US012002558B2

United States Patent
Blasetto et al.

(10) Patent No.: US 12,002,558 B2
(45) Date of Patent: *Jun. 4, 2024

(54) SYSTEMS AND METHODS FOR DISPENSING A STATIN MEDICATION OVER THE COUNTER

(71) Applicant: ASTRAZENECA UK LIMITED, Cambridge (GB)

(72) Inventors: James Blasetto, Chadds Ford, PA (US); Judy Firor, Landenberg, PA (US); David Guiga, West Chester, PA (US); William Mongan, Malvern, PA (US); Robert Prybolsky, West Chester, PA (US); Richard L. Skelly, Flourtown, PA (US)

(73) Assignee: ASTRAZENECA UK LIMITED, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 17/898,115

(22) Filed: Aug. 29, 2022

(65) Prior Publication Data

US 2023/0005584 A1    Jan. 5, 2023

Related U.S. Application Data

(63) Continuation of application No. 17/132,731, filed on Dec. 23, 2020, now Pat. No. 11,430,555, which is a
(Continued)

(51) Int. Cl.
*G16H 20/10* (2018.01)
*A61K 31/505* (2006.01)
*G16H 50/30* (2018.01)

(52) U.S. Cl.
CPC .......... *G16H 20/10* (2018.01); *A61K 31/505* (2013.01); *G16H 50/30* (2018.01)

(58) Field of Classification Search
CPC ........ G16H 10/20; G16H 10/60; G16H 20/10; G16H 20/13; G16H 70/20; G16H 50/30
(Continued)

(56) References Cited

U.S. PATENT DOCUMENTS 7,493,264 B1    2/2009  Kelly et al.
2005/0108053 A1  5/2005  Jones
(Continued)

FOREIGN PATENT DOCUMENTS

WO    WO 2010/041052 A1    4/2010

OTHER PUBLICATIONS

Doyle, After heart attacks, most don't get enough statins, Jan. 29, 2015, Reuters Health, https://www.reuters.com/article/us-heart-statins-guidelines/after-heart-attacks-most-dont-get-enough-statins-idUSKBN0L22M320150129 (Year: 2015).*
(Continued)

*Primary Examiner* — Devin C Hein
(74) *Attorney, Agent, or Firm* — Brett A. Lovejoy; Andrew J. Antczak; Morgan, Lewis & Bockius LLP

(57) ABSTRACT

A method is provided for treatment of atherosclerotic cardiovascular disease in a subject in need thereof by administering a statin pharmaceutical composition to the subject when the subject is qualified for over-the-counter access to the statin pharmaceutical composition. In some embodiments, the statin pharmaceutical composition includes atorvastatin, fluvastatin, lovastatin, pitavastatin, pravastatin, rosuvastatin, or simvastatin as an active ingredient.

27 Claims, 41 Drawing Sheets

Related U.S. Application Data continuation of application No. 16/872,251, filed on May 11, 2020, now Pat. No. 10,910,091, which is a continuation-in-part of application No. 16/791,745, filed on Feb. 14, 2020, now Pat. No. 11,031,104, which is a continuation of application No. 15/385,747, filed on Dec. 20, 2016, now Pat. No. 10,600,502.

(58) Field of Classification Search
USPC .......................................................... 705/2, 3
See application file for complete search history.

(56) References Cited

U.S. PATENT DOCUMENTS

| | | | |
|---|---|---|---|
| 2009/0125324 A1 | 5/2009 | Keravich et al. | |
| 2011/0166876 A1 | 7/2011 | Chapman et al. | |
| 2011/0178812 A1 | 7/2011 | Lindsay | |
| 2012/0232922 A1* | 9/2012 | Elsayed | A61P 39/00 705/2 |
| 2015/0261934 A1* | 9/2015 | Miller | G16H 20/10 705/3 |

OTHER PUBLICATIONS

Goff et al. 2013 ACC/AHA guideline on the assessment of cardiovascular risk: a report of the American College of Cardiology/American Heart Association Task Force on Practice Guidelines. Circulation Jun. 24, 2014, 129 (25 Suppl 2): S49-73 (Year: 2014).*
A.Th.G. Blom, J.A.L. Rens, Information about over-the-counter medication: The role of the pharmacy, Patient Education and Counseling, vol. 14, Issue 3,1989, pp. 181-189, ISSN 0738-3991, https://doi.org/10.1016/0738-3991(89)90032-3. (Year: 1989).*
U.S. Appl. No. 15,385,747, filed Dec. 20, 2016, now U.S. Pat. No. 10,600,502.
U.S. Appl. No. 15/877,133, filed Jan. 22, 2018, now U.S. Pat. No. 10,325,678.
U.S. Appl. No. 16/791,745, filed Feb. 14, 2020; now U.S. Pat. No. 11,031,104.
U.S. Appl. No. 16/871,251, filed May 11, 2020, now U.S. Pat. No. 10,910,091.
U.S. Appl. No. 17/132,731, filed Dec. 23, 2020, now U.S. Pat. No. 11,430,555.
International Search Report and Written Opinion for International Patent Application No. PCT/EP2017/083774 dated May 7, 2018, 17 pages.
Ramkumar, S. et al., Acta Cardiol. Sin., 32(6):631-39 (2016).
Barlas S. FDA Considers a New Paradigm For Over-the-Counter Medications: More Power-but More Burdens-for Pharmacists and Pharmacies. P T. May 2012;37(5):300-5. PubMed PMID: 22876088; PubMed Central PMCID: PMC3411219.
Crestor, Full Prescribing Information, 2012, AstraZeneca Pharmaceuticals LP.
Dyer O., BMJ, 330(7484):164 (2005).
Powerpoint presentations from the Engelberg Center for Health Care Reform, May 9, 2013.
Pfizer Wants Atorvastatin Available Over the Counter—Medscape—Aug. 4, 2011, downloaded from the Internet Nov. 30, 2018.
PR Newswire Association, "Americans Should Pay More Attention to Over-the-Counter (OTC) medicine Labels According to New Survey", Oct. 15 (2015) (citing McNeil Consumer Healthcare research).
Ferris et al., "Over-the-Counter Antifungal Drug Misuse Associated With Patient-Diagnosed Vulvovaginal Candidiasis" The American College of Obstetricians and Gynecologists. Published by Elsevier Science Inc. vol. 99, No. 3, (2002).
Stomberg et al., "Utilization effects of Rx-OTC switches and implications for future switches" Health 5 (2013) 1667-1680.
D'Agostino et al., "General Cardiovascular Risk Profile for Use in Primary Care. The Framingham Heart Study" Circulation (2008): 743-753.
Both et al., "Perspective: Analysis of licensed over-the-counter (OTC) antibiotics in the European Union and Norway, 2012" Euro Surveill. 2015;20(34).
Chang et al., Prescription to over-the-counter switches in the United States. Journal of Research in Pharmacy Practice. (2016).
Ferris et al., Over-the-Counter Antifungal Drug Misuse Associated With Patient-Diagnosed Vulvovaginal Candidiasis. Antifungal Drug Misuse. Obstetrics & Gynecology. vol. 99, No. 3, (2002) The American College of Obstetricians and Gynecologists.
Kelley and Buggey 2021, "Study Shows Use of Technology Can Help Ensure Safe and Effective Access to Non-Prescription Statins" News Releases. https://newsroom.clevelandclinic.org/2021/09/06/study-shows-use-of-technology-can-help-ensure-safe-and-effective-access-to-non-prescription-statins.
Marathe et al., Over-the-counter medicines: Global perspective and Indian scenario, J Postgrad Med. Jan.-Mar. 2020; 66(1): 28-34.
Nissen et al., 2021, "Technology-Assisted Self-Selection of Candidates for Nonprescription Statin Therapy," Journal of American College of Cardiology 78:11.
O'Riordan, 2021, "Could an App Replace Statin Prescribing by Doctors?," News—Daily https://www.tctmd.com/news/could-app-replace-statin-prescribing-doctors.
Pagidipati et al. 2021 "Should Cardiovascular Preventive Therapy Be Over-the-Counter," Journal of the American College of Cardiology 78:11 at 1124.
Phend, 2021, "'Self-Service' Statin Prescribing? Study Suggests It's Possible" https://www.medpagetoday.com/cardiology/dyslipidemia/94381.
Ruiz, Risks of self-medication practices, Current Drug Safety, 2010, 5 (4): 315-323.
Stomberg et al., Utilization effects of Rx-OTC switches and implications for future switches. Health. vol. 5, No. 10, 1667-1680 (2013).
Yuen et al., Rx-to-OTC Switch—An Overview and its Implications to Public Health. Pharmacy Education & Practice. vol. 25, No. 4 (2018).

* cited by examiner

4000

(4002) Qualify a human subject for an over-the-counter provision of a statin pharmaceutical composition.

> (4004) The statin pharmaceutical composition includes rosuvastatin as an active ingredient.

> (4006) The statin pharmaceutical composition includes atorvastatin, fluvastatin, lovastatin, pitavastatin, pravastatin, or simvastatin as an active ingredient.

(4008) Provide an assessment survey for obtaining a first information set from the subject.

> (4010) The first information set includes a sex of the subject, an age of the subject when the subject is a female - whether the subject is pregnant or breastfeeding, whether the subject is taking one or more compositions that interact with the statin pharmaceutical composition, whether the subject has ever had a cardiac event, a total cholesterol level of the subject, a low-density lipoprotein (LDL) cholesterol level of the subject, a high-density lipoprotein (HDL) cholesterol level of the subject, a triglyceride level of the subject, a systolic blood pressure of the subject, a diastolic blood pressure of the subject, whether the subject has a liver condition, an alcohol consumption status of the subject, and whether the subject has had an adverse reaction to a cholesterol lowering composition.

Fig. 4A

(4012) Apply an algorithm to the first information set.

(4014) The algorithm runs all or a portion of the first information set against a first plurality of assessment filters. The subject is deemed not qualified for a statin treatment when a respective filter in the first plurality of assessment filters is fired and the method is terminated without authorizing provision of the statin pharmaceutical composition to the subject.

(4016) The first plurality of assessment filters includes an age filter that is fired at least when the first information set indicates the age of the subject fails to satisfy an age threshold for receiving the statin pharmaceutical composition.

(4018) The age filter is fired when the first information set indicates the subject is a woman of childbearing age.

(4020) The age filter is fired when the first information set indicates the subject is less than 20 years of age.

(4022) The age filter is fired when the first information set indicates the subject is less than 20 years of age and male or less than 50 years of age and female.

(4024) The age filter is fired when the first information set indicates the subject fails to satisfy a ceiling age threshold for receiving the statin pharmaceutical composition.

(4026) The age filter is fired when the first information set indicates the subject is more than 75 years of age.

(4028) The first plurality of assessment filters includes a pregnancy filter that is fired at least when the subject is female and the first information set indicates the subject is pregnant or breastfeeding.

(4030) The pregnancy filter is fired when the first information set indicates the subject is female and planning on becoming pregnant.

Fig. 4B

*(4014 continued)*

*(4032)* The first plurality of assessment filters includes a severe drug interaction filter that is fired at least when the first set of information indicates the subject is taking one or more compositions that interact with the statin pharmaceutical composition. The one or more compositions are each contraindicated for co-administration with the statin pharmaceutical composition.

*(4034)* The statin pharmaceutical composition includes an active ingredient selected from the group consisting of atorvastatin, fluvastatin, lovastatin, and pitavastatin. The severe drug interaction filter is fired at least when the first information set indicates the subject is taking cyclosporine.

*(4036)* The statin pharmaceutical composition includes an active ingredient selected from the group consisting of fluvastatin, lovastatin, and pravastatin. The severe drug interaction filter is fired at least when the first information set indicates the subject is taking a cholesterol-lowering medication or a triglyceride-lowering medication.

*(4038)* The statin pharmaceutical composition includes an active ingredient selected from the group consisting of lovastatin, pitavastatin, and simvastatin. The severe drug interaction filter is fired at least when the first information set indicates the subject is taking an anti-viral protease inhibitor.

*(4040)* The statin pharmaceutical composition includes fluvastatin as an active ingredient. The severe drug interaction filter is fired at least when the first information set indicates the subject is taking warfrin.

*(4042)* The statin pharmaceutical composition includes lovastatin or simvastatin as an active ingredient. The severe drug interaction filter is fired at least when the first information set indicates the subject is taking a strong CYP3A4 inhibitor.

*(4044)* The statin pharmaceutical composition includes rosuvastatin as an active ingredient. The severe drug interaction filter is fired at least when the first information set indicates the subject is taking a drug from the group consisting of cyclosporine, a cholesterol-lowering drug, a triglyceride-lowering drug, and warfarin.

Fig. 4C

(4014 continued)

(4046) The first plurality of assessment filters includes a cardiac event filter that is fired at least when the first information set indicates the subject has had a documented cardiac event.

(4048) The cardiac event filter is fired when the first information set indicates the subject has had a heart attack, had a stroke, undergone a heart procedure, or has developed peripheral artery disease.

(4050) The cardiac event filter is fired when the first information set indicates the subject is a young male with a familial history of premature heart disease.

(4052) The first plurality of assessment filters includes a total cholesterol filter that is fired at least when the first information set indicates the subject has a total cholesterol level that fails to satisfy a ceiling total cholesterol level threshold.

(4054) The total cholesterol filter is fired when the first information set indicates the total cholesterol level of the subject is greater than 320 mg/dL.

(4056) The total cholesterol filter is fired when the first information set indicates the subject has a total cholesterol level that fails to satisfy a total cholesterol level threshold.

(4058) The total cholesterol filter is fired when the first information set indicates the total cholesterol level of the subject is less than 130 mg/dL.

Fig. 4D

*(4014 continued)*

*(4060)* The first plurality of assessment filters includes a LDL cholesterol filter that is fired at least when the first information set indicates the subject has a LDL cholesterol level that fails to satisfy a ceiling LDL cholesterol level threshold.

*(4062)* The LDL cholesterol filter is fired when the first information set indicates the LDL cholesterol level of the subject is greater than 190 mg/dL.

*(4064)* The LDL cholesterol filter is fired when the first information set indicates the subject has a LDL cholesterol level that fails to satisfy a LDL cholesterol level threshold.

*(4066)* The LDL cholesterol filter is fired when the first information set indicates the LDL cholesterol level of the subject is less than 160 mg/dL

*(4068)* The LDL cholesterol filter is fired when the first information set indicates the LDL cholesterol level of the subject is less than 160 mg/dL when the subject is an older male or a female and less than 70 mg/dL when the subject is a younger male with a familial history of premature heart disease

*(4070)* The first plurality of assessment filters includes a HDL cholesterol filter that is fired at least when the first information set indicates the subject has a HDL cholesterol level that fails to satisfy a ceiling HDL cholesterol level threshold.

*(4072)* The HDL cholesterol filter is fired when the first information set indicates the HDL cholesterol level of the subject is greater than 100 mg/dL.

*(4074)* The HDL cholesterol filter is fired when the first information set indicates the subject has a HDL cholesterol level that fails to satisfy a HDL cholesterol level threshold

*(4076)* The HDL cholesterol filter is fired when the first information set indicates the HDL cholesterol level of the subject is less than 20 mg/dL

Fig. 4E

(4014 continued)

(4078) The first plurality of assessment filters includes a triglyceride filter that is fired at least when the first information set indicates the subject has a triglyceride level that fails to satisfy a ceiling triglyceride level threshold.

(4080) The triglyceride filter is fired when the first information set indicates the triglyceride level of the subject is greater than 500 mg/dL.

(4082) The first plurality of assessment filters includes a blood pressure filter that is fired at least when the first information set indicates the systolic blood pressure of the subject fails to satisfy a ceiling systolic blood pressure threshold or the diastolic blood pressure of the subject fails to satisfy a ceiling diastolic blood pressure threshold.

(4084) The blood pressure filter is fired when the first information set indicates the systolic blood pressure of the subject is greater than 180 mmHg.

(4086) The blood pressure filter is fired when the first information set indicates the subject has a systolic blood pressure that fails to satisfy a systolic blood pressure threshold.

(4088) The blood pressure filter is fired when the first information set indicates the systolic blood pressure of the subject is less than 90 mmHg.

(4090) The blood pressure filter is fired when the first information set indicates the diastolic blood pressure of the subject is greater than 120 mmHg.

Fig. 4F

*(4014 continued)*

*(4092)* The first plurality of assessment filters includes an ASCVD risk pooled cohort equation filter that is fired at least when an ASCVD risk derived from the first information set indicates the ASCVD risk of the subject fails to satisfy a ceiling ASCVD risk threshold.

*(4094)* The first information set further includes a race of the subject, whether the subject is taking a high blood pressure treatment, a diabetes status of the subject, and a smoking status of the subject. The ASCVD risk pooled cohort equation filter incorporates the age of the subject, the gender of the subject, the race of the subject, the total cholesterol of the subject, the triglyceride level of the subject, the systolic blood pressure of the subject, the diastolic blood pressure of the subject, whether the subject is taking a medication for hypertension, the diabetes status of the subject, and the smoking status of the subject to derive a risk for ASCVD.

*(4096)* The ASCVD risk pooled cohort equation is implemented as a multivariable Cox proportional hazard regression.

*(4098)* The ASCVD risk pooled cohort equation filter is fired when the first information set indicates the subject has an ASCVD risk that is greater than a 20% 10-year risk.

*(4100)* The ASCVD risk pooled cohort equation filter is fired when the first information set indicates the subject has an ASCVD risk that fails to satisfy an ASCVD risk threshold.

*(4102)* The ASCVD risk pooled cohort equation filter is fired when the first information set indicates the subject has an ASCVD risk that is less than a 5% 10-year risk.

*(4104)* The algorithm bypasses firing the ASCVD risk pooled cohort equation filter when the first information set indicates the subject has an ASCVD risk that fails to satisfy the ASCVD risk threshold, the subject has diabetes, and the age of the subject satisfies a first ceiling diabetes age threshold for receiving the statin pharmaceutical composition.

*(4106)* The first ceiling diabetes age threshold for receiving the statin pharmaceutical composition is 50 years of age when the subject is a male and 60 years of age when the subject is a female.

Fig. 4G

*(4014 continued)*

*(4100 continued)*

*(4108)* The ASCVD risk pooled cohort equation filter is fired when the first information set indicates the subject has diabetes and the age of the subject satisfies a second ceiling diabetes age threshold for receiving the statin pharmaceutical composition.

*(4110)* The second ceiling age threshold for receiving the statin pharmaceutical composition is 50 years of age when the subject is a male and 60 years of age when the subject is a female.

*(4112)* The first plurality of assessment filters includes a liver condition filter that is fired at least when the first information set indicates the subject has a liver condition.

*(4114)* The first plurality of assessment filters includes a risk enhancing factor filter that is fired unless the first information set indicates that the subject has at least one of a plurality of enhancing factors for high cholesterol.

*(4116)* The first plurality of assessment filters includes a risk enhancing factor filter that is fired unless the first information set indicates that the subject has at least two of a plurality of enhancing factors for high cholesterol.

*(4118)* The first plurality of assessment filters includes a risk enhancing factor filter that is fired when the first information set indicates the subject has an ASCVD risk that fails to satisfy an intermediate ASCVD risk threshold, unless the first information set indicates the subject has at least one of a plurality of risk enhancing factors for high cholesterol.

*(4120)* The first plurality of assessment filters includes a risk enhancing factor filter that is fired when the first information set indicates the subject has an ASCVD risk that fails to satisfy an intermediate ASCVD risk threshold, unless the first information set indicates the subject has at least two of a plurality of risk enhancing factors for high cholesterol.

Fig. 4H

*(4014 continued)*

*(4118 continued OR 4120 continued)*

*(4122)* The ASCVD risk of the subject is derived from a pooled cohort algorithm that incorporates the age of the subject, the gender of the subject, the race of the subject, the total cholesterol of the subject, the LDL of the subject, the HDL of the subject, the triglyceride level of the subject, the systolic blood pressure of the subject, the diastolic blood pressure of the subject, whether the subject is taking a medication for hypertension, the diabetes status of the subject, and the smoking status of the subject.

*(4124)* The ASCVD risk is derived from a pooled cohort algorithm implementing a Cox proportional hazard regression.

*(4126)* The intermediate ASCVD risk threshold is a 7.5% 10-year risk.

*(4114 continued through 4120 continued)*

*(4128)* The plurality of risk enhancing factors that prevent firing of the risk enhancing factor filter includes South Asian descent, a familial history of premature heart disease, a LDL cholesterol level of at least 160 mg/dL, a triglyceride level of at least 175 mg/dL, an inflammatory disease, preeclampsia, premature menopause, a C-Reactive Protein level of at least 2 mg/L, coronary artery calcium, and metabolic syndrome.

*(4130)* The subject is deemed to have the metabolic syndrome when the first information set indicates the subject has a HDL cholesterol level of less than 40 mg/dL; a triglyceride level of greater than 150 mg/dL; and a systolic blood pressure of at least 130 mmHg, a diastolic blood pressure of at least 85 mmHg, or a current blood pressure medication regiment when the subject has a systolic blood pressure of less than 130 mmHg and a diastolic blood pressure of less than 85 mmHg.

Fig. 41

(4012 continued)

(4014 continued)

(4130 continued)

(4132) The subject is deemed to have the metabolic syndrome when the first information set indicates the subject has a waist circumference of at last 35 inches for a female or at least 40 inches for a male, and at least two of: a HDL cholesterol level of less than 40 mg/dL; a triglyceride level of greater than 150 mg/dL; and a systolic blood pressure of at least 130 mmHg, a diastolic blood pressure of at least 85 mmHg, or a current blood pressure medication regiment when the subject has a systolic blood pressure of less than 130 mmHg and a diastolic blood pressure of less than 85 mmHg.

(4134) The algorithm runs all or a portion of the first information set against a second plurality of assessment filters. When a respective filter in the second plurality of assessment filters is fired, the subject is provided with a warning corresponding to the respective filter.

(4136) The second plurality of assessment filters includes an alcohol consumption filter that is fired at least when the alcohol consumption status of the subject in the first information set fails to satisfy a ceiling alcohol consumption threshold.

(4138) The ceiling amount of alcohol for firing the alcohol consumption filter is two alcoholic drinks per day.

(4140) The second plurality of assessment filters includes a first adverse reaction filter that is fired at least when the first information set indicates the subject has had an adverse reaction to a cholesterol-lowering drug.

Fig. 4J

(4134 continued)

(4142) The second plurality of assessment filters includes a moderate drug interaction filter that is fired at least when the first information set indicates the subject is taking one or more compositions that interact with the statin pharmaceutical composition. The one or more compositions are each associated with a warning, but are not contraindicated, for co-administration with the statin pharmaceutical composition.

(4144) The statin pharmaceutical composition includes rosuvastatin as an active ingredient. The moderate drug interaction filter is fired at least when the first information set indicates the subject is taking colchicine or an anti-viral protease inhibitor.

(4146) The second plurality of assessment filters further includes a second adverse reaction filter that is fired at least when the first information set indicates the subject has had an adverse reaction to the cholesterol-lowering composition.

(4150) The statin pharmaceutical composition includes rosuvastatin as an active ingredient. The second plurality of assessment filters includes a kidney disorder filter that is fired at least when the first information set indicates that the subject has kidney disease.

(4152) The statin pharmaceutical composition includes an active ingredient selected from the group consisting of atorvastatin, fluvastatin, and pitavastatin. The second plurality of assessment filters includes a kidney disorder filter that is fired at least when the first information set indicates that the subject has kidney disease.

*(4154)* The algorithm obtains acknowledgement from the subject confirming that the subject has discussed the risk factor associated with each warning issued to the subject by any filter in the second plurality of assessment filters with a physician.

*(4156)* The algorithm proceeds with a fulfillment process when no filter in the first plurality of assessment filters has been fired and the subject has acknowledged each warning associated with each filter in the second plurality of assessment filters that was fired.

*(4158)* The fulfillment process includes storing an indication in a subject profile of an initial order for the statin pharmaceutical composition, communication an over the counter drug facts label for the statin pharmaceutical composition to the subject, and authorizing, upon confirmation from the subject that the over the counter drug facts label has been received and read, provision of the statin pharmaceutical composition.

*(4160)* Upon confirmation from the subject that the over the counter drug facts label has been received and read, the subject is authorized for a dosage of from 2.5 mg to 15 mg of rosuvastatin per day.

*(4162)* Upon confirmation from the subject that the over the counter drug facts label has been received and read, the subject is authorized for a dosage of 5 mg of rosuvastatin per day.

*(4164)* Upon confirmation from the subject that the over the counter drug facts label has been received and read, the subject is authorized for a dosage of from 20 mg to 40 mg of fluvastatin per day.

*(4166)* Upon confirmation from the subject that the over the counter drug facts label has been received and read, the subject is authorized for a dosage of from 10 mg to 40 mg of atorvastatin per day.

*(4168)* Upon confirmation from the subject that the over the counter drug facts label has been received and read, the subject is authorized for a dosage of from 1 mg to 4 mg of pitavastatin per day.

*(4170)* Upon confirmation from the subject that the over the counter drug facts label has been received and read, the subject is authorized for a dosage of from 10 mg to 40 mg of lovastatin per day.

(4012 continued)

(4156 continued)

(4158 continued)

(4172) Upon confirmation from the subject that the over the counter drug facts label has been received and read, the subject is authorized for a dosage of from 10 mg to 40 mg of pravastatin per day.

(4174) Upon confirmation from the subject that the over the counter drug facts label has been received and read, the subject is authorized for a dosage of from 5 mg to 20 mg of simvastatin per day.

(4176) Administer, after authorization of the provision, the statin pharmaceutical composition to the subject.

(5002) Re-qualify a human subject for an over-the-counter provision of a statin pharmaceutical composition in response to receiving a re-order request from the subject.

> (5004) The statin pharmaceutical composition includes rosuvastatin as an active ingredient.

> (5006) The statin pharmaceutical composition includes atorvastatin, fluvastatin, lovastatin, pravastatin, pitavastatin, or simvastatin as an active ingredient.

(5008) Provide a re-assessment survey for obtaining a second information set from the subject.

> (5010) The second information set includes whether the subject has had a documented cardiac event since receiving their last provision of the statin pharmaceutical composition, when the subject is female – whether the subject is pregnant or breastfeeding, whether the subject is taking one or more compositions that interact with the statin pharmaceutical composition, whether the subject has experienced liver problems since receiving their last provision of the statin pharmaceutical composition, whether the subject has experienced a muscle irregularity since receiving a muscle irregularity since receiving their last provision of the statin pharmaceutical composition, and an alcohol consumption status of the subject since receiving their last provision of the statin pharmaceutical composition.

(5012) Apply an algorithm to the second information set.

> (5014) The algorithm runs all or a portion of the second information set against a first plurality of re-assessment filters. The subject is deemed not qualified for a statin treatment when a respective filter in the first plurality of re-assessment filters is fired and the method is terminated without authorizing provision of the statin pharmaceutical composition to the subject.
>
>> (5016) The first plurality of re-assessment filters includes a cardiac event filter that is fired at least when the second information set indicates the subject has had a documented cardiac event since receiving their last provision of the statin pharmaceutical composition.
>>
>>> (5018) The cardiac event filter is fired when the second information set indicates the subject had a heart attack, had a stroke, has undergone a heart procedure, or has developed peripheral artery disease since receiving their last provision of the statin pharmaceutical composition.

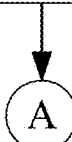

Fig. 5A

*(5014 continued)*

*(5020)* The first plurality of re-assessment filters includes a cholesterol status filter that is fired at least when the second information set indicates that a cholesterol level of the subject has not been reduced by a threshold amount.

> *(5022)* The algorithm bypasses the cholesterol status filter when the subject reported a reduction of their cholesterol by more than the threshold amount during a previous re-order of the statin pharmaceutical composition.

> *(5024)* The algorithm bypasses the cholesterol status filter when the second information set indicates the subject has not yet retested their cholesterol following their first provision of the statin pharmaceutical composition, and has ordered the statin pharmaceutical composition less than three times.

> *(5026)* The algorithm bypasses the cholesterol status filter when the second information set indicates the subject has not yet retested their cholesterol following their first provision of the statin pharmaceutical composition, and has ordered the statin pharmaceutical composition less than three times.

*(5028)* The first plurality of re-assessment filters includes a pregnancy filter that is fired at least when the subject is female and the second information set indicates the subject is pregnant or breastfeeding.

*(5030)* The first plurality of re-assessment filters includes a severe drug interaction filter that is fired at least when the second information set indicates the subject is taking one or more compositions that interact with the statin pharmaceutical composition. The one or more compositions are each contraindicated for co-administration with the statin pharmaceutical composition.

> *(5032)* The statin pharmaceutical composition includes an active ingredient selected from the group consisting of atorvastatin, fluvastatin, lovastatin, and pitavastatin. The severe drug interaction filter is fired at least when the second information set indicates the subject is taking cyclosporine.

Fig. 5B

*(5014 continued)*

*(5030 continued)*

*(5034)* The statin pharmaceutical composition includes an active ingredient selected from the group consisting of fluvastatin, lovastatin, and pravastatin. The severe drug interaction filter is fired at least when the second information set indicates the subject is taking a cholesterol-lowering medication or a triglyceride-lowering medication.

*(5036)* The statin pharmaceutical composition includes an active ingredient selected from the group consisting of lovastatin, pitavastatin, and simvastatin. The severe drug interaction filter is fired at least when the second information set indicates the subject is taking an anti-viral protease inhibitor.

*(5038)* The statin pharmaceutical composition includes fluvastatin as an active ingredient. The severe drug interaction filter is fired at least when the second information set indicates the subject is taking warfarin.

*(5040)* The statin pharmaceutical composition includes lovastatin or simvastatin as an active ingredient. The severe drug interaction filter is fired at least when the second information set indicates the subject is taking a strong CYP3A4 inhibitor.

*(5042)* The statin pharmaceutical composition includes rosuvastatin as an active ingredient. The severe drug interaction filter is fired at least when the second information set indicates the subject is taking a drug selected from the group consisting of cyclosporine, a cholesterol-lowering medication, a triglyceride-lowering medication, and warfarin.

*(5044)* The first plurality of re-assessment filters includes a liver condition filter that is fired at least when the second information set indicates the subject has developed a liver condition since receiving their last provision of the statin pharmaceutical composition.

*(5046)* The first plurality of re-assessment filters includes a muscle irregularity filter that is fired at least when the second information set indicates the subject has experienced unexplained muscle pain or weakness since receiving their last provision of the statin pharmaceutical composition.

Fig. 5C

*(5012 continued)*

*(5048)* The algorithm runs all or a portion of the second information set against a second plurality of re-assessment filters. When a respective filter in the second plurality of re-assessment filters is fired, the subject is provided with a warning corresponding to the respective filter.

*(5050)* The second plurality of re-assessment filters includes an alcohol consumption filter that is fired at least when the alcohol consumption status of the subject in the second information set fails to satisfy a ceiling alcohol consumption threshold.

*(5052)* The second plurality of re-assessment filters includes a moderate drug interaction filter that is fired at least when the second information set indicates the subject is taking one or more compositions that interact with the statin pharmaceutical composition. The one or more compositions are each associated with a warning, but are not contraindicated, for co-administration with the statin pharmaceutical composition.

*(5054)* The statin pharmaceutical composition includes rosuvastatin as an active ingredient. The moderate drug interaction filter is fired at least when the second information set indicates the subject is taking colchicine or an anti-viral protease inhibitor.

*(5056)* The statin pharmaceutical composition includes an active ingredient selected from the group consisting of atorvastatin, fluvastatin, pitavastatin, and rosuvastatin. The second plurality of re-assessment filters includes a kidney disorder filter that is fired at least when the second information set indicates the subject has developed kidney problems or experienced worsening of a previous kidney problem since receiving their last provision of the statin pharmaceutical composition.

*(5058)* The algorithm obtains acknowledgement from the subject confirming that the subject has discussed the risk factor associated with each warning issued to the subject by any filter in the second plurality of re-assessment filters with a physician.

Fig. 5D

(5012 continued)

(5060) The algorithm proceeds with a re-fulfillment process when no filter in the first plurality of re-assessment filters has been fired and the subject has acknowledged each warning associated with each filter in the second plurality of re-assessment filters that was fired.

(5062) The re-fulfillment process includes storing an indication in a subject profile of a re-order for the statin pharmaceutical composition, communication an over the counter drug facts label for the statin pharmaceutical composition to the subject, and authorizing, upon confirmation from the subject that the over the counter drug facts label has been received and read, re-provision of the statin pharmaceutical composition.

(5064) Upon confirmation from the subject that the over the counter drug facts label has been received and read, the subject is authorized for a dosage of from 2.5 mg to 15 mg of rosuvastatin per day.

(5066) Upon confirmation from the subject that the over the counter drug facts label has been received and read, the subject is authorized for a dosage of 5 mg of rosuvastatin per day.

(5068) Upon confirmation from the subject that the over the counter drug facts label has been received and read, the subject is authorized for a dosage of from 20 mg to 40 mg of fluvastatin per day.

(5070) Upon confirmation from the subject that the over the counter drug facts label has been received and read, the subject is authorized for a dosage of from 10 mg to 40 mg of atorvastatin per day.

(5072) Upon confirmation from the subject that the over the counter drug facts label has been received and read, the subject is authorized for a dosage of from 1 mg to 4 mg of pitavastatin per day.

(5074) Upon confirmation from the subject that the over the counter drug facts label has been received and read, the subject is authorized for a dosage of from 10 mg to 40 mg of lovastatin per day.

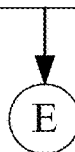

Fig. 5E

*(5012 continued)*

*(5060 continued)*

*(5062 continued)*

*(5076)* Upon confirmation from the subject that the over the counter drug facts label has been received and read, the subject is authorized for a dosage of from 10 mg to 40 mg of pravastatin per day.

*(5078)* Upon confirmation from the subject that the over the counter drug facts label has been received and read, the subject is authorized for a dosage of from 5 mg to 20 mg of simvastatin per day.

*(5080)* The method is terminated without authorizing re-provision of the statin pharmaceutical composition to the subject when more than a threshold period of time has passed since the subject received their first provision of the statin pharmaceutical composition without retesting their cholesterol.

*(5082)* The threshold period of time since the subject received their first provision of the statin pharmaceutical composition without retesting their cholesterol level, for terminating the method, is 90 days.

*(5084)* The method is terminated without authorizing re-provision of the statin pharmaceutical composition to the subject when less than a threshold period of time has passed since the subject received their last provision of the statin pharmaceutical composition.

*(5086)* The subject's last provision of the statin pharmaceutical composition included daily dosages of the statin pharmaceutical composition for a predetermined number of days. The threshold period of time since receiving their last provision of the statin pharmaceutical composition, for terminating the method, is a period of time greater than half the predetermined number of days.

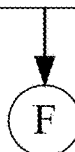

Fig. 5F

(5012 continued)

(5060 continued)

(5062 continued)

(5088) The method is terminated without authorizing re-provision of the statin pharmaceutical composition to the subject when the second information set indicates the subject has not yet retested their cholesterol following their first provision of the statin pharmaceutical composition, and has ordered the statin pharmaceutical composition at least three times.

(5090) Administer, after authorization of the re-provision, the statin pharmaceutical composition to the subject.

Fig. 5G

Have you ever had a heart attack, stroke, or an operation on your heart?

Users with a history of cardiac events are known to have adverse effects when taking with a statin pharmaceutical composition.

Please consult with your doctor to discuss whether taking a statin will be beneficial for you.

Do you have a history of kidney disease?

Users with compromised kidney function may experience adverse effects when taking a statin.

Have you discussed taking a statin with your doctor in view of your history of kidney disease?

— 702

Statin OTC may not be right for you. Based on your answers, it is important to talk to your doctor about potential risks of taking statin OTC. It may be helpful to have your summary of answers when talking to your doctor.

Has your doctor said it is OK for you to take statin OTC?

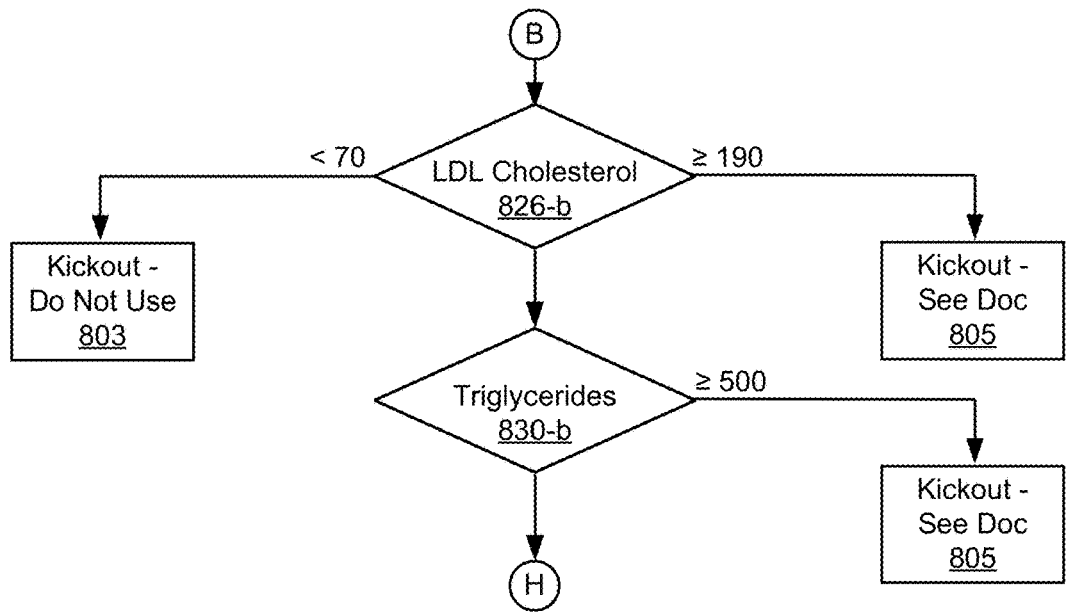
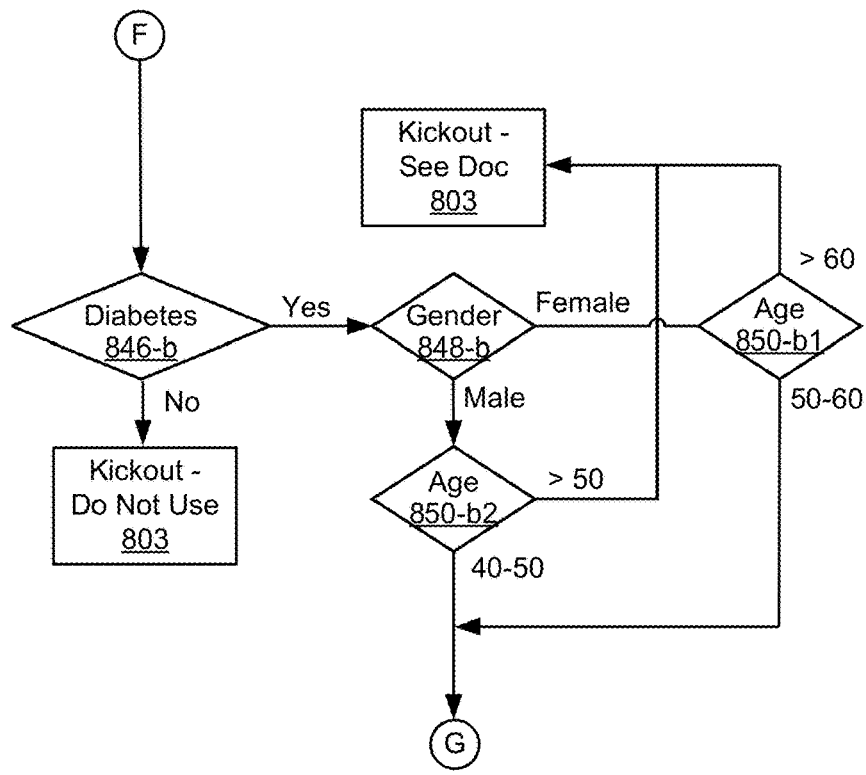
Fig. 8H

900

SYSTEMS AND METHODS FOR DISPENSING A STATIN MEDICATION OVER THE COUNTER

CROSS REFERENCE TO RELATED APPLICATIONS

This application is a continuation of U.S. patent application Ser. No. 17/132,731, filed Dec. 23, 2020, now U.S. Pat. No. 11,430,555, which is a continuation of U.S. patent application Ser. No. 16/872,251, filed May 11, 2020, now U.S. Pat. No. 10,910,091, which is a continuation-in-part of U.S. patent application Ser. No. 16/791,745, filed Feb. 14, 2020, now U.S. Pat. No. 11,031,104, which is a continuation of U.S. patent application Ser. No. 15/385,747, filed Dec. 20, 2016, now U.S. Pat. No. 10,600,502, each of which are hereby incorporated by reference in their entireties.

TECHNICAL FIELD

The present disclosure relates generally to methods for lowering cholesterol, e.g., thereby treating and/or preventing heart disease, by administering an over-the-counter statin pharmaceutical composition to a subject in need thereof, who has been qualified for over-the-counter access to the composition.

BACKGROUND

Cardiovascular disease remains the leading global cause of death, claiming more lives than all forms of cancer combined. The number of cardiovascular deaths is expected to increase to approximately 24 million annually by 2030. The direct and indirect annual costs total more than $316 billion dollars. This exceeds the entire gross domestic product (GDP) of all the world's countries except the top 30 countries.

Statins have been a cornerstone therapy for fighting heart disease for nearly three decades. The totality of evidence for reducing cardiovascular disease events is second to none in all of medicine. Statins are still the most prescribed class of medicine.

Despite the fact that many statins will be generically available off patent in the United States and other markets by 2017, it is expected that prevalence of cardiovascular disease will continue. That is, that heart disease will remain. The next-generation is showing clear signs they are going to develop cardiovascular disease at high prevalence levels and need help. Although novel therapies are materializing to address cardiovascular disease, it is expected that such novel therapies will be combined with statins, not replace them. Thus, it is expected that statins will remain a cornerstone therapy for cardiovascular disease for the foreseeable future.

Unfortunately, long-term trends demonstrate many people avoid prescription medications, including statins. One approach to making statins more available is to make then available without a prescription, e.g., over the counter ("OTC"). However, because statins cause serious adverse effects in certain patients, the population receiving the drug should be carefully selected and monitored. Ramkumar S. et al., Acta Cardiol. Sin., 32(6):631-39 (2016). This is why statin distribution has traditionally been regulated through exclusive prescription access. In order to ensure the safety of OTC distribution of statins, prospective patients must effectively self-select themselves for the drug. Recent studies, however, found that many prospective patients do not pay consistent attention to guidelines printed on the packaging of OTC drugs, to ensure safe and responsible use. PR Newswire Association, "Americans Should Pay More Attention to Over-the-Counter (OTC) medicine Labels According to New Survey", October 15 (2015) (citing McNeil Consumer Healthcare research). According to these studies, 40% of prospective patients consider the directions as just guidelines and 80% of patients do not re-read the label of an OTC medicine they have used before. Even more troubling, only 58% of men surveyed found it very important to pay attention to restrictions on an OTC label.

Currently, there are two regulatory pathways for legal marketing of an OTC drug in the United States. In the first pathway, marketing occurs in compliance with an OTC drug monograph, that sets regulatory standards for non-prescription drugs that are not covered by human drug applications, e.g., a New Drug Application (NDA) or Abbreviated New Drug Application (ANDA). An OTC monograph is created as a result of a three phase OTC drug review by the FDA. In phase I of the review, an advisory review panel determines whether ingredients in the proposed OTC composition could be generally recognized as safe and effective for use in self-treatment. In the second pathway, marketing occurs under the authority of an approved product-specific new drug application (NDA), or an abbreviated new drug application (ANDA). In order to support an over-the-counter label for a drug for which regulatory approval is being sought through an NDA, a consumer research study is required to assess the consumer's ability to select and deselect themselves as appropriate users of the drug, based on the proposed labeling for the drug. Oliver, A., Regulatory Rapporteur, 10(3):4-9 (2013), which is incorporated by reference herein.

However, attempts at switching distribution of cardiovascular drugs having potentially far-reaching benefits for societal health, from prescription-only to an OTC model, have repeatedly failed, in large part due to concerns over inappropriate patient selection and medication. Possibly the best documented cases relate to statins used to treat high cholesterol.

For instance, Merck has had at least three applications for sale of over the counter lovastatin rejected by the FDA, in 2000, 2005, and 2007. In 2005, their proposal to permit over the counter sales of lovastatin was rejected by an expert advisory panel at the FDA in 2005. The panel was concerned by a marketing study performed to support the proposal in which approximately one third of 3316 customers who were offered the drug over the counter decided they would purchase the drug. After reviewing the data, the panel concluded that 45% of the purchases would have been inappropriate for a variety of reasons, including the age of the subject, the subject's lack of knowledge about their condition, and contraindications associated with their condition. Dyer O., BMJ, 330(7484):164 (2005). In 2007, the board again concluded that the ability of consumers to appropriately self-select and to adequately comply with chronic MEVACOR® therapy without the intervention of a physician had not been demonstrated. Division of Metabolic and Endocrine Drug Products, 2005, "NDA 21-213 Non-prescription MEVACOR® 20 mg Joint Advisory Committee Meeting."

Similarly, Pfizer announced in 2011 its intention to switch LIPITOR® from prescription-only to OTC status. Sett OTC bulletin, 16 Nov. 2011, page 7. However, they abandoned their attempt in 2014 when a phase 3 "actual use" trial, intended to simulate the OTC use of LIPITOR® (atorvastatin calcium) 10 mg, failed to meet its primary objectives on the basis that patient compliance with the direction to check their low-density lipoprotein cholesterol (LDL-C) level and, after checking their LDL-C level, take appropriate action based on their test results was unsatisfactory. Pfizer Inc., "Pfizer Reports Second-Quarter 2015 Results," (2015).

In fact, in the nearly two decades since Bristol-Myers Squibb and Merck & Co first failed in their attempts to switch PRAVACHOL® and lovastatin, respectively, to OTC, a statin has never been granted OTC status in the United States. This is despite that nearly 40 million adults in the U.S. who are eligible for cholesterol-lowering medications, under the current guidelines, are not taking anything.

The information disclosed in this Background section is only for enhancement of understanding of the general background of the invention and should not be taken as an acknowledgment or any form of suggestion that this information forms the prior art already known to a person skilled in the art.

SUMMARY

Given the above background, systems and methods are needed for qualifying a human subject for delivery of a statin pharmaceutical composition over-the-counter to lower cholesterol, e.g., thereby, treating or preventing heart disease.

The present disclosure addresses the need in the art for systems and methods configured for qualifying a human subject for an over-the-counter provision of a statin pharmaceutical composition (e.g., a rosuvastatin pharmaceutical composition such as rosuvastatin calcium) in order to treat or prevent heart disease, e.g., by lowering cholesterol. In the present disclosure, systems and methods are provided for an over-the-counter provision of a statin pharmaceutical composition to a subject. An information set is obtained from the subject and applied to an algorithm. The algorithm runs the information set against a first plurality of filters. When a filter in the first plurality is fired, the subject is deemed not qualified for a statin treatment. The algorithm also runs the information set against a second plurality of filters. When a respective filter in the second plurality is fired, the subject is provided with a corresponding warning. The method proceeds to a fulfillment process when no filter in the first plurality is fired and the subject has acknowledged each warning associated with each fired filter in the second plurality of filters. The fulfillment process stores the composition order, communicates a drug facts label for the statin pharmaceutical composition to the subject, and authorizes, upon subject confirmation that the label has been read, provision of the statin pharmaceutical composition to the subject.

Accordingly, one aspect of the present disclosure provides a method for qualifying a subject for an over-the-counter provision of a statin pharmaceutical composition. The method includes providing an assessment survey of the subject in order to obtain a first information set. In some embodiments, the first information set include one or more of: a sex of the subject, an age of the subject, when the subject is female—whether the subject is pregnant or breast-feeding, whether the subject is taking one or more compositions that interact (e.g., via a pharmacokinetic interaction and/or a pharmacodynamic interaction) with the statin pharmaceutical composition, whether the subject has ever had a cardiac event, a cholesterol level of the subject (e.g., a total cholesterol level, a LDL cholesterol level, and a HDL cholesterol level), a triglyceride level of the subject, a blood pressure of the subject (e.g., a systolic blood pressure of the subject and/or a diastolic blood pressure of the subject), whether the subject has a liver condition, an alcohol consumption status of the subject, and whether the subject has had an adverse reaction to a cholesterol-lowering composition.

The method also includes applying an algorithm to the first information set. The algorithm runs all or a portion of the first information set against a first plurality of assessment filters. When a respective filter in the first plurality of assessment filters is fired, the subject is deemed not qualified for a statin treatment. The method is then terminated accordingly without authorizing provision of the statin pharmaceutical composition to the subject. In some embodiments, the first plurality of assessment filters includes one or more of an age filter, a pregnancy filter, a severe drug interaction filter, a cardiac event filter, a total cholesterol filter, a HDL cholesterol filter, a LDL cholesterol filter, a triglyceride level filter, a blood pressure filter, an atherosclerotic cardiovascular disease (ASCVD) risk pooled cohort equation filter, and a liver condition filter.

The algorithm also runs all or a portion of the first information set against a second plurality of assessment filters. When a respective filter in the second plurality of assessment filters is fired, the subject is provided with a warning corresponding to the respective filter. In some embodiments, the second plurality of assessment filters includes one or more of an alcohol consumption filter, a first adverse reaction filter, and a moderate drug interaction filter. However, unlike filters in the first plurality of assessment filters, filters in the second plurality of assessment filters do not automatically terminate the process without provision of the statin pharmaceutical composition to the subject.

The method continues by obtaining acknowledgment from the subject for the warning issued to the subject by any filter in the second plurality of assessment filters. In some embodiments, acknowledgment from the subject is a written acknowledgement, a verbal acknowledgment, or an electronic acknowledgment such as an electronic signature.

The method continues by proceeding with a fulfillment process when no filter in the first plurality of filters has been fired and the subject has acknowledged each warning associated with each filter in the second plurality of filters that was fired.

In some embodiments, the fulfillment process includes storing an indication in a subject profile of an initial order for the statin pharmaceutical composition, communicating an over-the-counter drug label for the statin pharmaceutical composition, and authorizing, upon confirmation from the subject that the over-the-counter drug label has been received and read, provision of the statin pharmaceutical composition to the subject.

In some embodiments, the statin pharmaceutical composition includes an active ingredient of rosuvastatin or a pharmaceutically acceptable salt thereof (e.g., rosuvastatin calcium, etc.) In some embodiments, the statin pharmaceutical composition includes an active ingredient of rosuvastatin calcium. In some embodiments, the statin pharmaceutical composition includes an active ingredient selected from the group consisting of atorvastatin, fluvastatin, lovastatin, pitavastatin, pravastatin, and simvastatin as an active ingredient.

In one aspect, the present disclosure provides a method for re-qualifying a subject for an over-the-counter provision (e.g., a subject who was previously qualified to receive a provision of the statin pharmaceutical composition) of the statin pharmaceutical composition (e.g., which is optionally performed in conjunction with a method for qualifying the subject for an initial order of the statin pharmaceutical composition). The method includes providing a re-assessment survey of the subject in order to obtain a second information set. In some embodiments, the second information set includes one or more of whether the subject has had a documented cardiac event since receiving their last provision of the statin pharmaceutical composition, when the subject is female—whether the subject is pregnant or breastfeeding, whether the subject is taking one or more compositions that interact with the statin pharmaceutical composition, whether the subject has experienced liver problems since receiving their last provision of the statin pharmaceutical composition, whether the subject has experienced a muscle irregularity since receiving their last provision of the statin pharmaceutical composition, and an alcohol consumption status of the subject.

The method also includes applying an algorithm to the second information set. The algorithm runs all or a portion of the second information set against a first plurality of re-assessment filters. When a respective filter in the first plurality of re-assessment filters is fired, the subject is deemed not qualified for a statin treatment. Accordingly, the method is terminated without authorizing re-provision of the statin pharmaceutical composition to the subject. In some embodiments, the first plurality of re-assessment filters includes one or more of a cardiac event filter, a cholesterol status filter, when the subject is female—a pregnancy filter, a severe drug interaction filter, a liver condition filter, and a muscle irregularity filter.

The algorithm also runs all or a portion of the second information set against a second plurality of re-assessment filters. When a respective filter in the second plurality of re-assessment filters is fired, the subject is provided with a warning corresponding to the respective filter. In some embodiments, the second plurality of re-assessment filters includes one or more of an alcohol consumption filter and a moderate drug interaction filter.

In some embodiments, the method includes storing an indication in the subject profile of a re-order for the statin pharmaceutical composition, communicating an over-the-counter drug facts label for the statin pharmaceutical composition to the subject, and authorizing, upon confirmation from the subject that the over-the-counter drug facts label has been received and read, re-provision of the statin pharmaceutical composition to the subject.

BRIEF DESCRIPTION OF THE DRAWINGS

FIGS. 4A, 4B, 4C, 4D, 4E, 4F, 4G, 4H, 4I, 4J, 4K, 4L, and 4M collectively provide a flow chart of processes for qualifying a human subject for an over-the-counter provision of a statin pharmaceutical composition to lower cholesterol, in accordance with various embodiments of the present disclosure.

FIGS. 5A, 5B, 5C, 5D, 5E, 5F, and 5G collectively provide a flow chart of processes for re-qualifying a human subject for an over-the-counter provision of a statin pharmaceutical composition to lower cholesterol, in accordance with various embodiments of the present disclosure.

FIGS. 8A, 8B, 8C, 8D, 8E, 8F, 8G, 8H, and 8I collectively illustrate an example method for qualifying a subject for an over-the-counter provision of a statin pharmaceutical composition, in accordance with various embodiments of the present disclosure.

Figure 1:
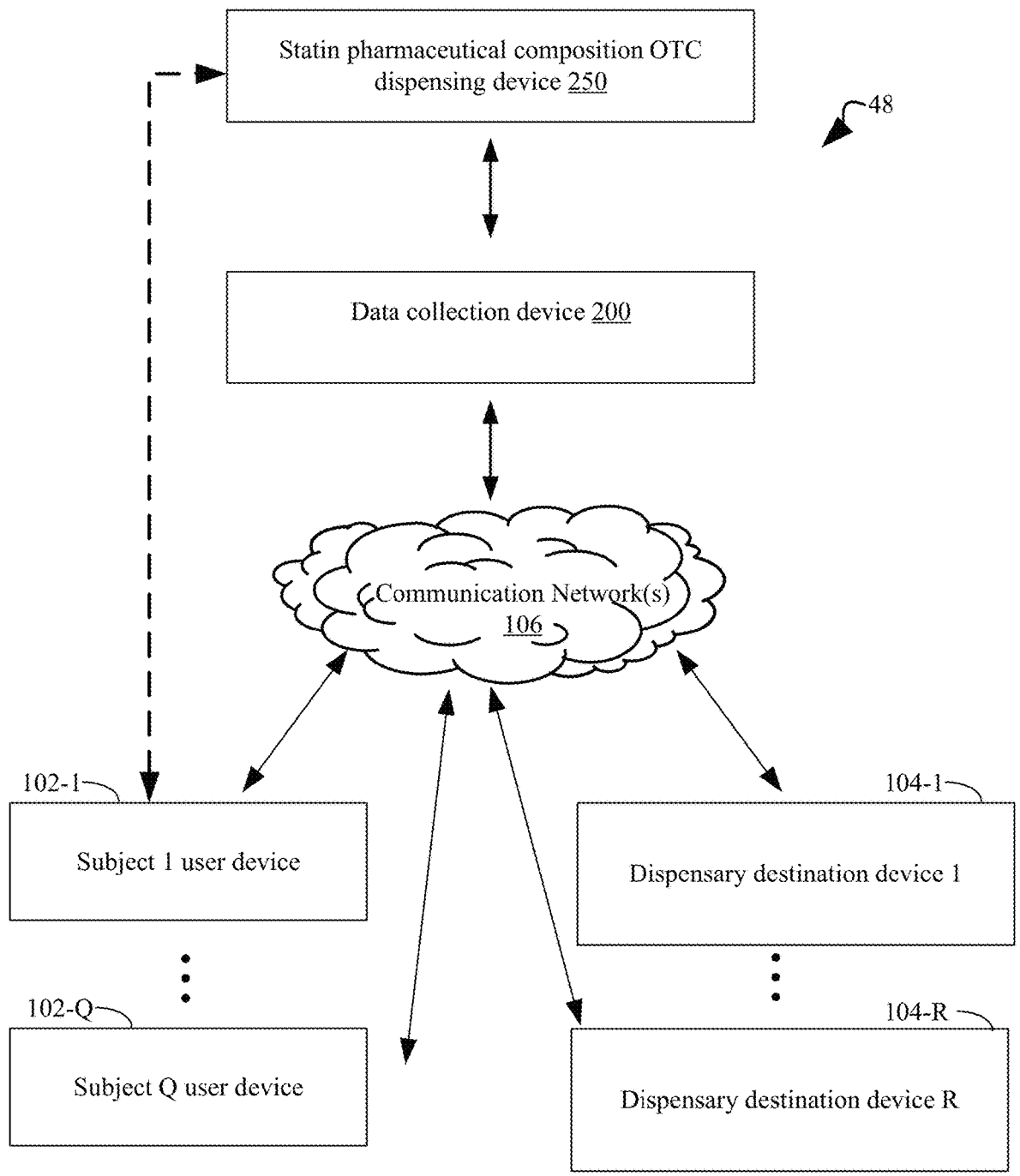
FIG. 1 illustrates an exemplary system topology that includes a statin pharmaceutical composition over-the-counter (OTC) dispensing device for qualifying a human subject for an over-the-counter provision of a statin pharmaceutical composition to lower cholesterol, a data collection device for collecting subject data, one or more user devices associated with human subjects, and one or more dispensary destinations for distributing the statin pharmaceutical composition over-the-counter, where the above-identified components are interconnected, optionally through a communications network, in accordance with various embodiments of the present disclosure.

In the figures, reference numbers refer to the same or equivalent parts of the present invention throughout the several figures of the drawing.

DETAILED DESCRIPTION

Hypercholesterolemia is a growing health problem, in the United States and worldwide. Although hypercholesterolemia can be effectively treated and/or prevented using established pharmaceutical compositions, access to these drugs is hindered by to the requirement for a prescription, as many individuals do not have adequate access and/or avoid the healthcare system for a variety of reasons. Accordingly, many people are not managing their hypercholesterolemia or conditions related to hypercholesterolemia appropriately. While over-the-counter alternatives to these prescription pharmaceuticals would increase access to these compositions, thereby improving population management of hypercholesterolemia and conditions related to hypercholesterolemia around the world, patients often have difficulty self-selecting themselves for an appropriate over-the-counter medication. Because inappropriate use of these drugs can result in ineffective treatment and/or serious side-effects, better systems and methods for selecting for, and treating patients with, other-the-counter hypercholesterolemia medications are needed. The present disclosure provides, among other aspects, methods, systems, and computer readable media that solve these problems.

Reference will now be made in detail to implementations, examples of which are illustrated in the accompanying drawings. In the following detailed description of implementations, numerous specific details are set forth in order to provide a thorough understanding of the present invention. However, it will be apparent to one of ordinary skill in the art that the present invention may be practiced without these specific details.

It will also be understood that, although the terms first, second, etc. may be used herein to describe various elements, these elements should not be limited by these terms. These terms are only used to distinguish one element from another. For example, a first filter could be termed a second filter, and, similarly, a second filter could be termed a first filter, without departing from the scope of the present disclosure. The first filter and the second filter are both filters, but they are not the same filter.

The terminology used in the present disclosure is for the purpose of describing particular embodiments only and is not intended to be limiting of the invention. As used in the description of the invention and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

As used herein, the term "over-the-counter" means to provide by retail purchase, subject to the constraints disclosed herein, but without a prescription or license from a physician or medical practitioner.

As used herein, the term "pharmaceutical compound" refers to any physical state of a material. Pharmaceutical compounds include but are not limited to capsules, tablets, liquids, topical formulations, and inhaled formulations.

As used herein, the term "contraindication" refers to a condition that makes a treatment, e.g., over-the-counter use of a statin pharmaceutical composition, inadvisable. Contraindications include physical characteristics of a subject, e.g., pregnancy or liver conditions, and contemporaneous drug use, e.g., statin pharmaceutical composition use. In the present context, identification of a contraindication fires a filter in a first plurality of filters, which prevents authorizing provision of a statin pharmaceutical composition, in accordance with some implementations of the methods, systems, and software disclosed herein.

As used herein, the term "risk factor" refers to a condition that makes a treatment, e.g., over-the-counter use of a statin pharmaceutical composition, possibly inadvisable. Risk factors include physical characteristics of a subject, e.g., a blood pressure reading, and contemporaneous drug use, e.g., use of a cholesterol-lowering composition. In the present context, identification of a risk factor fires a filter in a second plurality of filters, which prevents authorizing provision of a statin pharmaceutical composition without confirmation that the subject has discussed the risk factor with a medical professional, in accordance with some implementations of the methods, systems, and software disclosed herein.

As used herein, "drug interactions," e.g., with a statin pharmaceutical composition, include pharmacokinetic drug interactions and pharmacodynamics drug interactions. Generally, a pharmacokinetic drug interaction is an interaction between two drugs (e.g., a statin and a second drug) that result in alterations in the absorption, transport, distribution, metabolism, and/or excretion of either drug. Generally, a pharmacokinetic drug interaction is an interaction between two drugs (e.g., a statin and a second drug) that result in a direct change in the effect or either drug. For a more comprehensive summary of pharmacokinetic drug interactions and pharmacodynamics drug interactions, see, Cascorbi, I, Dtsch Arztebl Int., 109(33-34):546-55 (2012), the content of which is hereby incorporated by reference.

In the context of the present disclosure, classification of a condition as either a contraindication or a risk factor is specific to a particular identity and dose of a statin pharmaceutical composition being authorized for over-the-counter use. Classification of a particular condition, e.g., contemporaneous statin pharmaceutical composition use, may vary between different statin pharmaceutical compositions (e.g., it may be classified as a contraindication for a first statin, a risk factor for a second statin, and/or neither for a third statin). Likewise, a particular condition may be classified as a contraindication for use of a particular statin at a first over-the-counter dosage, classified as a risk factor for the same particular statin at a second (e.g., lower) over-the-counter dosage, and/or classified as neither for the same particular statin at a third (e.g., lowest) over-the-counter dosage.

As used herein, whether a subject "has developed" and/or "has experienced" a condition since receiving their last provision of a statin pharmaceutical composition refers to both conditions that are new to the subject, i.e., a condition that the subject did not have at the time they received their last provision of the statin pharmaceutical composition, and conditions that have been newly diagnosed, regardless of whether the condition existed when the subject received their last provision of the statin pharmaceutical composition, e.g., a condition that the subject was not aware of when they received their last provision of the statin pharmaceutical composition.

The term "salt(s)" includes salts of the compounds prepared by the neutralization of acids or bases, depending on the particular ligands or substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of base addition salts include sodium, potassium calcium, ammonium, organic amino, or magnesium salt, or a similar salt. Examples of acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids, and the like, as well as the salts derived from relatively nontoxic organic acids like acetic, propionic, isobutyric, butyric, maleic, malic, malonic, benzoic, succinic, suberic, fumaric, lactic, mandelic, phthalic, benzenesulfonic, p-tolylsulfonic, citric, tartaric, methanesulfonic, and the like. Certain specific compounds of the present invention contain both basic and acidic functionalities that allow the compounds to be converted into either base or acid addition salts. Hydrates of the salts are also included.

In one aspect of the present disclosure, a survey (e.g., an assessment survey and/or a re-assessment survey) of a subject is provided to obtain an information set in order to determine if the subject qualifies for an over-the-counter (OTC) provision of a statin pharmaceutical composition for lowering cholesterol, e.g., thereby, treating or preventing an atherosclerotic cardiovascular disease. The information set is used as the basis for running filters in a first plurality of filters. If the triggering conditions of any of the filters in the first plurality of filters are fired, the subject does not qualify for the OTC statin pharmaceutical composition. In some embodiments, the information set is also used as the basis for running filters of a second plurality of filters. If the triggering conditions of any of the filters in the second plurality of filters are fired, the subject is provided with warning messages associated with the respective filters of the second plurality of filters that have been fired. If none of the filters in the first plurality of filters are fired and the subject successfully addresses the warning messages associated with the respective filters of the second plurality of filters that have been fired a fulfillment process is initiated for an OTC provision of the statin pharmaceutical composition.

FIG. 1 illustrates an example of an integrated system 48 for providing one or more surveys (e.g., an assessment survey and/or a re-assessment survey) of one or more subjects in order to qualifying the subjects for an OTC provision of a statin pharmaceutical composition. The integrated system 48 includes one or more connected user devices 102 (e.g., first user device 102-1, second user device 102-2, . . . , $Q^{th}$ user device 102-Q). The user devices 102 are configured for entering survey data and making requests for the statin pharmaceutical composition. The system 48 also includes one or more dispensary destination devices 104 that are configured to receive instructions in order to provide the statin pharmaceutical composition to qualifying subjects. Furthermore, the system 48 includes a statin pharmaceutical composition over-the-counter (OTC) dispensing device 250 and one or more data collection devices 200 that are configured for collecting subject data.

Throughout the present disclosure, the data collection device 200 and the statin pharmaceutical composition OTC dispensing device 250 will be referenced as separate devices solely for purposes of clarity. That is, the disclosed functionality of the data collection device 200 and the disclosed functionality of the statin pharmaceutical composition OTC dispensing device 250 are contained in separate devices as illustrated in FIG. 1. However, it will be appreciated that, in fact, in some embodiments, the disclosed functionality of the data collection device 200 and the disclosed functionality of the statin pharmaceutical composition OTC dispensing device 250 are contained in a single device.

With the integrated system 48, information sets obtained from the subjects are run against a first plurality of filters, such as a first plurality of assessment filters (e.g., filter 216-1, filter 216-2, filter 216-11, etc.) and/or a first plurality of re-assessment filters (e.g., filter 216-12, filter 216-17, etc.). When a filter in the respective first plurality of filters (e.g., filter 216) is fired for a respective subject, the respective subject is deemed not qualified for the statin pharmaceutical composition. In some embodiments, the information set is also run against a second plurality of filters (e.g., filter 222-1, filter 222-2, filter 222-4, etc.) and/or a second plurality of re-assessment filters (e.g., filter 222-4, filter 222-5, etc.). When a respective filter in the respective second plurality is fired for a respective subject, the respective subject is provided with a warning (e.g., filter warning 226) associated with the respective filter. In some embodiments, the information set is run against the first plurality of filters and the second plurality of filters concurrently. In some embodiments, the information set is run against the first plurality of filters and then against the second plurality of filters (e.g., sequentially). For instance, in some embodiments the information set is obtained and then run against the plurality of filters. However, the present disclosure is not limited thereto. In some embodiments, each piece of information of the information set is run against a corresponding filter prior to a subsequent piece of information of the information set being obtained. This running prior to the subsequent piece prevents a user from unnecessarily providing a piece of information in accordance with a determination that the user is not qualified for the statin pharmaceutical composition (e.g., preserves privacy of a subject).

As used herein, unless expressly stated otherwise, a survey refers to both an assessment survey and/or a re-assessment survey. For instance, in some embodiments a first survey result corresponds to an assessment survey (e.g., a piece of information of a first information set), whereas in other embodiments a first survey results corresponds to a re-assessment survey (e.g., a piece of information of a second information set), without departing from the scope of the present disclosure.

The method enabled by the integrated system 48 proceeds to a fulfillment process, or similarly a re-fulfillment process, when no filter in the respective first plurality of filters fires and the subject has acknowledged, or otherwise successfully addressed, each warning associated with each filter in the respective second plurality of filters that fired. As part of the fulfillment process, or re-fulfillment process, the composition order is stored (e.g., in a user profile 234 associated with the subject to receive the pharmaceutical composition), a drug facts label (e.g., drug facts label 230) for the statin pharmaceutical composition is communicated to the qualifying subject. Upon subject confirmation that the label has been read, authorization is granted to provide a provision of the statin pharmaceutical composition.

Referring to FIG. 1, the statin pharmaceutical composition OTC dispensing device 250 qualifies a subject for an over-the-counter provision of a statin pharmaceutical composition to lower cholesterol. To accomplish the above, the data collection device 200, which is in electrical communication with the statin pharmaceutical composition OTC dispensing device 250, receives an information set (e.g., a first information set associated with an assessment survey and/or a second information set associated with a re-assessment survey) originating from one or more user devices 102 that are associated with corresponding subjects. In some embodiments, the data collection device 200 receives the respective information sets directly from the user devices 102. For instance, in some embodiments the data collection device 200 receives this data wirelessly through radio-frequency (RF) signals. In some embodiments, such signals are in accordance with an 802.11 (Wi-Fi), Bluetooth, or ZigBee standard. In some embodiments, the data collection device 200 receives such data directly, analyzes the data, and passes the analyzed data to statin pharmaceutical composition OTC dispensing device 250.

In some embodiments, the data collection device 200 and/or the statin pharmaceutical composition OTC dispensing device 250 is not proximate to the subject and/or does not have wireless capabilities or such wireless capabilities are not used for the purpose of acquiring survey results. In such embodiments, a communication network 106 may be used to communicate survey questions (e.g., survey questions 208, 212) from the statin pharmaceutical composition OTC dispensing device 250 to user devices 102 and the answers (e.g., the respective information set) to such survey questions from the user devices 102 to the data collection device 200 and/or the statin pharmaceutical composition OTC dispensing device 250. Further, in some embodiments the communication network 106 communicates authorization to dispense the statin survey questions from the statin pharmaceutical composition OTC dispensing device 250 to dispensary destination devices 104.

Examples of networks 106 include, but are not limited to, the World Wide Web (WWW), an intranet and/or a wireless network, such as a cellular telephone network, a wireless local area network (LAN) and/or a metropolitan area network (MAN), and other devices by wireless communication. The wireless communication optionally uses any of a plurality of communications standards, protocols and technologies, including but not limited to Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Wireless Fidelity (Wi-Fi) (e.g., IEEE 802.11a, IEEE 802.11ac, IEEE 802.11ax, IEEE 802.11b, IEEE 802.11g and/or IEEE 802.11n), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of the present disclosure.

Of course, other topologies of the system 48 are possible. For instance, rather than relying on a communications network 106, the one or more user devices 102 and the one or more dispensary destination devices 104 may communicate directly to the data collection device 200 and/or the statin pharmaceutical composition OTC dispensing device 250. Further, the data collection device 200 and/or the statin pharmaceutical composition OTC dispensing device 250 may constitute a portable electronic device, a server computer, or in fact constitute several computers that are linked together in a network, be a virtual machine in a cloud computing context, be a container in a cloud computer context, or a combination thereof. As such, the exemplary topology shown in FIG. 1 merely serves to describe the features of an embodiment of the present disclosure in a manner that will be readily understood to one of skill in the art.

Figure 2:
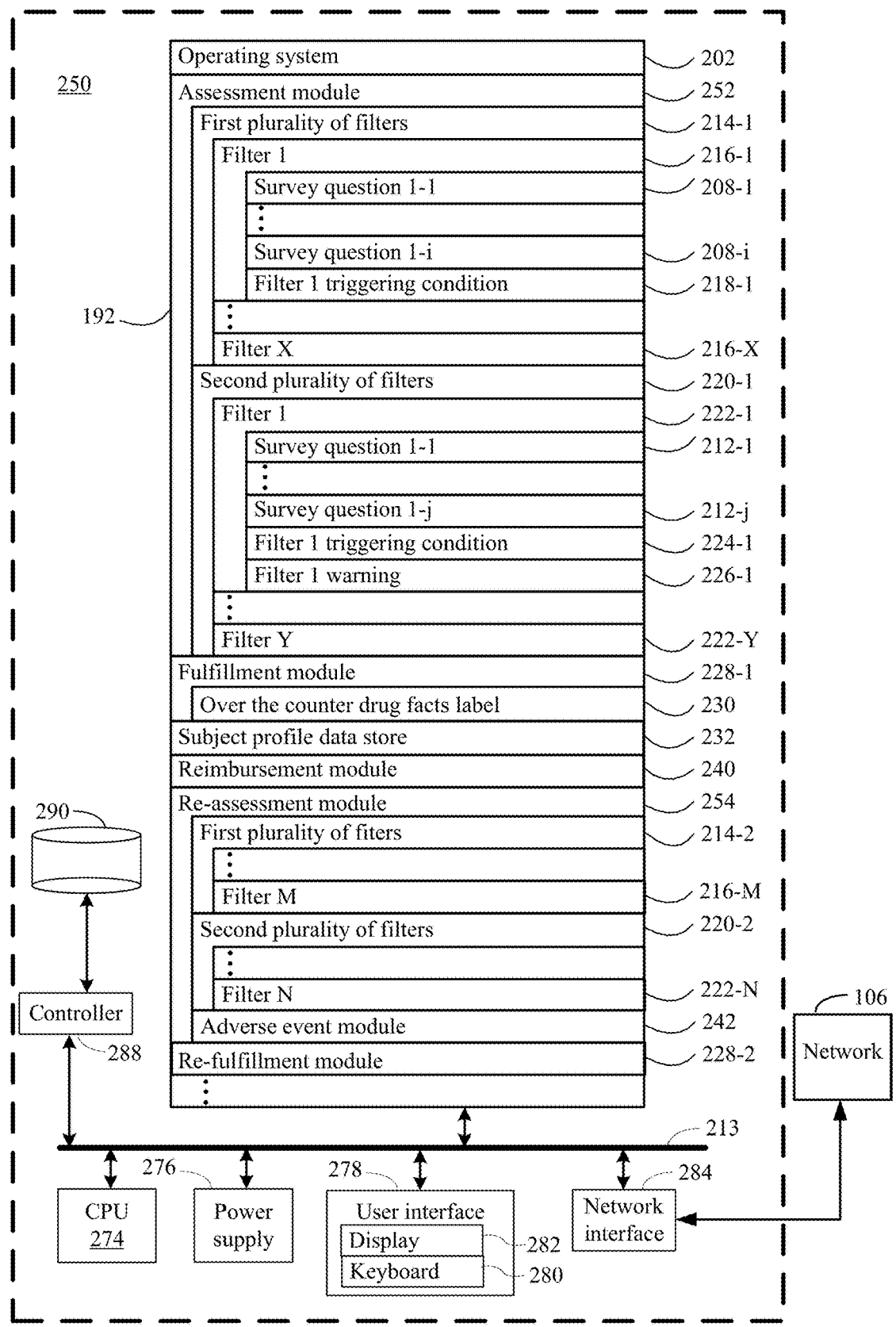
FIG. 2 illustrates an example device for qualifying a human subject for a provision of a statin pharmaceutical composition over-the-counter to lower cholesterol in accordance with various embodiments of the present disclosure.

Turning to FIG. 2 with the foregoing in mind, an exemplary statin pharmaceutical composition OTC dispensing device 250 configured for determining whether a subject is qualified for an OTC provision of a statin pharmaceutical composition is depicted. Referring to FIG. 2, in typical embodiments, the statin pharmaceutical composition OTC dispensing device 250 includes one or more computers. For purposes of illustration in FIG. 2, the statin pharmaceutical composition OTC dispensing device 250 is represented as a single computer that includes all of the functionality for qualifying a human subject for an over-the-counter provision of a statin pharmaceutical composition to lower cholesterol. However, the present disclosure is not limited thereto. In some embodiments, the functionality for qualifying a human subject for an over-the-counter provision of a statin pharmaceutical composition to lower cholesterol is spread across any number of networked computers and/or resides on each of several networked computers, is hosted on one or more virtual machines at a remote location accessible across the communications network 106, and/or is hosted on one or more containers at a remote location accessible across the communications network 106. One of skill in the art will appreciate that any of a wide array of different computer topologies are used for the present disclosure and all such topologies are within the scope of the present disclosure.

The statin pharmaceutical composition OTC dispensing device 250 of FIG. 2 is configured to conduct an assessment survey (e.g., using assessment module 252 to perform an initial qualification of the subject for a provision of a statin pharmaceutical composition) and/or a re-assessment survey (e.g., using re-assessment module 254 to perform a re-qualification of the subject for provision of a statin pharmaceutical composition). The assessment survey (e.g., the assessment) includes a variety of questions 208, 212 associated with assessment filters 216, 222 within a first plurality of assessment filters (e.g., filters 214) and a second plurality of assessment filters (e.g., filters 220), respectively. An algorithm is used to run answers to the questions in the assessment survey (e.g., a first information set) received by the device 250 against one or more assessment filters 216 in the first plurality of assessment filters 214-1 and/or, in some embodiments, one or more assessment filters 222 in the second plurality of assessment filters 220-1, respectively. Similarly, the re-assessment survey (e.g., the re-assessment) also includes a variety of questions 208, 212 associated with one or more re-assessment filters 216 in the first plurality of re-assessment filters 214-2 and/or, in some embodiments, one or more re-assessment filters 222 in the second plurality of re-assessment filters 220-2, respectively. Answers to the questions in the re-assessment survey (e.g., a second information set) received by the device 250 are run against one or more re-assessment filters in a first plurality of re-assessment filters 216-2 and re-assessment filters in a second plurality of re-assessment filters 220-2, e.g., within the first and second pluralities of re-assessment filters, respectively. Re-assessment filters 216 of the first plurality of re-assessment filters 214-2 are configured to terminate the re-qualification process when fired. Re-assessment filters 222 of the second plurality of re-assessment filters 220-2 are configured to provide the subject with a warning associated with a corresponding survey question. In other words, the device of FIG. 2 is configured to accumulate results (e.g., an information set) from a survey (e.g., survey questions 208 and survey questions 212 of an assessment survey module 252 and/or a re-assessment survey module 545) and apply an algorithm to the results by running the results against corresponding filters (e.g., assessment filters and/or re-assessment filters, respectively) in order to determine if a subject is qualified for an OTC provision of a statin pharmaceutical composition.

In the present disclosure, a plurality of filters refers to a series, or set, or filters in either the first plurality of filters or the second plurality of filters of a respective survey. For instance, in some embodiments, a plurality of filters of the first plurality of filters 214 can include any subset of filters 216 of the first plurality of filters (e.g., any subset of filters of the first plurality of assessment filters and the first plurality of re-assessment filters). As an example, in some embodiments a plurality of filters of the first plurality of filters includes filters 216-1, 216-2, 216-3, . . . , 216-i, or any combination thereof. Similarly, a plurality of filters of the second plurality of filters 220 can include any set of filters 222 of the second plurality of filters (e.g., any subset of filters of the second plurality of assessment filters and the second plurality of re-assessment filters). Moreover, in some embodiments a plurality of filters of the second plurality of filters includes filters 222-1, 222-2, 222-3, . . . , 222-i, or any combination thereof. However, the present disclosure is not limited thereto. For instance, in some embodiments filters of the first plurality of filters are categorized according to which survey the filter is associated with (e.g., the first plurality of filters is categorized by assessment filters and/or re-assessment filters, the second plurality of filters is categorized by assessment filters and/or re-assessment filters).

Continuing to refer to FIG. 2, in some embodiments, the dispensing device 250 includes one or more processing units (CPU's) 274, a network or other communications interface 284, a memory 192 (e.g., random access memory), one or more magnetic disk storage and/or persistent devices 290 optionally accessed by one or more controllers 288, one or more communication busses 213 for interconnecting the aforementioned components, a user interface 278, the user interface 278 including a display 282 and input 280 (e.g., a keyboard, a keypad, a touch screen, etc.), and a power supply 276 for powering the aforementioned components. In some embodiments, data in memory 192 is seamlessly shared with non-volatile memory 290 using known computing techniques such as caching. In some embodiments, memory 192 and/or memory 290 includes mass storage that is remotely located with respect to the central processing unit(s) 274. In other words, some data stored in memory 192 and/or memory 290 may in fact be hosted on computers that are external to the statin pharmaceutical composition OTC dispensing device 250 but that can be electronically accessed by the statin pharmaceutical composition OTC dispensing device 250 over an Internet, intranet, or other form of network or electronic cable (illustrated as element 106 in FIG. 2) using network interface 284.

In some embodiments, the memory 192 of the statin pharmaceutical composition OTC dispensing device 250 stores one or more of:

an operating system 202 that includes procedures for handling various basic system services;

an assessment module 252 for qualifying a subject for an initial over-the-counter provision of a statin pharmaceutical composition to lower cholesterol, e.g., treating or preventing heart disease, by communicating assessment survey questions, obtaining results therefrom, and utilizing an algorithm to apply the results to qualifying assessment filters, the assessment module including:

a first plurality of assessment filters 214-1, including assessment filters 216, each respective assessment filter 216 in the first plurality of assessment filters 214-1 associated with one or more assessment survey questions 208 and one or more triggering conditions 218;

a second plurality of assessment filters 220-1, including assessment filters 222, each respective assessment filter 222 in the second plurality of assessment filters 220-1 associated with one or more assessment survey questions 208, triggering conditions 224, and warnings 226;

a fulfillment module 228-1 for executing a fulfillment process when no assessment filter 216 in the first plurality of assessment filters 214-1 has been fired for a subject and the subject has acknowledged each warning 226 associated with each assessment filter 222 in the second plurality of assessment filters 220-1 that was fired as a result of answers by the subject to the assessment survey questions 208, where the fulfillment process includes communicating an over-the-counter drug facts label 230 for the statin pharmaceutical composition to the subject and receiving confirmation from the subject that the over-the-counter drug facts label has been received and read;

a re-assessment module 254 for re-qualifying a subject for an over-the-counter provision of a statin pharmaceutical composition to lower cholesterol, e.g., treating or preventing heart disease, by communicating re-assessment survey questions, obtaining results therefrom, and utilizing an algorithm to apply the results to qualifying re-assessment filters, the re-assessment module including:

a first plurality of re-assessment filters 214-2, including re-assessment filters 216, each respective re-assessment filter 216 in the first plurality of re-assessment filters 214-2 is associated with one or more re-assessment survey questions 208 and one or more triggering conditions 218;

a second plurality of re-assessment filters 220-2, including re-assessment filters 222, each respective filter 222 in the second plurality of re-assessment filters 220-2 is associated with one or more survey questions 212, triggering conditions 224, and warnings 226;

a re-fulfillment module 228-2 for executing a re-fulfillment process when no re-assessment filter 216 in the first plurality of re-assessment filters 214-2 has been fired for a subject and the subject has acknowledged each warning 226 associated with each re-assessment filter 222 in the second plurality of re-assessment filters 220-2 that was fired as a result of answers by the subject to the re-assessment survey questions 212, where the re-fulfillment process includes communicating an over-the-counter drug facts label 230 for the statin pharmaceutical composition to the subject and receiving confirmation from the subject that the over-the-counter drug facts label has been received and read;

a subject profile data store 232 including a user profile 234 for each of a plurality of subjects, each respective user profile 234 including information (e.g., shipping information, billing information, biometric information, etc.) about a corresponding subject in the plurality of subjects, an initial order date (e.g., an initial date for qualifying for a provision of a statin pharmaceutical composition) and/or destination 236, and any re-order date (e.g., a date for re-qualifying for a provision of a statin pharmaceutical composition) and/or the destination 238 for the statin pharmaceutical composition made by the corresponding subject using the statin pharmaceutical composition OTC dispensing device 250;

an adverse event module 242 for identifying and aggregating records of adverse events associated with a plurality of subjects, e.g., corresponding to the firing of a re-assessment filter 216 in the first plurality of re-assessment filters 214-2 during a re-fulfillment process;

a reimbursement module 240 for determining eligibility and/or communicating an insurance claim associated with provision of a statin pharmaceutical composition, e.g., based on insurance information stored in a respective user profile 234.

In some embodiments, the assessment module 252, the re-assessment module 254, and/or the fulfillment module 228 is accessible within any browser (e.g., phone, tablet, laptop/desktop, or smartwatch). In some embodiments, the assessment module 252, re-assessment module 254, and/or fulfillment module 228 run on native device frameworks, and is available for download onto a user device 102 running an operating system 202 such as Android, iOS, or WINDOWS.

In some embodiments, one or more of the above identified data elements or modules (e.g., assessment module 252, fulfillment module 228-1, etc.) of the statin pharmaceutical composition OTC dispensing device 250 for qualifying a human subject for an over-the-counter provision of a statin pharmaceutical composition to lower cholesterol is stored in one or more of the previously described memory devices, and correspond to a set of instructions for performing a function described above. The above-identified data, modules or programs (e.g., sets of instructions) need not be implemented as separate software programs, procedures or modules, and thus various subsets of these modules may be combined or otherwise re-arranged in various embodiments. In some embodiments, the memory 192 and/or 290 optionally stores a subset of the modules and data structures identified above. Furthermore, in some embodiments the memory 192 and/or 290 stores additional modules and data structures not described above.

In some embodiments, a statin pharmaceutical composition OTC dispensing device 250 for qualifying a human subject for an over-the-counter provision of a statin pharmaceutical composition to lower cholesterol is a smart phone (e.g., an iPhone, Blackberry, etc.), a laptop, a tablet computer, a desktop computer, a smart watch, or another form of electronic device (e.g., a gaming console, a kiosk, a virtual reality system, etc.). In some embodiments, the statin pharmaceutical composition OTC dispensing device 250 is not mobile. In some embodiments, the statin pharmaceutical composition OTC dispensing device 250 is mobile.

In some embodiments, the statin pharmaceutical composition OTC dispensing device 250 is not a smart phone but rather is a tablet computer, desktop computer, emergency vehicle computer, or other form or wired or wireless networked device. In the interest of brevity and clarity, only a few of the possible components of the statin pharmaceutical composition OTC dispensing device 250 are shown in FIG. 2 in order to better emphasize the additional software modules that are installed on the statin pharmaceutical composition OTC dispensing device 250.

Figure 3A:
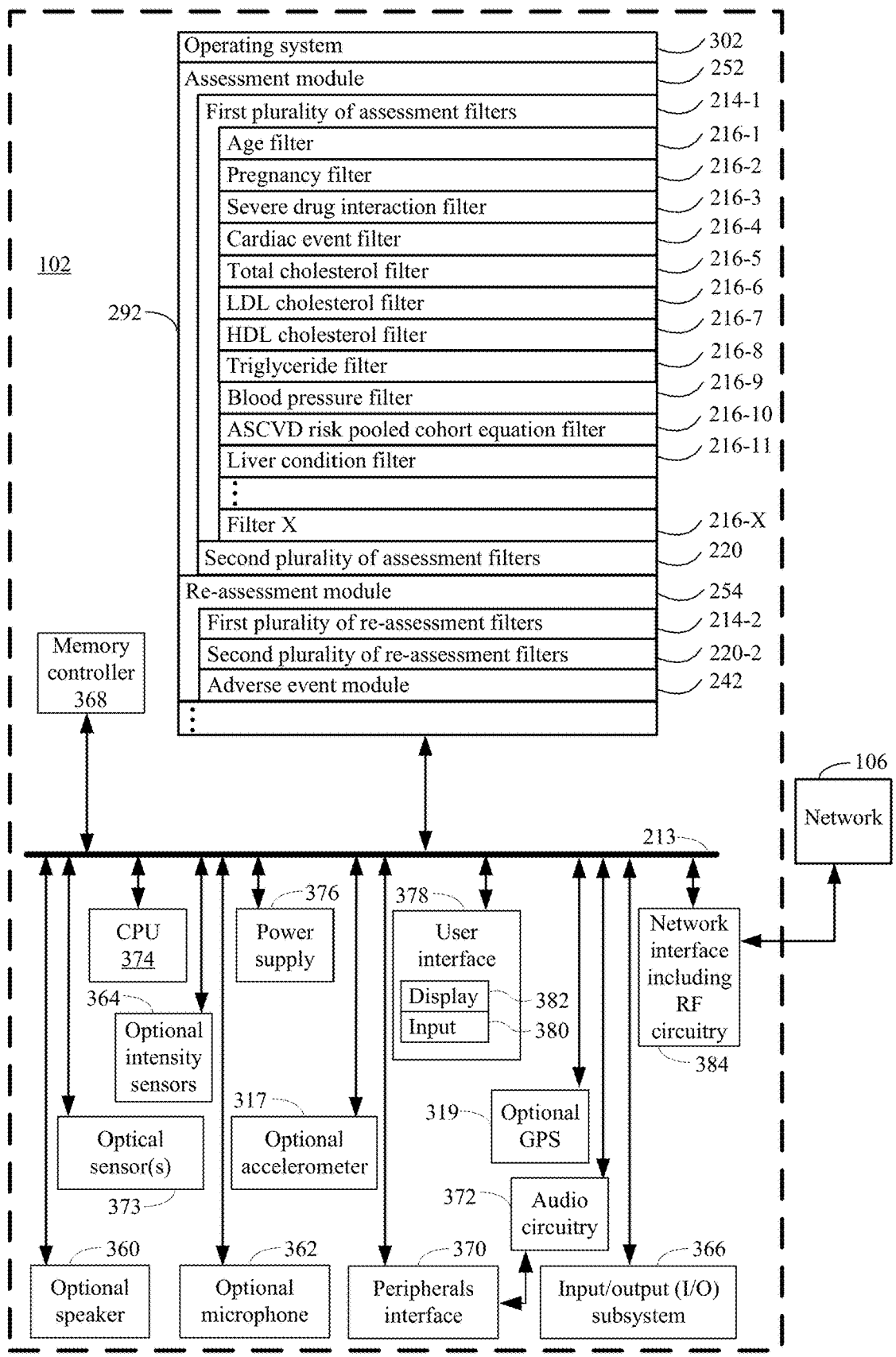
FIGS. 3A and 3B collectively illustrate an example device associated with a human subject for qualifying the human subject for an over-the-counter provision of a statin pharmaceutical composition for lowering cholesterol, e.g., thereby treating and/or preventing heart disease, in accordance with various embodiments of the present disclosure. In some embodiments, the example device of FIGS. 3A and 3B works in conjunction with the device of FIG. 2 to perform the methods illustrated in FIGS. 4, 5, 8, and 9 in some embodiments, providing the device of FIG. 2 with information sets and/or the results of firing filters of the present disclosure against such information sets. In some embodiments, the device of FIG. 2 performs all the methods of the present disclosure and the device of FIGS. 3A and 3B is not used. In other embodiments, the device of FIGS. 3A and 3B performs the methods of the present disclosure and the device of FIG. 2 is not used.
Figure 3B:
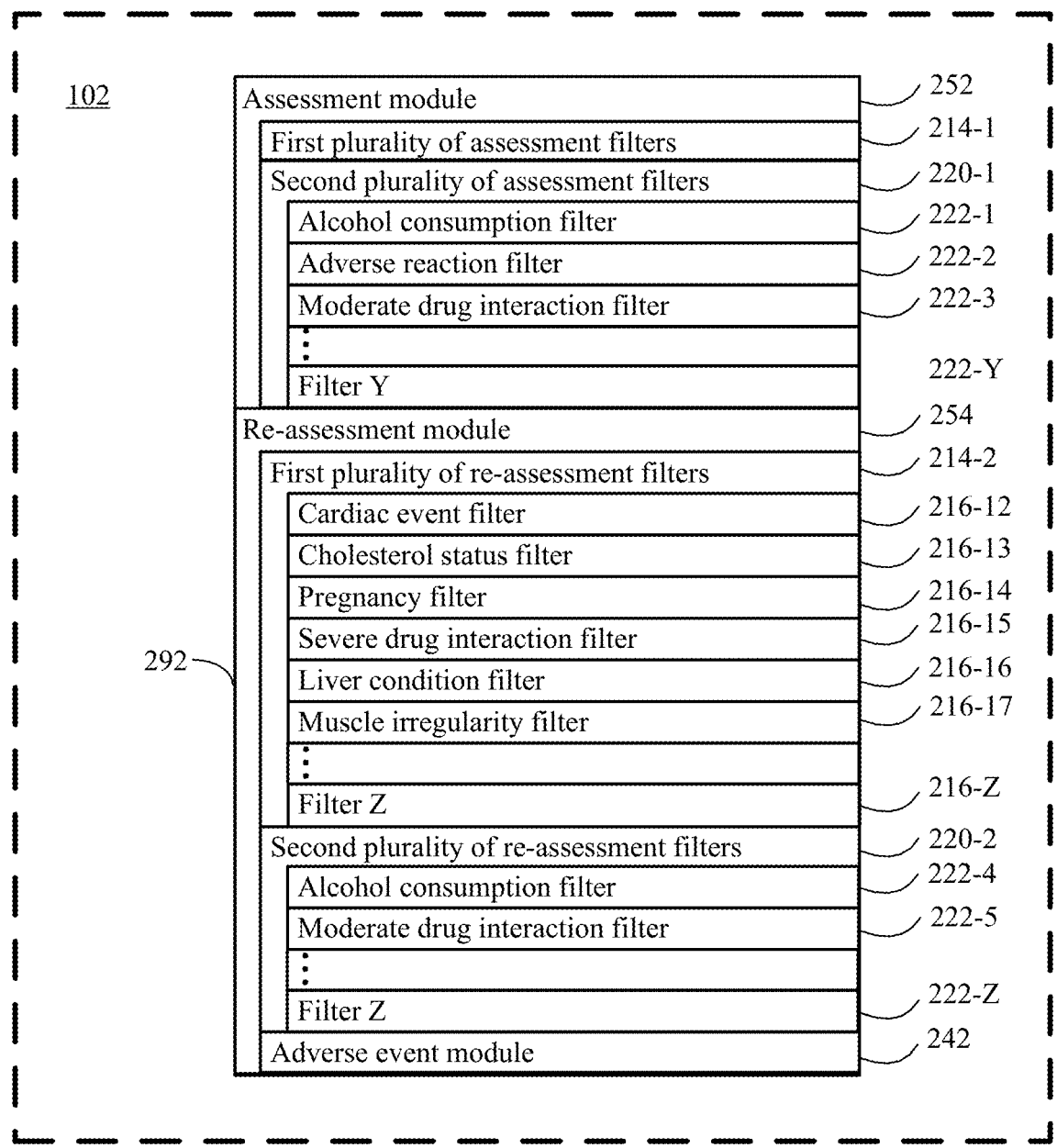

FIGS. 3A and 3B collectively provide a description of a user device 102 that can be used with the present disclosure. The user device 102 illustrated in FIGS. 3A and 3B has one or more processing units (CPU's) 374, peripherals interface 370, memory controller 368, a network or other communications interface 384, a memory 392 (e.g., random access memory), a user interface 378, the user interface 378 including a display 382 and input 380 (e.g., a keyboard, a keypad, a touch screen), an optional accelerometer 317, an optional GPS 319, optional audio circuitry 372, an optional speaker 360, an optional microphone 362, one or more optional intensity sensors 364 for detecting intensity of contacts on the user device 102 (e.g., a touch-sensitive surface such as a touch-sensitive display system 382 of the user device 102), an optional input/output (I/O) subsystem 366, one or more optional optical sensors 373, one or more communication busses 313 for interconnecting the aforementioned components, and a power supply 376 for powering the aforementioned components.

In some embodiments, the input 380 is a touch-sensitive display, such as a touch-sensitive surface. In some embodiments, the user interface 378 includes one or more soft keyboard embodiments. The soft keyboard embodiments may include standard (e.g., QWERTY) and/or non-standard configurations of symbols on the displayed icons.

The user device 102 illustrated in FIGS. 3A and 3B optionally includes, in addition to accelerometer(s) 317, a magnetometer and a GPS 319 (or GLONASS or other global navigation system) receiver for obtaining information concerning a location and/or an orientation (e.g., portrait or landscape) of the user device 102 and/or for determining an amount of physical exertion by the subject.

It should be appreciated that the user device 102 illustrated in FIGS. 3A and 3B is only one example of a multifunction device that may be used for performing a survey (e.g., assessment module 252) in order to qualify for an over-the-counter provision of a statin pharmaceutical composition to lower cholesterol, and that the user device 102 optionally has more or fewer components than shown, optionally combines two or more components, or optionally has a different configuration or arrangement of the components. The various components shown in FIGS. 3A and 3B are implemented in hardware, software, firmware, or a combination thereof, including one or more signal processing and/or application specific integrated circuits.

Memory 392 of the user device 102 illustrated in FIGS. 3A and 3B optionally includes high-speed random access memory and optionally also includes non-volatile memory, such as one or more magnetic disk storage devices, flash memory devices, or other non-volatile solid-state memory devices. Access to memory 392 by other components of the statin pharmaceutical composition OTC dispensing device 250, such as CPU(s) 374 is, optionally, controlled by the memory controller 368. In some embodiments, the memory 392 of the user device 102 illustrated in FIGS. 3A and 3B optionally includes:

an operating system 302 that includes procedures for handling various basic system services;

the assessment module 252 for qualifying a subject for an initial over-the-counter provision of a statin pharmaceutical composition, e.g., as described above in conjunction with the statin pharmaceutical composition OTC dispensing device 250, the assessment module including;

a first plurality of filters 214 (e.g., the first plurality of assessment filters 214-1), e.g., as described above in conjunction with the statin pharmaceutical composition OTC dispensing device 250, e.g., including one or more of an age filter 216-1, a pregnancy filter 216-2, a severe drug interaction filter 216-3, a cardiac event filter 216-4, a total cholesterol filter 216-5, a LDL cholesterol filter 216-6, a HDL cholesterol filter 216-7, a triglyceride filter 216-8, a blood pressure filter 216-9, an atherosclerotic cardiovascular disease (ASCVD) risk pooled cohort equation filter 216-10, and a liver condition filter 216-11;

the second plurality of filters 220 (e.g., the second plurality of assessment filters 220-1) used in conjunction with assessment module 252, e.g., as described above in conjunction with the statin pharmaceutical composition OTC dispensing device 250, e.g., including an alcohol consumption filter 222-1, an adverse reaction filter 222-2, and a moderate drug interaction filter 222-3;

a re-assessment module 254, e.g., as described above in conjunction with the statin pharmaceutical composition OTC dispensing device 250;

a re-assessment module 254 for re-qualifying a subject for an over-the-counter provision of a statin pharmaceutical composition to lower cholesterol, e.g., as described above in conjunction with the statin pharmaceutical composition OTC dispensing device 250, the re-assessment module including:

a first plurality of re-assessment filters 214-2, e.g., as described above in conjunction with the statin pharmaceutical composition OTC dispensing device 250, including re-assessment filters 216 associated with corresponding re-assessment survey questions 208 and one or more triggering conditions 218;

a second plurality of re-assessment filters 220-2, e.g., as described above in conjunction with the statin pharmaceutical composition OTC dispensing device 250, including re-assessment filters 222 associated with corresponding re-assessment survey questions 212, triggering conditions 224, and warnings 226.

In some embodiments, the optional accelerometer 317, optional GPS 319, and/or magnetometer of the user device 102 or such components are used to recommend to qualifying subjects one or more suitable destinations for delivery of a provision of the statin pharmaceutical composition over-the-counter. In some embodiments, the GPS 319 is used to determine if a subject is geographically restricted for an OTC provision of the statin pharmaceutical composition. Geographical restrictions include but are not limited to a subject residing outside of delivery or shipping regions, marketing restrictions, and/or government regulations.

The peripherals interface 370 can be used to couple input and output peripherals of the device to CPU(s) 374 and memory 392. The one or more processors 374 run or execute various software programs and/or sets of instructions stored in memory 392, such as the survey module 204, to perform various functions for the user device 102 and to process data.

In some embodiments, the peripherals interface 370, CPU(s) 374, and memory controller 368 are optionally implemented on a single chip. In some other embodiments, they are implemented on separate chips.

RF (radio frequency) circuitry of network interface 384 receives and sends RF signals, also called electromagnetic signals. In some embodiments, the survey module 252/254, survey questions 208/212, answers to survey questions 208/212 (e.g., information sets), and/or the over-the-counter drug facts label 230 are communicated to the subject device 102 using this RF circuitry. In some embodiments, the RF circuitry 384 converts electrical signals to/from electromagnetic signals and communicates with communications networks and other communications devices and/or the data collection device 200 and/or the statin pharmaceutical composition OTC dispensing device 250 via the electromagnetic signals. The RF circuitry 384 optionally includes well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth. RF circuitry 384 optionally communicates with the communication network 106. In some embodiments, the circuitry 384 does not include RF circuitry and, in fact, is connected to the network 106 through one or more hard wires (e.g., an optical cable, a coaxial cable, or the like).

In some embodiments, the audio circuitry 372, the optional speaker 360, and the optional microphone 362 provide an audio interface between the subject and the user device 102. The audio circuitry 372 receives audio data from the peripherals interface 370, converts the audio data to electrical signals, and transmits the electrical signals to the speaker 360. The speaker 360 converts the electrical signals to human-audible sound waves. In some embodiments, the speaker 360 converts the electrical signals to human-inaudible sound waves. The audio circuitry 372 also receives electrical signals converted by the microphone 362 from sound waves. The audio circuitry 372 converts the electrical signal to audio data and transmits the audio data to peripherals interface 370 for processing. Audio data is, optionally, retrieved from and/or transmitted to the memory 392 and/or the RF circuitry 384 by the peripherals interface 370.

In some embodiments, the power supply 376 optionally includes a power management system, one or more power sources (e.g., battery, alternating current (AC)), a recharging system, a power failure detection circuit, a power converter or inverter, a power status indicator (e.g., a light-emitting diode (LED)) and any other components associated with the generation, management and distribution of power in portable devices.

In some embodiments, the user device 102 optionally also includes one or more optical sensors 373. The optical sensor(s) 373 optionally include charge-coupled device (CCD) or complementary metal-oxide semiconductor (CMOS) phototransistors. The optical sensor(s) 373 receive light from the environment, projected through one or more lens, and converts the light to data representing an image. The optical sensor(s) 373 optionally capture still images and/or video. In some embodiments, an optical sensor is located on the back of the user device 102, opposite the display 382 on the front of the user device 102, so that the input 380 is enabled for use as a viewfinder for still and/or video image acquisition. In some embodiments, another optical sensor 373 is located on the front of the user device 102 so that an image of the subject is obtained (e.g., to verify the health, condition, or identity of the subject as part of qualifying the subject for an over-the-counter provision of a statin pharmaceutical composition to lower cholesterol), to help diagnose a subject's condition remotely, or to acquire visual physiological measurements of the subject, etc.)

As illustrated in FIGS. 3A and 3B, the user device 102 preferably includes an operating system 302 that includes procedures for handling various basic system services. The operating system 302 (e.g., iOS, DARWIN, RTXC, LINUX, UNIX, OS X, WINDOWS, or an embedded operating system such as VxWorks) includes various software components and/or drivers for controlling and managing general system tasks (e.g., memory management, storage device control, power management, etc.) and facilitates communication between various hardware and software components.

In some embodiments, the user device 102 is a smart phone or a smart watch. In other embodiments, the user device 102 is not a smart phone or a smart watch but rather is a tablet computer, a desktop computer, an emergency vehicle computer, or other form or wired or wireless networked device. In the interest of brevity and clarity, only a few of the possible components of the user device 102 are shown in FIGS. 3A and 3B in order to better emphasize the additional software modules that are installed on the user device 102.

While the system 48 disclosed in FIG. 1 can work standalone, in some embodiments it can also be linked with an electronic medical records system to exchange information in any way.

Now that details of a system 48 for qualifying a human subject for an over-the-counter provision of a statin pharmaceutical composition to lower cholesterol have been disclosed, details regarding methods (e.g., an assessment method 4000 of FIG. 4 and/or a re-assessment method 5000 of FIG. 5), including processes and features to be performed by the system, in accordance with an embodiment of the present disclosure, are disclosed with reference to FIGS. 4 and 5, respectively. In some embodiments, such processes and features of the system 48 are carried out by the assessment module 252, the re-assessment module 254, the fulfillment module 228-1, and/or the re-fulfillment module 228-2 illustrated in FIGS. 2 and 3. In some embodiments, the assessment module 252, the re-assessment module 254, the fulfillment module 228-1, and/or the re-fulfillment module 228-1 are a single software module.

In some embodiments, e.g., as described with reference to FIGS. 4 and 8 below, the disclosure provides a method for qualifying a subject for an over-the-counter provision of a statin pharmaceutical composition. The method includes obtaining an information set about the subject, e.g., by transmitting survey questions to the subject and/or accessing a database entry relating to the subject (such as an electronic health record and/or a private subject profile data store 232). In some embodiments, the information set includes a plurality of the example characteristics provided in Table 1. The method also includes applying some or all of the information set to a qualification algorithm that includes at least one filter of a first type and one filter of a second type. Filters of the first type interrogate information from the information set and when baseline qualification conditions are not met, the filter fires, preventing the subject from becoming qualified to receive a provision of the statin pharmaceutical composition. In some embodiments, a plurality of filters of the first type are applied. In some embodiments, the plurality of filters of the first type include a plurality of the example assessment filters provided in Table 2. Filters of the second type interrogate information from the information set and when baseline qualification conditions are not met, the filter fires, providing a warning to the subject of a risk factor associated with taking the statin pharmaceutical composition. However, upon confirmation of the warning from the subject, the filter does not prevent the subject from being qualified to receive a provision of the stain pharmaceutical composition. In some embodiments, a plurality of filters of the second type are applied. In some embodiments, the plurality of filters of the second type include a plurality of the example assessment filters provided in Table 4.

In some embodiments, the method further includes obtaining acknowledgment from the subject for each warning issued to the subject by any filter in the second plurality of assessment filters, e.g., confirming that the subject has discussed the risk factor associated with each warning issued to the subject by any filter in the second plurality of assessment filters with a physician. In some embodiments, the method then includes proceeding with a fulfillment process when (a) no filter in the first plurality of assessment filters has been fired and (b) the subject has acknowledged each warning associated with each filter in the second plurality of assessment filters that was fired. In some embodiments, the fulfillment process includes storing an indication in a subject profile of an initial order for the statin pharmaceutical composition, communicating an over the counter drug facts label for the statin pharmaceutical composition to the subject, and authorizing, upon confirmation from the subject that the over the counter drug facts label has been received and read, provision of the statin pharmaceutical composition to the subject. In some embodiments, the method also includes administering (which will typically be performed by the subject themselves), after authorization of the provision, the statin pharmaceutical composition to the subject.

In some embodiments, e.g., as described with reference to FIGS. 5 and 9 below, the disclosure provides a method for re-qualifying a subject for an over-the-counter provision of a statin pharmaceutical composition. The method includes obtaining an information set about the subject, e.g., by transmitting survey questions to the subject and/or accessing a database entry relating to the subject (such as an electronic health record and/or a private subject profile data store 232). In some embodiments, the information set includes a plurality of the example characteristics provided in Table 5. The method also includes applying some or all of the information set to a qualification algorithm that includes at least one filter of a first type and one filter of a second type. Filters of the first type interrogate information from the information set and when baseline qualification conditions are not met, the filter fires, preventing the subject from becoming re-qualified to receive a provision of the statin pharmaceutical composition. In some embodiments, a plurality of filters of the first type are applied. In some embodiments, the plurality of filters of the first type include a plurality of the example assessment filters provided in Table 6. Filters of the second type interrogate information from the information set and when baseline qualification conditions are not met, the filter fires, providing a warning to the subject of a risk factor associated with taking the statin pharmaceutical composition. However, upon confirmation of the warning from the subject, the filter does not prevent the subject from being qualified to receive a provision of the stain pharmaceutical composition. In some embodiments, a plurality of filters of the second type are applied. In some embodiments, the plurality of filters of the second type include a plurality of the example assessment filters provided in Table 7.

In some embodiments, the method further includes obtaining acknowledgment from the subject for each warning issued to the subject by any filter in the second plurality of assessment filters, e.g., confirming that the subject has discussed the risk factor associated with each warning issued to the subject by any filter in the second plurality of assessment filters with a physician. In some embodiments, the method then includes proceeding with a fulfillment process when (a) no filter in the first plurality of assessment filters has been fired and (b) the subject has acknowledged each warning associated with each filter in the second plurality of assessment filters that was fired. In some embodiments, the fulfillment process includes storing an indication in a subject profile of a re-order for the statin pharmaceutical composition, communicating an over the counter drug facts label for the statin pharmaceutical composition to the subject, and authorizing, upon confirmation from the subject that the over the counter drug facts label has been received and read, provision of the statin pharmaceutical composition to the subject. In some embodiments, the method also includes administering (which will typically be performed by the subject themselves), after authorization of the provision, the statin pharmaceutical composition to the subject.

FIG. 4 illustrates method 4000 for qualifying (4002) a human subject for an over-the-counter provision of a statin pharmaceutical composition for lowering cholesterol, e.g., thereby, treating and/or preventing heart disease, using a computer system such as a statin pharmaceutical composition OTC dispensing device 250. As illustrated in FIG. 2, the statin pharmaceutical composition OTC dispensing device (e.g., device 250) includes one or more processors (e.g., processor 274) and a memory (e.g., memory 192 and/or 290). The memory stores non-transitory instructions that, when executed by the one or more processors, perform a method.

Figure 10:
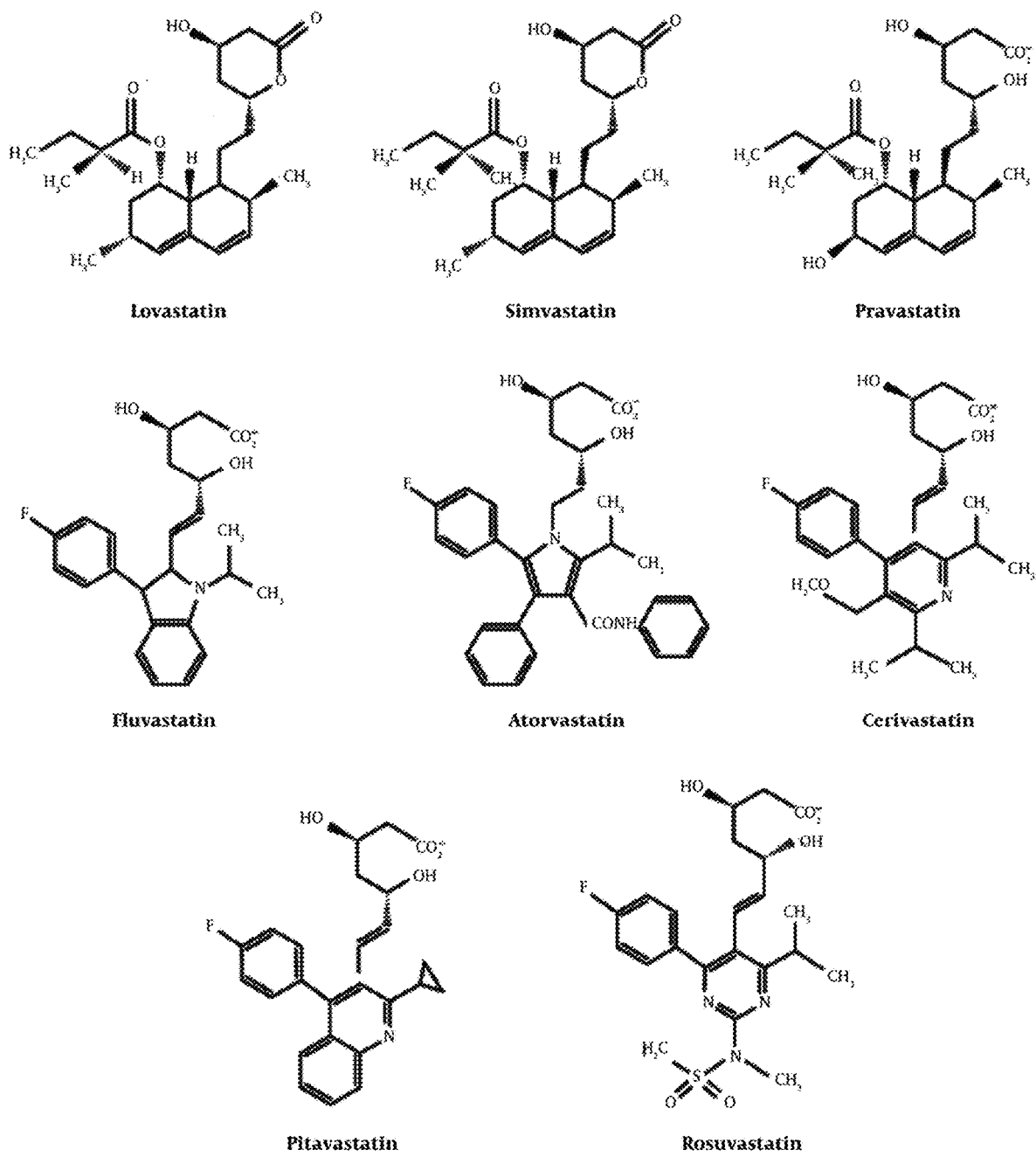
FIG. 10 illustrates example statins in accordance with the prior art.

As used herein, the term "statin" refers to a class of drugs commonly referred to as HMG CoA reductase inhibitors. The statins are used to reduce blood cholesterol levels in patients in need of such treatment. The site of action of the statins is in the liver. Examples of statins include, but are not limited, to atorvastatin (LIPITOR®), cerivastastin, fluvastatin (LESCOL®, LESCOL XL®), lovastatin (ALTOPREV®), pitavastatin (LIVALO®), pravastatin (PRAVACHOL®), simvastatin, rosuvastatin (CRESTOR®), and simvastatin (ZOCOR®). Example chemical structures of statins are disclosed in FIG. 10.

Method 4000 involves collecting relevant biographical and medical information about the subject, applying the collected information to an algorithm that applies the information against one or more filters of a first type and one or more filters of a second type, and providing access to a statin pharmaceutical composition when each of the filters is satisfied. The one or more filters of the first type terminate the process without qualifying the patient for access to an over-the-counter statin pharmaceutical agent when fired. The one or more filters of the second type trigger transmission of a warning to the subject when fired. The subject must confirm any transmitted warnings, which optionally include confirmation that certain conditions precedent have been met (such as having a discussion with a medical professional and receiving advice that the statin pharmaceutical composition is safe to take), before the subject is qualified to receive a provision of the statin pharmaceutical agent.

Referring to blocks 4004 and 4006 of FIG. 4A, in some embodiments the statin pharmaceutical composition includes rosuvastatin (CRESTOR®) as an active ingredient. In some embodiments, the statin pharmaceutical composition includes a composition disclosed in U.S. Pat. No. 6,316,460 or 6,858,618, each of which is hereby incorporated by reference, as an active ingredient.

In some embodiments, the statin pharmaceutical composition includes atorvastatin (LIPITOR®) as an active ingredient.

In some embodiments, the statin pharmaceutical composition includes fluvastatin (LESCOL®, LESCOL XL®) as an active ingredient. In some embodiments, the statin pharmaceutical composition includes a composition disclosed in U.S. Pat. No. 6,242,003, which is hereby incorporated by reference, as an active ingredient.

In some embodiments, the statin pharmaceutical composition includes lovastatin (ALTOPREV®) as an active ingredient.

In some embodiments, the statin pharmaceutical composition includes pitavastatin (LIVALO®) as an active ingredient. In some embodiments, the statin pharmaceutical composition includes a composition disclosed in U.S. Pat. Nos. 5,856,336, 7,022,713, or 8557993, each of which is hereby incorporated by reference, as an active ingredient.

In some embodiments, the statin pharmaceutical composition includes pravastatin (PRAVACHOL®) as an active ingredient.

In some embodiments, the statin pharmaceutical composition includes simvastatin (ZOCOR®) as an active ingredient.

In some embodiments, the statin pharmaceutical composition includes a statin composition described in Lee et al., 2007, "Comparison of Efficacy and Tolerability of Pitavastatin and Atorvastatin: an 8-Week, Multicenter, Randomized, Open-Label, Dose-Titration Study in Korean Patients with Hypercholesterolemia," Clin Ther. 2007; 29:2365-73; Bradford et al., 1990, "Expanded clinical evaluation of lovastatin (EXCEL) study design and patient characteristics of a double blind, placebo controlled study in patients with moderate hypercholesterolemia. American Journal of Cardiology 66: p. 44B-55B; Serruys et al., 2002, "Fluvastatin for Prevention of Cardiac Events Following Successful First Percutaneous Coronary Intervention: A Randomized Controlled Trial.," JAMA 287:p. 3215-3222; Sacks et al. 1996, "The effect of pravastatin on coronary events after myocardial infarction in patients with average cholesterol levels. Cholesterol and Recurrent Events Trial investigators," New England Journal of Medicine, 1996. 335(14): p. 001-9; *Anonymous*, 2002 "Heart Protection Study Collaborative Group, MRC/BHF Heart Protection Study of cholesterol lowering with simvastatin in 20,536 high-risk individuals: a randomised placebo-controlled trial," Lancet 360: p. 7-22; Jones et al., 2003, "Comparison of the efficacy and safety of rosuvastatin versus atorvastatin, simvastatin, and pravastatin across doses (STELLAR Trial)," Am J Cardiol. 92 (2): 152-60 each of which is hereby incorporated by reference.

In some embodiments, the statin pharmaceutical composition comprises a statin and another lipid-lowering drug, such as Atorvastatin/Ezetimibe (LIPTRUZET®), Lovastatin+Niacin (ADVICOR®), Simvastatin/Ezetimibe (VYTORIN®), or Simvastatin/Niacin-ER (SIMCOR®).

In some embodiments, the statin pharmaceutical composition is a prodrug. As used herein, a prodrug refers to a pharmaceutical composition that includes a biologically inactive compound that is metabolized in vivo to generate the active form of the drug. For instance, in some embodiments the prodrug statin pharmaceutical composition includes atorvastatin, fluvastatin, lovastatin, pitavastatin, pravastatin, rosuvastatin, or simvastatin.

In some embodiments, the statin pharmaceutical composition includes rosuvastatin (e.g., CRESTOR®) as an active ingredient, and the subject is authorized for a daily dosage of from about 2.5 mg to about 20 mg. In some embodiments, the subject is authorized for a daily dosage of from 2.5 mg to 15 mg rosuvastatin. In some embodiments, the subject is authorized for a daily dosage of from 5 mg to 15 mg rosuvastatin. In some embodiments, the subject is authorized for a daily dosage of from 5 mg to 10 mg rosuvastatin. In some embodiments, the subject is authorized for a daily dosage of 5 mg rosuvastatin. In some embodiments, the subject is authorized for a daily dosage of 10 mg rosuvastatin. In other embodiments, the subject is authorized for a daily dosage of 2.5 mg, 7.5 mg, 12.5 mg, 15 mg, 17.5 mg, or 20 mg rosuvastatin.

In some embodiments, the statin pharmaceutical composition includes a composition disclosed in U.S. Pat. No. 6,316,460 or 6,858,618, each of which is hereby incorporated by reference, as an active ingredient and the subject is authorized for a daily dosage of from about 2.5 mg to about 20 mg, a daily dosage of from 2.5 mg to 15 mg, a daily dosage of from 5 mg to 15 mg, a daily dosage of from 5 mg to 10 mg, a daily dosage of 5 mg, a daily dosage of 10 mg, or a daily dosage of 2.5 mg, 7.5 mg, 12.5 mg, 15 mg, 17.5 mg, or 20 mg of the active composition disclosed in U.S. Pat. No. 6,316,460 or 6,858,618.

In some embodiments, the statin pharmaceutical composition includes fluvastatin (e.g., LESCOL®) as an active ingredient, and the subject is authorized for a daily dosage of from about 5 mg to about 60 mg. In some embodiments, the subject is authorized for a daily dosage of from 5 mg to 40 mg fluvastatin. In some embodiments, the subject is authorized for a daily dosage of from 10 mg to 40 mg fluvastatin. In some embodiments, the subject is authorized for a daily dosage of from 20 mg to 40 mg fluvastatin. In some embodiments, the subject is authorized for a daily dosage of 20 mg fluvastatin. In some embodiments, the subject is authorized for a daily dosage of 40 mg fluvastatin. In other embodiments, the subject is authorized for a daily dosage of 5 mg, 10 mg, 30 mg, 50 mg, or 60 mg fluvastatin.

In some embodiments, the statin pharmaceutical composition includes an active composition disclosed in U.S. Pat. No. 6,242,003, which is hereby incorporated by reference, and the subject is authorized for a daily dosage of from about 5 mg to about 60 mg, a daily dosage of from 5 mg to 40 mg, a daily dosage of from 10 mg to 40 mg, a daily dosage of from 20 mg to 40 mg, a daily dosage of 20 mg, a daily dosage of 40 mg, or a daily dosage of 5 mg, 10 mg, 30 mg, 50 mg, or 60 mg of the active composition disclosed in U.S. Pat. No. 6,242,003.

In some embodiments, the statin pharmaceutical composition includes atorvastatin (e.g., LIPITOR®) as an active ingredient, and the subject is authorized for a daily dosage of from about 5 mg to about 60 mg. In some embodiments, the subject is authorized for a daily dosage of from 5 mg to 40 mg atorvastatin. In some embodiments, the subject is authorized for a daily dosage of from 10 mg to 40 mg atorvastatin. In some embodiments, the subject is authorized for a daily dosage of from 20 mg to 40 mg atorvastatin. In some embodiments, the subject is authorized for a daily dosage of 10 mg atorvastatin. In some embodiments, the subject is authorized for a daily dosage of 20 mg atorvastatin. In some embodiments, the subject is authorized for a daily dosage of 40 mg atorvastatin. In other embodiments, the subject is authorized for a daily dosage of 5 mg, 10 mg, 30 mg, 50 mg, or 60 mg atorvastatin.

In some embodiments, the statin pharmaceutical composition includes pitavastatin (e.g., LIVALO®) as an active ingredient, and the subject is authorized for a daily dosage of from about 0.5 mg to about 4 mg. In some embodiments, the subject is authorized for a daily dosage of from 1 mg to 4 mg pitavastatin. In some embodiments, the subject is authorized for a daily dosage of from 1 mg to 2 mg pitavastatin. In some embodiments, the subject is authorized for a daily dosage of 1 mg pitavastatin. In some embodiments, the subject is authorized for a daily dosage of 2 mg pitavastatin. In other embodiments, the subject is authorized for a daily dosage of 0.5 mg, 3 mg, or 40 mg pitavastatin.

In some embodiments, the statin pharmaceutical composition includes lovastatin (e.g., MEVACOR®) as an active ingredient, and the subject is authorized for a daily dosage of from about 5 mg to about 60 mg. In some embodiments, the subject is authorized for a daily dosage of from 5 mg to 40 mg lovastatin. In some embodiments, the subject is authorized for a daily dosage of from 10 mg to 40 mg lovastatin. In some embodiments, the subject is authorized for a daily dosage of from 20 mg to 40 mg lovastatin. In some embodiments, the subject is authorized for a daily dosage of 10 mg lovastatin. In some embodiments, the subject is authorized for a daily dosage of 20 mg lovastatin. In some embodiments, the subject is authorized for a daily dosage of 40 mg lovastatin. In other embodiments, the subject is authorized for a daily dosage of 5 mg, 10 mg, 30 mg, 50 mg, or 60 mg lovastatin.

In some embodiments, the statin pharmaceutical composition includes pravastatin (e.g., PRAVACHOL®) as an active ingredient, and the subject is authorized for a daily dosage of from about 5 mg to about 60 mg. In some embodiments, the subject is authorized for a daily dosage of from 5 mg to 40 mg pravastatin. In some embodiments, the subject is authorized for a daily dosage of from 10 mg to 40 mg pravastatin. In some embodiments, the subject is authorized for a daily dosage of from 20 mg to 40 mg pravastatin. In some embodiments, the subject is authorized for a daily dosage of 10 mg pravastatin. In some embodiments, the subject is authorized for a daily dosage of 20 mg pravastatin. In some embodiments, the subject is authorized for a daily dosage of 40 mg pravastatin. In other embodiments, the subject is authorized for a daily dosage of 5 mg, 10 mg, 30 mg, 50 mg, or 60 mg pravastatin.

In some embodiments, the statin pharmaceutical composition includes simvastatin (e.g., ZOCOR®) as an active ingredient, and the subject is authorized for a daily dosage of from about 2.5 mg to about 40 mg. In some embodiments, the subject is authorized for a daily dosage of from 5 mg to 40 mg simvastatin. In some embodiments, the subject is authorized for a daily dosage of from 5 mg to 20 mg simvastatin. In some embodiments, the subject is authorized for a daily dosage of from 5 mg to 10 mg simvastatin. In some embodiments, the subject is authorized for a daily dosage of 5 mg simvastatin. In some embodiments, the subject is authorized for a daily dosage of 10 mg simvastatin. In some embodiments, the subject is authorized for a daily dosage of 20 mg simvastatin. In other embodiments, the subject is authorized for a daily dosage of 2.5 mg, 30 mg or 40 mg simvastatin.

In some embodiments, the lowering of cholesterol is to treat and/or prevent heart disease. Typically, this treatment and/or prevention of heart disease is accomplished by inhibiting HMG-CoA reductase in the liver.

As described in detail below, method 4000 includes eliciting medical information about the user (e.g., information sets), which is used to qualify or disqualify the subject for an over-the-counter provision of the statin pharmaceutical composition. However, in some embodiments, before beginning to elicit this information, the system registers the subject and/or ensures that the subject is prepared to proceed through the qualification process. For example, in some embodiments, the system first determines whether the subject has already registered, was previously qualified, and/or previously received a provision of the over-the-counter provision of the statin pharmaceutical composition. This determination may occur by comparing the first information set and/or additional information provided by the subject with data of a subject profile data store (e.g., subject profile store 323 of FIG. 2).

When the subject has not yet registered with the system, device 250 registers the subject as a new user and creates a corresponding user profile (e.g., regardless of whether the subject previously received a prescription provision of the statin pharmaceutical composition). The system then performs an assessment method (e.g., assessment method 4000) to qualify the subject for a first over-the-counter provision of the statin pharmaceutical composition.

When the subject already has a user profile 234, e.g., as verified with a user password, the device registers the user as a returning customer. When the returning subject has previously received an over-the-counter provision of the statin pharmaceutical composition, the system performs a re-assessment method (e.g., re-assessment method 5000) to qualify the subject for a subsequent provision. When the returning subject has not previously received an over-the-counter provision of the statin pharmaceutical composition (e.g., because they did not previously qualify or choose not to purchase the composition after being qualified), the system performs an assessment method (e.g., assessment method 4000) to qualify the patient for a first over-the-counter provision of the statin pharmaceutical composition.

In some embodiments, when a new user does not already have a user profile 234 (e.g., the subject has not previously been qualified for an over-the-counter provision of the statin pharmaceutical composition) the device registers the user as a new user and creates a corresponding user profile, regardless of whether the subject previously received a prescription provision of the statin pharmaceutical composition. In some embodiments, when a new user has not previously been qualified for an over-the-counter provision of the statin pharmaceutical composition, but has received a prescription for the statin pharmaceutical composition, the device will consider the new user a returning user and will perform a re-order qualification (e.g., via method 5000), rather than an initial qualification (e.g., via method 4000).

In some embodiments, prior to eliciting medical information (e.g., some or all of the first information set) from the subject, the system prompts (e.g., 802 of FIG. 8A) to confirm that they have adequate privacy to provide sensitive medical information and/or that they are in possession of the medical information required to complete the qualification process. For example, in some embodiments the system prompts (e.g., 804 of FIG. 8A) the user to confirm that they have knowledge of their blood pressure, cardiovascular history, etc.

Blocks 4008 and 4010. Referring to block 4008 of FIG. 4A, the method includes providing an assessment survey that obtains an information set from the subject. By way of the assessment survey, a plurality of assessment survey results to survey questions 208, 212 (e.g., one or more of the survey questions set forth in Table 1) are obtained (e.g., the device 250 transmits one or more assessment survey questions to the user, prompting a response, and then receives a response to the one or more assessment survey questions back from the subject). In some embodiments, the information set include some or all of the characteristics listed in Table 1. For example, in some embodiments, the information set includes 2, 3, 4, 5, 6, 7, 8, 9, 10, 11, 12, 13, 14, 15, 16, 17, or all 18 of the characteristics listed in Table 1. In one embodiment, the plurality of assessment survey results includes at least characteristics 1-8 as provided in Table 1. In one embodiment, the plurality of assessment survey results includes at least characteristics 1-15 as provided in Table 1.

It will be appreciated that the survey questions 208, 212 and filters 216, 222 (e.g., first plurality of assessment filters 216-1 and second plurality of assessment filters 222-1) applied to the information set thereof may vary depending upon the statin pharmaceutical composition being distributed. This varying is due to differences in the contraindication profiles of the various the statin pharmaceutical compositions, e.g., due to different drug-drug interactions, routes of drug clearance, etc. of the different the statin pharmaceutical compositions. For example, co-administration of warfarin with a single oral dose of atorvastatin had no significant effect on the pharmacokinetics of atorvastatin. As such, in some embodiments, an assessment survey, or similarly a re-assessment survey, qualifying a subject for an OTC provision of simvastatin may ask whether the subject consumes warfarin, while a similar survey qualifying a subject for OTC use of rosuvastatin may not.

Referring to block 4010, and as further informed by the example workflow illustrated in FIG. 8, in some embodiments the first information set includes a sex of the subject (e.g., responsive to a survey question 208 that is associated with a decision point (806)), an age of the subject (e.g., responsive to a survey question 208 that is associated with (808-1 or 808-2) an age filter 216-1), when the subject is female—whether the subject is one of pregnant or breast-feeding (e.g., responsive to a survey question 208 that is associated with (810) a pregnancy filter 216-2), whether the subject is taking one or more compositions that interact with the statin pharmaceutical composition (e.g., responsive to a survey question 208 that is associated with (814) a severe drug interaction filter 216-3), whether the subject has ever had a cardiac event (e.g., responsive to a survey question 208 that is associated with (816 and/or 818) a cardiac event filter 216-4), a total cholesterol level of the subject (e.g., responsive to a survey question 208 that is associated with (824) a total cholesterol filter 216-5), a low-density lipoprotein (LDL) cholesterol level of the subject (e.g., responsive to a survey question 208 that is associated with (826) an LDL cholesterol filter 216-6), a high-density lipoprotein (HDL) cholesterol level of the subject (e.g., responsive to a survey question 208 that is associated with (828) an HDL cholesterol filter 216-7), a triglyceride level of the subject (e.g., responsive to a survey question 208 that is associated with (830) a triglyceride filter 216-8), a systolic blood pressure of the subject (e.g., responsive to a survey question 208 that is associated with (832) a blood pressure filter 216-9), a diastolic blood pressure of the subject (e.g., responsive to a survey question 208 that is associated with (834) a blood pressure filter 216-9), whether the subject has a liver condition (e.g., responsive to a survey question 208 that is associated with (852) a blood pressure filter 216-11), an alcohol consumption status of the subject (e.g., responsive to a survey question 212 that is associated with (856) an alcohol consumption filter 222-1), and whether the subject has had an adverse reaction to a cholesterol lowering composition (e.g., responsive to a survey question 212 that is associated with (858) an adverse reaction filter 222-1).

In some embodiments, the assessment survey includes questions that elicit responses providing some or all of the characteristics listed in Table 1. In some embodiments, the assessment survey includes questions corresponding to the information set required for the methods described herein. In other embodiments, the assessment survey includes questions corresponding to only a subset of the information set required for the methods described herein. In such embodiments, one or more portions of the information set required for the methods described herein are acquired through other means (e.g., upon registration/subscription for a service associated with qualifying the subject for over-the-counter medication, from a healthcare provider, from a prior survey, from a database associated with a pharmacy, from an electronic health record associated with the subject, from the subject profile data store 232, etc.) For example, in some embodiments, the subject provides a personal medical identification associated with an insurer, a hospital, or other healthcare provider and information about the subject required for the methods described herein, e.g., one or more survey results, is acquired from a preexisting database associated with the personal medical identification (e.g., a blood pressure measurement determined for the subject).

TABLE 1

Example Medical Information Elicited from Assessment Survey Questions

| Result | Example Characteristics |
|---|---|
| 1 | a sex of the subject |
| 2 | an age of the subject |
| 3 | when the subject is female - whether the subject is pregnant or breastfeeding, |
| 4 | whether the subject is taking one or more compositions that interact with the statin pharmaceutical composition |
| 5 | whether the subject has ever had a cardiac event |
| 6 | a total cholesterol level of the subject |
| 7 | a LDL cholesterol level of the subject |
| 8 | a HDL cholesterol level of the subject |
| 9 | a triglyceride level of the subject |
| 10 | a systolic blood pressure of the subject |
| 11 | a diastolic blood pressure of the subject |
| 12 | whether the subject has a lever condition |
| 13 | an alcohol consumption status of the subject |
| 14 | whether the subject has had an adverse reaction to a cholesterol lowering composition |
| 15 | a race of the subject |
| 16 | whether the subject is taking a high blood pressure treatment |
| 17 | a diabetes status of the subject |
| 18 | a smoking status of the subject |

It is contemplated that, in some embodiments, any one or more of characteristics listed in Table 1 will not be elicited by the assessment survey (e.g., will not be used for the assessment and/or will be obtained by other means). For example, in some embodiments, a characteristic associated with a particular survey question will be informative when qualifying a subject for one particular statin but not for another statin. For instance, in some embodiments, an assessment survey question is queried for lovastatin qualifying surveys but not for simvastatin qualifying surveys (e.g., the assessment survey question is not relevant for simvastatin). The skilled artisan will recognize that different statins carry different risk and drug interaction profiles. Accordingly, assessment survey information set (e.g., first information set) required for qualifying a subject for access to one statin with a known adverse drug interaction may not be necessary for qualifying the same subject for access to a second statin.

Accordingly, it is contemplated that the characteristics elicited by the assessment survey questions 208 include any subset of survey results provided in Table 1. For brevity, all possible combinations of the characteristics elicited by the assessment survey provided in Table 1 are not specifically delineated here. However, the skilled artisan will easily be able to envision any particular subset of the characteristics listed in Table 1. Likewise, the skilled artisan may know of other characteristics, not listed in Table 1, that may be combined with any subset of the characteristics listed in Table 1 to form the information elicited by the assessment survey questions used in the methods described herein.

In some embodiments, the assessment survey and/or the re-assessment survey is conducted by transmitting a plurality of respective questions to the subject, e.g., some or all of the respective survey questions, and receiving answers to the plurality of respective survey questions before applying any of the answers to respective filters. For example, with reference to the workflow in FIG. 8, in some embodiments, the device transmits questions relating to all of the assessment filters of the first plurality of assessment filters, all of the assessment filters of the second plurality of assessment filters, or all of the assessment filters in the workflow (e.g., as a virtual assessment survey where all of the questions are displayed in a single user interface, or as a series of questions displayed in consecutive user interfaces). After receiving answers to all of the assessment survey questions, the device then applies an algorithm to run assessment information set against the assessment filters (e.g., sequentially or concurrently) to determine whether the subject is qualified to receive a provision of the statin pharmaceutical composition. In alternative embodiments, the device transmits questions relating to relating to a subset of assessment filters of the first category class, e.g., for which it could not obtain answers to the questions from an electronic database associated with the subject such as electronic health record of the subject, and/or relating to a subset of assessment filters of the second category class, e.g., that it could not obtain answers to the questions from an electronic database associated with the subject (e.g., as a virtual assessment survey where such unanswered questions are displayed in a single user interface, or as a series of questions displayed in consecutive user interfaces). After receiving answers to all of the survey questions, the device then applies the answers to all of the filters (e.g., sequentially or concurrently) to determine whether the subject is qualified to receive provision of the statin pharmaceutical composition.

Figures 6A, 6B:
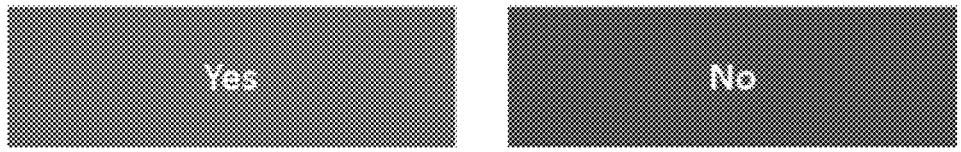
FIGS. 6A, 6B, 6C, and 6D illustrate example prompts and information associated with assessment and/or reassessment filters of a first type (FIGS. 6A and 6B) and filters of a second type (FIGS. 6C and 6D), in accordance with various embodiments of the present disclosure.

In some embodiments, the assessment survey and/or the re-assessment survey is conducted in a serial fashion, e.g., by transmitting a first question or a first group of survey questions (e.g., associated with a single respective filter) to the subject, receiving an answer to the single survey question or small group of survey questions, and applying an algorithm by running the answer or answers through a filter, prior to transmitting a second question or second group of questions to the subject. For example, with reference to the workflow in FIG. 8, in some embodiments the device transmits a first assessment question to the subject, relating to the cardiac event history of the subject (e.g., question 650 'Have you ever had any of the following: A heart attack, stroke, or an operation or procedure on your heart?Developed peripheral artery disease (PAD)?' in FIG. 6C). After receiving the answer to the survey question (e.g., 'yes or no'), the device applies the algorithm to the answer by running the answer through a cardiac event filter (816). If the cardiac event filter is fired (e.g., in response to a "yes" answer), the device terminates (805) the process, and optionally provides the user with a message relating to why they are being denied a provision of the statin pharmaceutical composition, a suggestion for following-up with a medical professional (e.g., as illustrated in FIG. 6B, when the survey answers indicate that the subject has had a history of cardiac events (816), the device optionally terminates the process (805) and advises that the subject seek guidance from a professional medical practitioner), and/or a suggestion to make a lifestyle change (e.g., when the survey answers indicate that the subject has slightly elevated blood pressure (832 and/or 834), the device terminates the process (803) and advises that the subject improve their diet or exercise routine which is consistent with current blood pressure treatment guidelines), to treat or manage their blood pressure. In other embodiments, the assessment survey and/or the reassessment survey is completed prior to applying any of the answers to the corresponding algorithm.

In some embodiments, one or more survey questions are not transmitted to a respective subject in accordance with a result to a previous survey question. For instance, in some embodiments where the ASCVD risk calculation is bypassed by an indication that the subject has a history of ASCVD (e.g., bypass mechanism 8443 in FIG. 8E), if an assessment survey result indicates that a subject has a history of ASCVD (e.g., at step 816 and/or 818 in FIG. 8B), one or more assessment survey questions related to an ASCVD pooled cohort equation filter are bypassed (e.g., not transmitted to the user) because the ASCVD pooled cohort filter can be bypassed.

As described in detail below, the methods disclosed herein include steps of applying information collected about a subject to a plurality of filters designed to identify contraindications—which render the subject unsuitable for treatment with the statin pharmaceutical composition generally or at least in the self-care environment (i.e., without physician supervision)—and risk factors—which render administration of the statin pharmaceutical composition unnecessarily risky without further physician consultation. The contraindication and risk factors described herein are non-exhaustive, as the skilled artisan will know of other possible contraindications or risk factors for a particular statin pharmaceutical composition. Moreover, as medical research progresses, new contraindications or risk factors may be discovered. Or, similarly, the classification of existing contraindications or risk factors may change with additional medical research or consideration. For example, a factor considered to be a contraindication may be reclassified as a risk factor, over time, or vice-a-versa.

Further, a contraindication for one statin pharmaceutical composition may only be a risk factor, or neither, for a different statin pharmaceutical composition, for example, based on different mechanisms, interaction, pharmacokinetic, and/or pharmacodynamics properties of the respective active ingredients. Similarly, a factor that is a contraindication or risk factor for a particular statin pharmaceutical composition when administered at one dose, e.g., a high, moderate, or low dose, may be classified differently when administered at a different dose. For example, a contraindication for a statin pharmaceutical composition administered at a high dose may only be a risk factor, or neither, when administered at a low dose. This is particularly true when the risk factor, e.g., a drug interaction, changes the bioavailability of the active ingredient by a certain factor, such that the bioavailability following high dose administration, but not low dose administration, would increase beyond a safe threshold.

Blocks 4012-4132. Referring to block 4012 of FIG. 4B, the method includes applying an algorithm to the information set obtained through, at least in part, the assessment survey. Referring to block 4014, all or a portion of the information set is run against a first plurality of assessment filters 214-1. As previously described, the first plurality of assessment filters 214-1 includes a subset of filters 216. When a respective filter in the first plurality of assessment filters 214-1 is fired (e.g., in accordance with a determination that a portion of the information set indicates that a triggering condition 218 has been met), the subject is deemed not qualified for provision of the statin pharmaceutical composition and the method is terminated without provision of the statin pharmaceutical composition.

For example, in some embodiments, the device transmits a prompt to provide information about a possible contraindication for statin use (e.g., prompt 650 "Have you ever had a heart attack, stroke, or an operation on your heart?," as illustrated in FIG. 6A), receives a response to the prompt, and then applies an algorithm to the response provided by the subject (e.g., through a pregnancy filter as described below). When the response indicates that a triggering condition has been met (e.g., the subject is pregnant), the filter is fired and the method is terminated without authorizing provision of the statin pharmaceutical composition to the subject. In some embodiments, the device transmits a message explaining why authorization of the statin pharmaceutical composition was denied. In some embodiments, the device transmits a message suggesting the subject consult with a medical professional, e.g., when the subject is deemed to need a stronger dosage of the statin pharmaceutical composition than available via the system and/or when the subject is deemed to be experiencing a medical emergency. For example, FIG. 6B illustrates an example message 652 provided to a subject who clinked "Yes" in response to prompt 650, informing them that users with a history of cardiac events can have adverse effects to statin therapy, and advising them to consult with a clinician to discuss whether statin therapy would benefit them.

In some embodiments, e.g., when the method is terminated without provision of the statin pharmaceutical composition, e.g., after a filter of the first type, the subject is prevented from attempting to re-qualify for the statin pharmaceutical composition for a predetermined period of time (e.g., 30 days, 60 days, 90 days, one year, two years, etc.). This prevents the subject from abusing the systems and methods of the present disclosure.

Referring to blocks 4016-4132 of FIGS. 4B-4J, example assessment filters 216 in the first plurality of assessment filters 214 and example triggering conditions 218 that cause the corresponding assessment filters to fire are described below.

TABLE 2

Example Assessment Filters of the First Plurality of Assessment Filters

| Filter | Type |
| --- | --- |
| 1a | an age filter |
| 2a | a pregnancy filter |
| 3a | a severe drug interaction filter |
| 4a | a cardiac event filter |
| 5a | a total cholesterol filter |
| 6a | a LDL cholesterol filter |
| 7a | a HDL cholesterol filter |
| 8a | a triglyceride filter |
| 9a | a blood pressure filter |
| 10a | an ASCVD risk pooled cohort equation filter |
| 11a | a liver condition filter |
| 12a | a risk enhancing factor filter |

In some embodiments, the first plurality of assessment filters 214 includes some or all of the filters 216 listed in Table 2. For example, in some embodiments, the first plurality of assessment filters 214-1 includes 2, 3, 4, 5, 6, 7, 8, 9, 10, 11, or all 12 of the filters listed in Table 2. In one embodiment, the first plurality of assessment filters includes at least filters 1a-11a as provided in Table 2. In some embodiments, where the information set indicates one or more particular risk enhancing factors, the first plurality of assessment filters further includes a risk enhancing factor filter 12a.

Accordingly, it is contemplated that in some embodiments the first plurality of assessment filters includes any sub-set of filters 216 provided in Table 2. Likewise, in some embodiments the skilled artisan may know of other filters 216, not provided in Table 2, which may be combined with any subset of the filters 216 provided in Table 2 to form the first plurality of assessment filters and corresponding information set used in the methods described herein. For brevity, all possible combinations of the assessment filters 216 provided in Table 2 are not specifically delineated here.

It is contemplated that, in some embodiments, any one or more of the assessment filters 216 provided in Table 2 will not be included in the first plurality of assessment filters. For example, in some embodiments, a characteristic associated with a particular survey result will be informative if qualifying a subject for one particular statin pharmaceutical composition but not for another statin pharmaceutical composition. In some embodiments, one or more of the filters 216 provided in Table 2 is implemented as a second type filter (e.g., included in a second plurality of assessment filters), as described below, which generates a warning to the user and/or requires the user confirm they have discussed an underlying risk triggering the filter with a medical professional, e.g., instead of automatically terminating the process without authorizing provision of the statin pharmaceutical composition. For example, in some cases, the decision to implement one of the filters listed in Table 2 as a second type filter will be based on a consideration specific to a particular statin compound and/or dosage of the statin compound. Similarly, in other cases, the decision to implement one of the filters listed in Table 2 as a second type filter will be based on a change in health and/or regulatory guidelines.

In some embodiments, the device is configured to conditionally bypass one or more of the filters 216 in the first plurality of assessment filters 214. For example, as illustrated in example implementation 800, when the device determines the subject is a male (e.g., as illustrated in step 806 in FIG. 8A) the pregnancy filter applied at step 810 is bypassed because it is not possible for the subject to become pregnant.

In some embodiments, where a filter is conditionally bypassed, one or more supplemental filters may be used to better refine which subjects are qualified for provision of the statin pharmaceutical composition. For example, as illustrated in example implementation 800, when the device determines the subject is a younger male with a family history of premature heart disease (e.g., as illustrated in steps 818 and 822 in FIG. 8B), filters relating to the calculation of an ASCVD risk (e.g., the cholesterol filters, triglyceride filter, blood pressure filters, and pooled cohort equation filters at steps 824-850 as illustrated in FIG. 8) are bypassed because the ASCVD pooled cohort equation cannot calculate an ASCVD risk for younger subjects. In some embodiments, this is a better option than merely excluding all younger subjects, because those with a family history of premature heart disease are more likely to develop premature heart disease themselves. However, it may be desirable to evaluate these subjects for signs of premature heart disease. For instance, as illustrated in steps 826-s and 830-s, supplemental LDL cholesterol and trigyceride filters are implemented as a replacement to similar bypassed filters. In this example, the supplemental LDL cholesterol filter sets a higher floor LDL cholesterol threshold of 160 mg/dL, rather than 70 mg/dL as used in the bypassed LDL cholesterol filter at step 826. The higher threshold in the supplemental filter helps to eliminate subjects that have a family history of premature heart disease, but do not show indications of developing premature heart disease themselves.

Age Filter

Referring to blocks 4016-4026 of FIG. 4B, in some embodiments the first plurality of assessment filters 214-1 includes an age filter (e.g., age filter 216-1 of FIG. 3A and/or filter 1a in Table 2). In some embodiments, the age assessment filter is configured to be fired when the information set indicates that the subject fails to satisfy an age threshold (e.g., when the subject is too young) to receive the statin pharmaceutical composition. Generally, the age threshold will be set on a jurisdiction-by-jurisdiction basis (e.g., a first subject in one geographic region is of age to receive the statin pharmaceutical composition while a second subject in another geographic region of the same age is not permitted to receiving the statin pharmaceutical composition). In some embodiments, the age threshold is 16 years of age. In some embodiments, the age threshold is 18 years of age. In some embodiments, the age threshold is 20 years of age. In some embodiments, the age threshold is at least 15, 16, 17, 18, 19, 20, 21, or more years of age.

In some embodiments, e.g., as in the embodiment illustrated in FIG. 8, the age threshold is set independently for men and women. For instance, in some embodiments, a first age threshold is set for men, e.g., considering generally a safe age of maturity for administration of the statin pharmaceutical agent, requiring the subject be at least 15, 16, 17, 18, 19, 20, 21, or older. Similarly, in some embodiments, a second age threshold is set for women, considering whether the woman is of child-bearing age, e.g., requiring that a woman is at least 45, 46, 47, 48, 49, 50, 51, 52, 53, 54, 55, or older to be qualified for the statin pharmaceutical composition. Accordingly, in some embodiments, where an age threshold is set in order to exclude women of child-bearing age from a provision of the statin pharmaceutical agent, a pregnancy filter is excluded from the workflow. However, in some embodiments, a pregnancy filter is still included, despite use of a more restrictive age threshold for women.

In some embodiments, the age filter is also configured to be fired when the first information indicates the subject fails to satisfy a ceiling age threshold (e.g., when the subject is too old). In some embodiments, the ceiling age threshold is 70 years old. In some embodiments, the ceiling age threshold is 75 years old. In some embodiments, the ceiling age threshold is 80 years old. In other embodiments, the ceiling age threshold is at least 65, 66, 67, 68, 69, 70, 71, 72, 73, 74, 75, 76, 77, 78, 79, 80, 81, 82, 83, 84, 85, or older.

In some embodiments, e.g., when implemented as a first type of filter, when the age filter is fired, the subject is not permitted to obtain provision of the statin pharmaceutical composition pharmaceutical composition over-the-counter (e.g., the method is terminated without authorizing provision of the statin pharmaceutical composition to the subject). In some embodiments, e.g., when implemented as a second type of filter, when the age filter is fired, the subject is issued a warning associated with the filter, but is eligible to obtain provision of the statin pharmaceutical composition pharmaceutical composition over-the-counter upon satisfying the acknowledgement criteria associated with the warning (e.g., by confirming that they have discussed the risk factor with a medical professional and/or the medical professional has advised that the subject should take a statin pharmaceutical agent despite the risk factor).

In some embodiments, age is also considered in combination with other characteristics of the subject in the information set. For example, in some embodiments, as illustrated at steps 818-820 in FIG. 8B, when the subject has not experienced a cardiac event and does not have a family history of premature cardiac disease, the device considers whether the subject is still relatively young, e.g., aged 20-39, and terminates (803) the process by firing a filter in the first class of filters. In some implementations of workflow 800, the process is terminated at this step because the pooled cohort equation used to evaluate the subject's ASCVD risk (e.g., a 10-year risk estimate for a hard ASCVD event using the pooled cohort equations provided in Goff, D C Jr. et al., Circulation (2013) performed at step 844) cannot be applied to younger subjects. Accordingly, when the subject does have a family history of premature coronary disease and is still relatively young, the system bypasses the pooled cohort equation filter at step 822. Similarly, as illustrated at steps 844-450 in FIG. 8E, in some embodiments, when the subject has a moderate ASCVD risk and is diabetic, the system evaluates whether the subject is older, e.g., at least 50 years old if a male and at least 60 years old if a female, and terminates the process (805) because of increased risks associated with statin use in older diabetics.

While these particular steps consider the age of the subject, they are not necessarily tied to a dedicated age filter. Rather, they function to more finely define which subjects would most benefit from statin therapy. For example, by facilitating eligibility for younger patients with a family history of premature coronary disease, who would otherwise not be eligible because of the limitations of the particular pooled cohort equation filter, and by safeguarding older diabetic patients that are at higher risk for adverse events.

Accordingly, in some embodiments, one or more of these supplemental age considerations are not included in the system, for instance, if all younger patients are disqualified by an age-specific filter (e.g., at step 808), if all diabetic patients are excluded or included, or if a pooled cohort equation that can be applied to younger subjects are used. Alternatively, some or all of the supplemental age considerations can be integrated as part of the age filter, e.g., at step 808.

Pregnancy Filter

Referring to blocks 4028-4030 of FIG. 4B, in some embodiments the first plurality of assessment filters includes a pregnancy filter (e.g., pregnancy filter 216-2 in FIG. 3A and/or filter 2a in Table 2). The pregnancy filter is configured to be fired at least when the first information set indicates the subject is pregnant or breastfeeding. In some embodiments, the pregnancy filter is also configured to be fired when the subject is planning to become pregnant. In some embodiments, the pregnancy filter is only applied when the information set indicates that the subject is female, e.g., the pregnancy filter is bypassed when the subject is male (e.g., as illustrated at steps 806-812 of workflow 800 in FIG. 8A).

In some embodiments, e.g., when implemented as a first type of filter, when the pregnancy filter is fired, the subject is not permitted to obtain provision of the statin pharmaceutical composition pharmaceutical composition over-the-counter (e.g., the method is terminated without authorizing provision of the statin pharmaceutical composition to the subject). In some embodiments, e.g., when implemented as a second type of filter, when the pregnancy filter is fired, the subject is issued a warning associated with the filter, but is eligible to obtain provision of the statin pharmaceutical composition pharmaceutical composition over-the-counter upon satisfying the acknowledgement criteria associated with the warning (e.g., by confirming that they have discussed the risk factor with a medical professional and/or the medical professional has advised that the subject should take a statin pharmaceutical agent despite the risk factor).

Severe Drug Interaction Filter

Referring to blocks 4032 through 4044 of FIG. 4C, in some embodiments, the first plurality of assessment filters includes a severe drug interaction filter (e.g., drug interaction filter 216-3 in FIG. 3 and/or filter 3a in Table 2). The severe drug interaction filter is configured to be fired at least when the information set indicates that the subject is taking one or more compositions that interacts with the statin pharmaceutical composition, e.g., a pharmacokinetic interaction and/or a pharmacodynamic interaction, and is contraindicated for co-administration with the statin pharmaceutical composition. Non-limiting examples of drugs that may be contraindicated for co-administration with a statin pharmaceutical composition, e.g., based on the particular statin, include cyclosporine, an anti-viral protease inhibitor, warfarin, a strong CYP3A4 inhibitor, and another cholesterol lowering medication.

In some embodiments, e.g., when implemented as a first type of filter, when the severe drug interaction filter is fired, the subject is not permitted to obtain provision of the statin pharmaceutical composition pharmaceutical composition over-the-counter (e.g., the method is terminated without authorizing provision of the statin pharmaceutical composition to the subject).

In some embodiments, e.g., when the statin pharmaceutical composition includes atorvastatin, fluvastatin, lovastatin, or pitavastatin as an active ingredient, the severe drug interaction filter is configured to be fired when the information set indicates that the subject is taking cyclosporine.

In some embodiments, e.g., when the statin pharmaceutical composition includes fluvastatin, lovastatin, or pravastatin as an active ingredient, the severe drug interaction filter is configured to be fired when the information set indicates the subject is already taking a cholesterol-lowering medication or a triglyceride-lowering medication.

In some embodiments, e.g., when the statin pharmaceutical composition includes lovastatin, pitavastatin, or simvastatin as an active ingredient, the severe drug interaction filter is configured to be fired when the information set indicates the subject is taking an anti-viral protease inhibitor.

In some embodiments, e.g., when the statin pharmaceutical composition includes fluvastatin as an active ingredient, the severe drug interaction filter is configured to be fired when the information indicates the subject is taking warfarin.

In some embodiments, e.g., when the statin pharmaceutical composition includes lovastatin or simvastatin as an active ingredient, the severe drug interaction filter is configured to be filed when the information set indicates the subject is taking a strong CYP3A4 inhibitor.

In some embodiments, e.g., when the statin pharmaceutical composition includes rosuvastatin as an active ingredient, the severe drug interaction filter is configured to be fired when the information set indicates the subject is taking cyclosporine, a cholesterol-lowering medication, a triglyceride-lowering medication, or warfarin.

As will be appreciated, compositions that are contraindicated, or represent a risk factor, for co-administration with a statin pharmaceutical composition vary from one statin pharmaceutical composition to another statin pharmaceutical composition. The skilled artisan will know, for example, of one or more compositions that interact with one statin pharmaceutical composition but not another. Inclusion of a composition within the severe drug interaction filter is dependent upon the identity and/or the dosage of the statin pharmaceutical composition being authorized for a provision of over-the-counter use.

As described further below, in some embodiments, use a drug that interacts with a statin pharmaceutical composition in a less severe fashion, e.g., which is a risk factor rather than a contraindication, is sufficient to trigger firing of a filter 222 in the second filter category class 220 (e.g., a moderate drug interaction filter), rather than the severe drug interaction filter 216 of the first plurality of assessment filters 214-1. For example, according to some embodiments, a particular composition is included in the severe drug interaction filter 216 (e.g., as a contraindication) for a first statin pharmaceutical composition, but included in a filter in the second plurality of assessment filters (e.g., as a risk factor) for a second statin pharmaceutical composition. A person skilled in the art will know whether to include a certain composition within the severe drug interaction filter 216-3 or as a separate filter 222 in the second plurality of assessment filters (e.g., a moderate drug interaction filter), based on the severity and risk of the drug interaction with the particular identity and dosage of the statin being authorized for provision of over-the-counter use.

Cardiac Event Filter

Referring to blocks 4046 through 4050 of FIG. 4D, in some embodiments the first plurality of assessment filters 214-1 includes a cardiac event filter (e.g., cardiac event filter 216-4 in FIG. 3A and/or filter 4a in Table 2). In some embodiments, the cardiac event filter is configured to be fired at least when the information set indicates the subject has had a documented cardiac event. In some embodiments, the cardiac event filter is fired when the first information set indicates the subject has had a heart attack, had a stroke, undergone a heart procedure, or developed peripheral artery disease (PAD). Examples of heart procedures that, in some embodiments, may fire the cardiac event filter include open-heart surgery, coronary artery bypass surgery, heart valve replacement and/or repair, surgery to treat heart arrhythmia, aneurysm repair surgery, coronary revascularization surgery, carotid endarterectomy, heart transplant, and the like.

In some embodiments, e.g., when implemented as a first type of filter, when the cardiac event filter is fired, the subject is not permitted to obtain provision of the statin pharmaceutical composition pharmaceutical composition over-the-counter (e.g., the method is terminated without authorizing provision of the statin pharmaceutical composition to the subject). In some embodiments, e.g., when implemented as a second type of filter, when the cardiac event filter is fired, the subject is issued a warning associated with the filter, but is eligible to obtain provision of the statin pharmaceutical composition pharmaceutical composition over-the-counter upon satisfying the acknowledgement criteria associated with the warning (e.g., by confirming that they have discussed the risk factor with a medical professional and/or the medical professional has advised that the subject should take a statin pharmaceutical agent despite the risk factor).

Total Cholesterol Filter

Referring to blocks 4052 through 4058 of FIG. 4D, in some embodiments the first plurality of assessment filters includes a total cholesterol filter (e.g., total cholesterol filter 216-5 in FIG. 3 and/or filter 5a in Table 2). In some embodiments, the total cholesterol filter is configured to be fired at least when the information set indicates the subject has a total cholesterol level that fails to satisfy a ceiling total cholesterol level threshold. For example, in some embodiments, the total cholesterol filter is fired when the first information set indicates the total cholesterol level of the subject is greater than 320 milligrams per deciliter (mg/dL), e.g., where the ceiling total cholesterol level threshold is 320 mg/dL. In other embodiments, the ceiling total cholesterol level threshold is at least 250 mg/dL, at least 275 mg/dL, at least 300 mg/dL, at least 325 mg/dL, or at least 350 mg/dL.

In some embodiments, the total cholesterol filter is configured to be fired, in addition to or instead of failing to satisfy a ceiling total cholesterol threshold, when the first information set indicates the subject has a total cholesterol level that fails to satisfy a floor total cholesterol level threshold. For example, in some embodiments, the total cholesterol filter is fired when the first information set indicates the total cholesterol level of the subject is less than 130 mg/dL, e.g., where the floor total cholesterol threshold is 130 mg/dL. In other embodiments, the ceiling total cholesterol level threshold is no more than 175 mg/dL, no more than 150 mg/dL, no more than 125 mg/dL, or no more than 100 mg/dL.

In some embodiments, the total cholesterol filter is bypassed under certain conditions. For example, as illustrated in example implementation 800, when the device determines the subject is a younger male with a family history of premature heart disease (e.g., as illustrated in steps 818 and 822 in FIG. 8B), filters relating to the calculation of an ASCVD risk (e.g., the cholesterol filters, triglyceride filter, blood pressure filters, and pooled cohort equation filters at steps 824-850 as illustrated in FIG. 8) are bypassed because the ASCVD pooled cohort equation cannot calculate an ASCVD risk for younger subjects. In some embodiments, a supplemental total cholesterol filter is used where the standard total cholesterol filter is bypassed.

In some embodiments, e.g., when implemented as a first type of filter, when the total cholesterol filter is fired, the subject is not permitted to obtain provision of the statin pharmaceutical composition pharmaceutical composition over-the-counter (e.g., the method is terminated without authorizing provision of the statin pharmaceutical composition to the subject). In some embodiments, e.g., when implemented as a second type of filter, when the total cholesterol filter is fired, the subject is issued a warning associated with the filter, but is eligible to obtain provision of the statin pharmaceutical composition pharmaceutical composition over-the-counter upon satisfying the acknowledgement criteria associated with the warning (e.g., by confirming that they have discussed the risk factor with a medical professional and/or the medical professional has advised that the subject should take a statin pharmaceutical agent despite the risk factor).

LDL Cholesterol Filter

Referring to blocks 4060 through 4068 of FIG. 4E, in some embodiments the first plurality of assessment filters includes a low-density lipoprotein (LDL) cholesterol filter (e.g., LDL cholesterol filter 216-6 in FIG. 3 and/or filter 6a in Table 2). In some embodiments, the LDL cholesterol filter is fired at least when the information set indicates the subject has a LDL cholesterol level that fails to satisfy a ceiling LDL cholesterol level threshold. For example, in some embodiments, the LDL cholesterol filter is fired when the first information set indicates the LDL cholesterol level of the subject is greater than 190 mg/dL, e.g., where the ceiling LDL cholesterol level threshold is 190 mg/dL. In other embodiments, the ceiling LDL cholesterol level threshold is at least 170 mg/dL, at least 180 mg/dL, at least 190 mg/dL, at least 200 mg/dL, or at least 210 mg/dL.

In some embodiments, the total cholesterol filter is configured to be fired, in addition to or instead of failing to satisfy a ceiling LDL cholesterol level threshold, when the first information set indicates the subject has a LDL cholesterol level that fails to satisfy a floor LDL cholesterol level threshold. For example, in some embodiments, the LDL cholesterol filter is fired when the first information set indicates the LDL cholesterol level of the subject is less than 70 mg/dL, e.g., where the floor LDL cholesterol level threshold is 70 mg/dL. In other embodiments, the LDL cholesterol level threshold is no more than 150 mg/dL, no more than 125 mg/dL, no more than 100 mg/dL, no more than 90 mg/dL, no more than 80 mg/dL, no more than 70 mg/dL, or no more than 60 mg/dL.

In some embodiments, the LDL cholesterol filter is bypassed under certain conditions. For example, as illustrated in example implementation 800, when the device determines the subject is a younger male with a family history of premature heart disease (e.g., as illustrated in steps 818 and 822 in FIG. 8B), filters relating to the calculation of an ASCVD risk (e.g., the cholesterol filters, triglyceride filter, blood pressure filters, and pooled cohort equation filters at steps 824-850 as illustrated in FIG. 8) are bypassed because the ASCVD pooled cohort equation cannot calculate an ASCVD risk for younger subjects.

In some embodiments, a supplemental LDL cholesterol filter is used where the standard total cholesterol filter is bypassed. For instance, as illustrated in steps 826-*s* and 830-*s*, in some embodiments a supplemental LDL cholesterol filter is implemented as a replacement to the bypassed LDL cholesterol filter. In some embodiments, the thresholds for the supplemental LDL filter are the same as the thresholds for the bypassed LDL cholesterol filter, e.g., a ceiling threshold of 160 mg/dL and a floor threshold of 70 mg/dL. In other embodiments, one or more thresholds in the supplemental LDL cholesterol filter are set differently. For instance, in some embodiments, the supplemental LDL cholesterol filter has a higher floor threshold, setting a more strict requirement for obtaining provision of the statin pharmaceutical composition. For example, in some embodiments, the floor threshold for the supplemental LDL cholesterol threshold is 160 mg/dL. The higher threshold in the supplemental filter helps to eliminate subjects that have a family history of premature heart disease, but do not show indications of developing premature heart disease themselves. In other embodiments, the floor threshold for the supplemental LDL cholesterol threshold at least 90 mg/dL, at least 100 mg/dL, at least 125 mg/dL, at least 150 mg/dL. In some embodiments, the ceiling threshold for the LDL cholesterol filter is the same as the ceiling threshold for the bypassed LSL cholesterol filter, e.g., 190 dL/mg.

In some embodiments, e.g., when implemented as a first type of filter, when the LDL cholesterol filter is fired, the subject is not permitted to obtain provision of the statin pharmaceutical composition pharmaceutical composition over-the-counter (e.g., the method is terminated without authorizing provision of the statin pharmaceutical composition to the subject). In some embodiments, e.g., when implemented as a second type of filter, when the LDL cholesterol filter is fired, the subject is issued a warning associated with the filter, but is eligible to obtain provision of the statin pharmaceutical composition pharmaceutical composition over-the-counter upon satisfying the acknowledgement criteria associated with the warning (e.g., by confirming that they have discussed the risk factor with a medical professional and/or the medical professional has advised that the subject should take a statin pharmaceutical agent despite the risk factor).

HDL Cholesterol Filter

Referring to blocks 4070 through 4076 of FIG. 4E, in some embodiments the first plurality of assessment filters includes a high-density lipoprotein (HDL) cholesterol filter (e.g., HDL cholesterol filter 216-7 in FIG. 3 and/or filter 7*a* in Table 2). In some embodiments, the HDL cholesterol filter is configured to be fired at least when the information set indicates the subject has a HDL cholesterol level that fails to satisfy a ceiling HDL cholesterol level threshold. For example, in some embodiments, the HDL cholesterol filter is fired when the first information set indicates the HDL cholesterol level of the subject is greater than 100 mg/dL, e.g., where the ceiling HDL cholesterol level threshold is 100 mg/dL. In other embodiments, the ceiling HDL cholesterol level threshold is at least 80 mg/dL, at least 90 mg/dL, at least 100 mg/dL, at least 110 mg/dL, or at least 120 mg/dL.

In some embodiments, the HDL cholesterol filter is configured to be fired, in addition to or instead of failing to satisfy a ceiling HDL cholesterol level threshold, when the first information set indicates the subject has a HDL cholesterol level that fails to satisfy a floor HDL cholesterol level threshold. For example, in some embodiments, the HDL cholesterol filter is fired when the first information set indicates the HDL cholesterol level of the subject is less than 20 mg/dL, e.g., where the floor HDL cholesterol level threshold is 20 mg/dL. In other embodiments, the ceiling total cholesterol level threshold is no more than 10 mg/dL, no more than 15 mg/dL, no more than 20 mg/dL, no more than 25 mg/dL, or no more than 30 mg/dL.

In some embodiments, the HDL cholesterol filter is bypassed under certain conditions. For example, as illustrated in example implementation 800, when the device determines the subject is a younger male with a family history of premature heart disease (e.g., as illustrated in steps 818 and 822 in FIG. 8B), filters relating to the calculation of an ASCVD risk (e.g., the cholesterol filters, triglyceride filter, blood pressure filters, and pooled cohort equation filters at steps 824-850 as illustrated in FIG. 8) are bypassed because the ASCVD pooled cohort equation cannot calculate an ASCVD risk for younger subjects. In some embodiments, a supplemental HDL cholesterol filter is used where the standard total cholesterol filter is bypassed.

In some embodiments, e.g., when implemented as a first type of filter, when the HDL cholesterol filter is fired, the subject is not permitted to obtain provision of the statin pharmaceutical composition pharmaceutical composition over-the-counter (e.g., the method is terminated without authorizing provision of the statin pharmaceutical composition to the subject). In some embodiments, e.g., when implemented as a second type of filter, when the HDL cholesterol filter is fired, the subject is issued a warning associated with the filter, but is eligible to obtain provision of the statin pharmaceutical composition pharmaceutical composition over-the-counter upon satisfying the acknowledgement criteria associated with the warning (e.g., by confirming that they have discussed the risk factor with a medical professional and/or the medical professional has advised that the subject should take a statin pharmaceutical agent despite the risk factor).

Triglyceride Filter

Referring to blocks 4078 and 4080 of FIG. 4F, in some embodiments the first plurality of assessment filters includes a triglyceride filter (e.g., triglyceride filter 216-8 in FIG. 3 and/or filter 8*a* in Table 2). In some embodiments, the triglyceride filter is configured to be fired when the when the information set indicates the subject has a triglyceride level that fails to satisfy a ceiling triglyceride level threshold. For example, in some embodiments, the triglyceride filter is fired when the information set indicates the triglyceride level of the subject is greater than 500 mg/dL, e.g., where the ceiling triglyceride level threshold is 500 mg/dL. In other embodiments, the ceiling triglyceride level threshold is at least 450 mg/dL, at least 475 mg/dL, at least 500 mg/dL, at least 525 mg/dL, or at least 550 mg/dL.

In some embodiments, the triglyceride filter is bypassed under certain conditions. For example, as illustrated in example implementation 800, when the device determines the subject is a younger male with a family history of premature heart disease (e.g., as illustrated in steps 818 and 822 in FIG. 8B), filters relating to the calculation of an ASCVD risk (e.g., the cholesterol filters, triglyceride filter, blood pressure filters, and pooled cohort equation filters at steps 824-850 as illustrated in FIG. 8) are bypassed because the ASCVD pooled cohort equation cannot calculate an ASCVD risk for younger subjects.

In some embodiments, a supplemental triglyceride filter is used where the standard triglyceride filter is bypassed. For instance, as illustrated in step 830-*s*, in some embodiments a supplemental triglyceride filter is implemented as a replacement to the bypassed triglyceride filter. In some embodiments, the threshold for the supplemental triglyceride is the same as the thresholds for the bypassed triglyceride filter, e.g., a ceiling threshold of 500 mg/dL, or at least 450 mg/dL, at least 475 mg/dL, at least 500 mg/dL, at least 525 mg/dL, or at least 550 mg/dL. In other embodiments, the threshold in the supplemental triglyceride filter is set differently than the threshold for the standard triglyceride filter.

In some embodiments, e.g., when implemented as a first type of filter, when the triglyceride filter is fired, the subject is not permitted to obtain provision of the statin pharmaceutical composition pharmaceutical composition over-the-counter (e.g., the method is terminated without authorizing provision of the statin pharmaceutical composition to the subject). In some embodiments, e.g., when implemented as a second type of filter, when the triglyceride filter is fired, the subject is issued a warning associated with the filter, but is eligible to obtain provision of the statin pharmaceutical composition pharmaceutical composition over-the-counter upon satisfying the acknowledgement criteria associated with the warning (e.g., by confirming that they have discussed the risk factor with a medical professional and/or the medical professional has advised that the subject should take a statin pharmaceutical agent despite the risk factor).

Blood Pressure Filter

Referring to blocks 4082 through 4090 of FIG. 4F, in some embodiments the first plurality of assessment filters includes a blood pressure filter (e.g., blood pressure filter 216-9 in FIG. 3 and/or filter 9*a* in Table 2). In some embodiments, the blood pressure filter evaluates the systolic blood pressure of the subject, the diastolic blood pressure of the subject, or both. In some embodiments, the rules underlying the blood pressure filter consider systolic and diastolic blood pressure readings separately, e.g., setting separate criteria for firing the filter. For example, as illustrated in example implementation 800 in FIG. 8D, the device first evaluates the systolic blood pressure of the subject (at step 832) and then evaluates the diastolic blood pressure of the subject (at step 834). In other embodiments, the rules underlying the blood pressure filter consider systolic and diastolic blood pressure at a single step, e.g., requiring a particular combination of systolic and diastolic blood pressures in order to qualify to receive provision of the statin pharmaceutical composition.

In some embodiments, the blood pressure filter is configured to be fired at least when the information set indicates that the systolic blood pressure of the subject fails to satisfy a ceiling systolic blood pressure threshold. For example, in some embodiments, the blood pressure filter is configured to be fired when the first information set indicates the systolic blood pressure of the subject is greater than 180 mmHg, e.g., where the ceiling systolic blood pressure threshold is 180 mmHg. In other embodiments, the ceiling systolic blood pressure threshold is at least 160 mmHg, at least 170 mmHg, at least 180 mmHg, at least 190 mmHg, or at least 200 mmHg. In some embodiments, the blood pressure filter is configured to be fired when the first information set indicates the subject is experiencing hypertensive crisis, e.g., as determined according to a set of healthcare guidelines, which may change over time, and/or vary on a jurisdiction-by-jurisdiction basis. For example, in the United States, the American College of Cardiology and the American Heart Association collaborated to provide guidance on management of high blood pressure. Whelton P K, et al., J Am Coll Cardiol., S0735-1097(17)41519-1 (2017), the contents of which are hereby expressly incorporated by reference.

In some embodiments, the blood pressure filter is configured to be fired, in addition to or instead of failing to satisfy a ceiling systolic blood pressure threshold, when the first information set indicates the subject has a systolic blood pressure that fails to satisfy a floor systolic blood pressure threshold. For example, in some embodiments, the blood pressure filter is configured to be fired when the first information set indicates the systolic blood pressure of the subject is less than 90 mmHg, e.g., where the floor systolic blood pressure threshold is 90 mmHg. In other embodiments, the floor systolic blood pressure threshold is no more than 80 mmHg, no more than 90 mmHg, no more than 100 mmHg, no more than 110 mmHg, or no more than 120 mmHg.

In some embodiments, the blood pressure filter is configured to be fired, in addition to or instead of failing to satisfy a systolic blood pressure threshold, when the first information set indicates the subject has a diastolic blood pressure that fails to satisfy a ceiling diastolic blood pressure threshold. For example, in some embodiments, the blood pressure filter is configured to be fired when the first information set indicates the diastolic blood pressure of the subject is greater than 120 mmHg, e.g., where the ceiling diastolic blood pressure threshold is 120 mmHg. In other embodiments, the ceiling diastolic blood pressure threshold is at least 100 mmHg, at least 110 mmHg, at least 120 mmHg, or at least 130 mmHg. In some embodiments, the blood pressure filter is configured to be fired when the first information set indicates the subject is experiencing hypertensive crisis, e.g., as determined according to a set of healthcare guidelines, which may change over time, and/or vary on a jurisdiction-by-jurisdiction basis. For instance, these guidelines change over time as medical research and advances in treatment better inform management of high blood pressure.

In some embodiments, the blood pressure filter is configured to be fired, in addition to or instead of failing to satisfy any of the blood pressure thresholds described above, when the first information set indicates the subject has a diastolic blood pressure that fails to satisfy a floor diastolic blood pressure threshold. For example, in some embodiments, the blood pressure filter is configured to be fired when the first information set indicates the diastolic blood pressure of the subject is less than 85 mmHg, e.g., where the floor diastolic blood pressure threshold is 85 mmHg. In other embodiments, the floor diastolic blood pressure threshold is no more than 70 mmHg, no more than 80 mmHg, or no more than 90 mmHg.

In some embodiments, the blood pressure filter is bypassed under certain conditions. For example, as illustrated in example implementation 800, when the device determines the subject is a younger male with a family history of premature heart disease (e.g., as illustrated in steps 818 and 822 in FIG. 8B), filters relating to the calculation of an ASCVD risk (e.g., the cholesterol filters, triglyceride filter, blood pressure filters, and pooled cohort equation filters at steps 824-850 as illustrated in FIG. 8) are bypassed because the ASCVD pooled cohort equation cannot calculate an ASCVD risk for younger subjects. In some embodiments, a supplemental blood pressure filter is used where the standard blood pressure filter is bypassed.

In some embodiments, e.g., when implemented as a first type of filter, when the blood pressure filter is fired, the subject is not permitted to obtain provision of the statin pharmaceutical composition pharmaceutical composition over-the-counter (e.g., the method is terminated without authorizing provision of the statin pharmaceutical composition to the subject). In some embodiments, e.g., when implemented as a second type of filter, when the blood pressure filter is fired, the subject is issued a warning associated with the filter, but is eligible to obtain provision of the statin pharmaceutical composition pharmaceutical composition over-the-counter upon satisfying the acknowledgement criteria associated with the warning (e.g., by confirming that they have discussed the risk factor with a medical professional and/or the medical professional has advised that the subject should take a statin pharmaceutical agent despite the risk factor).

ASCVD Risk Filter

Referring to blocks 4092 through 4110 of FIGS. 4G and 4H, in some embodiments the first plurality of assessment filters includes an atherosclerotic cardiovascular disease (ASCVD) risk pooled cohort equation filter (e.g., ASCVD risk pooled cohort equation filter 216-10 in FIG. 3 and/or filter 10a in Table 2). In some embodiments, the ASCVD risk pooled cohort equation filter is configured to be fired when the first information set indicates that the subject has a risk of experiencing a first hard ASCVD event, e.g., a nonfatal myocardial infarction, coronary heart disease death, nonfatal stroke, or fatal stroke, within a given time period that fails to satisfy a ceiling ASCVD risk threshold. In some embodiments, the ASCVD risk is calculated using a pooled cohort equation, e.g., as explained in further detail below. In some embodiments, the risk for the atherosclerotic cardiovascular disease calculated using the pooled cohort equation is a 10-year ASCVD risk. In other embodiments, the risk for the atherosclerotic cardiovascular disease calculated using the pooled cohort equation is 5-year risk, a 15-year risk, a 20-year risk, or a lifetime risk (e.g., or a period estimated to coincide with the subject's remaining estimated lifetime (e.g., 25, 30, 40, 50, 60, or more years). In some embodiments, the pooled cohort equation is implemented as a multivariable Cox proportional hazard regression.

In some embodiments, the ASCVD risk for the subject is calculated as a 10-year risk. In some embodiments, the pooled cohort equation filter is configured to be fired when the information set indicates the subject has a 10-year risk for a hard ASCVD event that is at least 20% (e.g., as determined by a pooled cohort equation), e.g., where the ceiling ASCVD risk threshold is a 20% ten-year risk. In other embodiments, the ceiling ASCVD risk threshold is at least a 15% ten-year risk, at least a 17.5% ten-year risk, at least a 20% ten-year risk, at least a 22.5% ten-year risk, or at least a 25% ten-year risk.

In some embodiments, the ASCVD risk pooled cohort equation filter is configured to be fired, in addition to or instead of failing to satisfy a ceiling total cholesterol threshold, when the first information set indicates the subject has a hard ASCVD event risk that fails to satisfy a floor ASCVD risk threshold. In some embodiments, the pooled cohort equation filter is configured to be fired when the information set indicates the subject has a 10-year risk for a hard ASCVD event that is less than 5%, e.g., where the floor ASCVD risk threshold is a 5% ten-year risk. In other embodiments, the floor ASCVD risk threshold is no more than a 2.5% ten-year risk, no more than a 5% ten-year risk, no more than a 7.5% ten-year risk, or no more than a 10% ten-year risk.

In some embodiments, the system is configured to forgo firing of the ASCVD risk pooled cohort equation filter-when the first information set indicates the subject has a hard ASCVD event risk that fails to satisfy a floor ASCVD risk threshold-when the first information set indicates that additional risk factors are present that warrant further evaluating the subject for treatment with a statin pharmaceutical composition. For example, in some embodiments, when the subject is determined to have an ASCVD risk falling below a floor ASCVD risk threshold, the system evaluates whether the subject has diabetes and is not of an advanced age (e.g., as illustrated at steps 246 to 250 in FIG. 8H). Accordingly, in some embodiments, when the first information set indicates the subject has an ASCVD risk that fails to satisfy the ASCVD risk threshold, the subject has diabetes, and the age of the subject satisfies a ceiling diabetes age threshold for receiving the statin pharmaceutical composition, the system forgoes firing the ASCVD risk pooled cohort equation filter. In some embodiments, the ceiling diabetes age threshold is 45, 50, 55, 60, 65, or 70 years of age. In some embodiments, the ceiling diabetes age threshold is set differently for man and women. For instance, in some embodiments, the ceiling diabetes age threshold is set to 50 years of age when the subject is a male and 60 years of age when the subject is a female. In some embodiments, the ceiling diabetes age threshold is at least 45, at least 50, at least 55, or at least 60 for a male. In some embodiments, the ceiling diabetes age threshold is at least 55, at least 60, at least 65, or at least 70 for a female.

In some embodiments, the ASCVD risk pooled cohort equation filter is configured to be fired-when the first information set indicates the subject has a hard ASCVD event risk that satisfies both a ceiling ASCVD risk threshold and a floor ASCVD risk threshold-when the first information set indicates that additional risk factors are present that warrant limiting access to the statin pharmaceutical composition, or require more careful monitoring by a health care professional. For example, in some embodiments, when the subject is determined to have an ASCVD risk falling between floor ASCVD risk threshold and a ceiling ASCVD risk threshold—which would otherwise facilitate access to the statin pharmaceutical composition—the system evaluates whether the subject has diabetes and is of an advanced age (e.g., as illustrated at steps 246-1 to 250 in FIG. 8E). Accordingly, in some embodiments, when the first information set indicates the subject has an ASCVD risk that otherwise satisfies all ASCVD risk thresholds, but the subject has diabetes and an age failing to satisfy a ceiling diabetes age threshold for receiving the statin pharmaceutical composition, the system fires the ASCVD risk pooled cohort equation filter. In some embodiments, the ceiling diabetes age threshold is 45, 50, 55, 60, 65, or 70 years of age. In some embodiments, the ceiling diabetes age threshold is set differently for man and women. For instance, in some embodiments, the ceiling diabetes age threshold is set to 50 years of age when the subject is a male and 60 years of age when the subject is a female. In some embodiments, the ceiling diabetes age threshold is at least 45, at least 50, at least 55, or at least 60 for a male. In some embodiments, the ceiling diabetes age threshold is at least 55, at least 60, at least 65, or at least 70 for a female.

In some embodiments, the ASCVD risk pooled cohort equation filter is configured to be fired when one or more values in the first information set does not enable calculation of an ASCVD event risk for the subject. For example, the ASCVD pooled cohort equation taught by Goff et al. is incalculable for subjects under the age of forty. Accordingly, in some embodiments when the Goff et al. equation is used, the ASCVD risk pooled cohort equation filter is configured to be fired when the first information set indicates that subject is less than forty years old. Alternatively, in some embodiments, when a value in the first information set does not enable calculation of an ASCVD event risk for the subject, the ASCVD risk pooled cohort equation acts as a filter in the second plurality of assessment filters 220-1. That is, when the ASCVD risk pooled cohort equation filter determines that a value used to calculate an ASCVD event risk is outside of the range required for the calculation, the device issues a warning to the subject (e.g., requiring the subject discuss taking a statin pharmaceutical composition with a medical professional) that must be acknowledged prior to being authorized a provision of the statin pharmaceutical composition, rather than automatically terminating the process, as would be done when the filter acts as a filter in the first plurality of assessment filters 214-1.

In other embodiments, the algorithm is configured such that one or more values falling outside of a range required for calculation of an ASCVD risk trigger firing of a related filter, such that they do not need to be considered when evaluating an ASCVD risk for the subject. For example, when the Goff et al. equation is used to calculate the ASCVD risk evaluated by this filter, a risk cannot be calculated for subjects younger than forty years of age. Accordingly, in some embodiments, an age filter placed upstream of the ASCVD risk pooled cohort equation is configured to be fired if the first information set indicates the subject is younger than forty years of age.

In some embodiments, the ASCVD risk pooled cohort equation filter is bypassed under certain conditions when one or more values fall outside of a range required for calculation of an ASCVD risk. For example, as illustrated in example implementation 800 illustrated in FIG. 8, when the device determines the subject is younger than forty years of age—such that an ASCVD risk cannot be calculated using the Goff et al. pooled cohort equation—the device determines whether the subject has other risk factors that might warrant administration of a statin pharmaceutical composition. For instance, in some embodiments, a family history of premature heart disease may warrant administering a statin pharmaceutical composition to a younger subject, despite that an ASCVD risk cannot be calculated for the subject. In some embodiments, the younger subject is a male, e.g., where younger females are disqualified because they are of child-bearing age. In some embodiments, the younger subject is less than 45 years old. In some embodiments, the younger subject is less than 40 years old. In some embodiments, the younger subject is greater than 16 years of age. In some embodiments, the younger subject is greater than 18 years of age. In some embodiments, the younger subject is greater than 20 years of age. In some embodiments, younger subject is from 20 years of age to 39 years of age. In other embodiments, the younger subject is from 16 years of age to 45 years of age, 18 years of age to 45 years of age, 18 years of age to 40 years of age, 20 years of age to 40 years of age, 20 years of age to 39 years of age, or 21 years of age to 39 years of age. In some embodiments, the subject is considered to have a familial history of premature heart disease when a father or a brother of the subject had a heart attack or a stroke before the age of 55 years of age, or when a mother or a sister of the subject had a heart attack or a stroke before the age of 65.

Figure 8A:
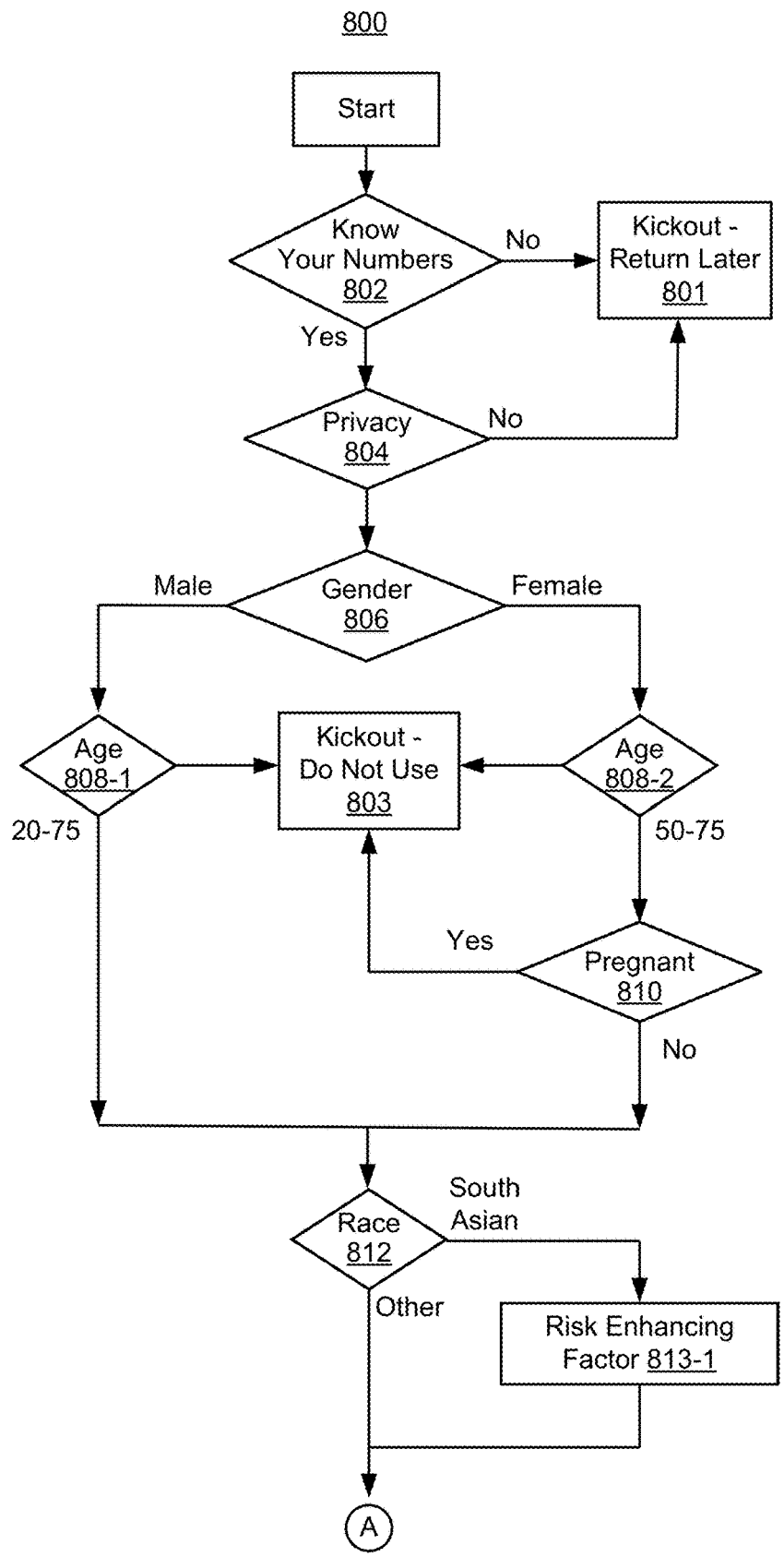
Figure 8B:
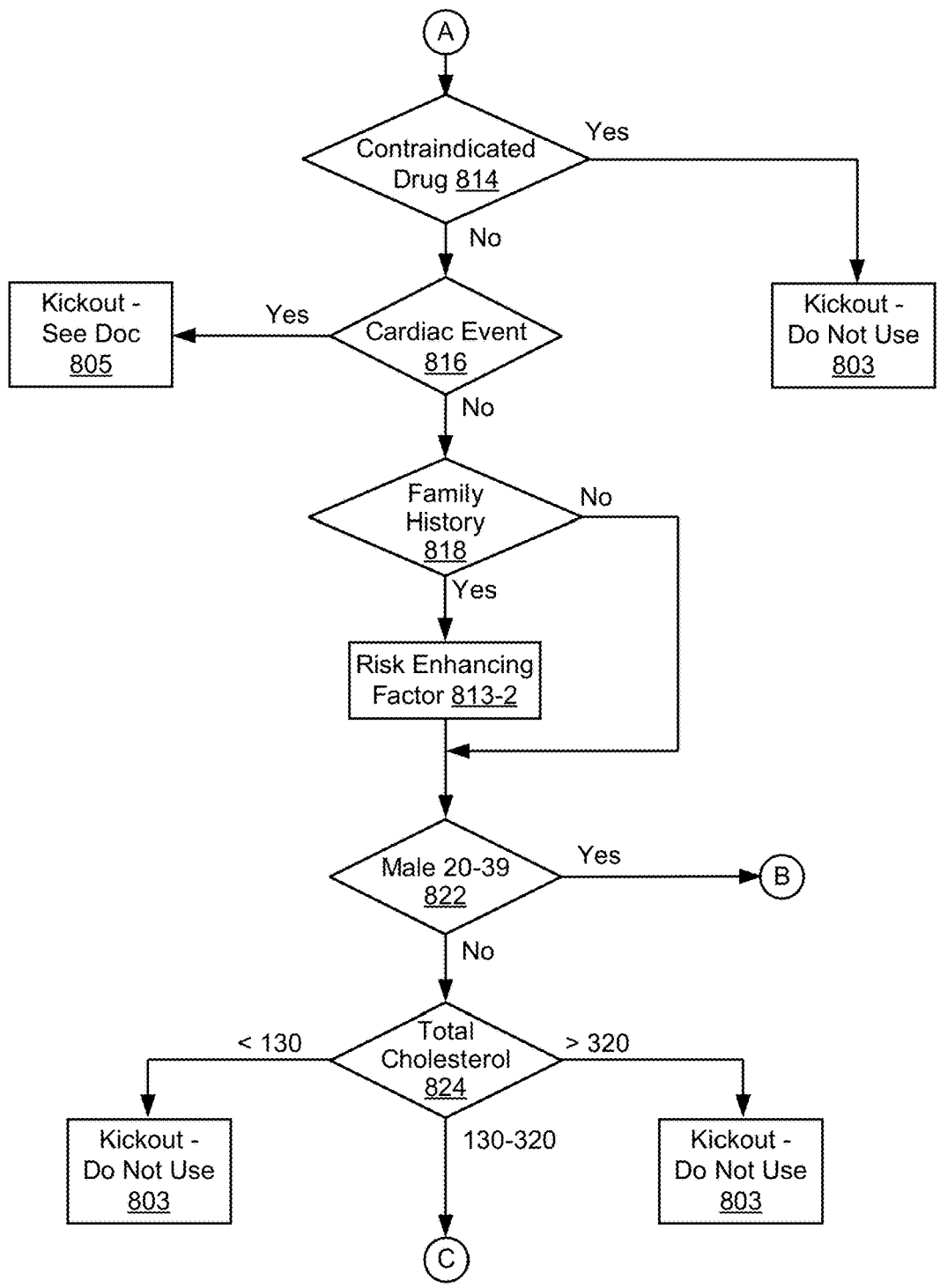
Figure 8C:
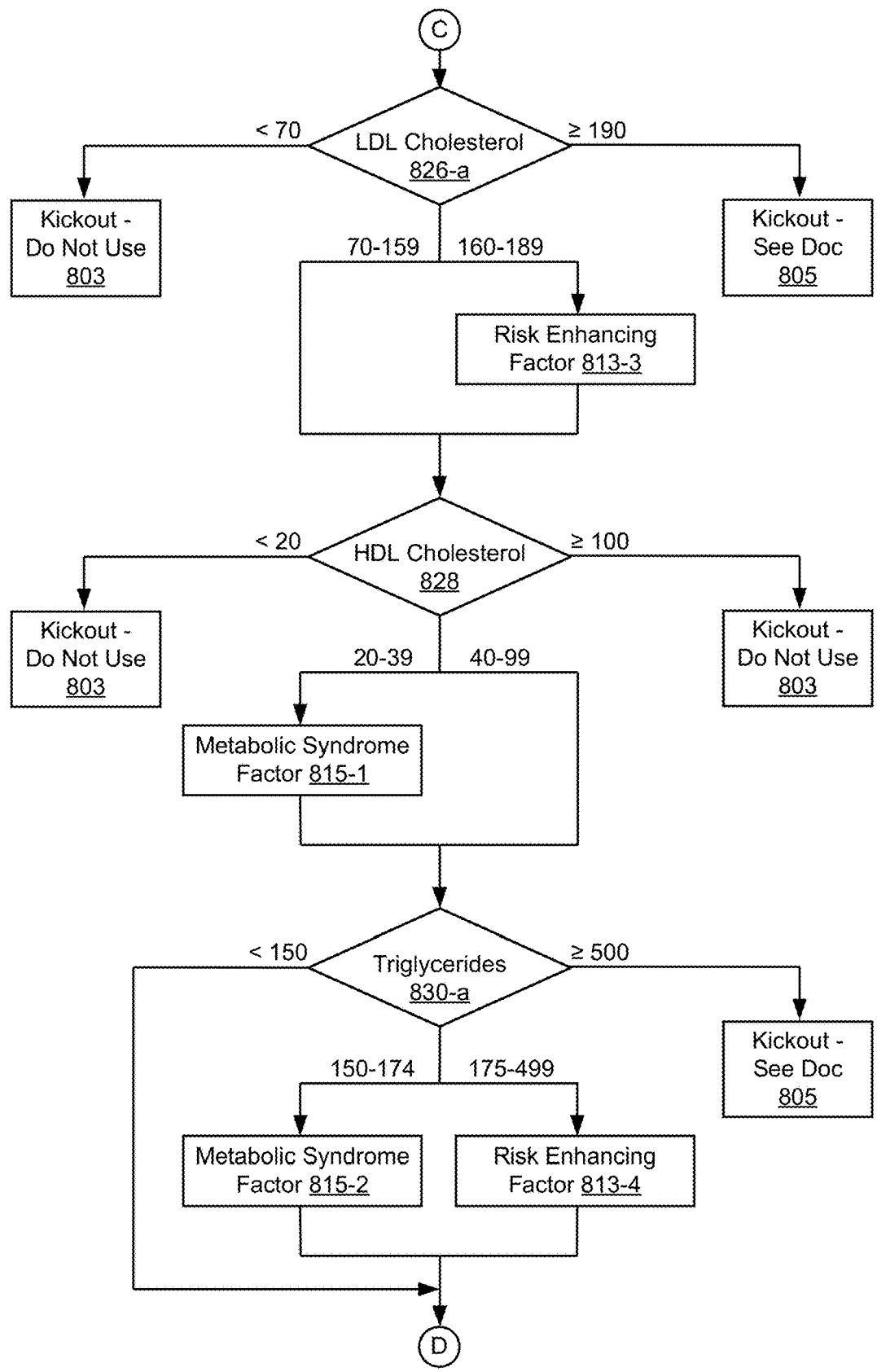
Figure 8D:
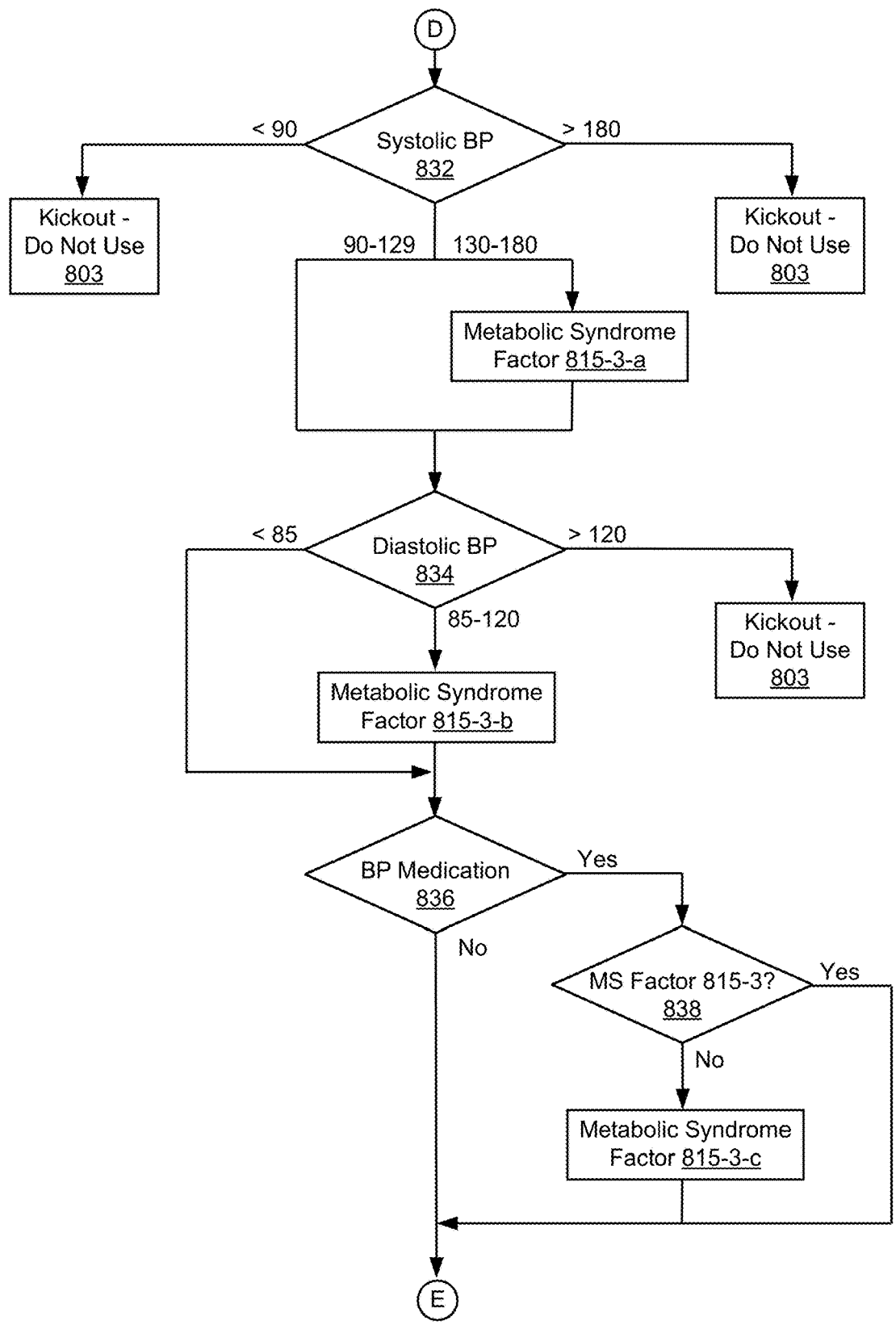
Figure 8E:
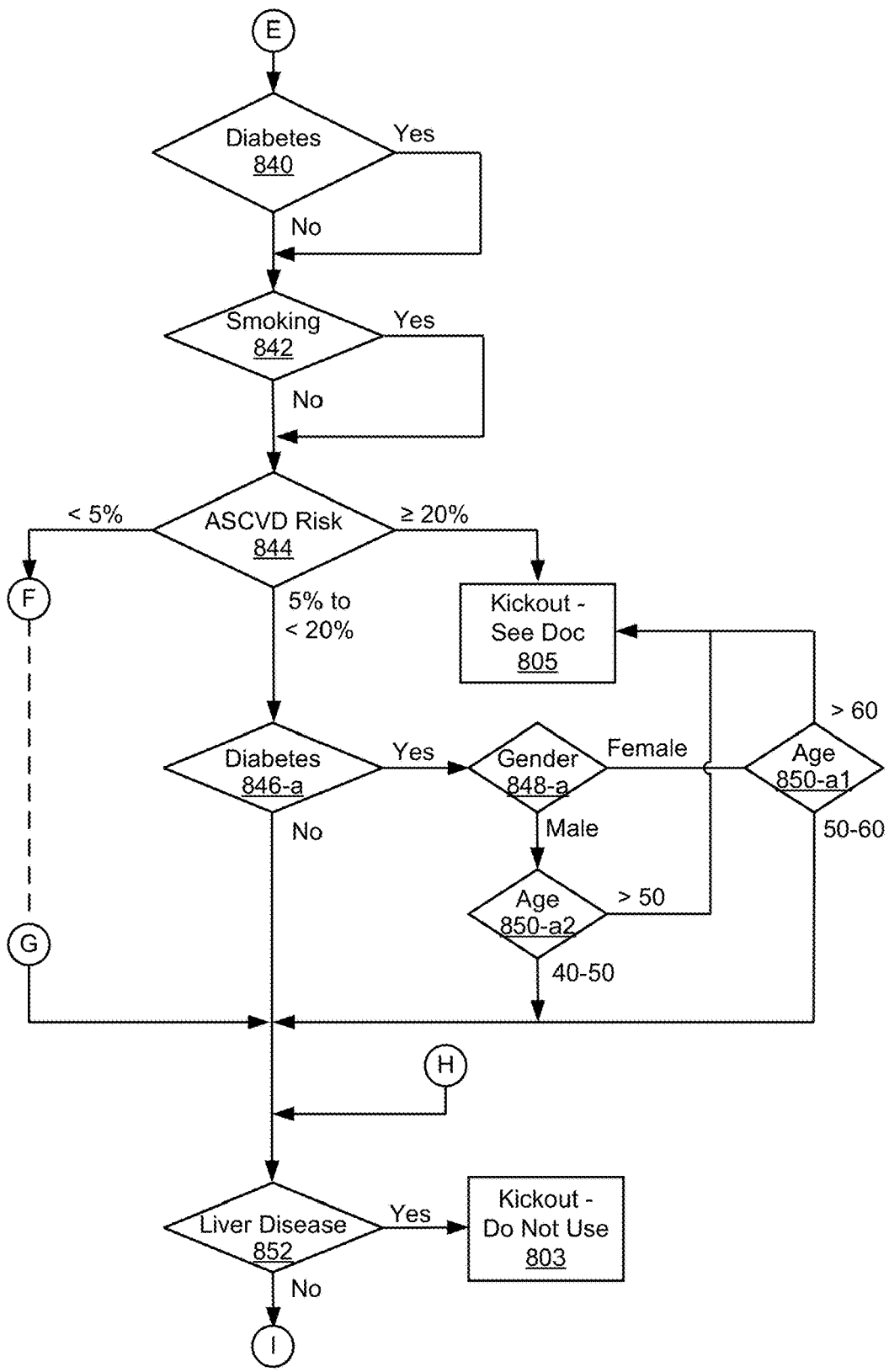

Accordingly, in some embodiments, e.g., as illustrated in steps 818 and 822 in FIG. 8B, filters relating to the calculation of an ASCVD risk (e.g., the cholesterol filters, triglyceride filter, blood pressure filters, and pooled cohort equation filters at steps 824-850 as illustrated in FIG. 8) are bypassed because the ASCVD pooled cohort equation cannot calculate an ASCVD risk for younger subjects. In some embodiments, one or more supplemental filters can be used in place of the bypassed filters, e.g., an LDL cholesterol filter, as implemented in step 826-*s* in FIG. 8H, and a triglyceride filter, as implemented in step 830-*s* in FIG. 8H, to further evaluate whether the subject has additional risk factors that support providing the subject with provision of the statin pharmaceutical composition.

In some embodiments, e.g., when implemented as a first type of filter, when the ASCVD risk pooled cohort equation filter is fired, the subject is not permitted to obtain provision of the statin pharmaceutical composition pharmaceutical composition over-the-counter (e.g., the method is terminated without authorizing provision of the statin pharmaceutical composition to the subject). In some embodiments, e.g., when implemented as a second type of filter, when the ASCVD risk pooled cohort equation filter is fired, the subject is issued a warning associated with the filter, but is permitted to obtain provision of the statin pharmaceutical composition pharmaceutical composition over-the-counter when the acknowledgement criteria associated with the warning (e.g., by confirming that they have discussed the risk factor with a medical professional and/or the medical professional has advised that the subject should take a statin pharmaceutical agent despite the risk factor).

In some embodiments the ASCVD risk pooled cohort equation filter incorporates the age of the subject, the sex of the subject, the race of the subject, the total cholesterol of the subject, the triglyceride level of the subject, the systolic blood pressure of the subject, the diastolic blood pressure of the subject, whether the subject is taking a medication for hypertension, the diabetes status of the subject, and the smoking status of the subject to derive a risk for atherosclerotic cardiovascular disease (e.g., a risk for experiencing an atherosclerotic cardiovascular disease (ASCVD) event within a certain timeframe, such as within five or ten years). In some embodiments, the pooled cohort equation also incorporates a familial history of premature heart or stroke (e.g., a familial history of heart attack or stroke before the age of forty-five, fifty, fifty-five, sixty, etc.). Accordingly, the first information set will include pertinent information required to calculate an ASCVD risk, as defined by a particular pooled cohort equation for the risk.

The pooled cohort equation estimates the probability of incurring a hard atherosclerotic cardiovascular disease (ASCVD) event in a given period of time, such as in the next 5 years, the next 10 years, or in the lifetime of a subject. In some embodiments, the pooled cohort equation for the pooled cohort equation filter is calculated using the guidelines set forth in Goff, D C Jr, et al., J. Am. Coll. Cardiol., 63:2935-59 (2014), the content of which is hereby incorporated by reference. Following the Goff et al. (Id.) calculation of the 10-year risk estimate for a hard ASCVD event using the pooled cohort equations is done as a series of steps. The natural log of the age of the subject, total cholesterol, HDL-C, and systolic blood pressure are first calculated with the systolic blood pressure being either a treated or untreated value. For example, calculation of the pooled cohort equations estimate the probability of a Caucasian male subject 55 years of age with total cholesterol 213 mg/dL, HDL-C 50 mg/dL, untreated systolic blood pressure 120 mm Hg, nonsmoker, and without diabetes determine the probability of a hard ASCVD event in the next 10 years using Goff Id. begins by first taking the natural log of the subject's age (4.01), the natural log of the subject's total cholesterol (5.36), the natural log of the subject's HDL-C (3.91), and the natural log of the subject's systolic blood pressure (4.79). These values are then multiplied by the coefficients from the equation ("Coefficient" column of Table A of Goff Id.) for the specific race-gender group of the individual to obtain "coefficient×values." That is:

multiply the natural log of the subject's age (4.01) by the coefficient 12.344 to obtain the "coefficient×value" of 49.47, multiply the natural log of the subject's total cholesterol (5.36) by the coefficient 11.853 to obtain the "coefficient×value" of 63.55, multiply the natural log of the subject's HDL-C (3.91) by the coefficient −7.990 to obtain the "coefficient×value" of −31.26, and multiply the natural log of the subject's systolic blood pressure (4.79) by the coefficient 1.764 to obtain the "coefficient×value" of 8.45.

Any appropriate interaction terms are also calculated. Following Goff Id., in the case of the Caucasian male subject 55 years of age, the interaction terms are:

the Log Age (4.01)×Log total Cholesterol (5.36) multiplied by the coefficient −2.664 to obtain the "coefficient×value" of −57.24 and Log Age (4.01)×Log HDL-C (3.91) multiplied by the coefficient 1.769 to obtain the "coefficient×value" of 27.73.

The sum of these "coefficient×values" is then calculated for the individual (49.47+63.55−31.26+8.45−57.24+27.73=60.69). The estimated 10-year risk of a first hard ASCVD event is formally calculated as 1 minus the baseline survival rate at 10 years for the gender/race (in this example Caucasian male), raised to the power of the exponent of the "Coefficient×Value" sum calculated above minus the race (Caucasian) and gender (Male) specific overall mean "Coefficient×Value" sum; or, in equation form:

$$1 - 0.9144^{e^{(60.69 - 61.18)}}$$

where the number 0.9144 is the baseline survival rate at 10 years for Caucasian males from Goff Id., the number 60.69 is the "coefficient×value" calculated for the particular subject as detailed above, and the number 61.18 is the race (Caucasian) and gender (Male) specific overall mean "Coefficient×Value" from Goff Id. This equates to a 5.3% probability of a first hard ASCVD event within 10 years.

In some embodiments, using the Goff et al. calculation, the risk for the fatal cardiovascular disease used in calculating the pooled cohort equation is a 10-year risk, and a first threshold value, e.g., a threshold value which when the risk of the subject is determined to be less than fires the filter, is about 10% risk. In some embodiments, the risk for the fatal cardiovascular disease used in calculating the pooled cohort equation is a 10-year risk, and the first threshold value is a 10% risk.

In some embodiments, the pooled cohort equation filter incorporates some or all of the characteristics listed in Table 3, e.g., as determined from a set of survey results, to derive a subject risk for atherosclerotic cardiovascular disease. For example, in some embodiments, the plurality of assessment survey results includes 2, 3, 4, 5, 6, 7, 8, 9, 10, or all 11 of the characteristics listed in Table 3. The pooled cohort equation filter is fired when the subject's risk for atherosclerotic cardiovascular disease exceeds a threshold level of risk.

TABLE 3

Example Characteristics Used for Pooled Cohort Equation Filter

| Result | Exemplary Characteristics |
|---|---|
| 1 | a gender of the subject |
| 2 | an age of the subject |
| 3 | a total cholesterol level of the subject |
| 4 | a HDL cholesterol count of the subject |
| 5 | a systolic blood pressure of the subject |
| 6 | a race of the subject |
| 7 | whether the subject is taking one or more medications for hypertension |
| 8 | a smoking status of the subject |
| 9 | a diabetes status of the subject |
| 10 | whether the subject has a family history of heart or stroke before the age of 60 |
| 11 | a hsCRP level of the subject |

In some embodiments, the pooled cohort equation used to calculate a risk of fatal cardiovascular disease for the pooled cohort equation filter is calculated using the guidelines set forth in Perk J. et al., European Guidelines on cardiovascular disease prevention in clinical practice, European Heart Journal 33:1635-1701 (2012), which is hereby incorporated by reference herein. In some embodiments, the pooled cohort equation assessment filter follows a low CVD risk SCORE chart, which incorporates the gender of the subject, the age of the subject, the total cholesterol level of the subject, the systolic blood pressure of the subject, and a smoking status of the subject, as set forth in Perk J. et al., Supra. In some embodiments, a conversion factor is used to convert a risk of fatal cardiovascular disease to a risk of fatal plus nonfatal hard cardiovascular disease events, as set forth in Catapano A L et al., 2016 ESC/EAS Guidelines for the Management of Dyslipidaemias. Eur Heart J. 2016 Oct. 14; 37(39):2999-3058, which is hereby incorporated by reference herein. In one embodiment, the pooled cohort equation filter incorporates at least survey results 1-9 as provided in Table 3, e.g., according to the method described in Goff, D C Jr, et al., J. Am. Coll. Cardiol., 63:2935-59 (2014). In another embodiment, the assessment survey results include at least survey results 1-10 as provided in Table 3. In another embodiment, the assessment survey results include at least survey results 1-9 and 11 as provided in Table 3. In another embodiment, the assessment survey results include at least survey results 1-11 as provided in Table 3.

In some embodiments, using the SCORE guidelines, the risk for the fatal cardiovascular disease used in calculating the pooled cohort equation is a 10-year risk, and a first threshold value, e.g., a threshold value which when the risk of the subject is determined to be less than fires the filter, is a 5% risk. In some embodiments, the risk for the fatal cardiovascular disease used in calculating the pooled cohort equation is a 10-year risk, and the first threshold value is a 10% risk.

In some embodiments, the pooled cohort equation used to calculate a risk of a cardiovascular disease-related death for the pooled cohort equation filter is calculated using the guidelines set forth in Teramoto et al., Japan Atherosclerosis Society. Executive summary of the Japan Atherosclerosis Society (JAS) guidelines for the diagnosis and prevention of atherosclerotic cardiovascular diseases in Japan-2012 version, J Atheroscler Thromb., 2013; 20(6):517-23, which is hereby incorporated by reference herein. In some embodiments, the pooled cohort equation assessment filter follows the NIPPON DATA80 absolute risk assessment charts, which incorporate the gender of the subject, the age of the subject, the total cholesterol level of the subject, the systolic blood pressure of the subject, and a smoking status of the subject, as set forth in Teramoto et al., Supra. In some embodiments, the pooled cohort equation also incorporates a glucose level of the subject.

In some embodiments, using the NIPPON DATA80 guidance, the risk for the coronary artery death used in calculating the pooled cohort equation is a 10-year risk, and a first threshold value, e.g., a threshold value which when the risk of the subject is determined to be less than fires the filter, is a 0.5% risk. In some embodiments, the risk for the fatal cardiovascular disease used in calculating the pooled cohort equation is a 10-year risk, and the first threshold value is a 1% risk. In some embodiments, the risk for the fatal cardiovascular disease used in calculating the pooled cohort equation is a 10-year risk, and the first threshold value is a 2% risk. In other embodiments, the risk for the fatal cardiovascular disease used in calculating the pooled cohort equation is a 10-year risk, and the first threshold value is a 3%, 4%, or 5% risk.

In some embodiments, the pooled cohort equation used to calculate a risk of atherosclerotic cardiovascular disease for the pooled cohort equation assessment filter is calculated using the guidelines set forth in Yang X. et al., Predicting the 10-Year Risks of Atherosclerotic Cardiovascular Disease in Chinese Population: The China-PAR Project (Prediction for ASCVD Risk in China). Circulation. 2016 Nov. 8; 134(19): 1430-1440, which is hereby incorporated by reference herein. In some embodiments, the pooled cohort equation assessment filter follows the China-PAR gender specific equations, which incorporate the gender of the subject (e.g., to determine which equation to use), the age of the subject, the systolic blood pressure of the subject, a blood pressure treatment status of the subject, the total cholesterol level of the subject, a smoking status of the subject, a diabetes mellitus status of the subject, the waist circumference of the subject, a geographic residential-region of the subject (e.g., for Chinese residents only, either northern China or southern China), an urbanization residential-region of the subject (e.g., for men residing in China only, either urban or rural), and family history of atherosclerotic cardiovascular disease (e.g., for men only), as set forth in Yang X. et al., Supra and at Supplemental Information. In some embodiments, the pooled cohort equation also incorporates an HDL cholesterol level of the subject and/or a cholesterol treatment status of the subject.

In some embodiments, using the China-PAR guidance, the risk for the atherosclerotic cardiovascular disease used in calculating the pooled cohort equation is a 10-year risk, and a first threshold value, e.g., a threshold value which when the risk of the subject is determined to be less than fires the filter, is a 5% risk. In some embodiments, the risk for the atherosclerotic cardiovascular disease used in calculating the pooled cohort equation is a 10-year risk, and the first threshold value is a 7.5% risk. In some embodiments, the risk for the atherosclerotic cardiovascular disease used in calculating the pooled cohort equation is a 10-year risk, and the first threshold value is a 7.5% risk.

In some embodiments, the pooled cohort equation used to calculate a risk of atherosclerotic cardiovascular disease for the pooled cohort equation assessment filter 216-5 is calculated using the guidelines set forth in National Vascular Disease Prevention Alliance, Guidelines for the management of absolute cardiovascular disease risk, 2012, which is hereby incorporated by reference herein. In some embodiments, the pooled cohort equation assessment filter follows the Australian cardiovascular risk charts, which incorporate the gender of the subject, the age of the subject, the systolic blood pressure of the subject, the ratio of total cholesterol to HDL levels of the subject, and a smoking status of the subject, as set forth in Absolute cardiovascular disease risk management: Quick reference guide for health professionals, 2012, National Stroke Foundation. In some embodiments, the pooled cohort equation also incorporates the decent of the subject (e.g., in Australia only, for Aboriginal, Torres Strait Islander, or other populations).

In some embodiments, using the Australian cardiovascular risk charts, the risk for the atherosclerotic cardiovascular disease used in calculating the pooled cohort equation is a 5-year risk, and a first threshold value, e.g., a threshold value which when the risk of the subject is determined to be less than fires the filter, is a 5% risk. In some embodiments, the risk for the atherosclerotic cardiovascular disease used in calculating the pooled cohort equation is a 5-year risk, and the first threshold value is a 10% risk. In some embodiments, the risk for the atherosclerotic cardiovascular disease used in calculating the pooled cohort equation is a 5-year risk, and the first threshold value is a 16% risk. In some embodiments, the risk for the atherosclerotic cardiovascular disease used in calculating the pooled cohort equation is a 5-year risk, and the first threshold value is a 20% risk. In some embodiments, the risk for the atherosclerotic cardiovascular disease used in calculating the pooled cohort equation is a 5-year risk, and the first threshold value is a 25% risk.

In some embodiments, the pooled cohort equation used to calculate a risk of atherosclerotic cardiovascular disease for the pooled cohort equation assessment filter 216-5 is calculated using the guidelines set forth in Anderson T J et al., 2016 Canadian Cardiovascular Society Guidelines for the Management of Dyslipidemia for the Prevention of Cardiovascular Disease in the Adult, Can J Cardiol. 2016 November; 32(11):1263-1282, which is hereby incorporated by reference herein. In some embodiments, the pooled cohort equation assessment filter follows a Framingham Heart Study Risk Score equation (FRS), which incorporates the gender of the subject, the age of the subject, the systolic blood pressure of the subject, a blood pressure treatment status of the subject, the total cholesterol level of the subject, and an HDL cholesterol level of the subject, a smoking status of the subject, a diabetes mellitus status of the subject, and a CVD event incident status of the subject, as set forth in D'Agostino R B Sr et al., General cardiovascular risk profile for use in primary care: the Framingham Heart Study. Circulation. 2008 Feb. 12; 117(6):743-53, which is hereby incorporated by reference herein. In some embodiments, the pooled cohort equation assessment filter follows a modified Framingham Heart Study Risk Score equation (FRS), which incorporates the gender of the subject, the age of the subject, the systolic blood pressure of the subject, a blood pressure treatment status of the subject, the total cholesterol level of the subject, and an HDL cholesterol level of the subject, a smoking status of the subject, a diabetes mellitus status of the subject, and a CVD event incident status of the subject, and a family history status of premature cardiovascular disease, as set forth in Anderson T J et al., Supra. In some embodiments, the pooled cohort equation assessment filter follows a Cardiovascular Life Expectancy Model (CLEM), as set forth in Grover S A et al., Estimating the benefits of modifying risk factors of cardiovascular disease: a comparison of primary vs secondary prevention. Arch Intern Med. 1998 Mar. 23; 158(6):655-62, which is hereby incorporated by reference herein.

In some embodiments, using the Canadian Cardiovascular Society guidance, the risk for the atherosclerotic cardiovascular disease used in calculating the pooled cohort equation is a 10-year risk, and a first threshold value, e.g., a threshold value which when the risk of the subject is determined to be less than fires the filter, is a 5% risk. In some embodiments, the risk for the atherosclerotic cardiovascular disease used in calculating the pooled cohort equation is a 10-year risk, and the first threshold value is a 10% risk. In some embodiments, the risk for the atherosclerotic cardiovascular disease used in calculating the pooled cohort equation is a 10-year risk, and the first threshold value is a 15% risk.

In some embodiments, a probability of the occurrence of a hard ASCVD event in a given period of time (e.g., within the next 10 years), e.g., as calculated above, is modified by considering one or both of the familial history of the subject for premature heart attacks or strokes and the hsCRP level of the subject. This inclusion is to reduce a likelihood of over-predicting adverse events, e.g., in subjects without a familial history of adverse events and/or with healthy hsCRP levels.

Liver Condition Filter

Referring to block 4112 of FIG. 4H, in some embodiments the first plurality of assessment filters includes a liver condition filter (e.g., liver condition filter 216-11 in FIG. 3A and/or filter 11a of Table 2). In some embodiments, the liver condition filter is configured to be fired when the first information set indicates that the subject has an adverse liver condition. In some embodiments, an adverse liver condition that is capable of firing the liver condition filter includes symptoms and/or conditions such as inflammation of the liver, fibrosis, cirrhosis, end-stage liver disease (ESLD), cancer of the liver, and/or liver failure. In some embodiments, when the liver condition filter is fired, the subject is provided a recommendation to discuss taking a lower dosage of the statin pharmaceutical composition with a medical practitioner.

In some embodiments, e.g., when implemented as a first type of filter, when the liver condition filter is fired, the subject is not permitted to obtain provision of the statin pharmaceutical composition pharmaceutical composition over-the-counter (e.g., the method is terminated without authorizing provision of the statin pharmaceutical composition to the subject). In some embodiments, e.g., when implemented as a second type of filter, when the liver condition filter is fired, the subject is issued a warning associated with the filter, but is eligible to obtain provision of the statin pharmaceutical composition pharmaceutical composition over-the-counter upon satisfying the acknowledgement criteria associated with the warning (e.g., by confirming that they have discussed the risk factor with a medical professional and/or the medical professional has advised that the subject should take a statin pharmaceutical agent despite the risk factor).

Risk Enhancing Factor Filter

Referring to blocks 4114 through 4132 of FIGS. 4H through 4J, in some embodiments the plurality of assessment filters includes a risk enhancing factor filter (e.g., filter 12a of Table 2). In some embodiments, the risk enhancing factor filter is fired unless the first information set indicates that the subject has at least one of a plurality of enhancing factors for high cholesterol. In some embodiments, the risk enhancing factor filter is fired unless the first information set indicates that the subject has at least two of a plurality of enhancing factors for high cholesterol. In some embodiments, the risk enhancing factor filter is fired unless the first information set indicates that the subject has at least three of a plurality of enhancing factors for high cholesterol. In other embodiments, the risk enhancing factor filter is fired unless the first information set indicates that the subject has at least four, five, six, or more of a plurality of enhancing factors for high cholesterol. In some embodiments, the risk enhancing factors that prevent firing of the risk enhancing factor filter include one or more of South Asian descent (e.g., from Afghanistan, Bangladesh, Bhutan, India, Maldives, Pakistan, Nepal or Sri Lanka), a familial history of premature heart disease, an elevated LDL cholesterol level, an elevated triglyceride level, a chronic kidney disease, an inflammatory disease (e.g., rheumatoid arthritis, psoriasis, or HIV/AIDS), a history of preeclampsia, premature menopause (e.g., before 35, 40, or 45 years of age), an elevated C-Reactive Protein level, the presence of coronary artery calcium (e.g., any coronary artery calcium), an elevated lipoprotein (a) level, an elevated apoB level, a low ankle-brachial index, and metabolic syndrome.

In some embodiments, a subject has a familial history of premature heart disease when a father or a brother of the subject had a heart attack or a stroke before the age of 55 years of age, or when a mother or a sister of the subject had a heart attack or a stroke before the age of 65. In some embodiments, a subject has a familial history of premature heart disease when a father or a brother of the subject had a heart attack or a stroke before the age of 50 years of age, 55 years of age, or 60 years of age. In some embodiments, a subject has a familial history of premature heart disease when a mother or a sister of the subject had a heart attack or a stroke before the age of 60 years of age, 65 years of age, or 70 years of age.

In some embodiments, a subject has an elevated LDL cholesterol level when their LDL cholesterol level is at least 160 mg/dL. In some embodiments, a subject has an elevated LDL cholesterol level when their LDL cholesterol level is between about 160 and about 189 mg/dL. In other embodiments, a subject has elevated LDL cholesterol when their LDL cholesterol level is at least 140 mg/dL, at least 150 mg/dL, at least 170 mg/dL, or at least 180 mg/dL. In some embodiments, for the purposes of the methods described herein, a subject has an elevated LDL cholesterol level when their non-HDL-C level is at least 190 mg/dL. In some embodiments, a subject has an elevated LDL cholesterol level when their non-HDL-C level is between about 190 and about 219 mg/dL. In other embodiments, a subject has elevated LDL cholesterol when their non-HDL-C level is at least 170 mg/dL, at least 180 mg/dL, at least 190 mg/dL, at least 200 mg/dL, or at least 210 mg/dL.

In some embodiments, a subject has an elevated triglyceride level when their triglyceride level is at least 175 mg/dL. In other embodiments, a subject has an elevated triglyceride level when their triglyceride level is at least 150 mg/dL, at least 160 mg/dL, at least 170 mg/dL, at least 180 mg/dL, at least 190 mg/dL, or at least 200 mg/dL.

In some embodiments, a subject has kidney disease when they have an estimated Glomerular Filtration Rate (eGFR) of less than about 60 mL/min/1.73 m$^2$. In other embodiments, a subject has kidney disease when they have an estimated Glomerular Filtration Rate of less than about 70, 65, 55, 50, or 45 mL/min/1.73 m$^2$. In some embodiments, chronic kidney disease is classified as meeting the kidney disease requirement (e.g., having less than a threshold eGFR level) for at least two months. In some embodiments, chronic kidney disease is classified as meeting the kidney disease requirement (e.g., having less than a threshold eGFR level) for at least three months. In some embodiments, e.g., where a particular statin pharmaceutical agent is contraindicated for use in a subject with kidney disease, chronic kidney disease is not used as a risk enhancing factor filter.

In some embodiments, a subject has an elevated C-Reactive Protein level when their C-Reactive Protein level is at least 2 mg/dL. In other embodiments, a subject has an elevated C-Reactive Protein level when their C-Reactive Protein level is at least 1 mg/dL, at least 1.5 mg/dL, at least 2.5 mg/dL, or at least 3 mg/dL.

In some embodiments, the presence of any coronary artery calcium constitutes a risk enhancing factor. In other embodiments, the presence of at least a threshold amount of coronary artery calcium constitutes a risk enhancing factor. For instance, in some embodiments, the threshold level is set at a preselected Agatston score, e.g., of at least 5, 10, 11, 20, 25, or more. In one embodiment, the threshold level is an Agatston score of at least 11. In some embodiments, a range of Agatston scores is used to identify a risk enhancing factor, e.g., where a score below the range does not constitute a risk enhancing factor and a score above the range fires a filter, preventing the subject from obtaining the statin pharmaceutical composition and recommending the subject consult a physician. For instance, in some embodiments, the range is from 1 to 400. In some embodiments, the range is from 1 to 100. In other embodiments, the range is from about 10 to about 400, or about 10 to about 100. The skilled artisan will know how to select an appropriate range for a particular statin composition and dosage.

In some embodiments, the subject has an elevated lipoprotein (a) level when their lipoprotein (a) level is at least 50 mg/dL (about 125 nmol/L). In other embodiments, an elevated lipoprotein (a) level is at least 40 mg/dL, at least 45 mg/dL, at least 55 mg/dL, or at least 60 mg/dL.

In some embodiments, the subject has an elevated apoB level when their apoB level is at least 130 mg/dL. In other embodiments, an elevated apoE level is at least 110 mg/dL, at least 120 mg/dL, at least 140 mg/dL, or at least 150 mg/dL.

In some embodiments, the subject has a low ankle-brachial index when their ankle-brachial index is less than 0.9. On other embodiments, a low ankle-brachial index is less than 1.1, less than 1.0, less than 0.8, or less than 0.7. In some embodiments, a range of ankle-brachial index is used to identify a risk enhancing factor, e.g., where a score above the range does not constitute a risk enhancing factor and a score below the range fires a filter, preventing the subject from obtaining the statin pharmaceutical composition and recommending the subject consult a physician. For instance, in some embodiments, the range is from about 0.4 to about 0.9. In other embodiments the range starts between about 0.3 and about 0.6 and ends between about 0.7 and ends about 1.1. The skilled artisan will know how to select an appropriate range for a particular statin composition and dosage.

Metabolic syndrome is a cluster of conditions that occur together, increasing the risk of heart disease, stroke, and type 2 diabetes. In some embodiments, a subject is deemed to have metabolic syndrome when the information set indicates the subject has at least two indicators of metabolic syndrome. In some embodiments, the subject is deemed to have metabolic syndrome when the information set indicates the subject has at least three indicators of metabolic syndrome. In some embodiments, the subject is deemed to have metabolic syndrome when the information set indicates the subject has at least four indicators of metabolic syndrome. In some embodiments, the indicators of metabolic syndrome include one or more of an elevated waist circumference, an elevated serum triglyceride level, a reduced HDL cholesterol level, an elevated blood pressure, and an elevated fasting glucose level. That is, in some embodiments, the subject is deemed to have metabolic syndrome when the information set indicates that the subject has a plurality (e.g., two, three, four, or more) of elevated waist circumference, an elevated serum triglyceride level, reduced HDL cholesterol level, elevated blood pressure, and an elevated fasting glucose level.

Generally, the threshold for a waist circumference that is an indicator of metabolic syndrome is determined differently for men and women. For example, in some embodiments, a waist circumference of at least 40 inches indicates that a man has a metabolic syndrome while a waist circumference of at least 35 inches indicates that a woman has a metabolic syndrome (e.g., where the predetermined threshold is set at 40 inches for men and 35 inches for women). In some embodiments, the predetermined threshold for men's waist circumference is at least 38 inches, at least 39 inches, at least 40 inches, at least 41 inches, or at least 42 inches. In some embodiments, the predetermined threshold for women's waist circumference is at least 33 inches, at least 34 inches, at least 35 inches, at least 36 inches, or at least 37 inches.

In some embodiments, an HDL cholesterol level of less than 40 mg/dL is an indicator that the subject has a metabolic syndrome. In other embodiments, an HDL cholesterol level of less than 50 mg/dL, less than 45 mg/dL, less than less than 40 mg/dL, less than 35 mg/dL, or less than 30 mg/dL, is an indication that the subject has a metabolic syndrome.

In some embodiments, a triglyceride level of greater than 150 mg/dL is an indicator that the subject has a metabolic syndrome. In other embodiments, a triglyceride level of greater than 125 mg/dL, greater than 150 mg/dL, greater than 175 mg/dL, or greater than 200 mg/dL, is an indicator that the subject has a metabolic syndrome.

In some embodiments, an HDL cholesterol level of less than 50 mg/dL is an indicator that the subject has a metabolic syndrome. In some embodiments, an HDL cholesterol level of less than 40 mg/dL is an indicator that the subject has a metabolic syndrome. In other embodiments, an HDL cholesterol level of less than 55 mg/dL, less than 45 mg/dL, or less than 35 mg/dL is an indicator that the subject has a metabolic syndrome. In some embodiments, the threshold for an HDL cholesterol level that is an indicator of metabolic syndrome is determined differently for men and women. For example, in some embodiments, an HDL cholesterol level of less than 40 mg/dL indicates that a man has a metabolic syndrome while an HDL cholesterol level of less than 50 mg/dL indicates that a woman has a metabolic syndrome. In some embodiments, the threshold for men's HDL cholesterol level is less than 50 mg/dL, less than 45 mg/dL, less than 35 mg/dL, or less than 30 mg/dL. In some embodiments, the threshold for women's HDL cholesterol level is less than 60 mg/dL, less than 55 mg/dL, less than 45 mg/dL, or less than 40 mg/dL.

In some embodiments, a subject's blood pressure is an indicator that the subject has metabolic disease when either the subject's systolic blood pressure or the subject's diastolic blood pressure is above a predetermined threshold. In some embodiments, the predetermined threshold for a systolic blood pressure is at least 130 mm Hg. In other embodiments, the predetermined threshold for a systolic threshold is at least 120 mm Hg, at least 125 mm Hg, at least 135 mm Hg, or at least 14 mmHg. In some embodiments, the predetermined threshold for a diastolic blood pressure is at least 85 mmHg. In other embodiments, the predetermined threshold for a diastolic blood pressure is at least 75 mm Hg, at least 80 mm Hg, at least 90 m Hg, or at least 95 Hg. Generally, if both of a subject's systolic and diastolic blood pressures satisfy a predetermined threshold, a single indicator of metabolic disease is counted. However, in other embodiments, each would be counted as a separate indicator.

In some embodiments, a fasting glucose level of at least 100 mg/dL is an indicator that the subject has a metabolic syndrome. In other embodiments, a fasting glucose level of greater than 80 mg/dL, greater than 90 mg/dL, greater than 110 mg/dL, or greater than 120 mg/dL, is an indicator that the subject has a metabolic syndrome.

Figure 8F:
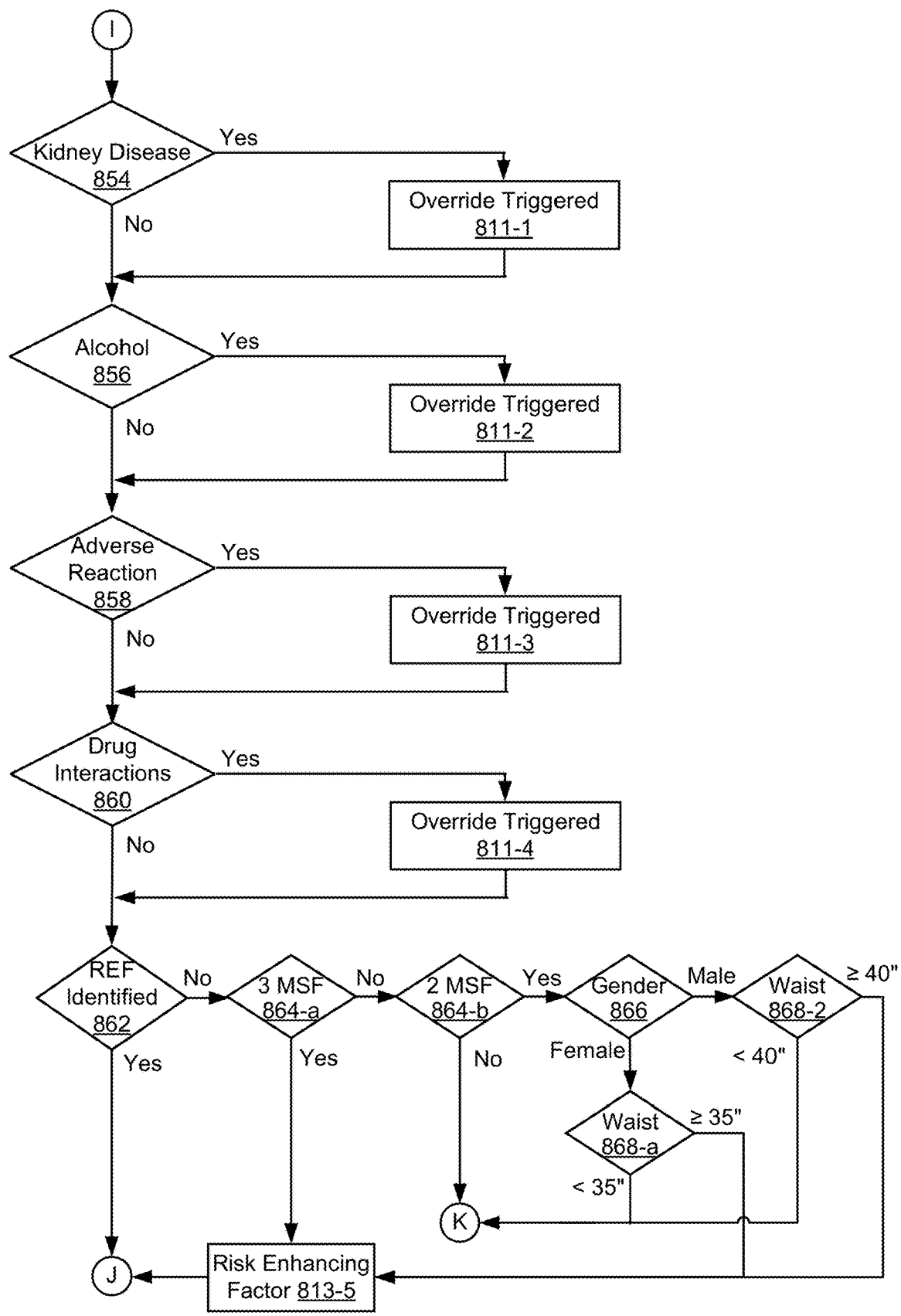
Figure 8G:
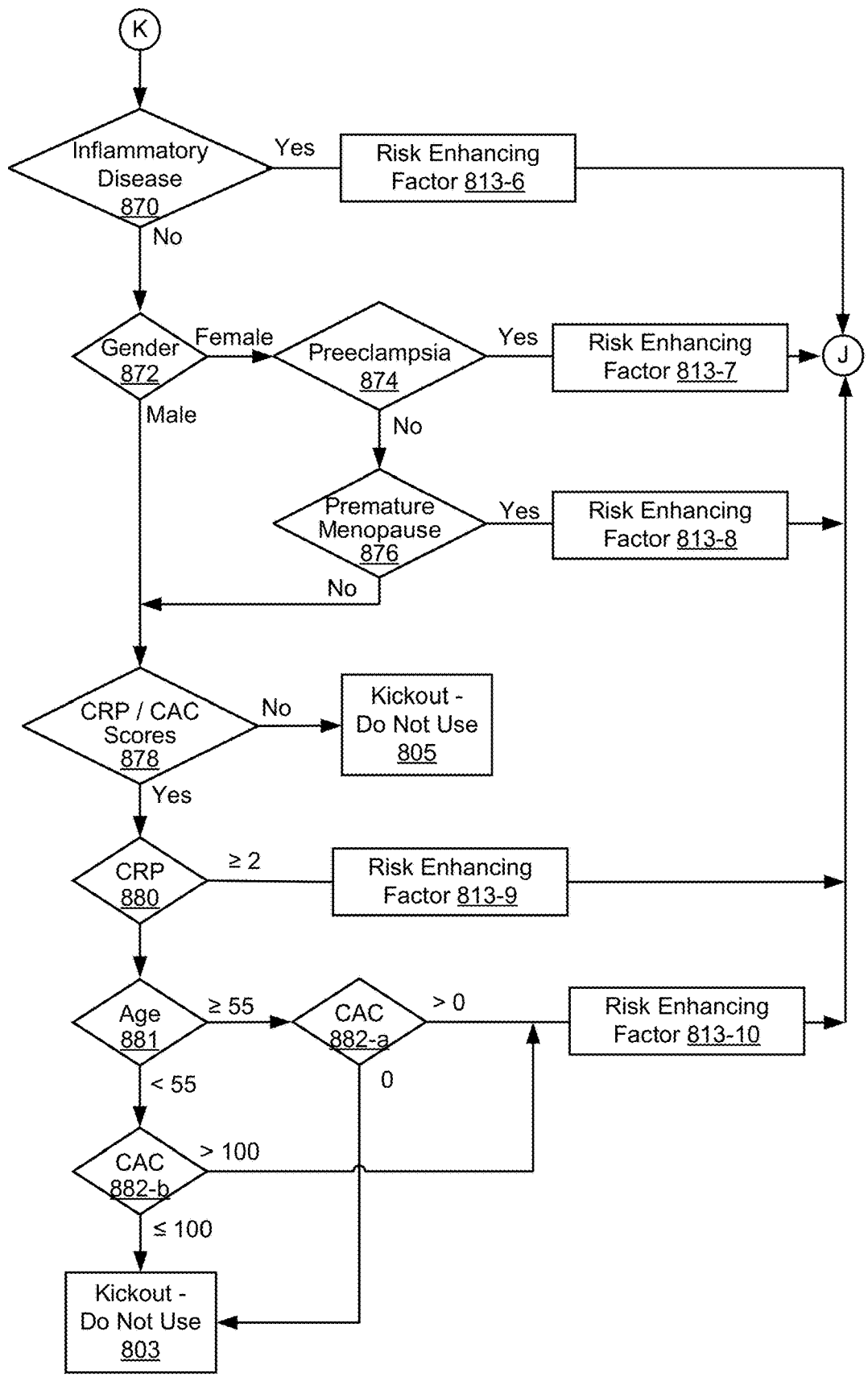
Figure 8I:
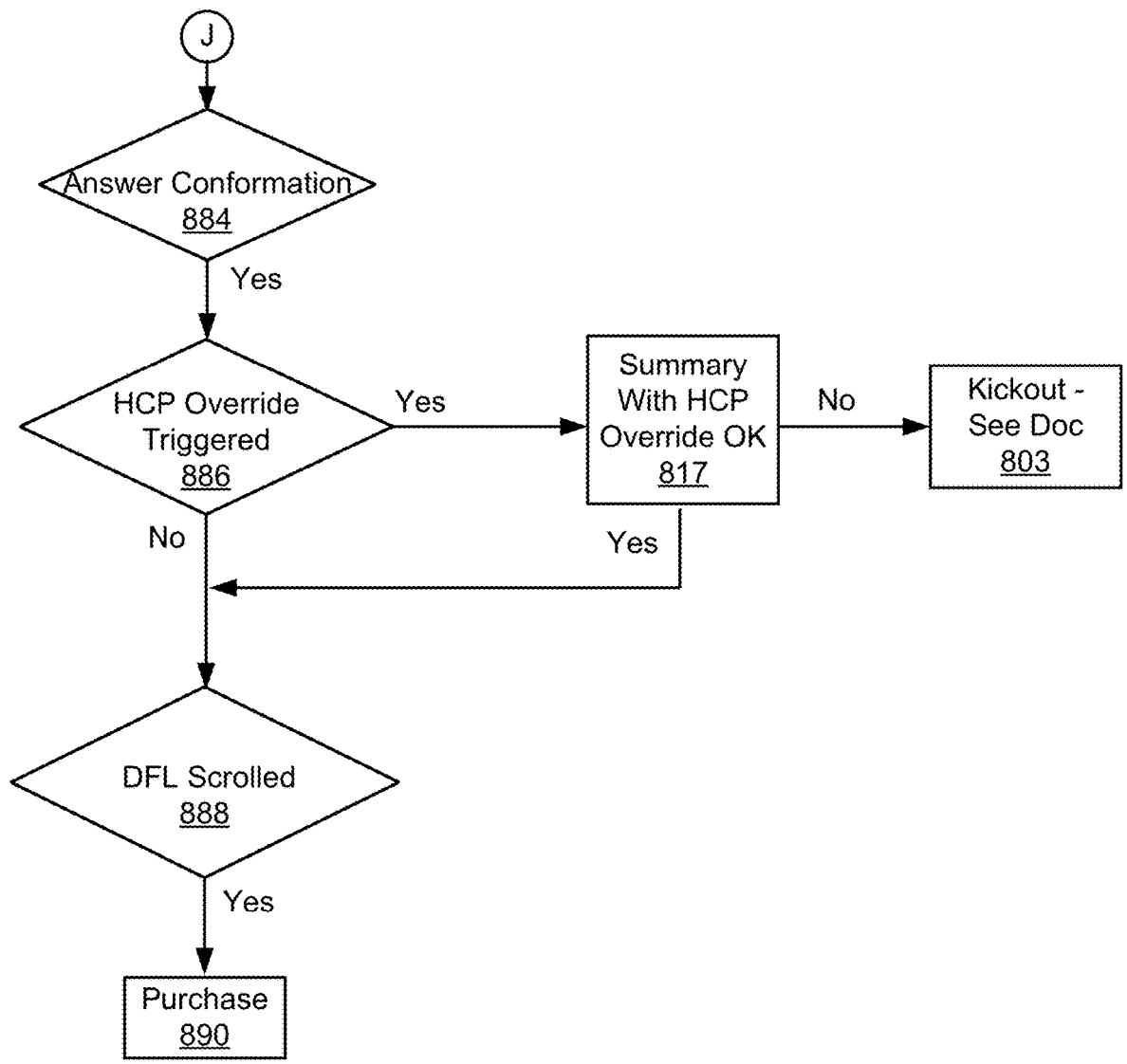

Referring to block 4134 of FIG. 4J, in some embodiments the method also includes using the algorithm to run all or a portion of the information set against a second plurality of assessment filters 220-1. When a respective filter in the second plurality of assessment filters 220-1 is fired, the subject is provided with a warning 226 corresponding to the respective filter (e.g., filter warning 228-4 corresponds to filter 222-4). In some embodiments, the warning 226 is provided as a next step, e.g., prior to applying the algorithm the information set or any subsequent filters, after the corresponding filter is fired. For example, with respect to FIG. 8F, in some embodiments, e.g., when the alcohol consumption filter is triggered at 856, the device would provide the subject with a warning prior to proceeding to the adverse reaction filter at 858, e.g., requiring the subject confirm the warning (e.g., confirming they have discussed their alcohol consumption status with a health care provider and the healthcare provider still recommends taking a statin pharmaceutical composition) prior to continuing. In some embodiments, the warning 226 is provided at a later time, e.g., after applying the information set to all subsequent filters, but prior to qualifying the subject for access to the statin pharmaceutical agent. For example, as illustrated in FIG. 8F, in some embodiments, e.g when the alcohol consumption filter is triggered at 856, the device would proceed to the adverse reaction filter at 858 prior to transmitting a warning to the subject, and then transmit all warnings corresponding to filters of the second plurality of filters 220-1, at 884 and/or 886, after the algorithm has applied the information set all subsequent filters.

Figure 6C:
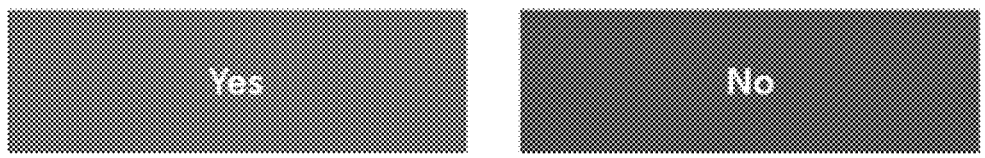

For example, in some embodiments, the device transmits a prompt to provide information about a possible risk factor for statin use (e.g., prompt 654 "Do you have a history of kidney disease?," as illustrated in FIG. 6C), receives a response to the prompt, and then applies an algorithm to the response provided by the subject (e.g., through a kidney disease filter as described below).

Figure 6D:
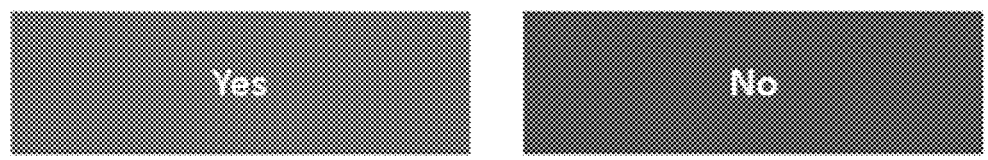

When the response indicates that a triggering condition has been met (e.g., the subject has a history of kidney disease), the filter is fired and the device transmits a warning associated with the filter to the subject. If the subject confirms the warning, the subject is still eligible to receive provision of the statin pharmaceutical agent. If the subject does not confirm the warning, the process is terminated without authorizing provision of the statin pharmaceutical composition to the subject. For example, FIG. 6D illustrates an example warning 656 provided to a subject who clicked "Yes" in response to prompt 654, asking whether they have discussed taking a statin with their doctor in view of their history of kidney disease. In some embodiments, the warning includes a message explaining the risk factor. For instance, warning 656 tells the subject that users with compromised kidney function may experience adverse effects when taking a statin.

Referring to blocks 4134-4152 of FIGS. 4J-4K, example assessment filters 222 in the second plurality of assessment filters 220 and example triggering conditions 224 that cause the corresponding assessment filters to fire are described.

TABLE 4

Example Filters of the Second Plurality of Assessment Filters

| Filter | Example Criteria |
|---|---|
| 1b | an alcohol consumption filter |
| 2b | a first adverse reaction filter |
| 3b | a moderate drug interaction filter |
| 4b | a second adverse reaction filter |
| 5b | a kidney disorder filter |

In some embodiments, the second plurality of assessment filters 220 includes some or all of the filters 222 listed in Table 4. For example, in some embodiments, the second plurality of assessment filters 220 includes 2, 3, 4, or all 5 of the filters listed in Table 4. In one embodiment, the second plurality of assessment filters includes at least filters 1b-3b as provided in Table 4. In some embodiments, e.g., where the particular statin pharmaceutical agent is primarily eliminated by renal excretion, the second plurality of assessment filters further includes a kidney disorder filter 5b. Thus, in some embodiments, the second plurality of assessment filters includes at least filters 1b-3b and 5b as provided in Table 4. In some embodiments, a second adverse drug reaction filter that is specific for adverse reactions against the particular statin compound being provided is implemented, e.g., in place of or in addition to the first adverse reaction filter which refers more generally to cholesterol-lowering medications. Accordingly, in some embodiments, the second plurality of assessment filters includes at least filters 1b, 3b and 4b as provided in Table 4.

Accordingly, it is contemplated that in some embodiments the second plurality of assessment filters includes any subset of filters 222 provided in Table 4. Likewise, in some embodiments the skilled artisan may know of other filters 222, not are provided in Table 4, which may be combined with any subset of the filters 222 provided in Table 4 to form the second plurality of assessment filters and corresponding information set used in the methods described herein. For brevity, all possible combinations of the assessment filters 222 provided in Table 4 are not specifically delineated here.

It is contemplated that, in some embodiments, any one or more of the filters provided in Table 4 will not be included in the second plurality of assessment filters. For example, in some embodiments, a characteristic associated with a portion of an information set will be informative when qualifying a subject for one particular statin pharmaceutical composition but not for another statin pharmaceutical composition. In some embodiments, one or more of the filters 222 provided in Table 4 is implemented as a first type filter (e.g., included in a first plurality of assessment filters), as described above, which automatically terminates the process without authorizing provision of the statin pharmaceutical composition when fired. For example, in some cases, the decision to implement one of the filters listed in Table 4 as a first type filter will be based on a consideration specific to a particular statin compound and/or dosage of the statin compound. Similarly, in other cases, the decision to implement one of the filters listed in Table 4 as a first type filter will be based on a change in health and/or regulatory guidelines.

Alcohol Consumption Filter

Referring to blocks 4136 and 4138, in some embodiments the second plurality of assessment filters 220 includes an alcohol consumption filter (e.g., alcohol consumption filter 222-1 in FIG. 3B and/or filter 1b in Table 4). The alcohol consumption filter is configured to be fired at least when the information set indicates that the alcohol consumption status of the subject fails to satisfy a ceiling alcohol consumption threshold. In some embodiments, the ceiling alcohol consumption threshold is an average daily consumption. For instance, in some embodiments, the ceiling alcohol consumption threshold is an average daily consumption of no more than two alcoholic drinks. That is, in such embodiments, the alcohol consumption filter is configured to be fired when the information set indicates the subject consumes three or more alcoholic drinks per day. In other embodiments, the ceiling alcohol consumption threshold is an average daily consumption of no more than one alcoholic drink, no more than three alcoholic drinks, or no more than four alcoholic drinks. In some embodiments, the alcohol consumption filter is also configured to be fired when the information set indicates the subject partakes in binge drinking more frequently than a threshold frequency, e.g., at least once a week, at least 2, 3, 4, 5, 6, or more times per month.

In some embodiments, e.g., when implemented as a first type of filter, when the alcohol consumption filter is fired, the subject is not permitted to obtain provision of the statin pharmaceutical composition pharmaceutical composition over-the-counter (e.g., the method is terminated without authorizing provision of the statin pharmaceutical composition to the subject). In some embodiments, e.g., when implemented as a second type of filter, when the alcohol consumption filter is fired, the subject is issued a warning associated with the filter, but is eligible to obtain provision of the statin pharmaceutical composition pharmaceutical composition over-the-counter upon satisfying the acknowledgement criteria associated with the warning (e.g., by confirming that they have discussed the risk factor with a medical professional and/or the medical professional has advised that the subject should take a statin pharmaceutical agent despite the risk factor).

First Adverse Reaction Filter

Referring to block 4140 of FIG. 4J, in some embodiments the second plurality of assessment filters 220-1 includes a first adverse reaction filter (e.g., first adverse reaction filter 222-2 in FIG. 3B and/or filter 2b in Table 4). The first adverse reaction filter is configured to be fired at least when the information set indicates that the subject has had an adverse reaction to a cholesterol-lowering drug.

In some embodiments, e.g., when implemented as a first type of filter, when the first adverse reaction filter is fired, the subject is not permitted to obtain provision of the statin pharmaceutical composition pharmaceutical composition over-the-counter (e.g., the method is terminated without authorizing provision of the statin pharmaceutical composition to the subject). In some embodiments, e.g., when implemented as a second type of filter, when the first adverse reaction filter is fired, the subject is issued a warning associated with the filter, but is eligible to obtain provision of the statin pharmaceutical composition pharmaceutical composition over-the-counter upon satisfying the acknowledgement criteria associated with the warning (e.g., by confirming that they have discussed the risk factor with a medical professional and/or the medical professional has advised that the subject should take a statin pharmaceutical agent despite the risk factor).

Moderate Drug Interaction Filter

Referring to block 4142 and 4144 of FIG. 4K, in some embodiments the second plurality of assessment filters 220-1 includes a moderate drug interaction filter (e.g., moderate drug interaction filter 222-3 in FIG. 3B and/or filter 3b in Table 4). The moderate drug interaction filter is configured to be fired at least when the information set indicates that the subject is taking one or more compositions that interacts with the statin pharmaceutical composition, e.g., a pharmacokinetic interaction and/or a pharmacodynamic interaction, but is not necessarily contraindicated for co-administration with the statin pharmaceutical composition. For example, a composition associated with a warning for co-administration with the statin pharmaceutical composition. Non-limiting examples of drugs that may be associated with warnings when co-administered with a statin pharmaceutical composition, e.g., based on the particular statin, include colchicine and an anti-viral protease inhibitor.

In some embodiments, e.g., when implemented as a second type of filter, when the moderate drug interaction filter is fired, the subject is issued a warning associated with the filter, but is eligible to obtain provision of the statin pharmaceutical composition pharmaceutical composition over-the-counter upon satisfying the acknowledgement criteria associated with the warning (e.g., by confirming that they have discussed the risk factor with a medical professional and/or the medical professional has advised that the subject should take a statin pharmaceutical agent despite the risk factor).

As will be appreciated, compositions that are contraindicated, or represent a risk factor, for co-administration with a statin pharmaceutical composition vary from one statin pharmaceutical composition to another statin pharmaceutical composition. The skilled artisan will know, for example, of one or more compositions that interact with one statin pharmaceutical composition but not another. Inclusion of a composition within the moderate drug interaction filter is dependent upon the identity and/or the dosage of the statin pharmaceutical composition being authorized for a provision of over-the-counter use.

As described above, in some embodiments, use a drug that interacts with a statin pharmaceutical composition in a more severe fashion, e.g., which is a contraindication, may trigger firing of a filter 216 in the first filter category class 214 (e.g., a severe drug interaction filter), rather than the moderate drug interaction filter 222 of the second plurality of assessment filters 220-1. For example, according to some embodiments, a particular composition is included in the severe drug interaction filter 216 (e.g., as a contraindication) for a first statin pharmaceutical composition, but included in a filter in the second plurality of assessment filters (e.g., as a risk factor) for a second statin pharmaceutical composition. A person skilled in the art will know whether to include a certain composition within the severe drug interaction filter 216-3 or as a separate filter 222 in the second plurality of assessment filters (e.g., a moderate drug interaction filter), based on the severity and risk of the drug interaction with the particular identity and dosage of the statin being authorized for provision of over-the-counter use.

Second Adverse Reaction Filter

Referring to block 4146 of FIG. 4K, in some embodiments the second plurality of assessment filters 220-1 includes a second adverse reaction filter (e.g., filter 4b in Table 4). The second adverse reaction filter is configured to be fired at least when the information set indicates that the subject has had an adverse reaction to the active ingredient of the statin pharmaceutical composition under consideration.

In some embodiments, e.g., when implemented as a first type of filter, when the second adverse reaction filter is fired, the subject is not permitted to obtain provision of the statin pharmaceutical composition pharmaceutical composition over-the-counter (e.g., the method is terminated without authorizing provision of the statin pharmaceutical composition to the subject). In some embodiments, e.g., when implemented as a second type of filter, when the second adverse reaction filter is fired, the subject is issued a warning associated with the filter, but is eligible to obtain provision of the statin pharmaceutical composition pharmaceutical composition over-the-counter upon satisfying the acknowledgement criteria associated with the warning (e.g., by confirming that they have discussed the risk factor with a medical professional and/or the medical professional has advised that the subject should take a statin pharmaceutical agent despite the risk factor).

Kidney Disorder Filter

Referring to blocks 4150 and 4152 of FIG. 4K, in some embodiments the second plurality of assessment filters includes a kidney disorder filter (e.g., filter 5b in Table 4). For instance, in some embodiments when the statin pharmaceutical composition includes rosuvastatin, atorvastatin, fluvastatin, and/or pitavastatin, the algorithm applies the kidney condition filter to the information set. The kidney disorder filter is configured to be fired at least when the information set indicates that the subject has had a kidney problem (e.g., has had kidney disease). In some embodiments, the kidney disorder filter is configured to be fired at least when the information set indicates that the subject has been diagnosed with kidney disease. In some embodiments, symptoms of a kidney problem capable of firing the kidney disorder filter include fatigue, a feeling of coldness, shortness of breath, a feeling of faintness, dizziness, weakness, a feeling of itchiness, and/or swelling of the hands and feet.

In some embodiments, e.g., when implemented as a first type of filter, when the kidney disorder filter is fired, the subject is not permitted to obtain provision of the statin pharmaceutical composition pharmaceutical composition over-the-counter (e.g., the method is terminated without authorizing provision of the statin pharmaceutical composition to the subject). In some embodiments, e.g., when implemented as a second type of filter, when the kidney disorder filter is fired, the subject is issued a warning associated with the filter, but is eligible to obtain provision of the statin pharmaceutical composition pharmaceutical composition over-the-counter upon satisfying the acknowledgement criteria associated with the warning (e.g., by confirming that they have discussed the risk factor with a medical professional and/or the medical professional has advised that the subject should take a statin pharmaceutical agent despite the risk factor).

The skilled artisan may know of other filters that could be implemented as second type filters. For example, in some embodiments, a South Asian decent filter could be implemented, e.g., when the statin compound under consideration is associated with an increased risk of adverse reactions in persons of South Asian descent. In some embodiments, South Asian descent refers to ancestry from a country on the Indian sub-continent, e.g., Indian, Afghani, Pakistani, or Bangladeshi descent, e.g., as opposed to ancestry from an Asian country not on the Indian sub-continent, e.g., Japanese, Pilipino, Chinese, or Korean descent.

Figure 7:
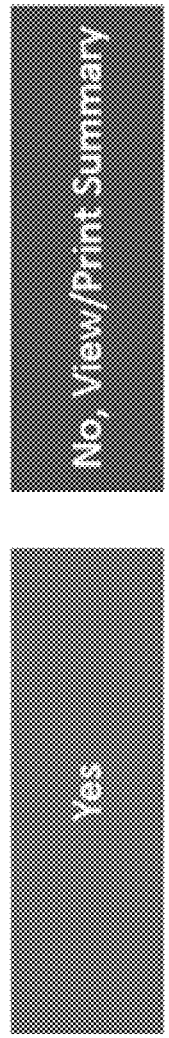
FIG. 7 illustrates feedback from a portion of an assessment survey, in accordance with various embodiments of the present disclosure.

Referring to block 4154 of FIG. 4L, in some embodiments the warning 226 corresponding to a respective filter 222 in the second plurality of assessment filters 220-1 includes a prompt for the subject to indicate whether they have discussed the risk factor underlying the respective filter in the second plurality of assessment filters that was fired with a health care practitioner (e.g., a licensed medical practitioner), e.g., and the health care practitioner indicated that the subject should take a statin pharmaceutical composition in view of the underlying risk factor. Accordingly, the algorithm obtains acknowledgement from the subject when the subject indicates that they have discussed the risk factor underlying the respective filter in the second plurality of assessment filters that was fired with a health care provider. For example, message 702 in FIG. 7 illustrates a warning that is generic to any fired filter of the second type. In some embodiments, the warning is specific to a particular filter (e.g., filter warning 656 in FIG. 6D), e.g., communicating to the user why the respective filter was fired.

In some embodiments, an acknowledgment from the user is verified by the health care practitioner (e.g., the method requires verification in order for authorization of the provision of the statin pharmaceutical composition), e.g., in order to verify an accuracy of the information set obtained. In some embodiments, e.g., when the acknowledgment is verified by the heath care practitioner, the subject is deemed a trusted subject, such that verification of future results is not required.

In some embodiments, the algorithm obtains acknowledgment from the subject for any warning 226 issued to the subject by any filter 222 in the second plurality of assessment filters. If a filter 216 in the first plurality of assessment filters fires, the subject is denied provision of the over-the-counter statin pharmaceutical composition.

Blocks 4156 through 4174. Referring to block 4156 of FIG. 4L, the algorithm proceeds to a fulfillment process when no filter 216 in the first plurality of assessment filters 214-1 has been fired and the subject has acknowledged each warning 226 associated with each filter 222 in the second plurality of assessment filters 220-1 that was fired. In some embodiments, the fulfillment process includes storing an indication in a user profile 234 of an initial order date and/or a destination for the statin pharmaceutical composition. The initial order date is utilized, for example, to verify at least a refill status of a provision of the statin pharmaceutical composition. The initial order date is also utilized, for example, to verify at least an elapsed period of time between an initial order and a future re-order (e.g., a provision of a re-assessment). Such verification is required in order to ensure that certain tests (e.g., blood pressure tests) are taken regularly.

The fulfillment process further includes communicating an over-the-counter drug facts label 230 for the statin pharmaceutical composition to the subject. In some embodiments, the drug facts label 230 is communicated to the subject in real-time, e.g., within the same user interface as used for the qualification assessment process.

In some embodiments, the over-the-counter drug facts label 230 specifies what the statin pharmaceutical composition is for (e.g., to lower cholesterol, to treat heart disease, etc.) and any risks associated with taking the statin pharmaceutical composition (e.g., drug-drug interactions, pharmacokinetic interactions, adverse reactions, etc.). For instance, in some embodiments, upon confirmation from the subject that the over the counter drug facts label 230 has been received and read, the subject is authorized for provision of a dosage of from 1 mg to 80 mg of statin pharmaceutical composition no more than once per day. In some embodiments, the subject is authorized for a provision of a dosage of from 2.5 mg to 15 mg of statin (e.g., rosuvastatin) no more than once per day (block 4160). In some embodiments, the subject is authorized for a provision of a dosage of 5 mg of statin (e.g., rosuvastatin) no more than once per day (block 4162). In some embodiments, the subject is authorized for a provision of a dosage of from 20 mg to 40 mg of statin (e.g., fluvastatin) no more than once per day (block 4164). In some embodiments, the subject is authorized for a provision of a dosage of from 10 mg to 40 mg of statin (e.g., atorvastatin) no more than once per day (block 4166). In some embodiments, the subject is authorized for a provision of a dosage of from 1 mg to 4 mg of statin (e.g., pitavastatin) no more than once per day (block 4168). In some embodiments, the subject is authorized for a provision of a dosage of from 10 mg to 40 mg of statin (e.g., lovastatin) no more than once per day (block 4170). In some embodiments, the subject is authorized for a provision of a dosage of from 10 mg to 40 mg of statin (e.g., pravastatin) no more than once per day (block 4172). In some embodiments, the subject is authorized for a provision of a dosage of from 5 mg to 20 mg of statin (e.g., simvastatin) no more than once per day (block 4174).

In some embodiments, the fulfillment process further includes authorizing provision of the statin pharmaceutical composition to the subject. The authorization occurs upon confirmation from the subject that the over-the-counter drug facts label 230 has been received and read by the subject. In some embodiments, this authorization includes a destination associated with the subject. In some embodiments, the destination associated with the subject is stored in the user profile 234. In some embodiments, the destination associated with the subject is a physical address including a street address, a Post Office box, a pharmacy associated with the subject, a health care provider associated with the subject, and/or one or more coordinates (e.g., longitude, latitude, elevation). In some embodiments, the provision of the statin pharmaceutical composition to the subject includes shipping the statin pharmaceutical composition to the physical address associated with the subject. In some embodiments, the provision of the statin pharmaceutical composition to the subject includes shipping the statin pharmaceutical composition to a pharmacy associated and/or a location associated with a health care provider of the subject and/or an office of a medical practitioner associated with the subject.

Referring to block 4176 of FIG. 4M, in some embodiments the method includes administering the statin pharmaceutical composition to the subject after authorization of the provision of the statin pharmaceutical composition. The administration will typically be performed by the subject themselves, just as it would be if the statin was provided by prescription.

FIG. 5 illustrates method 5000 for re-qualifying (5002) a human subject for an over-the-counter provision of a statin pharmaceutical composition for lowering cholesterol, e.g., thereby, treating and/or preventing heart disease, using a computer system such as a statin pharmaceutical composition OTC dispensing device 250. As illustrated in FIG. 2, the statin pharmaceutical composition OTC dispensing device (e.g., device 250) includes one or more processors (e.g., processor 274) and a memory (e.g., memory 192 and/or 290). The memory stores non-transitory instructions that, when executed by the one or more processors, perform a method.

Method 5000 involves to collecting relevant biographical and medical information about the subject, applying the collected information to an algorithm that applies the information against one or more filters of a first type and one or more filters of a second type, and providing access to a statin pharmaceutical composition when each of the filters is satisfied. The one or more filters of the first type terminate the process without re-qualifying the patient for access to an over-the-counter statin pharmaceutical agent when fired. The one or more filters of the second type trigger transmission of a warning to the subject when fired. The subject must confirm any transmitted warnings, which optionally include confirmation that certain conditions precedent have been met (such as having a discussion with a medical professional and receiving advice that the statin pharmaceutical composition is safe to take), before the subject is qualified to receive a reorder provision of the statin pharmaceutical agent.

In some embodiments the statin pharmaceutical composition includes rosuvastatin (CRESTOR®) as an active ingredient. In some embodiments, the statin pharmaceutical composition includes an active ingredient selected from the group consisting of atorvastatin (LIPITOR®), fluvastatin (LESCOL®, LESCOL XL®), lovastatin (ALTOPREV®), pitavastatin (LIVALO®), pravastatin (PRAVACHOL®), and simvastatin (ZOCOR®). These statin pharmaceutical compositions are described in Lee et al., 2007, "Comparison of Efficacy and Tolerability of Pitavastatin and Atorvastatin: an 8-Week, Multicenter, Randomized, Open-Label, Dose-Titration Study in Korean Patients with Hypercholesterolemia," Clin Ther. 2007; 29:2365-73; Bradford et al., 1990, "Expanded clinical evaluation of lovastatin (EXCEL) study design and patient characteristics of a double blind, placebo controlled study in patients with moderate hypercholesterolemia. American Journal of Cardiology 66: p. 44B-55B; Serruys et al., 2002, "Fluvastatin for Prevention of Cardiac Events Following Successful First Percutaneous Coronary Intervention: A Randomized Controlled Trial.," JAMA 287: p. 3215-3222; Sacks et al. 1996, "The effect of pravastatin on coronary events after myocardial infarction in patients with average cholesterol levels. Cholesterol and Recurrent Events Trial investigators," New England Journal of Medicine, 1996. 335(14): p. 001-9; Anonymous, 2002 "Heart Protection Study Collaborative Group, MRC/BHF Heart Protection Study of cholesterol lowering with simvastatin in 20,536 high-risk individuals: a randomised placebo-controlled trial," Lancet 360: p. 7-22; Jones et al., 2003, "Comparison of the efficacy and safety of rosuvastatin versus atorvastatin, simvastatin, and pravastatin across doses (STELLAR Trial)," Am J Cardiol. 92 (2): 152-60 each of which is hereby incorporated by reference. In some embodiments, the statin pharmaceutical composition comprises a statin and another lipid-lowering drug, such as Atorvastatin/Ezetimibe (LIPTRUZET®), Lovastatin+Niacin (ADVICOR®), Simvastatin/Ezetimibe (VYTORIN®), or Simvastatin/Niacin-ER (SIMCOR®). Further information regarding possible statin pharmaceutical compositions is provided above, e.g., with respect to method 4000, and is not repeated here for brevity.

Blocks 5000 through 5006. Referring to block 5002 of FIG. 5A, a goal of the present disclosure is to re-qualify subjects (e.g., a re-fulfillment process) for provision of an over-the-counter statin pharmaceutical composition to lower cholesterol, e.g., thereby, treating and/or preventing heart disease, using a computer system such as a statin pharmaceutical composition OTC dispensing device 250. As illustrated in FIG. 2, the statin pharmaceutical composition OTC dispensing device (e.g., device 250) includes one or more processors (e.g., processor 274) and a memory (e.g., memory 192 and/or 290). The memory stores non-transitory instructions that, when executed by the one or more processors, perform a method (e.g., method 5000 of FIG. 5). In some embodiments, the present disclosure provides a method for qualifying a subject for a re-order (e.g., a re-assessment) of a provision of a statin pharmaceutical composition. In some embodiments, the qualification for a re-order of the statin pharmaceutical composition follows an initial qualification (e.g., an assessment) of the subject, as described herein. In some embodiments, the qualification for a refill of the statin pharmaceutical composition follows issuance of a prescription to the subject for the statin pharmaceutical composition. For example, in some embodiments, a subject who is new to the qualification process is asked whether they previously received a prescription for the statin pharmaceutical composition. Accordingly, if the subject indicates that they have not previously received a prescription, the subject is directed to an initial qualification method (e.g., method 4000 of FIG. 4) and, if the subject indicates that they have previously received a prescription, the subject is directed to the re-fill qualification method, e.g., as described below.

In some embodiments, a re-fulfillment procedure is performed (e.g., re-qualifying a human subject for an over-the-counter provision of a statin pharmaceutical composition). The re-fulfillment procedure is responsive to receiving a re-order request from the subject for the statin pharmaceutical composition. In some embodiments, a prompt to initiate the re-fulfillment procedure is sent to a user device 102 associated with the subject after a predetermined amount of time associated with a duration of dosages previously delivered to the subject (e.g., the user is reminded to fulfill their order of the statin pharmaceutical composition just before, or just after, the user is scheduled to run out of a previously delivered provision.

In some embodiments, the statin pharmaceutical composition includes an active ingredient of atorvastatin, fluvastatin, lovastatin, pitavastatin, pravastatin, rosuvastatin, or simvastatin. In some embodiments, the lowering of cholesterol is to treat and/or prevent heart disease.

Referring to blocks 5008 and 5010 of FIG. 5A, in some embodiments the re-fulfillment procedure includes providing a re-assessment survey for obtaining an information set from the subject (e.g., a second information set). This information set is derived from corresponding re-assessment survey questions (e.g., the device 250 transmits one or more re-assessment survey questions to the user, prompting a response, and then receives a response (e.g., a portion of the information set) to the one or more re-assessment survey questions back from the subject). In some embodiments, the information set includes some or all of the characteristics listed in Table 5. For example, in some embodiments, the information set includes 1, 2, 3, 4, 5, 6, 7, or all 8 of the characteristic listed in Table 5. In one embodiment, the information set includes at least characteristics 1-6 as provided in Table 5. In one embodiment, the information set includes at least characteristics 2-6 as provided in Table 5. In one embodiments, the information set also includes the LCL cholesterol level of the subject. For example, in some embodiments, the information set includes at least characteristics 1-6 and 8, as provided in Table 5. Similarly, in some embodiments, the information set includes at least characteristics 2-6 and 8, as provided in Table 5. In some embodiments, the information set also includes a kidney function status of the subject. For example, in some embodiments, the information set includes at least characteristics 1-7, as provided in Table 5. Similarly, in some embodiments, the information set includes at least characteristics 2-7, as provided in Table 5. Similarly, in some embodiments, the information set includes at least characteristics 2-8, as provided in Table 5.

It will be appreciated that the survey questions 208, 212 and filters 216, 222 (e.g., second plurality of re-assessment filters 216-2 and second plurality of re-assessment filters 222-2) applied to the information set thereof may vary depending upon the statin pharmaceutical composition being distributed. This varying is due to differences in the contraindication profiles of the various the statin pharmaceutical compositions, e.g., due to different drug-drug interactions, routes of drug clearance, etc. of the different the statin pharmaceutical compositions. For example, co-administration of warfarin with a single oral dose of atorvastatin had no significant effect on the pharmacokinetics of atorvastatin. As such, in some embodiments, an assessment survey, or similarly a re-assessment survey, qualifying a subject for an OTC provision of simvastatin may ask whether the subject consumes warfarin, while a similar survey qualifying a subject for OTC use of rosuvastatin may not.

Referring to block 5010, and as further informed by the example workflow illustrated in FIG. 9, in some embodiments, the information set includes whether the subject has had a documented cardiac event since receiving their last provision of the statin pharmaceutical composition (e.g., responsive to a re-assessment survey question that is associated with and/or applied to (908) a cardiac event filter 216-12 in a first plurality of re-assessment filters 214-2), when the subject is female—whether the subject is pregnant or breastfeeding (e.g., responsive to a re-assessment survey question that is associated with and/or applied to (920) a pregnancy filter 216-14 in a first plurality of re-assessment filters 214-2), whether the subject is taking one or more compositions that interact with the statin pharmaceutical composition (e.g., responsive to a re-assessment survey question that is associated with and/or applied to either or both (922 and/or 936) a severe drug interaction filter 216-15 in a first plurality of re-assessment filters 214-2 and/or a moderate drug interaction filter 222-5 in a second plurality of re-assessment filters 220-2), whether the subject has experienced liver problems since receiving their last provision of the statin pharmaceutical composition (e.g., responsive to a re-assessment survey question that is associated with and/or applied to (924) a liver condition filter 216-16 in a first plurality of re-assessment filters 214-2), whether the subject has experienced a muscle irregularity since receiving their last provision of the statin pharmaceutical composition (e.g., responsive to a re-assessment survey question that is associated with and/or applied to (926) a muscle irregularity filter 216-17 in a first plurality of re-assessment filters 214-2), and an alcohol consumption status of the subject since receiving their last provision of the statin pharmaceutical composition (e.g., responsive to a re-assessment survey question that is associated with and/or applied to (934) an alcohol consumption filter 222-4 in a second plurality of re-assessment filters 220-2).

In some embodiments, the re-assessment survey includes questions that elicit responses providing some or all of the characteristics listed in Table 5. In some embodiments, the re-assessment survey includes questions corresponding to the information set required for the methods described herein. In other embodiments, the reassessment survey includes questions corresponding to only a subset of the information set required for the methods described herein. In such embodiments, one or more portions of the information set required for the methods described herein are acquired through other means (e.g., upon registration/subscription for a service associated with qualifying the subject for over-the-counter medication, from a healthcare provider, from a prior survey, from a database associated with a pharmacy, from an electronic health record associated with the subject, from the subject profile data store 232, etc.) For example, in some embodiments, the subject provides a personal medical identification associated with an insurer, a hospital, or other healthcare provider and information about the subject required for the methods described herein, e.g., one or more survey results, is acquired from a preexisting database associated with the personal medical identification (e.g., a recent LDL cholesterol level measurement determined for the subject).

TABLE 5

Example Medical Information Elicited from the Re-assessment Information Set

| Result | Example Characteristics |
|---|---|
| 1 | whether the subject has had a documented cardiac event since receiving their last provision of the statin pharmaceutical composition |
| 2 | when the subject is female - whether the subject is pregnant or breastfeeding |
| 3 | whether the subject is taking one or more compositions that interact with the statin pharmaceutical composition |
| 4 | whether the subject has experienced liver problems since receiving their last provision of the statin pharmaceutical composition |
| 5 | whether the subject has experienced muscle irregularity since receiving their last provision of the statin pharmaceutical composition |
| 6 | an alcohol consumption status of the subject since receiving their last provision of the statin pharmaceutical composition |
| 7 | whether the subject has developed kidney problems or experienced worsening of a previous kidney problem since receiving their last provision of the statin pharmaceutical composition |
| 8 | a LDL cholesterol level of the subject |

It is contemplated that, in some embodiments, any one or more of the survey questions provided in Table 5 will not be elicited by the re-assessment survey (e.g., will not be used for the re-assessment and/or will be obtained by other means). For example, in some embodiments, a characteristic associated with a particular survey question will be informative when qualifying a subject for one particular statin but not for another statin. For instance, a re-assessment survey question is queried for simvastatin qualifying re-assessment surveys but not for rosuvastatin qualifying re-assessment surveys (e.g., the assessment survey question is not relevant for rosuvastatin). The skilled artisan will recognize that different statin pharmaceutical compositions carry different risk and drug interaction profiles. Accordingly, survey information required for qualifying a subject for access to one statin pharmaceutical composition with a known adverse drug interaction may not be necessary for qualifying the same subject for access to a second statin pharmaceutical composition.

Accordingly, it is contemplated that the characteristics elicited by the re-assessment survey questions include any sub-set of the information set provided in Table 5. For brevity, all possible combinations of the characteristics provided in Table 5 are not specifically delineated here. However, the skilled artisan will easily be able to envision any particular subset of survey questions designed to elicit responses to any subset of characteristics provided in Table 5. Likewise, the skilled artisan may know of other survey questions, not provided in Table 5, that may be combined with any subset of the survey questions provided in Table 5 to form the re-assessment survey questions used in the methods described herein.

In some embodiments, the assessment survey and/or the re-assessment survey is conducted by transmitting a plurality of respective questions to the subject, e.g., some or all of the respective survey questions, and receiving answers to the plurality of respective survey questions before applying any of the answers to respective filters. For example, with reference to the workflow in FIG. 9, in some embodiments, the device transmits questions relating to all of the re-assessment filters of the first plurality of re-assessment filters, all of the re-assessment filters of the second plurality of re-assessment filters, or all of the re-assessment filters in the workflow (e.g., as a virtual re-assessment survey where all of the questions are displayed in a single user interface, or as a series of questions displayed in consecutive user interfaces). After receiving answers to all of the re-assessment survey questions, the device then applies an algorithm to run assessment information set against the re-assessment filters (e.g., sequentially or concurrently) to determine whether the subject is re-qualified to receive a provision of the statin pharmaceutical composition. In alternative embodiments, the device transmits questions relating to a subset of re-assessment filters of the first category class, e.g., for which it could not obtain answers to the questions from an electronic database associated with the subject such as electronic health record of the subject, and/or relating to a subset of re-assessment filters of the second category class, e.g., that it could not obtain answers to the questions from an electronic database associated with the subject (e.g., as a virtual re-assessment survey where such unanswered questions are displayed in a single user interface, or as a series of questions displayed in consecutive user interfaces). After receiving answers to all of the survey questions, the device then applies the answers to all of the filters (e.g., sequentially or concurrently) to determine whether the subject is re-qualified to receive provision of the statin pharmaceutical composition.

In some embodiments, the assessment survey and/or the re-assessment survey is conducted in a serial fashion, e.g., by transmitting a first question or a first group of survey questions (e.g., associated with a single respective filter) to the subject, receiving an answer to the single survey question or small group of survey questions, and applying an algorithm by running the answer or answers through a filter, prior to transmitting a second question or second group of questions to the subject. For example, with reference to the workflow in FIG. 9, in some embodiments the device transmits a first re-assessment question to the subject, relating to contraindicated drugs. After receiving the answer to the survey question, the device applies the algorithm to the answer by running (922) the answer through a severe drug interaction filter cardiac event filter. If the severe drug interaction filter is fired, the device terminates (909) the process, and optionally provides the user with a message relating to why they are being denied a provision of the statin pharmaceutical composition, a suggestion for following-up with a medical professional, and/or a suggestion to make a lifestyle change. In other embodiments, the assessment survey and/or the reassessment survey is completed prior to applying any of the answers to the corresponding algorithm.

Figure 9A:
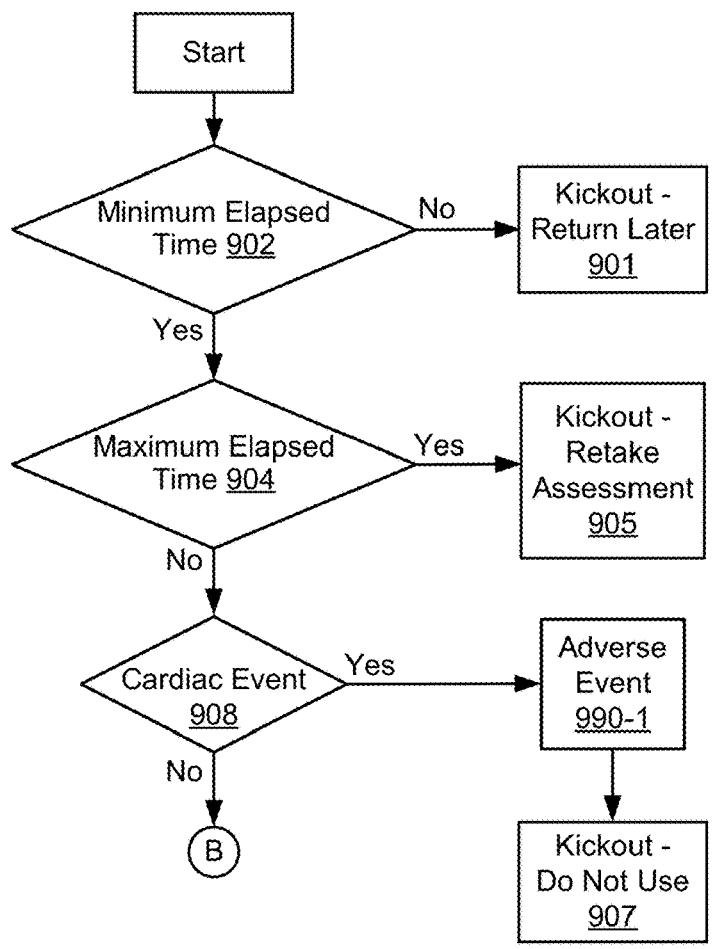
FIGS. 9A, 9B, 9C, and 9D collectively illustrate an example method for re-qualifying a subject for an over-the-counter provision of a statin pharmaceutical composition, in accordance with various embodiments of the present disclosure.
Figure 9B:
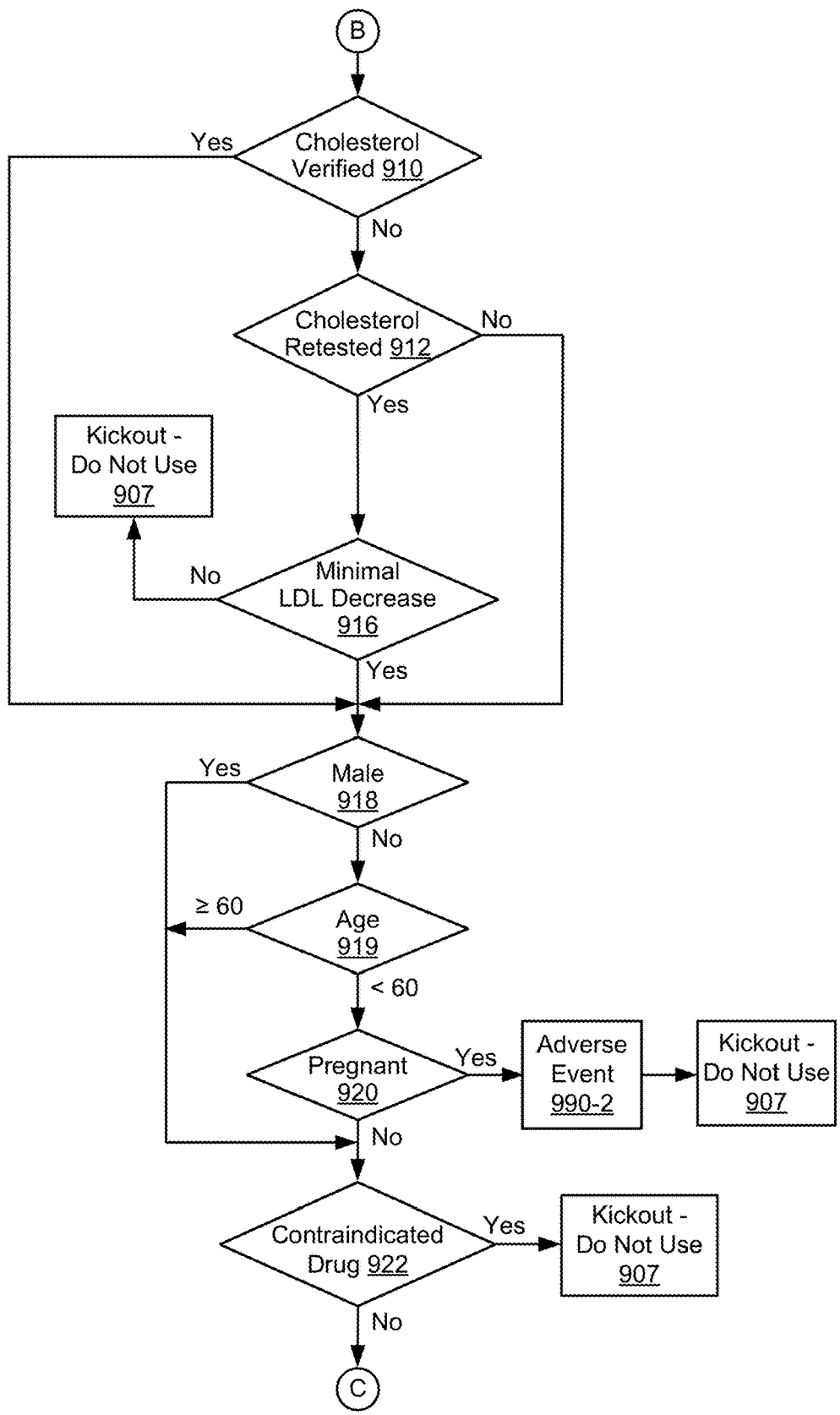
Figure 9C:
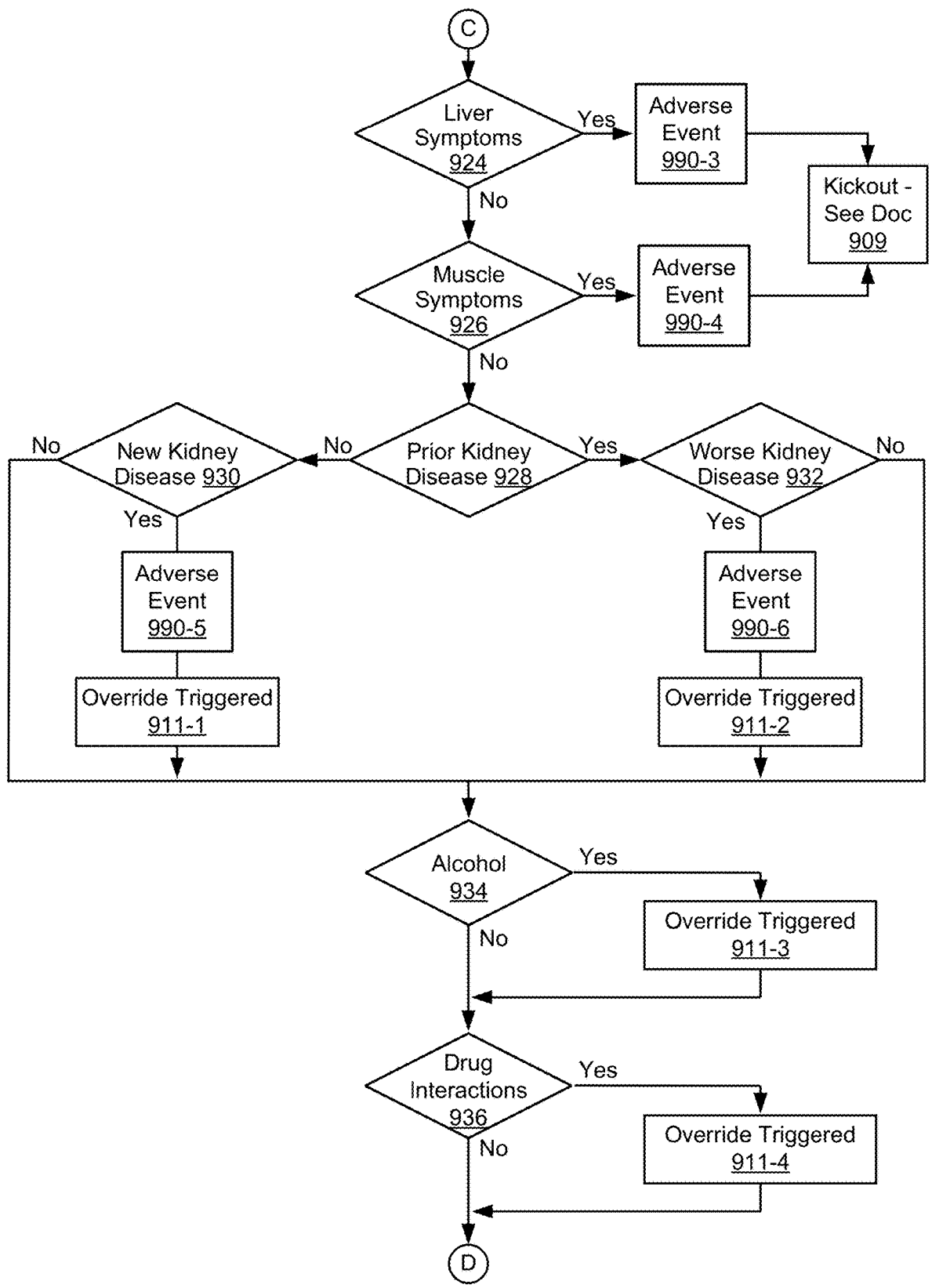
Figure 9D:
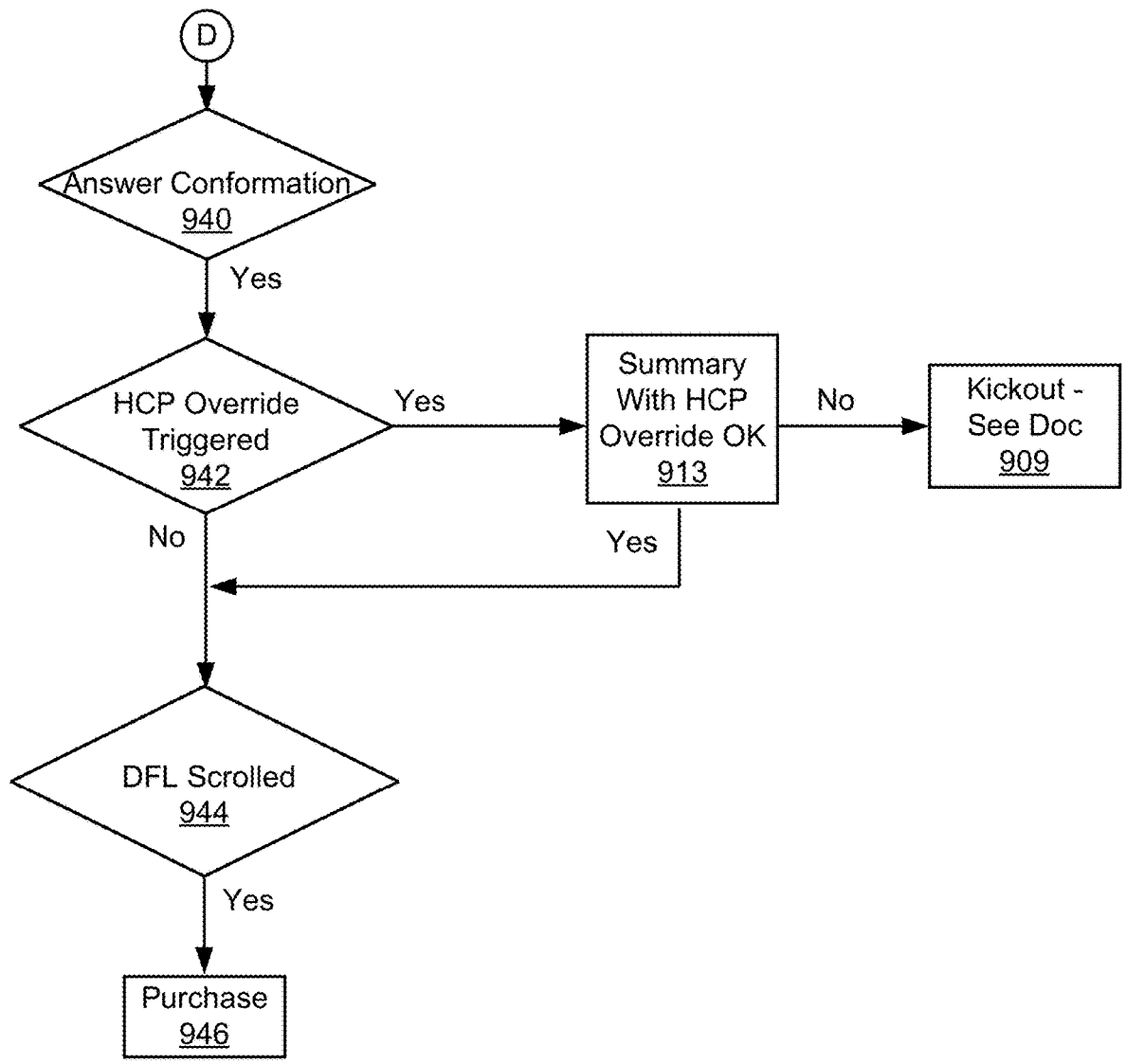

In some embodiments, one or more survey questions are not transmitted to a respective subject in accordance with a result to a previous survey question. For instance, in some embodiments the pregnancy filter is bypassed because the subject is male (e.g., as shown in FIG. 9B) and, consequently, one or more re-assessment survey questions related to pregnancy are bypassed (e.g., not transmitted to the user).

As described in detail below, the methods disclosed herein include steps of applying information collected about a subject to a plurality of filters designed to identify contraindications—which render the subject unsuitable for treatment with the statin pharmaceutical composition generally or at least in the self-care environment (i.e., without physician supervision)—and risk factors—which render administration of the statin pharmaceutical composition unnecessarily risky without further physician consultation. The contraindication and risk factors described herein are non-exhaustive, as the skilled artisan will know of other possible contraindications or risk factors for a particular statin pharmaceutical composition. Moreover, as medical research progresses, new contraindications or risk factors may be discovered. Or, similarly, the classification of existing contraindications or risk factors may change with additional medical research or consideration. For example, a factor considered to be a contraindication may be reclassified as a risk factor, over time, or vice-a-versa.

Further, a contraindication for one statin pharmaceutical composition may only be a risk factor, or neither, for a different statin pharmaceutical composition, for example, based on different mechanisms, interaction, pharmacokinetic, and/or pharmacodynamics properties of the respective active ingredients. Similarly, a factor that is a contraindication or risk factor for a particular statin pharmaceutical composition when administered at one dose, e.g., a high, moderate, or low dose, may be classified differently when administered at a different dose. For example, a contraindication for a statin pharmaceutical composition administered at a high dose may only be a risk factor, or neither, when administered at a low dose. This is particularly true when the risk factor, e.g., a drug interaction, changes the bioavailability of the active ingredient by a certain factor, such that the bioavailability following high dose administration, but not low dose administration, would increase beyond a safe threshold.

Referring to blocks 5012 and 5014 of FIG. 5A, the method includes applying an algorithm to the information set obtained through, at least in part, the re-assessment survey. The algorithm runs all or a portion of the information set against a first plurality of re-assessment filters 214-2. When a respective re-assessment filter in the first plurality of reassessment filters 214-2 is fired (e.g., when a re-assessment survey result indicates that a triggering condition 218 has been met), the subject is deemed not qualified for the statin pharmaceutical composition and the method is terminated without authorizing provision of the statin blocker pharmaceutical composition.

Referring to blocks 5016 through 5046 of FIGS. 5A and 5C, example re-assessment filters in the first plurality of re-assessment filters and example triggering conditions that cause the corresponding filters to fire are described below.

TABLE 6

Example Re-Assessment Filters of the First Plurality of Re-Assessment Filters

| Filter | Type |
|---|---|
| 1c | a cardiac event filter |
| 2c | a cholesterol status filter |
| 3c | a pregnancy filter |
| 4c | a severe drug interaction filter |
| 5c | a liver condition filter |
| 6c | a muscle irregularity filter |

In some embodiments, the first plurality of re-assessment filters includes some or all of the filters listed in Table 6. For example, in some embodiments, the first plurality of re-assessment filters includes 2, 3, 4, 5, or all 6 of the filters listed in Table 6. In some embodiments, the first plurality of re-assessment filters includes at least filters 1c, 3c, 4c, and 6c. In some embodiments, the first plurality of re-assessment filters includes at least filters 1c-4c and 6c. In some embodiments, the first plurality of re-assessment filters includes at least filters 1c and 3c-6c. In some embodiments, the first plurality of re-assessment filters includes at least filters 1c-6c.

Accordingly, it is contemplated that in some embodiments the first plurality of re-assessment filters includes any subset of filters provided in Table 6. Likewise, in some embodiments the skilled artisan may know of other filters, not provided in Table 6, which may be combined with any subset of the filters provided in Table 6 to form the first plurality of re-assessment filters and corresponding information set used in the methods described herein. For brevity, all possible combinations of the re-assessment filters provided in Table 6 are not specifically delineated here.

It is contemplated that, in some embodiments, any one or more of the re-assessment filters provided in Table 6 will not be included in the first plurality of re-assessment filters 214-2. For example, in some embodiments, a characteristic associated with a particular survey result will be informative when qualifying a subject for one particular statin pharmaceutical composition but not for another statin pharmaceutical composition. In some embodiments, one or more of the filters provided in Table 6 is implemented as a second type filter (e.g., included in a second plurality of re-assessment filters), as described below, which generates a warning to the user and/or requires the user confirm they have discussed an underlying risk triggering the filter with a medical professional, e.g., instead of automatically terminating the process without authorizing provision of the statin pharmaceutical composition. For example, in some cases, the decision to implement one of the filters listed in Table 6 as a second type filter will be based on a consideration specific to a particular statin compound and/or dosage of the statin compound. Similarly, in other cases, the decision to implement one of the filters listed in Table 6 as a second type filter will be based on a change in health and/or regulatory guidelines.

In some embodiments, the device is configured to conditionally bypass one or more of the filters in the first plurality of re-assessment filters. For example, as illustrated in example implementation 900, when the device determines the subject is a male (e.g., as illustrated in step 918 in FIG. 9B) the pregnancy filter applied at step 920 is bypassed because it is not possible for the subject to become pregnant.

Cardiac Event Filter

Referring to block 5016 and 5018 of FIG. 5A, in some embodiments the first plurality of re-assessment filters 214-2 includes a cardiac event filter 216-12. In some embodiments, the cardiac event filter 216-12 is as described above in relation to the cardiac event filter 216-4. In some embodiments, the cardiac event filter is configured to be fired at least when the information set indicates that the subject has had a documented cardiac event since receiving their last provision of the statin pharmaceutical composition. In some embodiments, the cardiac event filter is fired when the information set indicates the subject had a heart attack, had a stroke, has undergone a heart procedure, or has developed peripheral artery disease since receiving their last provision of the statin pharmaceutical composition. Examples of heart procedures that, in some embodiments, may fire the cardiac event filter include open-heart surgery, coronary artery bypass surgery, heart valve replacement and/or repair, surgery to treat heart arrhythmia, aneurysm repair surgery, coronary revascularization surgery, carotid endarterectomy, heart transplant, and the like.

In some embodiments, e.g., when implemented as a first type of filter, when the cardiac event filter is fired, the subject is not permitted to obtain provision of the statin pharmaceutical composition pharmaceutical composition over-the-counter (e.g., the method is terminated without authorizing provision of the statin pharmaceutical composition to the subject). In some embodiments, e.g., when implemented as a second type of filter, when the cardiac event filter is fired, the subject is issued a warning associated with the filter, but is eligible to obtain provision of the statin pharmaceutical composition pharmaceutical composition over-the-counter upon satisfying the acknowledgement criteria associated with the warning (e.g., by confirming that they have discussed the risk factor with a medical professional and/or the medical professional has advised that the subject should take a statin pharmaceutical agent despite the risk factor).

Cholesterol Status Filter

Referring to blocks 5020 through 5026 of FIG. 5B, in some embodiments the first plurality of re-assessment filters 214-2 includes a cholesterol status filter 216-13. In some embodiments, the cholesterol status filter 216-13 is configured to be fired at least when the information set indicates that a cholesterol level of the subject has not been reduced by at least a threshold amount since receiving their first dosage of the statin pharmaceutical agent. In some embodiments, the cholesterol level is an LDL cholesterol level. In some embodiments, the threshold amount is 10%. In other embodiments, the threshold amount is about 1%, 2%, 3%, 4%, 5%, 6%, 7%, 8%, 9%, 10%, 15%, 20%, 25%, or more. In some embodiments, the threshold amount is variable, depending upon the starting cholesterol level of the subject. For instance, in some embodiments, the threshold amount of cholesterol reduction is set higher for subjects starting with a significantly elevated cholesterol level and lower for subjects starting with a mildly elevated cholesterol level. Generally, the subject is prompted to input their last cholesterol level (e.g., last LDL cholesterol level) and the system will compare that level to a previous cholesterol level, e.g., stored in subject profile data store 232.

In some embodiments, the cholesterol status filter is bypassed under certain conditions. For example, as illustrated in example implementation 900, when the device determines that a reduction in the subject's cholesterol level was previously verified (910), the cholesterol status filter implemented at step 912 is bypassed. Similarly, as also illustrated in example implementation 900, when the device determines that the subject has not retested their cholesterol levels since receiving their first provision of the statin pharmaceutical agent, the cholesterol status filter implemented at step 912 is bypassed. However, in some embodiments, if the device determines that the subject has not retested their cholesterol levels since receiving their first provision of the statin pharmaceutical agent, the device will prompt the subject to re-test their cholesterol level, particularly when a significant period of time has passed since receiving their first provision of the statin pharmaceutical agent.

In some embodiments, e.g., when implemented as a first type of filter, when the cholesterol status filter is fired, the subject is not permitted to obtain provision of the statin pharmaceutical composition pharmaceutical composition over-the-counter (e.g., the method is terminated without authorizing provision of the statin pharmaceutical composition to the subject). In some embodiments, e.g., when implemented as a second type of filter, when the cholesterol status filter is fired, the subject is issued a warning associated with the filter, but is eligible to obtain provision of the statin pharmaceutical composition pharmaceutical composition over-the-counter upon satisfying the acknowledgement criteria associated with the warning (e.g., by confirming that they have discussed the risk factor with a medical professional and/or the medical professional has advised that the subject should take a statin pharmaceutical agent despite the risk factor).

Pregnancy Filter

Referring to block 5028 of FIG. 5B, in some embodiments the first plurality of re-assessment filters 214-2 includes a pregnancy filter 216-14. In some embodiments, the pregnancy filter 214-14 is as described above in relation to the pregnancy assessment filter 216-2. In some embodiments, the pregnancy filter 216-14 is configured to be fired at least when the information set indicates that the subject is pregnant or the subject is breastfeeding. In some embodiments, the pregnancy filter 216-14 is also configured to be fired when the information set indicates that the subject is planning on becoming pregnant. In some embodiments, the pregnancy filter is only applied when the information set indicates that the subject is female, e.g., the pregnancy filter is bypassed when the subject is male (e.g., as illustrated at steps 918-922 of workflow 900 in FIG. 9B).

In some embodiments, e.g., when implemented as a first type of filter, when the pregnancy filter is fired, the subject is not permitted to obtain provision of the statin pharmaceutical composition pharmaceutical composition over-the-counter (e.g., the method is terminated without authorizing provision of the statin pharmaceutical composition to the subject). In some embodiments, e.g., when implemented as a second type of filter, when the pregnancy filter is fired, the subject is issued a warning associated with the filter, but is eligible to obtain provision of the statin pharmaceutical composition pharmaceutical composition over-the-counter upon satisfying the acknowledgement criteria associated with the warning (e.g., by confirming that they have discussed the risk factor with a medical professional and/or the medical professional has advised that the subject should take a statin pharmaceutical agent despite the risk factor).

Severe Drug Interaction Filter

Referring to block 5030 through 5042 of FIGS. 5B and 5C, in some embodiments, the first plurality of re-assessment filters includes a severe drug interaction filter 216-15. In some embodiments, the severe drug interaction filter 216-15 is as described above in relation to the severe drug interaction filter 226-3. In some embodiments, the severe drug interaction filter 216-15 is configured to be fired at least when the information set indicates that the subject is taking (e.g, has started taking) one or more compositions that interact with the statin pharmaceutical composition e.g., a pharmacokinetic interaction and/or a pharmacodynamic interaction, and is contraindicated for co-administration with the statin pharmaceutical composition. Non-limiting examples of drugs that may be contraindicated for co-administration with a statin pharmaceutical composition, e.g., based on the particular statin, include cyclosporine, an anti-viral protease inhibitor, warfarin, a strong CYP3A4 inhibitor, and another cholesterol lowering medication.

As previously described, these interactions can be pharmacodynamic drug-drug interactions or pharmacokinetic drug-drug interactions. Typically, the interactions (e.g., triggering conditions 224) that are capable of firing the severe drug interaction filter 216-15 are the same as the interactions that are capable of firing the severe drug interaction filter 216-3 assuming that statin pharmaceutical composition is the same between the fulfillment process and the re-fulfillment process.

In some embodiments, e.g., when implemented as a first type of filter, when the severe drug interaction filter is fired, the subject is not permitted to obtain provision of the statin pharmaceutical composition pharmaceutical composition over-the-counter (e.g., the method is terminated without authorizing re-provision of the statin pharmaceutical composition to the subject).

In some embodiments, e.g., when the statin pharmaceutical composition includes atorvastatin, fluvastatin, lovastatin, or pitavastatin as an active ingredient, the severe drug interaction filter is configured to be fired when the information set indicates that the subject is taking cyclosporine.

In some embodiments, e.g., when the statin pharmaceutical composition includes fluvastatin, lovastatin, or pravastatin as an active ingredient, the severe drug interaction filter is configured to be fired when the information set indicates the subject is already taking a cholesterol-lowering medication or a triglyceride-lowering medication.

In some embodiments, e.g., when the statin pharmaceutical composition includes lovastatin, pitavastatin, or simvastatin as an active ingredient, the severe drug interaction filter is configured to be fired when the information set indicates the subject is taking an anti-viral protease inhibitor.

In some embodiments, e.g., when the statin pharmaceutical composition includes fluvastatin as an active ingredient, the severe drug interaction filter is configured to be fired when the information indicates the subject is taking warfarin.

In some embodiments, e.g., when the statin pharmaceutical composition includes lovastatin or simvastatin as an active ingredient, the severe drug interaction filter is configured to be filed when the information set indicates the subject is taking a strong CYP3A4 inhibitor.

In some embodiments, e.g., when the statin pharmaceutical composition includes rosuvastatin as an active ingredient, the severe drug interaction filter is configured to be fired when the information set indicates the subject is taking cyclosporine, a cholesterol-lowering medication, a triglyceride-lowering medication, or warfarin.

As will be appreciated, compositions that are contraindicated, or represent a risk factor, for co-administration with a statin pharmaceutical composition vary from one statin pharmaceutical composition to another statin pharmaceutical composition. The skilled artisan will know, for example, of one or more compositions that interact with one statin pharmaceutical composition but not another. Inclusion of a composition within the severe drug interaction filter is dependent upon the identity and/or the dosage of the statin pharmaceutical composition being authorized for a provision of over-the-counter use.

As described further below, in some embodiments, use a drug that interacts with a statin pharmaceutical composition in a less severe fashion, e.g., which is a risk factor rather than a contraindication, is sufficient to trigger firing of a filter in the second filter category class (e.g., a moderate drug interaction filter), rather than the severe drug interaction filter of the first plurality of re-assessment filters. For example, according to some embodiments, a particular composition is included in the severe drug interaction filter (e.g., as a contraindication) for a first statin pharmaceutical composition, but included in a filter in the second plurality of re-assessment filters (e.g., as a risk factor) for a second statin pharmaceutical composition. A person skilled in the art will know whether to include a certain composition within the severe drug interaction filter or as a separate filter in the second plurality of re-assessment filters (e.g., a moderate drug interaction filter), based on the severity and risk of the drug interaction with the particular identity and dosage of the statin being authorized for provision of over-the-counter use.

Liver Condition Filter

Referring to block 5044 of FIG. 5C, in some embodiments the first plurality of re-assessment filters includes a liver condition filter 216-16. In some embodiments, the liver condition filter 214-16 is as described above in relation to the liver condition filter 216-11. In some embodiments, the liver condition filter 216-16 is configured to be fired at least when the information set indicates that the subject has developed or been newly diagnosed with a liver condition since receiving their last provision of the statin pharmaceutical composition. In some embodiments, a new liver condition is identified based on new symptoms provided in the information set, e.g., inflammation of the liver, fibrosis, cirrhosis, end-stage liver disease (ESLD), cancer of the liver, and/or liver failure.

In some embodiments, e.g., when implemented as a first type of filter, when the liver condition filter is fired, the subject is not permitted to obtain provision of the statin pharmaceutical composition pharmaceutical composition over-the-counter (e.g., the method is terminated without authorizing re-provision of the statin pharmaceutical composition to the subject). In some embodiments, e.g., when implemented as a second type of filter, when the liver condition filter is fired, the subject is issued a warning associated with the filter, but is eligible to obtain re-provision of the statin pharmaceutical composition pharmaceutical composition over-the-counter upon satisfying the acknowledgement criteria associated with the warning (e.g., by confirming that they have discussed the risk factor with a medical professional and/or the medical professional has advised that the subject should take a statin pharmaceutical agent despite the risk factor).

Muscle Irregularity Filter

Referring to block 5046 of FIG. 5C, in some embodiments the first plurality of re-assessment filters includes a muscle irregularity filter 216-16. In some embodiments, the muscle irregularly filter 216-17 is configured to be fired at least when the information set indicates that the subject has experienced unexplained muscle pain and/or weakness since receiving their last provision of the statin pharmaceutical composition.

In some embodiments, e.g., when implemented as a first type of filter, when the muscle irregularity filter is fired, the subject is not permitted to obtain provision of the statin pharmaceutical composition pharmaceutical composition over-the-counter (e.g., the method is terminated without authorizing re-provision of the statin pharmaceutical composition to the subject). In some embodiments, e.g., when implemented as a second type of filter, when the muscle irregularity filter is fired, the subject is issued a warning associated with the filter, but is eligible to obtain re-provision of the statin pharmaceutical composition pharmaceutical composition over-the-counter upon satisfying the acknowledgement criteria associated with the warning (e.g., by confirming that they have discussed the risk factor with a medical professional and/or the medical professional has advised that the subject should take a statin pharmaceutical agent despite the risk factor).

Referring to block 5048 of FIG. 5D, in some embodiments the method also includes using the algorithm to run all or a portion of the information set against a second plurality of re-assessment filters 220-2. When a respective filter 222 in the second plurality of re-assessment filters 220-2 is fired, the subject is provided with a warning corresponding to the respective filter. In some embodiments, the warning is provided as a next step, e.g., prior to applying the information set to any subsequent filters, after the corresponding filter is fired. For example, with respect to FIGS. 9A and 9B, in some embodiments, the device would provide the subject with a warning prior to proceeding to the proceeding filter, e.g., requiring the subject confirm they have discussed the warning with a health care provider and the healthcare provider still recommends taking a statin pharmaceutical composition. In some embodiments, the warning is provided after applying the information set to all subsequent filters. Further details on possible implementations of these second type filters is described above with respect to the assessment workflow, and is not repeated here for brevity.

Referring to FIG. 5, example re-assessment filters 222 in the second plurality of assessment filters 220 and example triggering conditions 224 that cause the corresponding re-assessment filters to fire are described.

TABLE 7

Example Second Plurality of Re-Assessment Filters

| Filter | Exemplary Criteria |
| --- | --- |
| 1d | an alcohol consumption filter |
| 2d | a moderate drug interaction filter |
| 3d | a kidney disorder filter |

In some embodiments, the second plurality of re-assessment filters 220 includes some or all of the filters 222 listed in Table 7. For example, in some embodiments, the second plurality of re-assessment filters 220 includes 1, 2, or all 3 of the filters listed in Table 4. In some embodiment, the second plurality of assessment filters includes at least filter 1d. In some embodiments, the second plurality of assessment filters includes at least filter 2d. In some embodiments, the second plurality of assessment filters includes at least filter 3d. In some embodiments, the second plurality of assessment filters includes at least filters 1d and 2d. In some embodiments, the second plurality of assessment filters includes at least filters 1d and 3d. In some embodiments, the second plurality of assessment filters includes at least filters 2d and 3d. In some embodiments, the second plurality of assessment filters includes at least filters 1d-3d.

Accordingly, it is contemplated that in some embodiments the second plurality of re-assessment filters includes any sub-set of filters provided in Table 7. Likewise, in some embodiments the skilled artisan may know of other filters, not provided in Table 7, which may be combined with any subset of the filters provided in Table 7 to form the second plurality of re-assessment filters and corresponding information set used in the methods described herein.

It is contemplated that, in some embodiments, any one or more of the re-assessment filters provided in Table 7 will not be included in the second plurality of re-assessment filters. For example, in some embodiments, a characteristic associated with a particular survey result will be informative when qualifying a subject for one particular statin pharmaceutical composition but not for another statin pharmaceutical composition. In some embodiments, one or more of the filters provided in Table 7 is implemented as a first type filter (e.g., included in a first plurality of re-assessment filters), as described above, which automatically terminates the process without authorizing provision of the statin pharmaceutical composition when fired. For example, in some cases, the decision to implement one of the filters listed in Table 7 as a first type filter will be based on a consideration specific to a particular statin compound and/or dosage of the statin compound. Similarly, in other cases, the decision to implement one of the filters listed in Table 7 as a first type filter will be based on a change in health and/or regulatory guidelines.

Alcohol Consumption Filter

Referring to block 5050 of FIG. 5D, in some embodiments the second plurality of re-assessment filters 220-2 includes an alcohol consumption filter 222-5 (e.g., filter 1d in Table 7). In some embodiments, the alcohol consumption filter 222-5 is as described above in relation to the alcohol consumption filter 222-1. The alcohol consumption filter is configured to be fired at least when the information set indicates that the alcohol consumption status of the subject fails to satisfy a ceiling alcohol consumption threshold. In some embodiments, the ceiling alcohol consumption threshold is an average daily consumption. For instance, in some embodiments, the ceiling alcohol consumption threshold is an average daily consumption of no more than two alcoholic drinks. That is, in such embodiments, the alcohol consumption filter is configured to be fired when the information set indicates the subject consumes three or more alcoholic drinks per day. In other embodiments, the ceiling alcohol consumption threshold is an average daily consumption of no more than one alcoholic drink, no more than three alcoholic drinks, or no more than four alcoholic drinks. In some embodiments, the alcohol consumption filter is also configured to be fired when the information set indicates the subject partakes in binge drinking more frequently than a threshold frequency, e.g., at least once a week, at least 2, 3, 4, 5, 6, or more times per month.

In some embodiments, e.g., when implemented as a first type of filter, when the alcohol consumption filter is fired, the subject is not permitted to obtain re-provision of the statin pharmaceutical composition pharmaceutical composition over-the-counter (e.g., the method is terminated without authorizing provision of the statin pharmaceutical composition to the subject). In some embodiments, e.g., when implemented as a second type of filter, when the alcohol consumption filter is fired, the subject is issued a warning associated with the filter, but is eligible to obtain re-provision of the statin pharmaceutical composition pharmaceutical composition over-the-counter upon satisfying the acknowledgement criteria associated with the warning (e.g., by confirming that they have discussed the risk factor with a medical professional and/or the medical professional has advised that the subject should take a statin pharmaceutical agent despite the risk factor).

Moderate Drug Interaction Filter

Referring to blocks 5050 through 5054 of FIG. 5D, in some embodiments the second plurality of re-assessment filters 220-2 includes a moderate drug interaction filter 222-6 (e.g., filter 2d in Table 7). In some embodiments, the moderate drug interaction filter 222-6 is as described with respect to the moderate drug interaction filter 222-3. The moderate drug interaction filter is configured to be fired at least when the information set indicates that the subject is taking one or more compositions that interacts with the statin pharmaceutical composition, e.g., a pharmacokinetic interaction and/or a pharmacodynamic interaction, but is not necessarily contraindicated for co-administration with the statin pharmaceutical composition. For example, a composition associated with a warning for co-administration with the statin pharmaceutical composition. Non-limiting examples of drugs that may be associated with warnings when co-administered with a statin pharmaceutical composition, e.g., based on the particular statin, include colchicine and an anti-viral protease inhibitor.

In some embodiments, e.g., when implemented as a second type of filter, when the moderate drug interaction filter is fired, the subject is issued a warning associated with the filter, but is eligible to obtain re-provision of the statin pharmaceutical composition pharmaceutical composition over-the-counter upon satisfying the acknowledgement criteria associated with the warning (e.g., by confirming that they have discussed the risk factor with a medical professional and/or the medical professional has advised that the subject should take a statin pharmaceutical agent despite the risk factor).

As will be appreciated, compositions that are contraindicated, or represent a risk factor, for co-administration with a statin pharmaceutical composition vary from one statin pharmaceutical composition to another statin pharmaceutical composition. The skilled artisan will know, for example, of one or more compositions that interact with one statin pharmaceutical composition but not another. Inclusion of a composition within the moderate drug interaction filter is dependent upon the identity and/or the dosage of the statin pharmaceutical composition being authorized for a provision of over-the-counter use.

As described above, in some embodiments, use a drug that interacts with a statin pharmaceutical composition in a more severe fashion, e.g., which is a contraindication, may trigger firing of a filter 216 in the first filter category class 214 (e.g., a severe drug interaction filter), rather than the moderate drug interaction filter 222 of the second plurality of re-assessment filters 220. For example, according to some embodiments, a particular composition is included in the severe drug interaction filter 216 (e.g., as a contraindication) for a first statin pharmaceutical composition, but included in a filter in the second plurality of re-assessment filters (e.g., as a risk factor) for a second statin pharmaceutical composition. A person skilled in the art will know whether to include a certain composition within the severe drug interaction filter 216-3 or as a separate filter 222 in the second plurality of re-assessment filters (e.g., a moderate drug interaction filter), based on the severity and risk of the drug interaction with the particular identity and dosage of the statin being authorized for provision of over-the-counter use.

Kidney Disorder Filter

Referring to block 5056 of FIG. 5D, in some embodiments the second plurality of assessment filters includes a kidney disorder filter (e.g., filter 3d in Table 7). For instance, in some embodiments when the statin pharmaceutical composition includes rosuvastatin, atorvastatin, fluvastatin, and/or pitavastatin, the algorithm applies the kidney condition filter to the information set. The kidney disorder filter is configured to be fired at least when the information set indicates that the subject has developed kidney problems (e.g., kidney disease) or experienced worsening of a previous kidney problem since receiving their last provision of the statin pharmaceutical composition. In some embodiments, the kidney disorder filter is configured to be fired at least when the information set indicates that the subject has been newly diagnosed with kidney disease. In some embodiments, symptoms of a kidney problem capable of firing the kidney disorder filter include fatigue, a feeling of coldness, shortness of breath, a feeling of faintness, dizziness, weakness, a feeling of itchiness, and/or swelling of the hands and feet.

In some embodiments, e.g., when implemented as a first type of filter, when the kidney disorder filter is fired, the subject is not permitted to obtain re-provision of the statin pharmaceutical composition pharmaceutical composition over-the-counter (e.g., the method is terminated without authorizing re-provision of the statin pharmaceutical composition to the subject). In some embodiments, e.g., when implemented as a second type of filter, when the kidney disorder filter is fired, the subject is issued a warning associated with the filter, but is eligible to obtain re-provision of the statin pharmaceutical composition pharmaceutical composition over-the-counter upon satisfying the acknowledgement criteria associated with the warning (e.g., by confirming that they have discussed the risk factor with a medical professional and/or the medical professional has advised that the subject should take a statin pharmaceutical agent despite the risk factor).

Referring to block 5058 of FIG. 5D, in some embodiments the algorithm obtains acknowledgment from the subject for each warning issued to the subject by any filter in the second plurality of re-assessment filters 220-2. As described with respect to the warnings issued in conjunction with the second plurality of assessment filters 220-1, in some embodiments, the warning includes a prompt for the subject to indicate whether they have discussed the risk factor underlying the respective filter in the second plurality of re-assessment filters 220-2 that was fired with a health care practitioner (e.g., a licensed medical practitioner), e.g., and the health care practitioner indicated that the subject should take a statin pharmaceutical composition in view of the underlying risk factor. Accordingly, acknowledgement is obtained from the subject when the subject indicates that they have discussed the risk factor underlying the respective filter in the second plurality of re-assessment filters 220-2 that was fired with a health care provider.

Referring to block 5060 of FIG. 5E, in some embodiments algorithm proceeds with a re-fulfillment process when the re-fulfillment process is not already terminated by the firing of a filter in the first plurality of re-assessment filters 214-2 (e.g., the pregnancy filter 216-14). Moreover, in order for the re-fulfillment process to complete, the subject is required to acknowledge each warning associated with each filter 222 in the second plurality of re-assessment filters 220-2 that was fired.

Referring to block 5062 of FIG. 5E, in some embodiments when a respective filter in the first plurality of re-assessment filters 214-2 or the second plurality of re-assessment filters 220-2 is fired, a record associated with the firing of the respective filter is stored (e.g., memorializing an adverse event that is required to be reported to a regulatory agency). This record is stored in an adverse event module 242 which includes records of filter firing events associated with a plurality of subjects (e.g., an aggregation of adverse events associated with the statin pharmaceutical composition across a population of subjects taking the statin pharmaceutical composition over-the-counter). In some embodiments, an indication of the adverse event is communicated to a third party (e.g., a medical practitioner associated with the subject, a health care provider of the subject, and/or a manufacturer/promoter of the statin pharmaceutical composition). In some embodiments, the indication is automatically stored in the adverse event module 242 when submitted by a subject as part of the re-assessment survey.

In some embodiments, an adverse event that is required to be reported includes an allergic reaction (e.g., a side effect and/or a drug interaction including a severe and/or a moderate drug interaction) of any type or kind as described above. In some embodiments, an adverse event that is required to be reported includes an anticipated and/or recent change in pregnancy status of a respective subject. In some embodiments, an adverse event that is required to be reported includes an indication that a respective subject has had a documented cardiac event. In some embodiments, an adverse event that is required to be reported includes an indication that a respective subject has developed a liver condition. In some embodiments, an adverse event that is required to be reported includes an indication that a respective subject has experienced unexplained muscle pain or weakness. Furthermore, in some embodiments an adverse event that is required to be reported includes an indication that a respective subject has developed a kidney problem or experienced a worsening of a previous kidney problem.

Referring to block 5062 of FIG. 5E, in some embodiments the re-fulfillment process also includes storing an indication in the user profile 234 of the subject of a re-order 238 for the statin pharmaceutical composition. The re-fulfillment process further includes communicating an over-the-counter drug facts label 230 for the statin pharmaceutical composition to the subject. As previously described, the communication of the over-the-counter drug facts label 230 can occur in a variety of means. Upon confirmation from the subject that the over-the-counter drug facts label 230 has been received and read, the method includes authorizing a re-order provision of the statin pharmaceutical composition to the subject. In some embodiments, this re-order provision includes the destination of the subject.

Referring to block 5084 and 5088 of FIGS. 5F and 5G, in some embodiments the method (e.g., method 5000) is terminated without authorizing re-provision of the statin pharmaceutical composition to the subject when less than a threshold period of time has passed since the subject received their last provision of the statin pharmaceutical composition. In some embodiments, the subject's last provision of the statin pharmaceutical composition included daily dosages of the statin pharmaceutical composition for a predetermined number of days. Accordingly, the threshold period of time since receiving their last provision of the statin pharmaceutical composition, for terminating the method, is a period of time greater than half the predetermined number of days. In some embodiments, the method is terminated without authorizing re-provision of the statin pharmaceutical composition to the subject when the second information set indicates the subject has not yet retested their cholesterol following their first provision of the statin pharmaceutical composition, and has ordered the statin pharmaceutical composition at least three times.

Referring to block 5090 of FIG. 5F, in some embodiments the method includes administering the statin pharmaceutical composition to the subject after authorization of the re-provision of the statin pharmaceutical composition.

Example Implementations

Having described methods for qualifying (4000) and re-qualifying (5000) subjects to receive an over-the-counter statin pharmaceutical composition above, example implementations for these processes are described below. The example implementations below are not meant to limit the scope of the disclosure, but rather to assist with understanding methods 4000 and 5000 described herein. In some embodiments, methods 4000 and 5000 include specific pieces of the example implementation described below, without being limited to the entirety of the example implementation. For example, in some embodiments, methods 4000 and/or 5000 include a step of determining (e.g., 804) whether the subject has adequate privacy to continue with the qualification process. Although described below as an iterative data collection and analysis work flow, the method can also be implemented by collecting some or all required information from the subject prior to applying the relevant filters, as described above.

FIG. 8 illustrates an example method (800) (e.g., performed at an electric device) for qualifying a subject for a provision of an over-the-counter statin pharmaceutical composition. In some embodiments, the method of FIG. 8 is utilized when the subject has not been previously qualified for the medication (e.g., an assessment for the medication). In some embodiments, the method of FIG. 8 is utilized when the subject was previously qualified for the statin pharmaceutical composition but a predetermined period of time elapsed since the previous qualification occurred (e.g., the most recent qualification of the subject was greater than one year ago).

Referring to FIG. 8, the device prompts (802) the user to confirm that they know at least their blood pressure and cholesterol levels (e.g., because in some embodiments the subject must know their blood pressure and their total cholesterol, including their HDL, values in order to complete the qualification process). If the subject indicates they do not know their blood pressure and/or cholesterol level, the process terminates (801) without authorizing provision of the statin pharmaceutical composition, and optionally transmits advice to the user to return later, e.g., once they know their blood pressure and cholesterol levels. If the subject indicates they know their blood pressure and cholesterol levels, the process continues, with the device prompting (804) the subject to acknowledge a privacy notice. Since the present disclosure requires the subject to know and input sensitive medical information (e.g., information only the subject and a medical practitioner have access to), privacy of this information is important. Once the subject has acknowledged they have the requisite privacy for continuing, the process continues.

The device prompts the subject to provide information their gender and then applies (806) the answer received from the subject to a gender filter. The process continues, with the device prompting the subject to provide information regarding their age and then applies (808-1 and/or 808-2) the answer received from the subject to an age filter (e.g., age filter 216-1 of FIG. 3A and/or filter 1a in Table 2). When the age filter is fired (e.g., when the answer indicates the subject is female and of childbearing age or the subject is male and is younger than 20 years of age or older than 75 years of age), the device terminates (803) the qualification process without authorizing provision of the stain pharmaceutical composition and, optionally, transmits advice to the user as to why they should not take the statin pharmaceutical composition.

When the subject is female and of age, the device proceeds with the qualification process, prompting the subject to indicate whether the subject is pregnant or breastfeeding and then applies (810) the answer received from the subject to a pregnancy filter (e.g., pregnancy filter 216-2 of FIG. 3A and/or filter 2a in Table 2). When the pregnancy filter is fired (e.g., when the answer indicates the subject is pregnant, breastfeeding, or, optionally, planning to become pregnant), the device terminates (803) the qualification process without authorizing provision of the statin pharmaceutical agent and, optionally, transmits advice to the user as to why they should not take the statin pharmaceutical composition.

When the pregnancy filter is not fired (e.g., when the subject is male or the subject indicates a non-pregnant or non-breastfeeding status), the device proceeds with the qualification process, prompting (812) the subject to indicate their race. When the answer indicates the subject is of South Asian descent, the device creates a record (813-1) indicating that the user has a risk enhancing factor.

The device then proceeds with the qualification process, prompting the subject to indicate if they are taking a composition that interacts with the statin pharmaceutical composition and then applies (814) the answer received from the subject to a severe drug interaction filter (e.g., filter 216-3 of FIG. 3A and/or filter 3a in Table 2). When the severe drug interaction filter is fired (e.g., when the answer indicates the subject is taking a medication that has a severe interaction with the statin pharmaceutical composition), the device terminates (803) the qualification process without authorizing provision of the statin pharmaceutical composition and, optionally, transmits advice to the user as to why they should not take statin pharmaceutical composition.

When the drug interaction assessment filter is not fired, the device proceeds with the qualification process, prompting the subject indicate whether they have ever experienced a documented cardiac event and then applies (816) the answer received from the subject to a cardiac event filter (e.g., filter 216-4 of FIG. 3A and/or filter 4a in Table 2). When the cardiac event filter is fired (e.g., when the subject indicates a personal documented cardiac event), the device terminates (805) the qualification process without authorizing provision of the statin pharmaceutical composition and, optionally, transmits advice to the user to discuss taking a statin pharmaceutical composition with a medical professional.

When the cardiac event filter is not fired, the device prompts (818) the user to indicate whether there is a history of premature heart disease in their family (e.g., collecting information relevant to a risk enhancing factor filter). If the answer to whether there is a history of premature cardiac disease in the user's family is yes, the device creates a record (813-2) indicating that the user has a risk enhancing factor.

If the process has not yet been terminated, the device proceeds with the qualification process by evaluating whether the user is a male under a threshold age, e.g., 40, and if so follows bypass path B, which is continued in FIG. 8H. If the user is not a male under the threshold age, the device proceeds by prompting the subject to provide information about their total cholesterol level and then applies (824) the answer received from the subject to a total cholesterol filter (e.g., filter 216-5 of FIG. 3A and/or filter 5a in Table 2). When the total cholesterol filter is fired (e.g., when the subject indicates a total cholesterol level of less than 130 mg/dL or greater than 320 mg/dL), the device terminates (803) the qualification process without authorizing provision of the statin pharmaceutical composition and, optionally, transmits advice to the user as to why they should not take statin pharmaceutical composition.

When the total cholesterol filter is not fired, the device proceeds with the qualification process, prompting the subject to provide information about their LDL cholesterol level and then applies (826) the answer to an LDL cholesterol filter (e.g., filter 216-6 of FIG. 3A and/or filter 6a in Table 2). When the LDL cholesterol filter is fired (e.g., when the subject indicates an LDL cholesterol level of less than 70 mg/dL or at least 190 mg/dL), the device terminates (803 or 805) the qualification process without authorizing provision of the statin pharmaceutical composition and, optionally, transmits advice to the user as to why they should not take statin pharmaceutical composition and/or to discuss taking a statin pharmaceutical composition with a medical professional (e.g., where their LDL cholesterol level is at least 190 mg/dL). If the subject's answer indicates their LDL cholesterol level is intermediately elevated (e.g., between 160 mg/dL and 190 mg/dL), the device creates a record (813-3) indicating that the user has a risk enhancing factor.

When the LDL cholesterol filter is not fired, the device proceeds by prompting the subject to provide information about their HDL cholesterol level and then applies (828) the answer to an HDL cholesterol filter (e.g., filter 216-7 of FIG. 3A and/or filter 7a in Table 2). When the HDL cholesterol filter is fired (e.g., when the subject indicates an HDL cholesterol level of less than 20 mg/dL or at least 100 mg/dL), the device terminates (803) the qualification process without authorizing provision of the statin pharmaceutical composition and, optionally, transmits advice to the user as to why they should not take statin pharmaceutical composition. If the subject's answer indicates their LDL cholesterol level is intermediately decreased (e.g., between 20 mg/dL and 40 mg/dL), the device creates a record (815-1) indicating that the user has an indicator of metabolic disease.

When the HDL cholesterol filter is not fired, the device proceeds by prompting the subject to provide information about their triglyceride level and applies (830) the answer received from the subject to a triglyceride level filter (e.g., filter 216-8 of FIG. 3A and/or filter 8a in Table 2). When the triglyceride level filter is fired (e.g., when the subject indicates a triglyceride level of at least 500 mg/dL), the device terminates (805) the qualification process without authorizing provision of the statin pharmaceutical composition and, optionally, transmits advice to the user as to why they should not take statin pharmaceutical composition and/or to discuss taking a statin pharmaceutical composition with a medical professional. If the subject's answer indicates their triglyceride level is intermediately elevated (e.g., between 175 mg/dL and 500 mg/dL), the device creates a record (813-4) indicating that the user has a risk enhancing factor. If the subject's answer indicates their triglyceride level is slightly elevated (e.g., between 150 mg/dL and 175 mg/dL), the device creates a record (815-2) indicating that the user has an indicator of metabolic disease.

When the triglyceride filter is not fired, the device proceeds by prompting the subject to provide information about blood pressure and applies (832) the answer received from the subject to a blood pressure filter (e.g., filter 216-9 of FIG. 3A and/or filter 9a in Table 2). When the blood pressure filter is fired (e.g., when the answer indicates the subject has a systolic blood pressure of less an 90 mmHg or greater than 180 mmHg, or the subject has a diastolic blood pressure of greater than 120 mmHg), the device terminates (803) the qualification process without authorizing provision of the statin pharmaceutical composition, and, optionally, transmits advice for the subject as to why they should not use a statin pharmaceutical composition and/or to seek immediate medical attention for hypertensive crisis (e.g., when the subject indicates they have a systolic blood pressure of greater than 180 mmHg or a diastolic blood pressure of greater than 120 mmHg). If the subject's answer indicates their systolic blood pressure or diastolic blood pressure is moderately elevated (e.g., a systolic blood pressure of between 130 mmHg and 180 mmHg or a diastolic blood pressure of between 85 mmHg and 120 mmHg), the device creates a record (815-3) indicating that the user has an indicator of metabolic disease.

When the blood pressure filter is not fired, the device proceeds with the qualification process, prompting the subject to provide information about whether they are currently taking blood pressure medication (836), whether they have diabetes (840), and their history of smoking (842). If the subject's answers indicate they are currently taking a blood pressure medication, and the subject did not have a blood pressure indicative of metabolic disease (e.g., no record was created (815-3), as described above), the device creates a record (815-3) indicating that the user has an indicator of metabolic disease. The device then calculates an atherosclerotic cardiovascular disease (ASCVD) event risk for the subject (e.g., based on the answers to previous prompts, including characteristics discussed above with respect to Table 3) and applies (844) the calculated risk to an ASCVD pooled cohort equation filter (e.g., filter 216-10 of FIG. 3A and/or filter 10*a* in Table 2). When the ASCVD pooled cohort equation filter is fired (e.g., when the risk of an ASCVD event is less than 5% or at least 20%), the device terminates (803 or 805) the qualification process without authorizing provision of the statin pharmaceutical composition and, optionally, transmits advice to the user to discuss taking a statin pharmaceutical composition with a medical professional (e.g., where their risk of an ASCVD event is at least 20%).

In some embodiments, when the subject's risk of an ASCVD event is below a floor risk threshold, that would otherwise fire the ASCVD pooled cohort equation filter, the device evaluates whether the subject should still be eligible for provision of the statin pharmaceutical composition because of increased risk associated with diabetes. The device prompts the subject to indicate whether they have diabetes and then evaluates (846-*b*) the answer in view of the subject's gender (848-*b*) and age (850-*b*). When the device determines the subject has an increased risk of an ASCVD event, the device bypasses firing the ASCVD filter.

Similarly, in some embodiments, when the subject's risk of an ASCVD event is between a floor risk threshold and a ceiling risk threshold, that would otherwise not file the ASCVD pooled cohort equation filter, the device evaluates whether the subject should seek further guidance from a medical professional because of increased risk associated with diabetes. The device prompts the subject to indicate whether they have diabetes and then evaluates (846-*a*) the answer in view of the subject's gender (848-*a*) and age (850-*a*). When the device determines the subject has an increased risk of an ASCVD event, the device fires the ASCVD pooled cohort equation filter and the device terminates (805) the qualification process without authorizing provision of the statin pharmaceutical composition and, optionally, transmits advice to the user to discuss taking a statin pharmaceutical composition with a medical professional.

Alternatively, when the device has followed bypass path B, the device bypasses the total cholesterol filter, the LDL cholesterol filter, the HDL cholesterol filter, the triglyceride filter, the blood pressure filter, and the ASCVD pooled cohort equation filter, as described above. Rather, the device proceeds by prompting the subject to provide information about their LDL cholesterol level and then applies (826-*b*) the answer to an alternate LDL cholesterol filter (e.g., an alternate version of filter 216-6 of FIG. 3A and/or filter 6*a* in Table 2). When the alternative LDL cholesterol filter is fired (e.g., when the subject indicates an LDL cholesterol level of less than 70 mg/dL or at least 190 mg/dL), the device terminates (803 or 805) the qualification process without authorizing provision of the statin pharmaceutical composition and, optionally, transmits advice to the user as to why they should not take statin pharmaceutical composition and/or to discuss taking a statin pharmaceutical composition with a medical professional (e.g., where their LDL cholesterol level is at least 190 mg/dL). When the alternative LDL cholesterol filter is not fired, the device proceeds by prompting the subject to provide information about their triglyceride level and applies (830-*b*) the answer received from the subject to a triglyceride level filter (e.g., an alternate filter 216-8 of FIG. 3A and/or filter 8*a* in Table 2). When the alternate triglyceride level filter is fired (e.g., when the subject indicates a triglyceride level of at least 500 mg/dL), the device terminates (805) the qualification process without authorizing provision of the statin pharmaceutical composition and, optionally, transmits advice to the user as to why they should not take statin pharmaceutical composition and/or to discuss taking a statin pharmaceutical composition with a medical professional.

When the ASCVD pooled cohort equation filter or alternate triglyceride level filter is not fired, the proceeds with the qualification process, prompting the subject to indicate whether they have had a liver condition and then applies (852) the answer received from the subject to a liver condition filter (e.g., filter 216-11 in FIG. 3A and/or filter 11*a* in Table 2). When the liver condition filter is fired (e.g., when the answer indicates the subject has had a liver condition), the device the terminates (803) the qualification process without authorizing provision of the statin pharmaceutical composition and, optionally, transmits advice to the user as to why they should not take statin pharmaceutical composition.

When the liver condition filter is not fired, the device proceeds with the qualification process, prompting the subject to indicate whether they have a kidney problem and applies (854) the answer received from the subject to a kidney disorder filter (e.g., filter 5*b* in Table 4). When the kidney disorder filter is fired (e.g., when the answer indicates the subject has had a kidney problem), the device initiates (811-1) an override procedure (e.g., creating a record indicating that the user must confirm they have discussed taking a statin pharmaceutical composition with a health care provider).

The device proceeds with the qualification process, prompting the subject to indicate their alcohol consumption status and applies (856) the answer received from the subject to alcohol consumption filter (e.g., filter 222-1 of FIG. 3B and/or filter 1*b* of Table 4). When the alcohol consumption filter is fired (e.g., when the answer indicates the subject consumes alcoholic drinks at a frequency above a ceiling frequency), the device initiates (811-2) an override procedure (e.g., creating a record indicating that the user must confirm they have discussed taking a statin pharmaceutical composition with a health care provider).

The device proceeds with the qualification process, prompting the subject to indicate whether the subject has had an adverse reaction to a cholesterol lowering drug and applies (858) the answer received from the subject to an adverse reaction filter (e.g., filter 222-2 of FIG. 3B and/or one of filters 2*b* and 4*b* in Table 4). When the adverse reaction filter is fired (e.g., when the answer indicates the subject has had an adverse reaction to a cholesterol lowering medication), the device initiates (811-3) an override procedure (e.g., creating a record indicating that the user must confirm they have discussed taking a statin pharmaceutical composition with a health care provider).

The device proceeds with the qualification process, prompting the subject to indicate if they are taking a composition that interacts with the statin pharmaceutical composition, and/or evaluates previous answers about the medications the subject is taking, and then applies (860) the answer received from the subject to a moderate drug interaction filter (e.g., filter 222-3 of FIG. 3B and/or filter 3*b* in Table 4). When the moderate drug interaction filter is fired (e.g., when the answer indicates the subject is taking a medication that constitutes a risk factor for co-administration of the statin pharmaceutical composition), the device initiates (811-4) an override procedure (e.g., creating a record indicating that the user must confirm they have discussed taking a statin pharmaceutical composition with a health care provider).

The device then proceeds by evaluating whether the subject has risk enhancing factors sufficient to justify treatment with the statin pharmaceutical composition. The device first applies (862) all records created (813) for risk enhancing factors based on the subject's previous answers (e.g., relating to their race, family history of premature cardiovascular disease, LDL cholesterol level, and triglyceride level) to a risk enhancing factor filter (e.g., filter 12*a* in Table 2). When the subject's information collected to that point does not indicate the subject has a risk enhancing factor, justifying statin therapy, the device begins determining if the subject has other risk enhancing factors.

For instance, the device evaluates (864-*a*) whether the subject has metabolic syndrome based on the subject's previous answers (e.g., relating to HDL cholesterol level, triglyceride level, and blood pressure). When it's determined the subject has metabolic syndrome, the device creates a record (813-5) indicating that the user has a risk enhancing factor, and proceeds along pathway J. If not, the device evaluates (864-*b*) whether the subject has at least two indicators of metabolic syndrome based on the subject's previous answers. When it's determined the subject has at least two indicators of metabolic syndrome, the device determines (866) whether the subject is a male or female, prompts the user to indicate their waist size, and evaluates (868) the answer. When the answer indicates the subject has a waist size indicative of metabolic syndrome, the device creates a record (813-5) indicating that the user has a risk enhancing factor, and proceeds along pathway J.

Similarly, the device prompts the subject to indicate whether they have an inflammatory disease and evaluates (870) the answer received from the subject. When the answer indicates the subject has an inflammatory disease, the device creates a record (813-6) indicating that the user has a risk enhancing factor, and proceeds along pathway J.

Similarly, the device determines (872) whether the subject is female, and then prompts the subject to indicate whether they have experienced preeclampsia and evaluates (874) the answer received from the subject. When the answer indicates the subject has experienced preeclampsia, the device creates a record (813-7) indicating that the user has a risk enhancing factor, and proceeds along pathway J. Optionally, the device then prompts the subject to indicate whether they have experienced premature menopause and evaluates (874) the answer received from the subject. When the answer indicates the subject has premature menopause, the device creates a record (813-8) indicating that the user has a risk enhancing factor, and proceeds along pathway J.

Similarly, the device determines (878) whether the subject knows their C-reactive protein and/or coronary artery calcium levels. When the scores are known, the device prompts the user to indicate their C-reactive protein level and evaluates (880) the answer received from the subject. When the answer indicates the subject has elevated C-reactive protein levels, the device creates a record (813-9) indicating that the user has a risk enhancing factor, and proceeds along pathway J. Optionally, the device then prompts the user to indicate their coronary artery calcium level and evaluates (882) the answer received from the subject. When the answer indicates the subject has a sufficiently elevated coronary artery calcium level score (e.g., any coronary artery calcium for an older subject or significantly elevated coronary artery calcium levels in younger subjects), the device creates a record (813-10) indicating that the user has a risk enhancing factor, and proceeds along pathway J.

When the risk enhancing factor filter is fired (e.g., when the answers indicate the subject still does not have sufficient risk enhancing factors to justify statin therapy), the device the terminates (805) the qualification process without authorizing provision of the statin pharmaceutical composition and, optionally, transmits advice to the user as to why they should not take statin pharmaceutical composition.

When the risk enhancing factor filter is not fired, the device proceeds along pathway J by prompting the subject to confirm the answers they have provided (884). Upon confirmation, the device proceeds with the qualification process, determining (886) whether the override procedure has been triggered (e.g., by firing one or more of the kidney disease filter, the alcohol consumption filter, the adverse reaction filter, or the moderate drug interaction filter). If the override procedure has been triggered, the device prompts (817) the user to confirm that they have spoken with a medical professional about taking a statin pharmaceutical composition (e.g., in view of the underlying risk factor that triggered the respective filter) and the medical professional recommended taking the statin pharmaceutical composition. If the user's response indicates they have not spoken with a medical professional or the medical professional did not recommend taking the statin pharmaceutical composition, the device terminates (805) the process and, optionally, transmits advice for the subject to consult a medical professional.

If the override procedure was not triggered, or the override procedure was triggered and the subject's response indicated that a medical professional recommended they take a statin pharmaceutical composition (e.g., in view of the underlying risk factor triggering the override procedure), the device transmits (888) a drug facts label for the statin pharmaceutical composition and prompts the user to read the drug facts label. If the subject confirms they have read the drug facts label, the device proceeds to authorize (890) purchase of the statin pharmaceutical composition.

FIG. 9 illustrates an example method for qualifying a subject for a re-fill (e.g, a re-assessment) of a provision for an over-the-counter statin pharmaceutical composition (e.g., following a prescription from a medical professional or initial qualification for an over-the-counter statin pharmaceutical composition, e.g., according to a method described herein). Referring to FIG. 9, the device determines the period of time that has elapsed since the subject most recently received provision of the statin pharmaceutical composition and evaluates (902) whether a minimum amount of time has passed. If a minimum amount of time has not passed since the subject last received a provision of the statin pharmaceutical agent, the device terminates (901) the re-qualification process without authorizing provision of the statin pharmaceutical composition and, optionally, transmits advice to the user to return at a later date (e.g., once the floor elapsed period of time has passed). The device then evaluates (904) whether more than a maximum amount of time has passed. If a maximum amount of time has passed since the subject last received a provision of the statin pharmaceutical agent, the device terminates (905) and, optionally, directs the subject to retake the initial qualification assessment (e.g., as described with respect to FIGS. 4 and 8 above).

When a minimum amount of time, but not a maximum amount of time, has passed since the subject last received a provision of the statin pharmaceutical agent, the device proceeds with the qualification process, prompting the subject to indicate whether the subject has had a documented cardiac event since receiving their last provision of the statin pharmaceutical agent, and then applies (908) the answer received from the subject to a cardiac event filter (e.g., filter 216-12 of FIG. 3B). In some embodiments, when the cardiac event filter is fired (e.g., when the answer indicates the subject has had a documented cardiac event), the device creates (990-1) a record of an adverse event (e.g., aggregated in an adverse event data store having records of adverse events from a plurality of users), terminates (907) the qualification process without authorizing re-provision of the statin pharmaceutical composition and, optionally, transmits advice to the user as to why they should not take the statin pharmaceutical composition.

When the cardiac event filter is not fired, the device proceeds with the qualification process, by evaluating whether the statin pharmaceutical agent has sufficiently lowered the subject's cholesterol level. The device determines (910) whether it was already confirmed that the subject's cholesterol level was lowered, e.g., by evaluating records (e.g., in subject profile data store 232) from previous reorder requests. When it was previously confirmed that taking the statin pharmaceutical agent has lowered the subject's cholesterol levels, the device bypasses additional evaluation of the subject's cholesterol level (e.g., bypasses a cholesterol status filter). When it was not previously confirmed that taking the statin pharmaceutical agent has lowered the subject's cholesterol level, the device prompts the subject to indicate whether they retested their cholesterol level since receiving a provision of the statin pharmaceutical agent and evaluates (912) their answer. When the answer indicates the subject has not retested their cholesterol since receiving a provision of the statin pharmaceutical composition, the device bypasses additional evaluation of the subject's cholesterol level. When the answer indicates the subject has retested their cholesterol since receiving a provision of the statin pharmaceutical composition, the device prompts the subject to provide information about their retested cholesterol level and applies (916) their answer(s) to a cholesterol status filter (e.g., filter 216-13 of FIG. 3B and/or filter 2c in Table 6). When the cholesterol status filter is fired (e.g., when the answer indicates the subject's cholesterol level has not decreased by at least 10% since beginning statin therapy), the device terminates (907) the requalification process without authorizing provision of the statin pharmaceutical agent and, optionally, transmits advice to the user as to why they should not take the statin pharmaceutical composition.

When the cholesterol status filter is not fired, the device proceeds with the requalification process, evaluating whether the subject has become pregnant or started breast feeding. The device determines (918) the gender of the subject (e.g., by evaluating information previously provided to the system, e.g., in subject profile data store 232). When the subject is a male, the device bypasses further evaluation of whether the subject has become pregnant (e.g., bypasses the pregnancy filter). When the subject is female, the device determines (919) the age of the subject, (e.g., by evaluating information previously provided to the system, e.g., in subject profile data store 232). When the subject is not of child-bearing age (e.g., over 60 years of age), the subject bypasses further evaluation of whether the subject has become pregnant (e.g., bypasses the pregnancy filter). When the subject is female and of child bearing age, the device prompts the subject to indicate their pregnancy status and then applies (920) the answer to a pregnancy filter (e.g., filter 216-14 of FIG. 3B and/or filter 3c in Table 6). When the pregnancy filter is fired (e.g., when the answer indicates the subject is pregnant or breastfeeding), the device creates (990-2) a record of an adverse event (e.g., aggregated in an adverse event data store having records of adverse events from a plurality of users), terminates (909) the requalification process without authorizing provision of the statin pharmaceutical agent and, optionally, transmits advice to the user as to why they should not take the statin pharmaceutical composition.

When the pregnancy filter was bypassed or not fired, the device proceeds by prompting the subject to provide information related to their current pharmaceutical composition use and then applies (922) the answer to a severe drug interaction filter (e.g., filter 216-15 of FIG. 3B and/or filter 4c in Table 6). When the severe drug interaction filter is fired (e.g., when the answer indicates the subject is taking a drug that is contraindicated for co-administration with the statin pharmaceutical composition), the device terminates (907) the requalification process without authorizing provision of the statin pharmaceutical composition and, optionally, transmits advice to the user as to why they should not take the statin pharmaceutical composition.

When the severe drug interaction filter is not fired, the device proceeds by prompting the subject to indicate whether they have developed a liver condition and then applies (924) the answer received from the subject to a liver condition filter. When the liver condition filter is fired (e.g., when the answer indicates the subject has developed a liver condition since receiving their last provision of the statin pharmaceutical composition), the device creates (990-3) a record of an adverse event (e.g., aggregated in an adverse event data store having records of adverse events from a plurality of users) and terminates (909) the requalification process without authorizing a provision of the statin pharmaceutical composition and, optionally, transmits advice to the user to discuss receiving the statin pharmaceutical composition with a medical professional.

When the liver condition filter is not fired, the device proceeds with the qualification process, prompting the subject to indicate whether they have experienced unexplained muscle weakness or pain and then applies (926) the answer received from the subject to a muscle irregularity filter. When the muscle irregularity filter is fired (e.g., when the answer indicates the subject has experienced unexplained muscle weakness or pain since receiving their last provision of the statin pharmaceutical composition), the device creates (990-4) a record of an adverse event (e.g., aggregated in an adverse event data store having records of adverse events from a plurality of users) and terminates (909) the requalification process without authorizing a provision of the statin pharmaceutical composition and, optionally, transmits advice to the user to discuss receiving the statin pharmaceutical composition with a medical professional.

When the muscle irregularity filter is not fired, the device proceeds by evaluating (928) whether the subject previously reported a kidney problem (e.g., by evaluating information previously provided to the system, e.g., in subject profile data store 232). When the subject has not previously reported kidney problems, the device prompts the subject to indicate whether they have developed a kidney problem since receiving their last provision of the statin pharmaceutical composition and applies (930) the answer to a kidney disorder filter (e.g., filter 3*d* in Table 7). When the answer indicates the subject has developed kidney disease, the device the device creates (990-5) a record of an adverse event (e.g., aggregated in an adverse event data store having records of adverse events from a plurality of users) and initiates (911-1) an override procedure (e.g., creates a record indicating that the user must confirm they have discussed taking a statin pharmaceutical composition with a health care provider). When the subject has previously reported kidney problems, the device prompts the subject to indicate whether they have experienced worsening of their symptoms since receiving their last provision of the statin pharmaceutical composition and applies (932) the answer to a kidney disorder filter (e.g., filter 3*d* in Table 7). When the answer indicates the subject's kidney disease has progressed, the device the device creates (990-6) a record of an adverse event (e.g., aggregated in an adverse event data store having records of adverse events from a plurality of users) and initiates (911-2) an override procedure (e.g., creates a record indicating that the user must confirm they have discussed taking a statin pharmaceutical composition with a health care provider).

The device proceeds then with the qualification process, prompting the subject to provide an alcohol consumption status and then applies (934) the answer to an alcohol consumption filter (e.g., filter 222-5 of FIG. 3B and/or filter Id in Table 7). When the alcohol consumption filter is fired (e.g., when the answer indicates the subject consumes more than a threshold amount of alcohol), the device initiates (911-3) an override procedure (e.g., creates a record indicating that the user must confirm they have discussed taking a statin pharmaceutical composition with a health care provider).

The device proceeds with the qualification process, evaluating (936) whether the subject is currently taking any medications that moderately interact with the statin pharmaceutical composition, using a moderate drug interaction filter (e.g., filter 222-6 of FIG. 3B and/or filter 2*d* in Table 7), e.g., by evaluating answers provided in conjunction with the severed drug interaction filter and/or by prompting the subject for more information about what medications they are currently taking. When the moderate drug interaction filter is fired (e.g., when the subject's answers indicate they are currently taking a medication that moderately interacts with the statin pharmaceutical composition), the device initiates (911-3) an override procedure (e.g., creates a record indicating that the user must confirm they have discussed taking a statin pharmaceutical composition with a health care provider).

The device then proceeds with the qualification process, prompting the subject to confirm the answers they have provided (940). Upon confirmation, the device proceeds by determining (942) whether the override procedure has been triggered (e.g., by firing one or more of the alcohol consumption filter, moderate drug interaction filter, or kidney disorder filter). If the override procedure has been triggered, the device prompts (913) the user to confirm that they have spoken with a medical professional about taking a statin pharmaceutical agent (e.g., in view of the underlying risk factor that triggered the respective filter) and the medical professional recommended taking the statin pharmaceutical composition. If the user's response indicates they have not spoken with a medical professional or the medical professional did not recommend taking the statin pharmaceutical composition, the device terminates (909) the process and, optionally, transmits advice for the subject to consult a medical professional.

If the override procedure was not triggered, or the override procedure was triggered and the subject's response indicated that a medical professional recommended they take a statin pharmaceutical composition (e.g., in view of the underlying risk factor triggering the override procedure), the device transmits (944) a drug facts label for the statin pharmaceutical composition and prompts the user to read the drug facts label. If the subject confirms they have read the drug facts label, the device proceeds to authorize (946) repurchase of the statin pharmaceutical composition.

SPECIFIC EMBODIMENTS

In one aspect, the disclosure provides methods, software, and computer systems for qualifying a human subject for an over-the-counter provision of a statin pharmaceutical composition to lower cholesterol, e.g., treating or preventing heart disease. In one embodiment, a computer system (e.g., computer system 250 in FIG. 2) includes instructions for providing an assessment survey of the subject (e.g., assessment module 252 in FIG. 2) to obtain an information set (e.g., first information set) about the subject necessary to run against at least two series of filters (e.g., a first plurality of assessment filters 214-1 and a second plurality of assessment filters 220-1). The computer system also includes instructions for running the information set against the assessment filters. Filters 216 in the first plurality of assessment filters 214-1 prevent authorization for provision of the OTC statin where the subject's information set identifies a contraindication for the OTC statin. Filters 222 in the second plurality of assessment filters 220-1 generate a warning 226 where the subject's information set identifies a risk factor for the OTC statin. In some embodiments, the warning 226 includes a prompt requiring the subject to confirm they have discussed the risk factor with a physician in order to proceed with qualification for the OTC statin.

In some embodiments, the computer system includes instructions for proceeding with a fulfillment process when no filter in the first plurality of assessment filters has been fired and the subject has acknowledged each warning associated with each filter in the second plurality of assessment filters that was fired. In some embodiments, the fulfillment process includes storing an indication in a subject profile of an initial order for the statin pharmaceutical composition, communicating an over the counter drug facts label for the statin pharmaceutical composition to the subject, and authorizing, upon confirmation from the subject that the over the counter drug facts label has been received and read, provision of the statin pharmaceutical composition to the subject In one aspect, the disclosure provides methods, software, and computer systems for qualifying a human subject for a re-order (e.g., re-assessment) for an over-the-counter provision of a statin pharmaceutical composition to lower cholesterol, e.g., treating or preventing heart disease. In one embodiment, a computer system includes instructions, responsive to receiving a re-order request from the subject for the statin pharmaceutical composition, performing a re-fulfillment procedure (e.g., re-assessment procedure) including, for providing a re-assessment survey of the subject to obtain an information set (e.g., second information set) for qualifying the subject for the re-order, e.g., associated with at least two series of filters (e.g., a first plurality of re-assessment filters 214-2 and a second plurality of re-assessment filters 220-2). The computer system also includes instructions for running the information set against the re-assessment filters. Filters 216 in the first plurality of re-assessment filters prevent authorization for delivery of the OTC statin where the subject's information set identifies a contraindication for the OTC statin. Filters 222 in the second plurality of re-assessment filters generate a warning 226 where the subject's information set identifies a risk factor for the OTC statin. In some embodiments, the warning 226 includes a prompt requiring the subject to confirm they have discussed the risk factor with a physician in order to proceed with qualification for the OTC statin.

In some embodiments, the computer system also includes instructions for proceeding with a re-fulfillment process when no filters in the first plurality of reassessment filters was fired and the subject acknowledges each warning associated with each filter in the second plurality of reassessment filters that was fired. In some embodiments, the re-fulfillment process includes storing an indication in a subject profile of a re-order for the statin pharmaceutical composition, communicating an over-the-counter drug facts label 230 for the statin pharmaceutical composition to the subject and, upon confirmation that the over-the-counter drug facts label has been received and read, authorizing provision of the OTC statin pharmaceutical composition to the subject.

In one aspect, the disclosure provides a method for qualifying a human subject for an over-the-counter provision of a statin pharmaceutical composition. The method includes providing an assessment survey for obtaining a first information set from the subject. The method includes applying an algorithm to the first information set. The algorithm runs all or a portion of the first information set against a first plurality of assessment filters. The subject is deemed not qualified for a statin treatment when a respective filter in the first plurality of assessment filters is fired and the method is terminated without authorizing provision of the statin pharmaceutical composition to the subject. The algorithm also runs all or a portion of the first information set against a second plurality of assessment filters. When a respective filter in the second plurality of assessment filters is fired, the subject is provided with a warning corresponding to the respective filter. Further, the algorithm obtains acknowledgment from the subject confirming that the subject has discussed the risk factor associated with each warning issued to the subject by any filter in the second plurality of assessment filters with a physician. The algorithm then proceeds with a fulfillment process when no filter in the first plurality of assessment filters has been fired and the subject has acknowledged each warning associated with each filter in the second plurality of assessment filters that was fired. The fulfillment process includes storing an indication in a subject profile of an initial order for the statin pharmaceutical composition, communicating an over the counter drug facts label for the statin pharmaceutical composition to the subject, and authorizing, upon confirmation from the subject that the over the counter drug facts label has been received and read, provision of the statin pharmaceutical composition to the subject.

In some embodiments, the information set includes information selected from the survey results listed in Table 1. In one embodiment, the information set includes: a sex of the subject, an age of the subject, when the subject is a female, whether the subject is pregnant or breastfeeding, whether the subject is taking one or more compositions that interact with the statin pharmaceutical composition, whether the subject has ever had a cardiac event, a total cholesterol level of the subject, a LDL cholesterol level of the subject, a HDL cholesterol level of the subject, a triglyceride level of the subject, a systolic blood pressure of the subject, a diastolic blood pressure of the subject, whether the subject has a liver condition, an alcohol consumption status of the subject, and whether the subject has had an adverse reaction to a cholesterol lowering composition.

In some embodiments, the first plurality of assessment filters includes a plurality of assessment filters selected from the filters listed in Table 2. In one embodiment, the first plurality of assessment filters includes an age filter, a pregnancy filter, a severe drug interaction filter, a cardiac event filter, a total cholesterol filter, a LDL cholesterol filter, a HDL cholesterol filter, a triglyceride level filter, a blood pressure filter, an ASCVD risk pooled cohort equation filter, and a liver condition filter.

In some embodiments, the second plurality of assessment filters includes a plurality of assessment filters selected from the filters listed in Table 4. In one embodiment, the second plurality of assessment filters includes an alcohol consumption filter, an adverse reaction filter, and a moderate drug interaction filter.

In some embodiments, the first and second plurality of assessment filters includes filters selected from the filters listed in Table 8. In some embodiments, the first plurality of assessment filters include a first sub-plurality of the filters listed in Table 8, for example, 2, 3, 4, 5, 6, 7, 8, 9, 10, 11, 12, 13, 14, or all 15 of the filters listed in Table 8, and the second plurality of assessment filters include a second sub-plurality of the filters listed in Table 8, which is different from the first sub-plurality of filters, for example, 2, 3, 4, 5, 6, 7, 8, 9, 10, 11, 12, 13, 14, or all 15 of the filters listed in Table 8. In some embodiments, each of the filters in the first sub-plurality of filters is different from each of the filters in the second sub-plurality of filters (e.g., no filter listed in Table 8 is included in both the first sub-plurality and the second sub-plurality of filters). In some embodiments, a system for qualifying a subject for delivery of a provision of an over-the-counter statin pharmaceutical composition includes instructions for applying only one plurality of filters, eg, only filters of a first plurality of assessment filters. In some embodiments, where the method, system, or software applies a single plurality of filters, the plurality of filters includes a plurality of filters selected from the filters listed in Table 8, e.g., at least 2, 3, 4, 5, 6, 7, 8, 9, 10, 11, 12, 13, 14, or all 15 of the filters listed in Table 8. In some embodiments, where a filter listed in Table 8 corresponds to a filter listed in Table 2 or Table 4, a threshold level sufficient to fire the corresponding filter listed in Table 2 or Table 4, as described in detail above, is sufficient to fire the filter listed in Table 8.

TABLE 8

Example Assessment Filters

| Filter | Exemplary Criteria |
|---|---|
| 1e | an age filter |
| 2e | a pregnancy filter |
| 3e | a severe drug interaction filter |
| 4e | a cardiac event filter |
| 5e | a total cholesterol filter |
| 6e | a LDL cholesterol filter |
| 7e | a HDL cholesterol filter |
| 8e | a triglyceride filter |
| 9e | a blood pressure filter |
| 10e | an ASCVD risk pooled cohort equation filter |

TABLE 8-continued

Example Assessment Filters

| Filter | Exemplary Criteria |
|---|---|
| 11e | a liver condition filter |
| 12e | a risk enhancing factor filter |
| 13e | an alcohol consumption filter |
| 14e | an adverse reaction filter |
| 15e | a moderate drug interaction filter |

In one aspect, the disclosure provides methods, software, and computer systems for qualifying a human subject for a re-order (e.g., a re-assessment) for an over-the-counter provision of a statin pharmaceutical composition to lower cholesterol, e.g, treating or preventing heart disease. In one embodiment, a method includes providing a re-assessment survey for obtaining a second information set from the subject. The method includes applying an algorithm to the second information set. The algorithm runs all or a portion of the second information set against a first plurality of re-assessment filters. The subject is deemed not qualified for a statin treatment when a respective filter in the first plurality of re-assessment filters is fired and the method is terminated without authorizing provision of the statin pharmaceutical composition to the subject. The algorithm also runs all or a portion of the second information set against a second plurality of re-assessment filters. When a respective filter in the second plurality of re-assessment filters is fired, the subject is provided with a warning corresponding to the respective filter. Further, the algorithm obtains acknowledgment from the subject confirming that the subject has discussed the risk factor associated with each warning issued to the subject by any filter in the second plurality of re-assessment filters with a physician. The algorithm then proceeds with a re-fulfillment process when no filter in the first plurality of re-assessment filters has been fired and the subject has acknowledged each warning associated with each filter in the second plurality of re-assessment filters that was fired. The re-fulfillment process includes storing an indication in a subject profile of a re-order for the statin pharmaceutical composition, communicating an over the counter drug facts label for the statin pharmaceutical composition to the subject, and authorizing, upon confirmation from the subject that the over the counter drug facts label has been received and read, provision of the statin pharmaceutical composition to the subject.

In some embodiments, the first plurality of re-assessment filters includes one or more filters listed in Table 6. In some embodiments, the first plurality of re-assessment filters includes a cardiac event filter, a cholesterol status filter, a pregnancy filter, a severe drug interaction filter, a liver condition filter, and a muscle irregularity filter.

In some embodiments, the second plurality of re-assessment filters includes one or more filters listed in Table 7. In some embodiments, the second plurality of re-assessment filters includes an alcohol consumption filter and a moderate drug interaction filter.

In some embodiments, the first and second pluralities of re-assessment filters includes filters selected from the filters listed in Table 9. In some embodiments, the first plurality of re-assessment filters includes a first sub-plurality of the filters listed in Table 9, for example, 2, 3, 4, 5, 6, 7, 8, or all 9 of the filters listed in Table 9, and the second plurality of re-assessment filters includes a second sub-plurality of the filters listed in Table 9, which is different from the first sub-plurality of filters, for example, 2, 3, 4, 5, 6, 7, 8, or all 9 of the filters listed in Table 9. In some embodiments, each of the filters in the first sub-plurality of filters is different from each of the filters in the second sub-plurality of filters (e.g., no filter listed in Table 9 is included in both the first sub-plurality and the second sub-plurality of filters). In some embodiments, a system for qualifying a subject for provision of an over-the-counter statin pharmaceutical composition includes instructions for applying only one plurality of re-assessment filters, e.g., only filters of a single plurality of re-assessment filters. In some embodiments, where the method, system, or software applies a single plurality of re-assessment filters, the plurality of re-assessment filters includes a plurality of re-assessment filters selected from the filters listed in Table 9, e.g., at least 2, 3, 4, 5, 6, 7, 8, or all 9 of the filters listed in Table 9. In some embodiments, where a filter listed in Table 9 corresponds to a filter listed in Table 2, Table 4, Table 6, or Table 7, a threshold level sufficient to fire the corresponding filter listed in Table 2, Table 4, Table 6, or Table 7, as described in detail above, is sufficient to fire the filter listed in Table 9.

TABLE 9

Example Re-assessment Filters

| Filter | Exemplary Criteria |
|---|---|
| 1f | a cardiac event filter |
| 2f | a cholesterol status filter |
| 3f | a pregnancy filter |
| 4f | a severe drug interaction filter |
| 5f | a liver condition filter |
| 6f | a muscle irregularity filter |
| 7f | an alcohol consumption filter |
| 8f | a moderate drug interaction filter |
| 9f | A kidney disorder filter |

In one aspect, the present disclosure provides a method for qualifying a human subject for an over-the-counter provision of a statin pharmaceutical composition. The method includes A) providing an assessment survey for obtaining a first information set from the subject, via a computer system having a processor programed to perform the assessment survey. The first information set including: a sex of the subject, an age of the subject, when the subject is a female, whether the subject is pregnant or breastfeeding, whether the subject is taking one or more compositions that interact with the statin pharmaceutical composition, whether the subject has ever had a cardiac event, a total cholesterol level of the subject, a low-density lipoprotein (LDL) cholesterol level of the subject, a high-density lipoprotein (HDL) cholesterol level of the subject, a triglyceride level of the subject, a systolic blood pressure of the subject, a diastolic blood pressure of the subject, whether the subject has a liver condition, an alcohol consumption status of the subject, and whether the subject has had an adverse reaction to a cholesterol lowering composition. The method includes B) applying an algorithm to the first information set, via a computer system having a processor programed to perform the algorithm. The algorithm i) runs all or a portion of the first information set against a first plurality of assessment filters. The subject is deemed not qualified for a statin treatment when a respective filter in the first plurality of assessment filters is fired and the method is terminated without authorizing provision of the statin pharmaceutical composition to the subject. The first plurality of assessment filters includes: an age filter that is fired at least when the first information set indicates the age of the subject fails to satisfy an age threshold for receiving the statin pharmaceutical composition, when the subject is a female, a pregnancy filter that is fired at least when the first information set indicates the subject is pregnant or breastfeeding, a severe drug interaction filter that is fired at least when the first information set indicates the subject is taking one or more compositions that interact with the statin pharmaceutical composition, wherein the one or more compositions are each contraindicated for co-administration with the statin pharmaceutical composition, a cardiac event filter that is fired at least when the first information set indicates the subject has had a documented cardiac event, a total cholesterol filter that is fired at least when the first information set indicates the subject has a total cholesterol level that fails to satisfy a ceiling total cholesterol level threshold, a LDL cholesterol filter that is fired at least when the first information set indicates the subject has a LDL cholesterol level that fails to satisfy a ceiling LDL cholesterol level threshold, a HDL cholesterol filter that is fired at least when the first information set indicates the subject has a HDL cholesterol level that fails to satisfy a ceiling HDL cholesterol level threshold, a triglyceride filter that is fired at least when the first information set indicates the subject has a triglyceride level that fails to satisfy a ceiling triglyceride level threshold, a blood pressure filter that is fired at least when the first information set indicates (i) the systolic blood pressure of the subject fails to satisfy a ceiling systolic blood pressure threshold or (ii) the diastolic blood pressure of the subject fails to satisfy a ceiling diastolic blood pressure threshold, an atherosclerotic cardiovascular disease (ASCVD) risk pooled cohort equation filter that is fired at least when an ASCVD risk derived from the first information set indicates the ASCVD risk of the subject fails to satisfy a ceiling ASCVD risk threshold, and a liver condition filter that is fired at least when the first information set indicates the subject has a liver condition. The algorithm also ii) runs all or a portion of the first information set against a second plurality of assessment filters. When a respective filter in the second plurality of assessment filters is fired, the subject is provided with a warning corresponding to the respective filter. The second plurality of assessment filters includes an alcohol consumption filter that is fired at least when the alcohol consumption status of the subject in the first information set fails to satisfy a ceiling alcohol consumption threshold, a first adverse reaction filter that is fired at least when the first information set indicates the subject has had an adverse reaction to a cholesterol-lowering drug, and a moderate drug interaction filter that is fired at least when the first information set indicates the subject is taking one or more compositions that interact with the statin pharmaceutical composition. The one or more compositions are each associated with a warning, but are not contraindicated, for co-administration with the statin pharmaceutical composition. The algorithm further iii) obtains acknowledgment from the subject confirming that the subject has discussed the risk factor associated with each warning issued to the subject by any filter in the second plurality of assessment filters with a physician; and iv) proceeds with a fulfillment process when (a) no filter in the first plurality of assessment filters has been fired and (b) the subject has acknowledged each warning associated with each filter in the second plurality of assessment filters that was fired. The fulfillment process including: storing an indication in a subject profile of an initial order for the statin pharmaceutical composition, communicating an over the counter drug facts label for the statin pharmaceutical composition to the subject, and authorizing, upon confirmation from the subject that the over the counter drug facts label has been received and read, provision of the statin pharmaceutical composition to the subject.

Initial Assessment

In some embodiments of the initial assessment methods, systems, and software described above, the age filter is fired when the first information set indicates the subject is a woman of childbearing age. In some embodiments, the age filter is fired when the first information set indicates the subject is less than 20 years of age. In some embodiments, the age filter is fired when the first information set indicates the subject is less than 20 years of age and male or less than 50 years of age and female. In some embodiments, the age filter is fired when the first information set indicates the age of the subject fails to satisfy a ceiling age threshold for receiving the statin pharmaceutical composition. In some embodiments, the age filter is fired when the first information set indicates the subject is more than 75 years of age.

In some embodiments of the initial assessment methods, systems, and software described above the pregnancy filter is fired when the first information set indicates the subject is female and planning on becoming pregnant.

In some embodiments of the initial assessment methods, systems, and software described above the second plurality of assessment filters includes a second adverse reaction filter that is fired at least when the first information set indicates that subject has had an adverse reaction to the cholesterol-lowering composition.

In some embodiments of the initial assessment methods, systems, and software described above, the statin pharmaceutical composition includes an active ingredient selected from the group consisting of fluvastatin, atorvastatin, pitavastatin, and lovastatin, and the severe drug interaction filter is fired at least when the first information set indicates the subject is taking cyclosporine.

In some embodiments of the initial assessment methods, systems, and software described above, the statin pharmaceutical composition includes an active ingredient selected from the group consisting of fluvastatin, lovastatin, and pravastatin, and the severe drug interaction filter is fired at least when the first information set indicates the subject is taking a cholesterol-lowering medication or a triglyceride-lowering medication.

In some embodiments of the initial assessment methods, systems, and software described above, the statin pharmaceutical composition includes an active ingredient selected from the group consisting of pitavastatin, lovastatin, and simvastatin, and the severe drug interaction filter is fired at least when the first information set indicates the subject is taking an anti-viral protease inhibitor.

In some embodiments of the initial assessment methods, systems, and software described above, the statin pharmaceutical composition includes fluvastatin as an active ingredient, and the severe drug interaction filter is fired at least when the first information set indicates the subject is taking warfarin.

In some embodiments of the initial assessment methods, systems, and software described above, the statin pharmaceutical composition includes lovastatin or simvastatin as an active ingredient, and the severe drug interaction filter is fired at least when the first information set indicates the subject is taking a strong CYP3A4 inhibitor.

In some embodiments of the initial assessment methods, systems, and software described above, the statin pharmaceutical composition includes rosuvastatin as an active ingredient, and the severe drug interaction filter is fired at least when the first information set indicates the subject is taking a drug selected from the group consisting of cyclosporine, a cholesterol-lowering medication, a triglyceride-lowering medication, and warfarin.

In some embodiments of the initial assessment methods, systems, and software described above, the cardiac event filter is fired when the first information set indicates the subject has had a heart attack, had a stroke, undergone a heart procedure, or has developed peripheral artery disease. In some embodiments, the cardiac event filter is fired when the first information set indicates that the subject is a young male without a familial history of premature heart disease.

In some embodiments of the initial assessment methods, systems, and software described above, the total cholesterol filter is fired when the first information set indicates the total cholesterol level of the subject is greater than 320 mg/dL. In some embodiments, the total cholesterol filter is fired when the first information set indicates the subject has a total cholesterol level that fails to satisfy a total cholesterol level threshold. In some embodiments, the total cholesterol filter is fired when the first information set indicates the total cholesterol level of the subject is less than 130 mg/dL.

In some embodiments of the initial assessment methods, systems, and software described above, the LDL cholesterol filter is fired when the first information set indicates the LDL cholesterol level of the subject is greater than 190 mg/dL. In some embodiments, the LDL cholesterol filter is fired when the first information set indicates the subject has a LDL cholesterol level that fails to satisfy a LDL cholesterol level threshold. In some embodiments, the LDL cholesterol filter is fired when the first information set indicates the LDL cholesterol level of the subject is less than 160 mg/dL. In some embodiments, the LDL cholesterol filter is fired when the first information set indicates the LDL cholesterol level of the subject is less than 160 mg/dL when the subject is an older male or a female and less than 70 mg/dL when the subject is a younger male with a familial history of premature heart disease.

In some embodiments of the initial assessment methods, systems, and software described above, the HDL cholesterol filter is fired when the first information set indicates the HDL cholesterol level of the subject is greater than 100 mg/dL. In some embodiments, the HDL cholesterol filter is fired when the first information set indicates the subject has a HDL cholesterol level that fails to satisfy a HDL cholesterol level threshold. In some embodiments, the HDL cholesterol filter is fired when the first information set indicates the HDL cholesterol level of the subject is less than 20 mg/dL.

In some embodiments of the initial assessment methods, systems, and software described above, the triglyceride filter is fired when the first information set indicates the triglyceride level of the subject is greater than 500 mg/dL.

In some embodiments of the initial assessment methods, systems, and software described above, the blood pressure filter is fired when the first information set indicates the systolic blood pressure of the subject is greater than 180 mmHg. In some embodiments, the blood pressure filter is fired when the first information set indicates the subject has a systolic blood pressure that fails to satisfy a systolic blood pressure threshold. In some embodiments, the blood pressure filter is fired when the first information set indicates the systolic blood pressure of the subject is less than 90 mmHg. In some embodiments, the blood pressure filter is fired when the first information set indicates the diastolic blood pressure of the subject is greater than 120 mmHg.

In some embodiments of the initial assessment methods, systems, and software described above, the first information set includes a race of the subject, whether the subject is taking a high blood pressure treatment, a diabetes status of the subject, and a smoking status of the subject. The ASCVD risk pooled cohort equation filter incorporates the age of the subject, the gender of the subject, the race of the subject, the total cholesterol level of the subject, the LDL cholesterol level of the subject, the HDL cholesterol level of the subject, the triglyceride level of the subject, the systolic blood pressure of the subject, the diastolic blood pressure of the subject, whether the subject is taking a medication for hypertension, the diabetes status of the subject, and the smoking status of the subject to derive a risk for ASCVD.

In some embodiments of the initial assessment methods, systems, and software described above, the ASCVD risk pooled cohort equation is implemented as a multivariable Cox proportional hazard regression.

In some embodiments of the initial assessment methods, systems, and software described above, the ASCVD risk pooled cohort equation filter is fired when the first information set indicates the subject has an ASCVD risk that is greater than a 20% 10-year risk. In some embodiments, the ASCVD risk pooled cohort equation filter is fired when the first information set indicates the subject has an ASCVD risk that fails to satisfy an ASCVD risk threshold. In some embodiments, the ASCVD risk pooled cohort equation filter is fired when the first information set indicates the subject has an ASCVD risk that is less than a 5% 10-year risk.

In some embodiments of the initial assessment methods, systems, and software described above, the algorithm bypasses firing the ASCVD risk pooled cohort equation filter when the first information set indicates, (i) the subject has an ASCVD risk that fails to satisfy the ASCVD risk threshold, (ii) the subject has diabetes, and (iii) the age of the subject satisfies a first ceiling diabetes age threshold for receiving the statin pharmaceutical composition. In some embodiments, the first ceiling diabetes age threshold for receiving the statin pharmaceutical composition is 50 years of age when the subject is a male and 60 years of age when the subject is a female.

In some embodiments of the initial assessment methods, systems, and software described above, the ASCVD risk pooled cohort equation filter is fired when the first information set indicates, (i) the subject has diabetes, and (ii) the age of the subject does not satisfy a second ceiling diabetes age threshold for receiving the statin pharmaceutical composition. In some embodiments, the second ceiling diabetes age threshold for receiving the statin pharmaceutical composition is 50 years of age when the subject is a male and 60 years of age when the subject is a female.

In some embodiments of the initial assessment methods, systems, and software described above, the algorithm bypasses the ASCVD risk pooled cohort equation filter when the first information set indicates when the subject is a younger male. In some embodiments, the algorithm bypasses the total cholesterol filter when the first information set indicates when the subject is a younger male. In some embodiments, the algorithm bypasses the HDL cholesterol filter when the first information set indicates when the subject is a younger male. In some embodiments, the algorithm bypasses the blood pressure filter when the first information set indicates when the subject is a younger male.

In some embodiments of the initial assessment methods, systems, and software described above, the statin pharmaceutical composition includes rosuvastatin as an active ingredient, and the second plurality of assessment filters includes a kidney disorder filter that is fired at least when the first information set indicates that the subject has kidney disease.

In some embodiments of the initial assessment methods, systems, and software described above, the statin pharmaceutical composition includes an active ingredient selected from the group consisting of fluvastatin, atorvastatin, and pitavastatin, and the second plurality of filters includes a kidney disorder filter that is fired at least when the first information set indicates that the subject has kidney disease.

In some embodiments of the initial assessment methods, systems, and software described above, the ceiling amount of alcohol for firing the alcohol consumption filter is two alcoholic drinks per day.

In some embodiments of the initial assessment methods, systems, and software described above, the statin pharmaceutical composition includes rosuvastatin as an active ingredient, and the moderate drug interaction filter is fired at least when the first information set indicates the subject is taking colchicine or an anti-viral protease inhibitor.

In some embodiments of the initial assessment methods, systems, and software described above, the first plurality of assessment filters includes a risk enhancing factor filter that is fired unless the first information set indicates that the subject has at least one of a plurality of risk enhancing factors for high cholesterol. In some embodiments, the first plurality of assessment filters includes a risk enhancing factor filter that is fired unless the first information set indicates that the subject has at least two of a plurality of risk enhancing factors for high cholesterol.

In some embodiments of the initial assessment methods, systems, and software described above, the first plurality of assessment filters includes a risk enhancing factor filter that is fired when the first information set indicates the subject has an ASCVD risk that fails to satisfy an intermediate ASCVD risk threshold, unless the first information set indicates the subject has at least one of a plurality of risk enhancing factors for high cholesterol.

In some embodiments of the initial assessment methods, systems, and software described above, the first plurality of assessment filters includes a risk enhancing factor filter that is fired when the first information set indicates the subject has an ASCVD risk that fails to satisfy an intermediate ASCVD risk threshold, unless the first information set indicates the subject has at least two of a plurality of risk enhancing factors for high cholesterol.

In some embodiments of the initial assessment methods, systems, and software described above, the ASCVD risk of the subject is derived from a pooled cohort algorithm that incorporates the age of the subject, the gender of the subject, the race of the subject, the total cholesterol level of the subject, the LDL cholesterol level of the subject, the HDL cholesterol level of the subject, the triglyceride level of the subject, the systolic blood pressure of the subject, the diastolic blood pressure of the subject, whether the subject is taking a medication for hypertension, the diabetes status of the subject, and the smoking status of the subject. In some embodiments, the ASCVD risk is derived from a pooled cohort algorithm implementing a multivariable Cox proportional hazard regression. In some embodiments, the intermediate ASCVD risk threshold is a 7.5% 10-year risk.

In some embodiments, the plurality of risk enhancing factors that prevent firing of the risk enhancing factor filter include South Asian descent, a familial history of premature heart disease, a LDL cholesterol level of at least 160 mg/dL, a triglyceride level of at least 175 mg/dL, an inflammatory disease, preeclampsia, premature menopause, a C-Reactive Protein (CRP) level of at least 2 mg/L, coronary artery calcium, and metabolic syndrome. In some embodiments, wherein the subject is deemed to have the metabolic syndrome when the first information set indicates the subject has: (i) an HDL cholesterol level of less than 40 mg/dL, (ii) a triglyceride level of greater than 150 mg/dL, and (iii) a systolic blood pressure of at least 130 mmHg, a diastolic blood pressure of at least 85 mmHg, or a current blood pressure medication regimen when the subject has a systolic blood pressure of less than 130 mmHg and a diastolic blood pressure of less than 85 mmHg.

In some embodiments, the subject is deemed to have the metabolic syndrome when the first information set indicates the subject has: (A) a waist circumference of at least 35 inches for a female or at least 40 inches for a male, and (B) at least two of: (i) a HDL cholesterol level of less than 40 mg/dL, (ii) a triglyceride level of greater than 150 mg/dL, and (iii) a systolic blood pressure of at least 130 mmHg, a diastolic blood pressure of at least 85 mmHg, or a current blood pressure medication regimen when the subject has a systolic blood pressure of less than 130 mmHg and a diastolic blood pressure of less than 85 mmHg.

In some embodiments, upon confirmation from the subject that the over the counter drug facts label has been received and read, the subject is authorized for provision of a dosage of from 2.5 mg to 15 mg of rosuvastatin per day.

In some embodiments, upon confirmation from the subject that the over the counter drug facts label has been received and read, the subject is authorized for provision of a dosage of 5 mg of rosuvastatin per day.

In some embodiments, upon confirmation from the subject that the over the counter drug facts label has been received and read, the subject is authorized for provision of a dosage of from 20 mg to 40 mg of fluvastatin per day.

In some embodiments, upon confirmation from the subject that the over the counter drug facts label has been received and read, the subject is authorized for provision of a dosage of from 10 mg to 40 mg of atorvastatin per day.

In some embodiments, upon confirmation from the subject that the over the counter drug facts label has been received and read, the subject is authorized for provision of a dosage of from 1 mg to 4 mg of pitavastatin per day.

In some embodiments, upon confirmation from the subject that the over the counter drug facts label has been received and read, the subject is authorized for provision of a dosage of from 10 mg to 40 mg of lovastatin per day.

In some embodiments, upon confirmation from the subject that the over the counter drug facts label has been received and read, the subject is authorized for provision of a dosage of from 10 mg to 40 mg of pravastatin per day.

In some embodiments, upon confirmation from the subject that the over the counter drug facts label has been received and read, the subject is authorized for provision of a dosage of from 5 mg to 20 mg of simvastatin per day.

In some embodiments, the method also includes administering, after authorization of the provision, the statin pharmaceutical composition to the subject.

Reassessment

In some embodiments of the reassessment methods, systems, and software described above, the method is terminated without authorizing re-provision of the statin pharmaceutical composition to the subject when more than a threshold period of time has passed since the subject received their first provision of the statin pharmaceutical composition without retesting their cholesterol level. In some embodiments, the threshold period of time since the subject received their first provision of the statin pharmaceutical composition without retesting their cholesterol level, for terminating the method, is 90 days.

In some embodiments of the reassessment methods, systems, and software described above, the method is terminated without authorizing re-provision of the statin pharmaceutical composition to the subject when less than a threshold period of time has passed since the subject received their last provision of the statin pharmaceutical composition. In some embodiments, the subject's last provision of the statin pharmaceutical composition included daily dosages of the statin pharmaceutical composition for a predetermined number of days, and the threshold period of time since the subject received their last provision of the statin pharmaceutical composition, for terminating the method, is a period of time greater than half the predetermined number of days.

In some embodiments of the reassessment methods, systems, and software described above, the cardiac event filter is fired when the second information set indicates the subject had a heart attack, had a stroke, has undergone a heart procedure, or has developed peripheral artery disease since receiving their last provision of the statin pharmaceutical composition.

In some embodiments of the reassessment methods, systems, and software described above, the algorithm bypasses the cholesterol status filter when the subject reported a reduction of their cholesterol by more than the threshold amount during a previous re-order of the statin pharmaceutical composition.

In some embodiments of the reassessment methods, systems, and software described above, the algorithm bypasses the cholesterol status filter when the second information set indicates the subject, (i) has not yet retested their cholesterol following their first provision of the statin pharmaceutical composition, and (ii) has ordered the statin pharmaceutical composition less than three times.

In some embodiments of the reassessment methods, systems, and software described above, the method is terminated without authorizing re-provision of the statin pharmaceutical composition to the subject when the second information set indicates the subject: (i) has not yet retested their cholesterol following their first provision of the statin pharmaceutical composition, and (ii) has ordered the statin pharmaceutical composition at least three times.

In some embodiments of the reassessment methods, systems, and software described above, the statin pharmaceutical composition includes an active ingredient selected from the group consisting of fluvastatin, atorvastatin, pitavastatin, and lovastatin, and the severe drug interaction filter is fired at least when the second information set indicates the subject is taking cyclosporine.

In some embodiments of the reassessment methods, systems, and software described above, the statin pharmaceutical composition includes an active ingredient selected from the group consisting of fluvastatin, lovastatin, and pravastatin, and the severe drug interaction filter is fired at least when the second information set indicates the subject is taking a cholesterol-lowering medication or a triglyceride-lowering medication.

In some embodiments of the reassessment methods, systems, and software described above, the statin pharmaceutical composition includes an active ingredient selected from the group consisting of pitavastatin, lovastatin, and simvastatin, and the severe drug interaction filter is fired at least when the second information set indicates the subject is taking an anti-viral protease inhibitor.

In some embodiments of the reassessment methods, systems, and software described above, the statin pharmaceutical composition includes fluvastatin as an active ingredient, and the severe drug interaction filter is fired at least when the second information set indicates the subject is taking warfarin.

In some embodiments of the reassessment methods, systems, and software described above, the statin pharmaceutical composition includes lovastatin or simvastatin as an active ingredient, and the severe drug interaction filter is fired at least when the second information set indicates the subject is taking a strong CYP3A4 inhibitor.

In some embodiments of the reassessment methods, systems, and software described above, the statin pharmaceutical composition includes rosuvastatin as an active ingredient, and the severe drug interaction filter is fired at least when the second information set indicates the subject is taking a drug selected from the group consisting of cyclosporine, a cholesterol-lowering medication, a triglyceride-lowering medication, and warfarin.

In some embodiments of the reassessment methods, systems, and software described above, the statin pharmaceutical composition includes rosuvastatin as an active ingredient, and the second plurality of re-assessment filters includes a kidney disorder filter that is fired at least when the second information set indicates the subject has developed kidney problems or experienced worsening of a previous kidney problem since receiving their last provision of the statin pharmaceutical composition.

In some embodiments of the reassessment methods, systems, and software described above, the statin pharmaceutical composition includes an active ingredient selected from the group consisting of fluvastatin, atorvastatin, and pitavastatin, and the second plurality of re-assessment filters includes a kidney disorder filter that is fired at least when the second information set indicates the subject has developed kidney problems or experienced worsening of a previous kidney problem since receiving their last provision of the statin pharmaceutical composition.

In some embodiments of the reassessment methods, systems, and software described above, the statin pharmaceutical composition includes rosuvastatin as an active ingredient, and the moderate drug interaction filter is fired at least when the second information set indicates the subject is taking colchicine or an anti-viral protease inhibitor.

In some embodiments, upon confirmation from the subject that the over the counter drug facts label has been received and read, the subject is authorized for provision of a dosage of from 2.5 mg to 15 mg of rosuvastatin per day.

In some embodiments, upon confirmation from the subject that the over the counter drug facts label has been received and read, the subject is authorized for provision of a dosage of 5 mg of rosuvastatin per day.

In some embodiments, upon confirmation from the subject that the over the counter drug facts label has been received and read, the subject is authorized for provision of a dosage of from 20 mg to 40 mg of fluvastatin per day.

In some embodiments, upon confirmation from the subject that the over the counter drug facts label has been received and read, the subject is authorized for provision of a dosage of from 10 mg to 40 mg of atorvastatin per day.

In some embodiments, upon confirmation from the subject that the over the counter drug facts label has been received and read, the subject is authorized for provision of a dosage of from 1 mg to 4 mg of pitavastatin per day.

In some embodiments, upon confirmation from the subject that the over the counter drug facts label has been received and read, the subject is authorized for provision of a dosage of from 10 mg to 40 mg of lovastatin per day.

In some embodiments, upon confirmation from the subject that the over the counter drug facts label has been received and read, the subject is authorized for provision of a dosage of from 10 mg to 40 mg of pravastatin per day.

In some embodiments, upon confirmation from the subject that the over the counter drug facts label has been received and read, the subject is authorized for provision of a dosage of from 5 mg to 20 mg of simvastatin per day.

In some embodiments, the method also includes administering, after authorization of the provision, the statin pharmaceutical composition to the subject.

EXAMPLES

The following examples provide example implementations of the methods, systems, and software described herein for various statin pharmaceutical compositions. However, these examples do not imply that these are the only useful implementations of the methods, systems, and software described herein for each individual statin pharmaceutical agent. The skilled artisan will know how to change each of these implementations according to their particular goals and desired safety profiles, e.g., based on the identity and/or dosage of the statin active ingredient. For instance, kidney disease filters are not included in some of the examples given below. However, in some embodiments the skilled artisan may be motivated to add such a filter to a particular system. For instance, while renal impairment is not a classical risk factor for low dose pravastatin pharmaceutical compositions, severe renal impairment is a known predisposition factor for myopathy and, thus, the skilled artisan may choose to implement a kidney disease filter in a system for qualifying patients to receive OTC pravastatin.

Example 1: A computer system is prepared for qualifying a human subject for delivery of a rosuvastatin pharmaceutical composition (e.g., low-dose CRESTOR) over the counter to treat or prevent an atherosclerotic cardiovascular disease (e.g., by lowering cholesterol).

The computer system includes instructions for conducting a survey of the subject, to obtain an age of the subject, a gender of the subject, if the subject is female, whether they are (i) pregnant, (ii) breastfeeding, or (iii) planning to become pregnant, a race of the subject, whether the subject is taking one or more medications that interact with the statin pharmaceutical composition (e.g., cyclosporine, warfarin, colchicine, lipid-lowering medications such as fibrates, and/or an anti-viral protease inhibitors), whether the subject has ever had an atherosclerotic cardiovascular event or had a heart procedure, whether the subject has a family history of premature ASCVD events, a total cholesterol level of the subject, an LDL cholesterol level of the subject, an HDL cholesterol level of the subject, a triglyceride level of the subject, a systolic blood pressure of the subject, a diastolic blood pressure of the subject, whether the subject is taking a medication for high blood pressure, whether the subject has diabetes, whether the subject is a smoker, whether the subject has or has ever had liver disease, whether the subject has or has ever had kidney disease, an alcohol consumption status of the subject, and whether the subject has ever has an adverse reaction to a cholesterol lowering medication.

The computer system runs survey results against a first series of filters that each prevents authorization for delivery of the OTC rosuvastatin where the subject's survey results identify a contraindication for the OTC rosuvastatin. The first series of filters includes an age filter, a pregnancy filter, a severe drug interaction filter, a cardiac event filter, a total cholesterol level filter, an LDL cholesterol level filter, an HDL cholesterol level filter, a triglyceride level filter, a blood pressure filter, an ASCVD risk filter, a liver disease filter, and a risk enhancement factor filter.

The computer system runs survey results against a second series of filters that each generates a warning where the subject's survey results identify a risk factor for OTC rosuvastatin. The second series of filters includes a kidney disease filter, an alcohol consumption filter, an adverse reaction filter, and a moderate drug interaction filter. The computer system then prompts the subject to acknowledge or deny having discussed any warning generated by the second series of filters with a medical professional (e.g., their physician).

The computer system then proceeds with a fulfillment process only when (i) none of the first series of filters was fired (ii) the subject acknowledged that they discussed each warning issued in association with the second series of filters that was fired. The computer system stores an indication of an initial order of the OTC rosuvastatin in a subject profile, and communicates an over the counter drug facts label for the rosuvastatin pharmaceutical composition to the subject. Upon confirmation from the subject that they have received and read the over the counter drug facts label, the computer system authorizes provision of the OTC rosuvastatin pharmaceutical composition to the subject.

Example 2: A computer system is prepared for qualifying a human subject for delivery of an atorvastatin pharmaceutical composition (e.g., low-dose LIPITOR) over the counter to treat or prevent an atherosclerotic cardiovascular disease (e.g., by lowering cholesterol).

The computer system includes instructions for conducting a survey of the subject, to obtain an age of the subject, a gender of the subject, if the subject is female, whether they are (i) pregnant, (ii) breastfeeding, or (iii) planning to become pregnant, a race of the subject, whether the subject is taking one or more medications that interact with the statin pharmaceutical composition (e.g., cyclosporine, colchicine, lipid-lowering medications such as fibrates, and/or an anti-viral protease inhibitors), whether the subject has ever had an atherosclerotic cardiovascular event or had a heart procedure, whether the subject has a family history of premature ASCVD events, a total cholesterol level of the subject, an LDL cholesterol level of the subject, an HDL cholesterol level of the subject, a triglyceride level of the subject, a systolic blood pressure of the subject, a diastolic blood pressure of the subject, whether the subject is taking a medication for high blood pressure, whether the subject has diabetes, whether the subject is a smoker, whether the subject has or has ever had liver disease, whether the subject has or has ever had kidney disease, an alcohol consumption status of the subject, and whether the subject has ever has an adverse reaction to a cholesterol lowering medication.

The computer system runs survey results against a first series of filters that each prevents authorization for delivery of the OTC atorvastatin where the subject's survey results identify a contraindication for the OTC atorvastatin. The first series of filters includes an age filter, a pregnancy filter, a severe drug interaction filter, a cardiac event filter, a total cholesterol level filter, an LDL cholesterol level filter, an HDL cholesterol level filter, a triglyceride level filter, a blood pressure filter, an ASCVD risk filter, a liver disease filter, and a risk enhancement factor filter.

The computer system runs survey results against a second series of filters that each generates a warning where the subject's survey results identify a risk factor for OTC atorvastatin. The second series of filters includes a kidney disease filter, an alcohol consumption filter, an adverse reaction filter, and a moderate drug interaction filter. The computer system then prompts the subject to acknowledge or deny having discussed any warning generated by the second series of filters with a medical professional (e.g., their physician).

The computer system then proceeds with a fulfillment process only when (i) none of the first series of filters was fired (ii) the subject acknowledged that they discussed each warning issued in association with the second series of filters that was fired. The computer system stores an indication of an initial order of the OTC atorvastatin in a subject profile, and communicates an over the counter drug facts label for the atorvastatin pharmaceutical composition to the subject. Upon confirmation from the subject that they have received and read the over the counter drug facts label, the computer system authorizes provision of the OTC atorvastatin pharmaceutical composition to the subject.

Example 3: A computer system is prepared for qualifying a human subject for delivery of a simvastatin pharmaceutical composition (e.g., low-dose Zocor) over the counter to treat or prevent an atherosclerotic cardiovascular disease (e.g., by lowering cholesterol).

The computer system includes instructions for conducting a survey of the subject, to obtain an age of the subject, a gender of the subject, if the subject is female, whether they are (i) pregnant, (ii) breastfeeding, or (iii) planning to become pregnant, a race of the subject, whether the subject is taking one or more medications that interact with the statin pharmaceutical composition (e.g., cyclosporine, warfarin, colchicine, lipid-lowering medications such as fibrates, strong CYP3A4 inhibitors, and/or an anti-viral protease inhibitors), whether the subject has ever had an atherosclerotic cardiovascular event or had a heart procedure, whether the subject has a family history of premature ASCVD events, a total cholesterol level of the subject, an LDL cholesterol level of the subject, an HDL cholesterol level of the subject, a triglyceride level of the subject, a systolic blood pressure of the subject, a diastolic blood pressure of the subject, whether the subject is taking a medication for high blood pressure, whether the subject has diabetes, whether the subject is a smoker, whether the subject has or has ever had liver disease, an alcohol consumption status of the subject, and whether the subject has ever has an adverse reaction to a cholesterol lowering medication.

The computer system runs survey results against a first series of filters that each prevents authorization for delivery of the OTC simvastatin where the subject's survey results identify a contraindication for the OTC simvastatin. The first series of filters includes an age filter, a pregnancy filter, a severe drug interaction filter, a cardiac event filter, a total cholesterol level filter, an LDL cholesterol level filter, an HDL cholesterol level filter, a triglyceride level filter, a blood pressure filter, an ASCVD risk filter, a liver disease filter, and a risk enhancement factor filter.

The computer system runs survey results against a second series of filters that each generates a warning where the subject's survey results identify a risk factor for OTC simvastatin. The second series of filters includes an alcohol consumption filter, an adverse reaction filter, and a moderate drug interaction filter. The computer system then prompts the subject to acknowledge or deny having discussed any warning generated by the second series of filters with a medical professional (e.g., their physician).

The computer system then proceeds with a fulfillment process only when (i) none of the first series of filters was fired (ii) the subject acknowledged that they discussed each warning issued in association with the second series of filters that was fired. The computer system stores an indication of an initial order of the OTC simvastatin in a subject profile, and communicates an over the counter drug facts label for the simvastatin pharmaceutical composition to the subject. Upon confirmation from the subject that they have received and read the over the counter drug facts label, the computer system authorizes provision of the OTC simvastatin pharmaceutical composition to the subject.

Example 4: A computer system is prepared for qualifying a human subject for delivery of a pravastatin pharmaceutical composition (e.g., low-dose PRAVACHOL) over the counter to treat or prevent an atherosclerotic cardiovascular disease (e.g., by lowering cholesterol).

The computer system includes instructions for conducting a survey of the subject, to obtain an age of the subject, a gender of the subject, if the subject is female, whether they are (i) pregnant, (ii) breastfeeding, or (iii) planning to become pregnant, a race of the subject, whether the subject is taking one or more medications that interact with the statin pharmaceutical composition (e.g., cyclosporine, colchicine, and/or lipid-lowering medications such as fibrates), whether the subject has ever had an atherosclerotic cardiovascular event or had a heart procedure, whether the subject has a family history of premature ASCVD events, a total cholesterol level of the subject, an LDL cholesterol level of the subject, an HDL cholesterol level of the subject, a triglyceride level of the subject, a systolic blood pressure of the subject, a diastolic blood pressure of the subject, whether the subject is taking a medication for high blood pressure, whether the subject has diabetes, whether the subject is a smoker, whether the subject has or has ever had liver disease, an alcohol consumption status of the subject, and whether the subject has ever has an adverse reaction to a cholesterol lowering medication.

The computer system runs survey results against a first series of filters that each prevents authorization for delivery of the OTC pravastatin where the subject's survey results identify a contraindication for the OTC pravastatin. The first series of filters includes an age filter, a pregnancy filter, a severe drug interaction filter, a cardiac event filter, a total cholesterol level filter, an LDL cholesterol level filter, an HDL cholesterol level filter, a triglyceride level filter, a blood pressure filter, an ASCVD risk filter, a liver disease filter, and a risk enhancement factor filter.

The computer system runs survey results against a second series of filters that each generates a warning where the subject's survey results identify a risk factor for OTC pravastatin. The second series of filters includes a an alcohol consumption filter, an adverse reaction filter, and a moderate drug interaction filter. The computer system then prompts the subject to acknowledge or deny having discussed any warning generated by the second series of filters with a medical professional (e.g., their physician).

The computer system then proceeds with a fulfillment process only when (i) none of the first series of filters was fired (ii) the subject acknowledged that they discussed each warning issued in association with the second series of filters that was fired. The computer system stores an indication of an initial order of the OTC pravastatin in a subject profile, and communicates an over the counter drug facts label for the pravastatin pharmaceutical composition to the subject. Upon confirmation from the subject that they have received and read the over the counter drug facts label, the computer system authorizes provision of the OTC pravastatin pharmaceutical composition to the subject.

Example 5: A computer system is prepared for qualifying a human subject for delivery of a fluvastatin pharmaceutical composition (e.g., low-dose LESCOL XL) over the counter to treat or prevent an atherosclerotic cardiovascular disease (e.g., by lowering cholesterol).

The computer system includes instructions for conducting a survey of the subject, to obtain an age of the subject, a gender of the subject, if the subject is female, whether they are (i) pregnant, (ii) breastfeeding, or (iii) planning to become pregnant, a race of the subject, whether the subject is taking one or more medications that interact with the statin pharmaceutical composition (e.g., cyclosporine, warfarin, colchicine, lipid-lowering medications such as fibrates, an anti-fungal agent such as fluconazole, and/or an anti-epileptic agent such as phenytoin), whether the subject has ever had an atherosclerotic cardiovascular event or had a heart procedure, whether the subject has a family history of premature ASCVD events, a total cholesterol level of the subject, an LDL cholesterol level of the subject, an HDL cholesterol level of the subject, a triglyceride level of the subject, a systolic blood pressure of the subject, a diastolic blood pressure of the subject, whether the subject is taking a medication for high blood pressure, whether the subject has diabetes, whether the subject is a smoker, whether the subject has or has ever had liver disease, whether the subject has or has ever had kidney disease, an alcohol consumption status of the subject, whether the subject has thyroid problems, and whether the subject has ever has an adverse reaction to a cholesterol lowering medication.

The computer system runs survey results against a first series of filters that each prevents authorization for delivery of the OTC fluvastatin where the subject's survey results identify a contraindication for the OTC fluvastatin. The first series of filters includes an age filter, a pregnancy filter, a severe drug interaction filter, a cardiac event filter, a total cholesterol level filter, an LDL cholesterol level filter, an HDL cholesterol level filter, a triglyceride level filter, a blood pressure filter, an ASCVD risk filter, a liver disease filter, and a risk enhancement factor filter.

The computer system runs survey results against a second series of filters that each generates a warning where the subject's survey results identify a risk factor for OTC fluvastatin. The second series of filters includes a kidney disease filter, an alcohol consumption filter, an adverse reaction filter, a thyroid problem filter, and a moderate drug interaction filter. The computer system then prompts the subject to acknowledge or deny having discussed any warning generated by the second series of filters with a medical professional (e.g., their physician).

The computer system then proceeds with a fulfillment process only when (i) none of the first series of filters was fired (ii) the subject acknowledged that they discussed each warning issued in association with the second series of filters that was fired. The computer system stores an indication of an initial order of the OTC fluvastatin in a subject profile, and communicates an over the counter drug facts label for the fluvastatin pharmaceutical composition to the subject. Upon confirmation from the subject that they have received and read the over the counter drug facts label, the computer system authorizes provision of the OTC fluvastatin pharmaceutical composition to the subject.

Example 6: A computer system is prepared for qualifying a human subject for delivery of a pitavastatin pharmaceutical composition (e.g., low-dose LIVALO) over the counter to treat or prevent an atherosclerotic cardiovascular disease (e.g., by lowering cholesterol).

The computer system includes instructions for conducting a survey of the subject, to obtain an age of the subject, a gender of the subject, if the subject is female, whether they are (i) pregnant, (ii) breastfeeding, or (iii) planning to become pregnant, a race of the subject, whether the subject is taking one or more medications that interact with the statin pharmaceutical composition (e.g., cyclosporine, colchicine, and/or lipid-lowering medications such as fibrates), whether the subject has ever had an atherosclerotic cardiovascular event or had a heart procedure, whether the subject has a family history of premature ASCVD events, a total cholesterol level of the subject, an LDL cholesterol level of the subject, an HDL cholesterol level of the subject, a triglyceride level of the subject, a systolic blood pressure of the subject, a diastolic blood pressure of the subject, whether the subject is taking a medication for high blood pressure, whether the subject has diabetes, whether the subject is a smoker, whether the subject has or has ever had liver disease, and whether the subject has ever has an adverse reaction to a cholesterol lowering medication.

The computer system runs survey results against a first series of filters that each prevents authorization for delivery of the OTC pitavastatin where the subject's survey results identify a contraindication for the OTC pitavastatin. The first series of filters includes an age filter, a pregnancy filter, a severe drug interaction filter, a cardiac event filter, a total cholesterol level filter, an LDL cholesterol level filter, an HDL cholesterol level filter, a triglyceride level filter, a blood pressure filter, an ASCVD risk filter, a liver disease filter, and a risk enhancement factor filter.

The computer system runs survey results against a second series of filters that each generates a warning where the subject's survey results identify a risk factor for OTC pitavastatin. The second series of filters includes an adverse reaction filter and a moderate drug interaction filter. The computer system then prompts the subject to acknowledge or deny having discussed any warning generated by the second series of filters with a medical professional (e.g., their physician).

The computer system then proceeds with a fulfillment process only when (i) none of the first series of filters was fired (ii) the subject acknowledged that they discussed each warning issued in association with the second series of filters that was fired. The computer system stores an indication of an initial order of the OTC pitavastatin in a subject profile, and communicates an over the counter drug facts label for the pitavastatin pharmaceutical composition to the subject. Upon confirmation from the subject that they have received and read the over the counter drug facts label, the computer system authorizes provision of the OTC pitavastatin pharmaceutical composition to the subject.

Example 7: A computer system is prepared for qualifying a human subject for delivery of a lovastatin pharmaceutical composition (e.g., low-dose MEVACOR) over the counter to treat or prevent an atherosclerotic cardiovascular disease (e.g., by lowering cholesterol).

The computer system includes instructions for conducting a survey of the subject, to obtain an age of the subject, a gender of the subject, if the subject is female, whether they are (i) pregnant, (ii) breastfeeding, or (iii) planning to become pregnant, a race of the subject, whether the subject is taking one or more medications that interact with the statin pharmaceutical composition (e.g., cyclosporine, colchicine, lipid-lowering medications such as fibrates, strong CYP3A inhibitors, and/or an anti-viral protease inhibitors), whether the subject has ever had an atherosclerotic cardiovascular event or had a heart procedure, whether the subject has a family history of premature ASCVD events, a total cholesterol level of the subject, an LDL cholesterol level of the subject, an HDL cholesterol level of the subject, a triglyceride level of the subject, a systolic blood pressure of the subject, a diastolic blood pressure of the subject, whether the subject is taking a medication for high blood pressure, whether the subject has diabetes, whether the subject is a smoker, whether the subject has or has ever had liver disease, an alcohol consumption status of the subject, and whether the subject ever has an adverse reaction to a cholesterol lowering medication.

The computer system runs survey results against a first series of filters that each prevents authorization for delivery of the OTC lovastatin where the subject's survey results identify a contraindication for the OTC lovastatin. The first series of filters includes an age filter, a pregnancy filter, a severe drug interaction filter, a cardiac event filter, a total cholesterol level filter, an LDL cholesterol level filter, an HDL cholesterol level filter, a triglyceride level filter, a blood pressure filter, an ASCVD risk filter, a liver disease filter, and a risk enhancement factor filter.

The computer system runs survey results against a second series of filters that each generates a warning where the subject's survey results identify a risk factor for OTC lovastatin. The second series of filters includes an alcohol consumption filter, an adverse reaction filter, and a moderate drug interaction filter. The computer system then prompts the subject to acknowledge or deny having discussed any warning generated by the second series of filters with a medical professional (e.g., their physician).

The computer system then proceeds with a fulfillment process only when (i) none of the first series of filters was fired (ii) the subject acknowledged that they discussed each warning issued in association with the second series of filters that was fired. The computer system stores an indication of an initial order of the OTC lovastatin in a subject profile, and communicates an over the counter drug facts label for the lovastatin pharmaceutical composition to the subject. Upon confirmation from the subject that they have received and read the over the counter drug facts label, the computer system authorizes provision of the OTC lovastatin pharmaceutical composition to the subject.

REFERENCES CITED AND ALTERNATIVE EMBODIMENTS

All references cited herein are incorporated herein by reference in their entirety and for all purposes to the same extent as if each individual publication or patent or patent application was specifically and individually indicated to be incorporated by reference in its entirety for all purposes.

The present invention can be implemented as a computer program product that includes a computer program mechanism embedded in a non-transitory computer readable storage medium. For instance, the computer program product could contain the program modules shown in any combination of FIGS. 1, 2, and 3 and/or described in FIG. 4 or 5. These program modules can be stored on a CD-ROM, DVD, magnetic disk storage product, USB key, or any other non-transitory computer readable data or program storage product.

Many modifications and variations of this invention can be made without departing from its spirit and scope, as will be apparent to those skilled in the art. The specific embodiments described herein are offered by way of example only. The embodiments were chosen and described in order to best explain the principles of the invention and its practical applications, to thereby enable others skilled in the art to best utilize the invention and various embodiments with various modifications as are suited to the particular use contemplated. The invention is to be limited only by the terms of the appended claims, along with the full scope of equivalents to which such claims are entitled.

What is claimed is:

1. A method of managing cholesterol in a subject, the method comprising:
    at a computer system comprising one or more processors and a memory, the memory comprising non-transitory instructions which, when executed by the one or more processor, perform an algorithm comprising:
        a) receiving a request for a statin pharmaceutical composition;
        b) obtaining information, about the subject, comprising:
            an age of the subject,
            a gender of the subject,
            when the subject is female, whether the subject is pregnant or breastfeeding,
            a race with which the subject identifies,
            whether the subject is taking one or more medications that interact with the statin pharmaceutical composition,
            whether the subject has had an atherosclerotic cardiovascular event;
            data required by a pooled cohort equation that calculates a risk of the subject developing an atherosclerotic disease;
            whether the subject has liver disease,
            an alcohol consumption status of the subject, and
            whether the subject has had an adverse reaction to a cholesterol lowering medication;
        c) comparing all or a portion of the information about the subject against a plurality of filters, wherein the plurality of filters comprises a filter of a first type and a filter of a second type and, when a respective filter in the plurality of filters is fired by the comparing, the subject is deemed unqualified for delivery of the statin pharmaceutical composition when the respective filter is of the first type or the subject is provided with a warning corresponding to the respective filter when the respective filter is of the second type, and wherein the plurality of filters comprises:
            an age filter,
            a pregnancy filter,
            a drug interaction filter,
            an atherosclerotic cardiovascular event filter;
            a pooled cohort equation filter,
            a liver disease filter,
            an alcohol consumption filter, and
            an adverse reaction filter; and
        d) when each filter in the plurality of filters that is configured to deem the subject unqualified for delivery of the statin pharmaceutical composition when fired has not been fired:
            obtaining a corresponding acknowledgement from the subject for each respective warning associated with each filter in the plurality of filters that was fired in the comparing c) that is not configured to deem the subject unqualified for delivery of the statin pharmaceutical composition when fired, wherein the corresponding acknowledgment is confirmation that the subject has discussed the respective warning with a medical practitioner, and
            authorizing a provision of the statin pharmaceutical composition; the method further comprising:
    administering the statin pharmaceutical composition to the subject, upon authorization of the provision, to manage cholesterol in the subject.

2. The method of claim 1, wherein the information further comprises whether the subject, when female, is planning to become pregnant.

3. The method of claim 1, wherein the information further comprises whether the one or more medications that interact with the statin pharmaceutical composition includes cyclosporine.

4. The method of claim 1, wherein the information further comprises whether the atherosclerotic cardiovascular event includes having a heart procedure.

5. The method of claim 1, wherein the data required by the pooled cohort equation comprises:
 a total cholesterol level of the subject,
 an HDL cholesterol count of the subject,
 a systolic blood pressure of the subject,
 whether the subject is taking a high blood pressure medication,
 a diabetes status of the subject, and
 a smoking status of the subject.

6. The method of claim 1, wherein the plurality of filters further comprises a total cholesterol level filter.

7. The method of claim 1, wherein the algorithm further comprises communicating an over-the-counter facts label for the statin pharmaceutical composition to the subject before the authorization of the provision.

8. The method of claim 7, wherein the algorithm further comprises receiving confirmation from the subject that the over-the-counter facts label for the statin pharmaceutical composition has been received and read by the subject before the authorization of the provision.

9. The method of claim 1, wherein the authorizing d) further comprises storing an indication in a subject profile of the order for the statin pharmaceutical composition.

10. The method of claim 1, wherein the subject has a coronary heart disease, a cerebrovascular disease, a peripheral artery disease, or an aortic atherosclerotic disease.

11. The method of claim 1, wherein the age filter is fired when the information indicates that the subject is over the age of 75.

12. The method of claim 1 wherein, when the age filter is fired, the subject is provided with a warning.

13. The method of claim 1, wherein the pregnancy filter is fired when the information indicates that the subject is (i) pregnant, (ii) breastfeeding, or (iii) planning to become pregnant.

14. The method of claim 13, wherein when the pregnancy filter is fired the pregnancy filter deems the subject unqualified for delivery of the statin pharmaceutical composition.

15. The method of claim 1, wherein the drug interaction filter is fired when the information indicates that the subject is taking an HIV/AIDS medication, colchicine, or a hepatitis medication.

16. The method of claim 1 wherein, when the drug interaction filter is fired, the subject is provided with a warning.

17. The method of claim 1, wherein
 the atherosclerotic cardiovascular event filter is fired when the information indicates the subject has had a heart attack, a stroke, or a heart procedure, and
 when the atherosclerotic cardiovascular event filter is fired, the subject is provided with a warning.

18. The method of claim 1, wherein
 the pooled cohort equation filter is fired when the information indicates that the subject has a 10-year risk of atherosclerotic cardiovascular disease of less than five percent, and
 when the pooled cohort equation filter is fired the subject is provided with a warning.

19. The method of claim 1, wherein
 the pooled cohort equation filter incorporates the sex of the subject, the race of the subject, the age of the subject, the total cholesterol level of the subject, the HDL cholesterol count of the subject, the systolic blood pressure of the subject, whether the subject is taking a medication that interacts with a statin, the smoking status of the subject, and the diabetes status of the subject to derive a risk for the atherosclerotic cardiovascular disease, and
 when the pooled cohort equation filter is fired, the subject is provided with a warning.

20. The method of claim 1, wherein:
 the liver disease filter is fired when the information indicates that subject has liver disease, and
 when the liver disease filter is fired the liver disease filter deems the subject unqualified for delivery of the statin pharmaceutical composition.

21. The method of claim 1, wherein
 the alcohol consumption filter is fired when the information indicates the subject consumes an average of three or more servings of alcohol per day and,
 when the alcohol consumption filter is fired, the subject is provided with a warning.

22. The method of claim 1, wherein
 the adverse reaction filter is fired when the information indicates that the subject has had an adverse reaction to a cholesterol lowering medication and
 when the adverse reaction filter is fired, the subject is provided with a warning.

23. The method of claim 1 wherein,
 the information further comprises whether the subject has a kidney disease, and
 the plurality of filters includes a kidney disease filter that is fired when the information indicates that the subject has kidney disease.

24. The method of claim 1, wherein
 the plurality of filters includes an Asian descent filter that is fired when the information indicates that the subject identifies with Asian descent.

25. The method of claim 1, wherein the statin pharmaceutical composition comprises lovastatin, fluvastatin, atorvastatin, rosuvastatin, simvastatin, pravastatin, or pitavastatin.

26. The method of claim 1, wherein
 the statin pharmaceutical composition comprises rosuvastatin and the subject is administered a daily dosage of from 4 mg to 11 mg,
 the statin pharmaceutical composition comprises atorvastatin and the subject is administered a daily dosage of 10 mg,
 the statin pharmaceutical composition comprises lovastatin and the subject is administered a daily dosage of from 15 mg to 25 mg,
 the statin pharmaceutical composition comprises simvastatin and the subject is administered a daily dosage of from 10 mg to 25 mg,
 the statin pharmaceutical composition comprises pravastatin and the subject is administered a daily dosage of from 10 mg to 80 mg,
 the statin pharmaceutical composition comprises fluvastatin and the subject is administered a daily dosage of from 20 mg to 40 mg, or the statin pharmaceutical composition comprises pitavastatin and the subject is administered a daily dosage of from 1 mg to 4 mg.

27. The method of claim 1, wherein, at least two of the filters in the plurality of filters deem the subject unqualified for delivery of the statin pharmaceutical composition when fired, and at least two of the filters in the plurality of filters provide the subject with a warning when fired.

* * * * *